US006486155B1

(12) United States Patent
Pamukcu et al.

(10) Patent No.: US 6,486,155 B1
(45) Date of Patent: Nov. 26, 2002

(54) METHOD OF INHIBITING NEOPLASTIC CELLS WITH ISOQUINOLINE DERIVATIVES

(75) Inventors: Rifat Pamukcu, Spring House, PA (US); Gary A. Piazza, Doylestown, PA (US)

(73) Assignee: Cell Pathways Inc, Horsham, PA (US)

( * ) Notice: Subject to any disclaimer, the term of this patent is extended or adjusted under 35 U.S.C. 154(b) by 0 days.

(21) Appl. No.: 09/198,413

(22) Filed: Nov. 24, 1998

(51) Int. Cl.$^7$ .......................................... A61K 31/535
(52) U.S. Cl. .......................................... 514/235.2
(58) Field of Search .......................................... 514/235.2

(56) References Cited

U.S. PATENT DOCUMENTS

| | | | | |
|---|---|---|---|---|
| 3,031,450 | A | 4/1962 | Fischer et al. | |
| 3,161,654 | A | 12/1964 | Shen | |
| 3,322,755 | A | 5/1967 | Roch et al. | |
| 3,517,005 | A | 6/1970 | Cronin et al. | |
| 3,594,480 | A | 7/1971 | Cronin et al. | |
| 3,647,858 | A | 3/1972 | Hinkley et al. | |
| 3,654,349 | A | 4/1972 | Shen et al. | |
| 3,780,040 | A | 12/1973 | Schnettler et al. | |
| 3,812,127 | A | 5/1974 | Cronin et al. | |
| 3,819,631 | A | 6/1974 | Broughton et al. | |
| 3,865,840 | A | 2/1975 | Carson | |
| 3,920,636 | A | 11/1975 | Takahasi et al. | |
| 4,001,237 | A | 1/1977 | Partyka et al. | |
| 4,001,238 | A | 1/1977 | Partyka et al. | |
| 4,039,544 | A | 8/1977 | Broughton et al. | |
| 4,060,615 | A | 11/1977 | Matier et al. | |
| 4,076,711 | A | 2/1978 | Ganguly et al. | |
| 4,079,057 | A | 3/1978 | Juby et al. | |
| 4,098,788 | A | 7/1978 | Crenshaw et al. | |
| 4,101,548 | A | 7/1978 | Crenshaw et al. | |
| 4,102,885 | A | 7/1978 | Crenshaw et al. | |
| 4,138,561 | A | 2/1979 | Crenshaw et al. | |
| 4,146,718 | A | 3/1979 | Jenks et al. | |
| 4,161,595 | A | 7/1979 | Kaplan et al. | |
| 4,171,363 | A | 10/1979 | Crenshaw et al. | |
| 4,208,521 | A | 6/1980 | Crenshaw et al. | |
| 4,209,623 | A | 6/1980 | Juby | |
| 4,423,075 | A | 12/1983 | Dvornik et al. | |
| 4,457,927 | A | 7/1984 | Biere et al. | |
| 4,460,590 | A | 7/1984 | Möller | |
| 4,460,591 | A | 7/1984 | DeGraw et al. | |
| 4,880,810 | A | 11/1989 | Lowe III et al. | |
| 4,885,301 | A | 12/1989 | Coates | |
| 4,923,874 | A | 5/1990 | McMahon et al. | |
| 4,950,680 | A | 8/1990 | Taylor et al. | |
| 4,971,972 | A | 11/1990 | Doll et al. | |
| 5,073,559 | A | 12/1991 | Coates | |
| 5,091,431 | A | 2/1992 | Tulshian et al. | |
| 5,147,875 | A | 9/1992 | Coates et al. | |
| 5,175,151 | A | 12/1992 | Afonso et al. | |
| 5,223,501 | A | 6/1993 | Chakravarty et al. | |
| 5,250,535 | A | 10/1993 | Verheyden et al. | |
| 5,254,571 | A | 10/1993 | Coates et al. | |
| 5,358,952 | A | 10/1994 | Moschel et al. | |
| 5,376,683 | A | 12/1994 | Klar et al. | |
| 5,393,755 | A | 2/1995 | Neustadt et al. | |
| 5,401,774 | A | 3/1995 | Pamukcu et al. | |
| 5,439,895 | A | 8/1995 | Lee et al. | |
| 5,488,055 | A | 1/1996 | Kumar et al. | |
| 5,614,530 | A | 3/1997 | Kumar et al. | |
| 5,614,627 | A | 3/1997 | Takase et al. | |
| 5,696,159 | A | 12/1997 | Gross et al. | 514/468 |
| 5,728,563 | A | 3/1998 | Tanaka | |
| 5,756,818 | A | 5/1998 | Buchmann et al. | |
| 5,852,035 | A | 12/1998 | Pamukcu et al. | |
| 5,858,694 | A | 1/1999 | Piazza et al. | |
| 5,874,440 | A | 2/1999 | Pamukcu et al. | |

FOREIGN PATENT DOCUMENTS

| | | | |
|---|---|---|---|
| DE | 3038166 | | 6/1981 |
| EP | 0 330 004 | A1 | 6/1989 |
| EP | 0 347146 | A2 | 12/1989 |
| EP | 0 349239 | A2 | 1/1990 |
| EP | 0 351058 | | 1/1990 |
| EP | 0 352960 | A2 | 1/1990 |
| EP | 0 395328 | A2 | 10/1990 |
| EP | 0 428268 | A2 | 5/1991 |
| EP | 0 463756 | A1 | 1/1992 |
| EP | 0 508586 | A1 | 10/1992 |
| EP | 0 526004 | A1 | 2/1993 |
| EP | 0 607439 | A1 | 7/1994 |
| EP | 0 722937 | A1 | 7/1996 |
| EP | 0 743304 | A1 | 10/1996 |
| GB | 807826 | | 1/1959 |
| GB | 2063249 | A | 6/1981 |
| JP | 56-53659 | A | 5/1981 |
| JP | 57-167974 | A | 10/1982 |
| JP | 8-311035 | | 11/1996 |
| WO | WO 92/03419 | | 3/1992 |
| WO | WO 93/07149 | | 4/1993 |
| WO | WO 93/12095 | | 6/1993 |
| WO | WO 94/05661 | | 3/1994 |
| WO | WO 94/19351 | | 9/1994 |
| WO | Wo 94/29277 | | 12/1994 |
| WO | WO 95 18969 | A | 7/1995 |
| WO | WO 95/19978 | | 7/1995 |
| WO | WO 95/26743 | | 10/1995 |
| WO | WO 97/03070 | | 1/1997 |
| WO | WO 97/03985 | | 2/1997 |
| WO | WO 97/24334 | | 7/1997 |
| WO | WO 98/14448 | | 4/1998 |
| WO | WO 98/15530 | | 4/1998 |
| WO | WO 98/16224 | | 4/1998 |
| WO | WO 98/16521 | | 4/1998 |
| WO | WO 98/17668 | | 4/1998 |
| WO | WO 98/08848 | | 5/1998 |
| WO | WO 98/23597 | | 6/1998 |
| WO | WO 98/38168 | | 9/1998 |
| WO | WO 96/32379 | | 10/1998 |
| WO | WO 00/15222 | | 3/2000 |

OTHER PUBLICATIONS

Blaya, C. et al., Effect of the protein kinase inhibitors, 1–(5–isoquinolinylsulfonyl)–2–methylpiperazine H–7 and N–(2–[methylamino]ethyl)–5–isoquinoline–sulfonamide H–8 on Lewis lung carcinoma tumor progression, European Journal of Pharmacology, 354, pp. 99–104 (1998).

(List continued on next page.)

*Primary Examiner*—Jerome D. Goldberg
(74) *Attorney, Agent, or Firm*—Robert W. Stevenson

(57) ABSTRACT

A method for inhibiting neoplasia, particularly cancerous and precancerous lesions by exposing the affected cells to isoquinoline derivatives.

2 Claims, No Drawings

OTHER PUBLICATIONS

Chang, W. et al., Sulindac Sulfone Modulates the Expression and Cellular Localization of b–Catenin in Human Colon Carcinoma Cells, Digestive Disease Week, Apr. 1, 1999.

Earnest, D. et al., Piroxicam and Other Cyclooxygenase Inhibitors: Potential for Cancer Chemoprevention, Journal of Cellular Biochemistry, Supplement 161:156–166 (1992).

Easwaran, V. et al., The Ubiquitin–Proteasome Pathway and Serine Kinase Activity Modulate Adenomatous Polyposis Coli Protein–mediated Regulation of β–Catenin–Lymphocyte Enhancer–binding Factor Signaling, The Journal of Biological Chemistry, vol. 274, No. 23, pp. 16641–16645, Jun. 4, 1999.

Jiang, X. et al., Inhibition of calmodulin–dependent phosphodiesterase induces apoptosis in human leukemic cells, Proc. Natl. Acad. Sci. USA, vol. 83, pp. 11236–11241, Oct. 1996.

Korinek, V. et al., Constitutive Transcriptional Activation by a β–Catenin–Tcf Complex in $APC^{-/-}$Colon Carcinoma, Science, vol. 275, pp. 1784–1786, Mar. 21, 1997.

Mahmoud, N. et al., Apc Gene Mutation is Associated with a Dominant–Negative Effect upon Intestinal Cell Migration, Cancer Research 57, pp. 5045–5050, Nov. 15, 1997.

Mahmoud, N. et al., Genotype–Phenotype Correlation in Murine Apc Mutation: Differences in Enterocyte Migration and Response to Sulindac, Cancer Research 59, pp. 353–359, Jan. 15, 1999.

Morin, P. et al., Activation of β–Catenin–Tcf Signaling in Colon Cancer by Mutations in β–Catenin or APC, Science, vol. 275, pp. 1787–1789, Mar. 21, 1997.

Peifer, M., β–Catenin as Oncogene: The Smoking Gun, Science, vol. 275, pp. 1752–1753, Mar. 21, 1997.

Rubinfeld, B. et al., Stabilization of β–Catenin by Genetic Defects in Melanoma Cell Lines, Science, vol. 275, pp. 1790–1792, Mar. 21, 1997.

Waddell, W.R. et al., Am. J. Surgery, vol. 157, pp. 175–179 (1989).

Gonzaga, R.A.F. et al., The Lancet, Mar. 30, 1985, p. 751.

Waddell, W.R. et al., J. Surg. Oncology, vol. 24, pp. 83–87 (1983).

Federation Proceedings (1972) of the Federation of American Societies for Experimental Biology abstract Nos. 2044 and 2045.

Gilman, S.C. et al., Nonsteroidal Anti–inflammatory Drugs in Cancer Therapy, (circa 1985).

Brogden, R.N. et al., Drugs, vol. 16, pp. 97–114 (1978).

Hucker, H.B. et al., Drug Metabolism & Disposition, vol. 1, No. 6, pp. 721–36 (1973).

Shen, T.Y. et al., Chemical and Biological Studies on Indomethacin, Sulindae and Their Analogs, pp. 107–178 (circa 1975).

Duggan, D.E. et al., Clin. Pharm. & Therapeutics, vol. 21, No. 3, pp. 326–335 (1976).

Duggan, D.E. et al., J. Pharm. & Exper. Therap., vol. 201, No. 1, pp. 8–13 (1977).

Glavin, G.B. et al., Toxicology and Applied Pharmacology, vol. 83, pp. 386–389 (1986).

Moorghen, M. et al., Journal of Pathology, vol. 156, pp. 341–347 (1988).

Moorghen, M. et al., Acta Histochemica, Suppl.–Band XXIX, S. 195–199 (1990).

Bjarnason et al., Gastroenterology, vol. 94, No. 4, pp. 1070–1074 (1988).

Badrieh, Y., et al., Chem. Ber., vol. 125, pp. 667–674 (1992).

Silvola, J. et al., Effects of nonsteroidal anti–inflammatory drugs on rat gastric mucosal phosphodiesterase activity, Agents and Actions, vol. 12.4, pp. 516–520 (1982).

Curtis–Prior, P.B. et al., Cyclic Nucleotide Phosphodiesterase Activity of Human Normal and Carcinomatous Lung Tissue, The Lancet, pp. 1225–1225 Dec. 4, 1976.

Pepin, P. et al., Effects of Sulindac and Oltipraz on the tumorigenicity of 4–(methylnitrosamino) 1–(3–pyridyl)–1–Butanone in A/J mouse lung, Carcinogenesis, vol. 13, No. 3, pp. 341–348 (1992).

Nicholson, C.D. et al. Differential modulation of tissue function and therapeutic of selective inhibitors of cyclic nucleotide Pharmacol. Sci. (TiPs), vol. 12, pp. 19–27 (1991).

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Luginer, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Turner, N.C. et al., Relaxation of guinea–pig trachea by cyclic AMP phosphodiesterase inhibitors and their enhancement by sodium mitroprusside, Br. J. Pharmacol. vol. III, pp. 1047–1052 (1994).

Weishaar, R.E. et al., Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Saeki, T. et al., Isolation of Cyclic Nucleotide Phosphodiesterase Isozymes From Pig Aorta, Biochem. Pharmacology, vol. 46, No. 5, pp. 833–839 (1993).

Turner, N.C. et al., Pulmonary effects of type V cyclic GMP specific phosphodiesterase inhibition in anaesthetized guinea–pig, Br. J. Pharmacol., vol. 111, 1198–1204 (1994).

Ferreira, S.H. et al., The molecular mechanism of action of peripheral morphone analgesia: stimulation of the cGMP system via nitric oxide release, European Journal of Pharmacology, 201 pp. 121–122 (1991).

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Tulshian, D. et al., Synthesis and Phosphodiesterase Activity of Carboxylic Acid Mimetics of Cyclic Guanosine 3",5"–Monophospate, J. Med. Chem, vol. 36, 1210–1220 (1993).

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073,2081 (1992).

Broughton, B.J. et al., Antiallergic Activity of 2–Phenyl–8–azapruin–6–ones, Journal of Medicinal Chemistry, vol. 18, No. 11, pp. 1117–1118 (1975).

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Zacharski L. R. et al., Effect of Mopidamol on Survival in Carcinoma of the Lung and Colon: Final Report of Veterans Administration Cooperative Study No. 188, J. of the Nat'l. Cancer Inst., vol. 80, No. 2, pp. 90–96 (1988).
Lichtner, R. B. et al., The Pyrimido–pyrimidine Derivatives RA 233 adn RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).
Janik, P. et al., Inhibition of Growth of Primary and Metastatic Lewis Lung Carcinoma Cells by the Phosphodiesterase Inhibitor Isobutylmethylxanthine, Cancer Res. vol. 40, pp. 1950–1954, (Jun., 1980).
Bergstrand, Hakan et al., Effects of Antiallergic Agents, Compound 48/80, and Some Reference Inhibitors on the Activity of Partially Purified Human Lung Tissue Adenosine Cyclic 3',5'–Monophosphate and Guanosine Cyclic 3',5'–Monophosphate Phosphodiesterases, Molecular Pharmacology, 13, pp. 38–43 (1976).
Drees, Markus et al., 3',5'–Cyclic Nucleotide Phosphodiesterase in Tumor Cells as Potential Target for Tumor Growth Inhibition, Cancer Research 53, pp. 3058–3061 (1993).
Semmler, J. et al., Xanthine derivatives: comparison between suppression of tumor necrosis factor–x production and inhibition of cAMP–phosphodiesterase activity, Immunology 78, pp. 520–525 (1993).
et al., Structure–Activity Relationships of Brassinin in Preventing the Development of Carcinogen–Induced Mammary Lesions in Organ Culture, Anticancer Research 14: 1209–1214 (1994).
Makaryan, A.P. et al., Cyclic Nucleotides in Patients with Malignant Neoplasms of the Colon, Laboratornoe Delo, vol. 8, pp. 31–33 (1991).
Carter et al., Chemotherapy of Cancer, $2^{nd}$ Ed., John Wiley & Sons, NY, NY, 1981, pp. 362–365.
Biddle, William et al., Antineoplastic Effect of the Pyrimido–Pyrimidine Derivative: RA 233, Pathologie Biologie, Jan., 1984, pp. 9–13.
Clarke, W.R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2), pp. 81–9, (1994).
Raeburn, David et al., Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–1151 (1993).
Marcoz, P. et al., Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–1035 (1993).
Barnett, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–812 (1993).
Molnar–Kimber, K. et al., Modulation of TNFa and IL–1B from indotoxin–stimulated monocytes by selective PDE isozyme inhibitors (Abstract Only), Agents Actiosn 39(Spec. Conf. Issue), C77–C79 (1993).
Giorgi, Mauro et al., Characterization of 3':5' cyclic nucleotide phosphodiesterase activities of mouse neuroblastoma N18TG2 cells (Abstract Only), FEBS Lett. 324 (1) pp. 76–80 (1993).
Porter, Roderick et al., Preparation of 6–phenyl–3–(5–tetrazoly)pyridin–2(H)–one derivatives as cyclic AMP–dependent protein kinase agonists (Abstract Only), PCT Int. Appl. WO9206085 A1, (Sep. 26, 1991).
Molnar–Kimber, K. L. et al., Differential regulation of TNF–a and IL–1B production from endotoxin stimulated human monocytes by phosphodiesterase inhibitors (Abstract Only), Mediators Inflammation 1(6) pp. 411–417 (1992).
Radomski, Marek W. et al., Human Colorectal adenocarcinoma cells: differential nitric oxide synthesis determines their ability of aggregate platelets (Abstract Only), Cancer Res. 51(22) pp. 6073–6078 (1991).
Anderson, Thomas L. G. et al., Interactions between isoprenaline, sodium nitroprusside, and isozyme–selective phosphodiesterase inhibitors on ADP–induced aggretation and cyclic Nucleotide levels in human platelets (Abstract Only), J. Cardiovasc, Pharmacol. 18(2) pp. 237–242 (1991).
Souness, John E. et al., Role of Selective cyclic GMP phosphodiesterase inhibition in the myorelaxant actions of M&B 22,943, MY–5445, vinpocetine and 1–methyl–3–isobutyl–8–(methylamino)xanthine (Abstract Only), Br. J. Pharmacol. 98(3) pp. 725–734 (1989).
Lichtner, Rosemarie B., The pyrimidopyrimidine derivatives RA233 and RX–RA85 affect cell cycle distribution of two murine tumor cell lines (Abstract Only), Eur. J. Cancer Clin. Oncol. 25(6), pp. 945–951 (1989).
Mamytbekova, A., et al., Antimetastatic effect of flurbiprofen and other platelet aggregation inhibitors (Abstract Only), Neoplasma 33(4), pp. 417–421 (1986).
Hagiwara, Masatoshi et al., Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–471 (1984).
Ho–Sam Ahn et al., Potent Tetracyclic Guanine Inhibitors of PDE1 and PDE5 Cyclic Guanosine Monophosphate Phosphodiesterases with Oral Antihypertensive Activity, J. Med. Chem. 1997, 40, pp. 2196–2210.
J.A. Mitchell et al., Selectivity of Nonsteroidal antiinflammatory drugs as inhibitors of constitutive and inducible cyclooxygenase; Proc. Natl. Acad. Sci. USA, vol. 90, Dec. 1994, pp. 11693–11697.
J.D. Gaffen et al.: Increased killing of malignant cells by giving indomethacin with methotrexate, p. 30; column 1; XP002084860Chemical Abstract, vol. 106, No. 11, Mar. 16, 1987, abstract No. 78377, J.D.
Tsou, K–C. et al. 5'–Nucleotide Phosphodiesterase Isozyme–V as a Marker for Liver Metastases in Breast Cancer Patients, Cancer 54:1788–1793, 1984.
Epstein P M et al.; Dep. Pharmacol., Univ. Tex. Med. Sch., M.D. Anderson Hosp., Houston, Tex. 88030, USA BIOSIS 78:140912, Increased Cyclic Nucleotide Phospho Di Esterase Activity Associated With Proliferation and Cancer in Human and Murine Lymphoid Cells, 1997.
Christian Schudt et al., "Phosphodiesterase Inhibitors" The Handbook of Immunopharmacology, Academic Press, 1996, pp. 65–134.

METHOD OF INHIBITING NEOPLASTIC CELLS WITH ISOQUINOLINE DERIVATIVES

TECHNICAL FIELD

This invention relates to a method for the selective inhibition of neoplastic cells, for example, for the treatment or prevention of precancerous lesions or other neoplasias in mammals.

BACKGROUND OF THE INVENTION

Each year in the United States alone, untold numbers of people develop precancerous lesions, which is a form of neoplasia, as discussed below. Such lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds that prevent or induce the remission of existing precancerous or cancerous lesions or carcinomas would greatly reduce illness and death from cancer.

For example, approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

In the breast, breast cancer is often treated surgically, often by radical mastectomy with its painful aftermath Such surgery is costly, too.

As indicated above, each lesion carries with it a chance that it will develop into a cancer. The likelihood of cancer is diminished if a precancerous lesion is removed. However, many of these patients demonstrate a propensity for developing additional lesions in the future. They must, therefore, be monitored periodically for the rest of their lives for reoccurrence.

In most cases (i.e. the cases of sporadic lesion formation, e.g. so-called common sporadic polyps), lesion removal will be effective to reduce the risk of cancer. In a small percentage of cases (i.e. cases where numerous lesions form, e.g. the so-called polyposis syndromes), removal of all or part of the effected area (e.g. the colon) is indicated. For example, the difference between common sporadic polyps and polyposis syndromes is dramatic. Common sporadic polyp cases are characterized by relatively few polyps which can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each lesion carries with it a palpable risk of cancerous development, patients who form many lesions (e.g. polyposis syndrome patients) invariably develop cancer if left untreated. Surgical removal of the colon is the conventional treatment in polyposis patients. Many polyposis patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because chemotherapy for cancer itself is often not effective and has severe side effects. Cancer chemoprevention is important for recovered cancer patients who retain a risk of cancer reoccurrence. Also, cancer prevention is important for people who have not yet had cancer, but have hereditary factors that place them at risk of developing cancer. With the development of new genetic screening technologies, it is easier to identify those patients with high-risk genetic factors, such as the potential for polyposis syndrome, who would greatly benefit from chemopreventative drugs. Therefore, finding such anti-cancer drugs that can be used for prolonged preventive use is of vital interest.

Known chemopreventative and chemotherapeutic drugs are believed to kill cancer cells by inducing apoptosis, or as sometimes referred to as "programmed cell death." Apoptosis naturally occurs in virtually all tissues of the body, and especially in self-renewing tissues such as bone marrow, immune cells, gut, liver and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis play a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long-term use, or use in otherwise healthy individuals with precancerous lesions, These side effects, which are a result of the high levels of cytotoxicity of the drugs, include hair loss, weight loss, vomiting, immune suppression and other toxicities. Therefore, there is a need to identify new drug candidates for therapy that do not have such serious side effects in humans.

In recent years, several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the prophylactic use of currently available NSAIDs, even in polyposis syndrome patients, is marked by severe side reactions that include gastrointestinal irritations, perforations, ulcerations and kidney toxicity. Once NSAID treatment is terminated due to such complications, the polyps return, particularly in polyposis syndrome patients.

Sulindac has been particularly well received among the NSAIDs for the polyp treatment. Sulindac is a sulfoxide compound that itself is believed to be inactive as an anti-arthritic agent. The sulfoxide is reportedly converted by liver enzymes to the corresponding sulfide, which is acknowledged to be the active moiety as a prostaglandin synthesis inhibitor. The sulfide, however, is associated with the side effects of conventional NSAIDs. The sulfoxide is also known to be metabolized to sulfone compound that has been found to be inactive as an inhibitor of prostaglandin synthesis but active as an inhibitor of precancerous lesions.

SUMMARY OF THE INVENTION

This invention includes a method of inhibiting neoplastic cells by exposing those cells to a pharmacologically effective amount of those compounds described below. Such compounds are effective in modulating apoptosis and eliminating and inhibiting the growth of neoplasias such as precancerous lesions, but are not characterized by the severe side reactions of conventional NSAIDs or other chemotherapeutics.

The compounds of that are useful in the methods of this invention include those of Formula I:

(I)

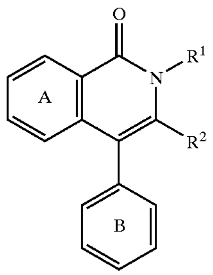

wherein

Ring A and Ring B are the same or different and each a substituted or unsubstituted benzene ring, R1 is (1) a hydrogen atom, (2) a substituted or unsubstituted lower alkyl group, (3) a substituted or unsubstituted cyclo-lower alkyl group, (4) a substituted or unsubstituted aryl group, (5) a substituted or unsubstituted heterocyclic group, or (6) an amino group optionally having one or two substituents, $R^2$ is a group of the formula —$COOR^3$ or —$CON(R^4)(R^5)$, $R^3$ is a hydrogen atom or an ester residue, and a group of the formula —$N(R^4)(R^5)$ is a substituted or unsubstituted nitrogen-containing aliphatic heterocyclic group or a substituted or unsubstituted amino group, provided that when $R^1$ is a hydrogen atom or a substituted or unsubstituted lower alkyl group, then at least one of Ring A and Ring B is a benzene ring which is substituted by two or more lower alkoxy groups, or a pharmaceutically acceptable salt thereof.

DETAILED DESCRIPTION OF THE PREFERRED EMBODIMENTS

As indicated above, this invention relates to a method for inhibiting neoplasia, particularly cancerous and precancerous lesions by exposing the affected cells to a compound of Formula I above.

Preferably, such compounds are administered without therapeutic amounts of an NSAID.

The present invention is also a method of treating mammals with precancerous lesions by administering a pharmacologically effective amount of an enterically coated pharmaceutical composition that includes compounds of this invention.

Also, the present invention is a method of inhibiting the growth of neoplastic cells by exposing the cells to an effective amount of compounds of Formula I, wherein $R_1$ through $R_3$ are defined as above.

In still another form, the invention is a method of inducing apoptosis in human cells by exposing those cells to an effective amount of compounds of Formula I to those cells sensitive to such a compound.

As used herein, the term "precancerous lesion" includes syndromes represented by abnormal neoplastic, including dysplastic, changes of tissue.

Examples include adenomatous growths in colonic, breast or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), prostatic dysplasia, bronchial dysplasia, breast, bladder and/or skin and related conditions (e.g., actinic keratosis), whether the lesions are clinically identifiable or not.

As used herein, the term "carcinomas" refers to lesions that are cancerous. Examples include malignant melanomas, breast cancer, and colon cancer.

As used herein, the term "neoplasm" refers to both precancerous and cancerous lesions.

Compounds useful in the methods of this invention may be formulated into compositions together with pharmaceutically acceptable carriers for oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g. pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories that may contain, in addition to the compounds of Formula I, excipients such as cocoa butter or a suppository wax.

The pharmaceutically acceptable carrier and compounds of this invention are formulated into unit dosage forms for administration to a patient. The dosage levels of active ingredient (i.e. compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The pharmaceutical compositions of this invention are preferably packaged in a container (e.g. a box or bottle, or both) with suitable printed material (e.g. a package insert) containing indications, directions for use, etc.

The dose of the compounds (I) for use in the present invention may vary in accordance with, for example, the administration routes, and the ages, weights and conditions of the patients. For example, when administered in an injection preparation, it is usually in the range of about 0.0001–0.5 mg/kg/day, preferably in the range of about 0.0005–0.1 mg/kg/day. When administered in an oral preparation, it is usually in the range of about 0.001–30 mg/kg/day, preferably in the range of about 0.05–10 mg/kg/day.

Among the compounds (1) useful in this present invention, a group of the formula —$COOR^3$ is ones wherein $R^3$ is a hydrogen atom, or an ester residue such as an aryl-lower alkyl group (e.g., benzyl, nitrobenzyl, a protected or unprotected amino-benzyl, a lower alkoxybenzyl), a lower alkyl group (e.g., methyl, ethyl, propyl, butyl), a cyclo-lower alkyl group (e.g., cyclopentyl), or a tri-lower alkylsilyl-lower alkyl group (e.g., trimethylsilylmethyl, tert-butyldimethylsilylmethyl). When $R^2$ is a group —$CON(R^4)(R^5)$, a group of the formula —$N(^4)(R^5)$ is, for example, a substituted or unsubstituted nitrogen-containing 5 or 6-membered aliphatic heterocyclic group (e.g., a hydroxy-lower alkylsubstituted piperazinyl group, a morpholino group, a pyrrolidinyl group, a piperidinyl group), or a substituted or unsubstituted amino group (e.g., an imidazolyl-substituted lower alkylamino group, a mono- or di-lower alkylamino group, amino group).

Ring A and Ring B of the compounds (I) useful in the practice of this invention are a benzene ring which may optionally have 1 to 4 substituents being the same or different, and such substituents of said Ring A and Ring B are, for example, a protected or unprotected hydroxy group, a lower alkylenedioxy group, a halogen atom, a lower alkyl group, a mono- or di-lower alkylcarbamoyloxy group, or a group of the formula $R^6$—$(CO)_n$—O—($R^6$ is a substituted or unsubstituted lower alkyl group, a substituted or unsubstituted lower alkenyl group, a substituted or unsubstituted cyclo-lower alkyl group, a substituted or unsubstituted aryl group, a substituted or unsubstituted arylsulfonyl group, or a substituted or unsubstituted heterocyclic group, and n is 0 or 1).

More particularly, Ring A of the compound (I) is a benzene ring which may optionally have 1 to 4 substituents being the same or different, and such substituents of Ring A are, for example, a protected or unprotected hydroxy group, a lower alkylenedioxy group, a halogen atom, a lower alkyl group, a mono- or di-lower alkylcarbamoyloxy group, or a group of the formula of the formula $R^6$—$(CO)_n$—O— ($R^6$ is a substituted or unsubstituted lower alkyl group, a substituted or unsubstituted lower alkenyl group, a substituted or unsubstituted cyclo-lower alkyl group, a substituted or unsubstituted aryl group, a substituted or unsubstituted arylsulfonyl group, or a substituted or unsubstituted heterocyclic group, and n is 0 or 1). Ring B of the compound (I) of the present invention is a benzene ring which may optionally have 1 to 4 substituents being the same or different, and such substituents of Ring B are, for example, a protected or unprotected hydroxy group, a lower alkoxy group, a lower alkyl group, a halogen atom, or a lower alkylenedioxy group.

The suitable examples of Ring A and Ring B of the compounds of the present invention are those wherein Ring A is a benzene ring of the formula:

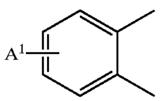

or

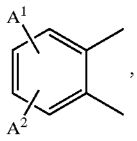

, and Ring B is a benzene ring of the formula:

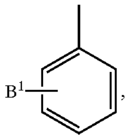

,

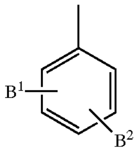

or

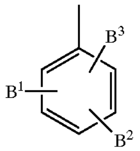

wherein $A^1$ and $A^2$ are the same or different and each a member selected from a hydrogen atom, a protected or unprotected hydroxy group, a lower alkylene-dioxy group, a halogen atom, a lower alkyl group, a mono- or di-lower alkyl-carbamoyloxy group, and a group of the formula $R^6$—$(CO)_n$—O—($R^6$ and n are the same as defined above), $B^1$, $B^2$ and $B^3$ are the same or different and each a member selected from a protected or unprotected hydroxy group, a lower alkoxy group, a lower alkyl group, a halogen atom and a lower alkylenedioxy group.

When Ring A and/or Ring B have a substituent of the formula $R^6$—CO)$_n$—O—$R^6$ is, for example, (1) a lower alkyl group which may optionally be substituted by 1 to 2 groups selected from a 5- to 10-membered heteromonocyclic or heterobicyclic group being optionally substituted by 1 to 4 groups selected from a hydroxy-substituted lower alkyl group, a lower alkyl group, an oxo group and a lower alkoxycarbonyl group; a 6- to 10-membered monocyclic or bicyclic aryl group being optionally substituted by 1 to 4 groups selected from a lower alkylenedioxy group, a carboxyl group, a lower alkoxycarbonyl group, a lower alkoxy group, a sulfamoyl group, a carbamoyl group, a nitro group, a protected or unprotected amino group, a phenyl group, a halogen atom, a mono-lower alkylamino group, a di-lower alkylamino group, a lower alkyl-piperazinocarbonyl group, a hydroxy-substituted lower alkyl group and a lower alkyl group; a cyano group; a carboxyl group; a mono- or di-lower alkylamino group; a lower alkoxy-substituted lower alkoxy group; a lower alkoxy group; a hydroxy group; a carbamoyl group; a lower alkoxycarbonyl group; a cyclo-lower alkyl group; and a benzoyl group, or (2) a 5- to 10-membered heteromonocyclic or heterobicyclic group which may optionally be substituted by 1 to 4 groups selected from a lower alkyl group, a cyano group, a carboxyl group, a mono- or di-lower alkylamino group, a lower alkoxy-substituted lower alkyl group, a hydroxy group, a lower alkoxy group, a carbamoyl group, a lower alkoxycarbonyl group and a nitro group.

The 6- to 10-membered monocyclic or bicyclic aryl group is, for example, a phenyl group, a naphthyl group, etc., and the 5- to 10-membered heteromonocyclic or heterobicyclic group is, for example, a pyridyl group, a pyrimidinyl group, a pyrazinyl group, a piperidyl group, a piperazinyl group, a pyrrolidinyl group, an isoquinolyl group, a quinolyl group, a tetrazolyl group, a thienyl group, a furyl group, a morpholino group, a pyrrolyl group, a benzimidazolyl group, an imidazolyl group, a quinazolyl group, a phtalazinyl group, etc.

Among Ring A and Ring B, more preferable examples of Ring A are a benzene ring of the formula:

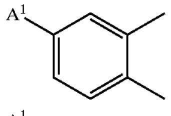

,

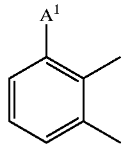

or

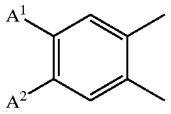

, and more preferable examples of Ring B are a benzene ring of the formula:

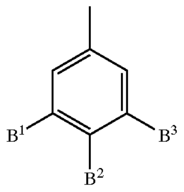

wherein $A^1$, $A^2$, $B^1$, $B^2$ and $B^3$ are the same as defined above.

Besides, among Ring A and Ring B, the most preferable examples of Ring

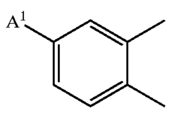

or

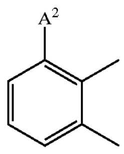

A are a benzene ring of the formula:

and the most preferable examples of Ring B are a benzene ring of the formula:

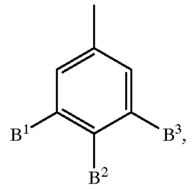

wherein $A^1$, $A^2$, $B^1$, $B^2$ and $B^3$ are the same as defined above.

Suitable examples of the substituents ($A^1$ and $A^2$) of Ring A are, for example, a protected or unprotected hydroxy group; a lower alkoxy group which may optionally be substituted by a group selected from a lower aklenedioxyphenyl group, a benzimidazolyl group, a lower alkyl-substituted imidazolyl group, a cyano group, a carboxyl group, a pyridyl group, an N-oxo-pyridyl group, a pyridyl group being substituted by a hydroxy-substituted lower alkyl group, a pyrrolidinyl group, an isoquinolyl group, a pyrimidinyl group, a pyrazinyl group, a quinazolyl group, a phthalazinyl group, a lower alkoxycarbonyl-substituted piperidyl group, a piperidyl group, a quinolyl group, a tetrazolyl group, a thienyl group, a furyl group, a pyrrolyl group being substituted by a lower alkyl group and a lower alkoxycarbonyl group, a mono-or di-lower alkyl amino group, a lower alkoxy-substituted lower alkoxy group, a lower alkoxy group, a hydroxy group, a carbamoyl group, a lower alkoxycarbonyl group, a cyclo-lower alkyl group, a hydroxy-lower alkyl group-substituted phenyl group, a carboxy-substituted phenyl group, a lower alkoxycarbonyl group-substituted phenyl group, a benzoyl group, a mono- or di-lower alkoxy-substituted phenyl group, a nitro-substituted phenyl group, a naphthyl group, a mono- or di-halogenophenyl group, a carbamoyl-substituted phenyl group, a sulfamoyl-substituted phenyl group, a phenyl group being substituted by one or two protected or unprotected amino groups, a biphenylyl group, a phenyl group being substituted by a halogen atom and a nitro group, a di-lower alkylamino-substituted phenyl group, and a lower alkyl-substituted phenyl group; a lower alkylenedioxy group; a halogen atom; a lower alkyl group; a cyclo-lower alkoxy group; a pyridyloxy group; a lower alkenyloxy group; a morpholinocarbonyloxy group; a lower alkyl-substituted piperazinylcarbonyloxy group; a pyrrolylcarbonyloxy group being substituted by a lower alkyl group and a nitro group; a pyrrolylcarbonyloxy group; a mono- or di-lower alkylcarbamoyloxy group; a lower alkyl-substituted phenylsulfonyloxy group; and a benzoyloxy group.

When $R^1$ of the present compounds (I) is a substituted or unsubstituted aryl group, the aryl group is, for example, a 6- to 14-membered partially saturated or unsaturated monocyclic, bicyclic or tricyclic aryl group. The monocyclic aryl group is, for example, a phenyl group, a cyclohexadienyl group, a cyclohexenyl group, etc. The bicyclic aryl group is, for example, a naphthyl group, an indenyl group, an indanyl group, an azulenyl group, etc. The tricyclic aryl group is, for example, a fluorenyl group, a phenanthrenyl group, an anthracenyl group, etc.

When $R^1$ of the present compounds (I) is a substituted or unsubstituted heterocyclic group, the heterocyclic group is, for example, a 5- to 12-membered partially saturated or unsaturated heteromonocyclic or heterobicyclic group, such as a 5- to 12-membered partially saturated or unsaturated aromatic heteromonocyclic or heterobicyclic group, or a 5- to 12-membered aliphatic heteromonocyclic or heterobicyclic group.

The 5- to 12-membered aromatic heteromonocyclic or heterobicyclic group is preferably a 5- to 10-membered aromatic heteromonocyclic or heterobicyclic group having 1 to 4 heteroatoms selected from a nitrogen atom, an oxygen atom and a sulfur atom, for example, a pyranyl group, an indazolyl group, a benzotriazolyl group, a pyrrolyl group, an imidazolyl group, a furyl group, a thienyl group, a thiazolyl group, an isoxazolyl group, an oxazolyl group, an oxazolinyl group, a pyrazolyl group, a phthalazinyl group, a quinazolinyl group, a thienopyrimidinyl group, a pyridyl group, a pyrimidinyl group, a pyridazinyl group, a pyrazinyl group, a triazinyl group, a tetrazolyl group, a quinolyl group, an isoquinolyl group, a quinoxalinyl group, an indolyl group, a benzothienyl group, a benzothiazolyl group, a benzoxazolyl group, or a benzimidazolyl group, and a partially saturated group of these groups.

The 5- to 12-membered aliphatic heteromonocyclic or heterobicyclic group is preferably a 5- to 10-membered aliphatic heteromonocyclic group having 1 to 4 heteroatoms selected from a nitrogen atom, an oxygen atom and a sulfur atom, for example, a piperazinyl group, a pyrrolidinyl group, a piperidyl group, a pyrazolidinyl group, a quinuclidinyl group, a thiomorpholino group, a morpholino group, a hexahydropyrimidinyl group, a tetrahydrofuranyl group, a tetrahydropyranyl group, and a dioxanyl group.

The substituent of the lower alkyl group for $R^1$ of the present compounds (I) is, for example, a piperidyl group, a pyridyl group, an imidazolyl group, a lower alkyl-substituted piperidyl group, a furyl group, a morpholino group, a tetrahydrofuryl group, a dihydropyridyl group being substituted by a lower alkyl group and an oxo group, a piperazinyl group, a lower alkoxycarbonyl-substituted piperazinyl group, a cyclo-lower alkyl group, a phenyl group, a lower alkylenedioxyphenyl group, a lower alkoxy-carbonyl group, a hydroxy group, a hydroxy-substituted lower alkoxy group, a caoxyl group, a lower alkoxy group, a protected or unprotected amino group, a carbamoyl group, a di-lower alkylamino group, and a pyridylcarbonyloxy group.

The lower alkyl group for $R^1$ may optionally have 1 to 3 substituents being the same or different, which are selected from the above groups.

The substituent of the cyclo-lower alkyl group for $R^1$ of the present compounds (I) is, for example, a lower alkoxy-carbonyl group, a hydroxy group, a carboxyl group, a lower alkyl group, a lower alkoxy group, a hydroxy-substituted lower alkyl group, or a protected or unprotected amino group.

The cyclo-lower alkyl group for $R^1$ may optionally have 1 to 3 substituents being the same or different, which are selected from the above groups.

The substituent of the aryl group for $R^1$ of the present compounds (I) is, for example, a halogen atom, a mono- or di-lower alkylamino group, a morpholino group, a lower alkyl-substituted pyrimidinyl group, a lower alkyl-substituted pyrazolyl group, a hydroxy-substituted lower alkyl group, a protected or unprotected amino group, a lower alkanoyl-substituted amino group, a lower alkoxy group, a lower alkyl group, a protected or unprotected hydroxy group, a carboxy-substituted lower alkyl group, a lower alkoxy-carbonyl-substituted lower alkyl group, a lower alkoxycarbonyl-substituted lower alkoxy group, a carbamoyl group, a carboxyl group, a lower alkylthio group, a lower alkoxycarbonyl group, a nitro group, a trihalogeno-lower alkyl group, a morpholinodarbonyl group, a carboxy-substituted lower alkoxy group, a di-(lower alkylsulfonyl) amino group, a morpholino-lower alkylcarbamoyl-substituted lower alkoxy group, a sulfamoyl group, a lower alkyl group being substituted by a protected or unprotected amino group, an amino group being substituted by a lower alkyl group and a protecting group for amino group, a lower alkylenedioxy group, a carbamoyl group being substituted by a protected or unprotected amino group, a lower alkyl-sulfinyl group, and a lower alkyl-sulfonyl group.

The aryl group for $R^1$ may optionally have 1 to 4 substituents being the same or different, which are selected from the above groups.

The substituent of the heterocyclic group for $R^1$ of the present compounds (I) is, for example, a hydroxy group, a halogen atom, a lower alkyl group, a phenyl-substituted lower alkyl group, a hydroxy-substituted lower alkyl group, an oxo group, a lower alkoxy group, a protected or unprotected amino group, a mono- or di-lower alkylamino group, a phenyl-lower alkoxy-carbonyl group, a lower alkoxycarbonyl group, a carboxyl group, and a carbamoyl group.

The heterocyclic group for $R^1$ may optionally have 1 to 4 substituents being the same or different, which are selected from the above groups.

The substituent of the amino group optionally having 1 or 2 substituents for $R^1$ of the present compounds (I) is, for example, a protecting group for amino group, a pyridyl group, a lower alkanoyl group, a lower alkyl group, a hydroxy-substituted lower alkyl group, a phenyl group, a lower alkanoyloxy-substituted lower alkyl group, and a trihalogeno-lower alkanoyl group, which are the same or different.

When the present compounds (I) have a protected amino group, the protecting group for amino group is, for example, a substituted or unsubstituted lower alkoxycarbonyl group, a lower alkanoyl group, etc., such as a benzyloxycarbonyl group, a 4-methoxybenzyloxycarbonyl group, a 9-fluorenylmethyloxy-carbonyl group, a tert-butoxycarbonyl group, a 2,2,2-trichloroethyloxycarbonyl group, a formyl group, an acetyl group, a propionyl group, and a butyryl group. Among these groups, the preferable one is an aryl-substituted lower alkoxy-carbonyl group and an unsubstituted lower alkoxycarbonyl group, for example, a benzyloxycarbonyl and a tert-butoxycarbonyl group.

When the present compounds (I) have a protected hydroxy group, the protecting group for hydroxy group is a conventional protecting group such as a substituted or unsubstituted aryl-lower alkyl group, and an acyl group. Among these groups, the preferable one is, for example, an unsubstituted aryl-lower alkyl group (e.g., benzyl, phenethyl), and an acyl group (e.g., formyl, acetyl, propionyl, malonyl, acryloyl, benzoyl).

Among the desired compounds (I) of the present invention, the preferable compounds are compounds of the formula (I) wherein the aryl group is a phenyl group, an indanyl group or a naphthyl group, the heterocyclic group is a piperazinyl group, a pyranyl group, a morpholino group, an indazolyl group, a pyrrolidinyl group, an indolyl group, a benzotriazolyl group, a pyrazinyl group, a pyridyl group, a thiomorpholino group, a pyrrolyl group, a quinolyl group, an isoquinolyl group, a phthalazinyl group, an isoxazolyl group, or a piperidyl group, and the nitrogen-containing aliphatic heterocyclic group is a piperazinyl group or a morpholino group.

The more preferable compounds of the present invention are compounds of the formula (I) wherein Ring A is a benzene ring of the formula:

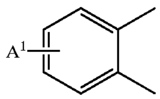
or
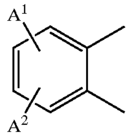

($A^1$ and $A^2$ are the same or different and each a member selected from a protected hydroxy group; a lower alkoxy group; a pridyl-lower alkoxy group; a hydroxy-lower alkyl group-substituted pyridyl-lower alkoxy group; an N-oxopyridyl-lower alkoxy group; a pyrazinyl-lower alkoxy group; a quinolyl-lower alkoxy group; a lower alkoxy group being substituted by an amino-substituted phenyl group; a lower alkoxy group being substituted by a mono or di-lower alkylamino-substituted phenyl group; a lower alkoxy group being substituted by a lower alkoxy-substituted phenyl group; a lower alkoxy group being substituted by a hydroxy-lower alkyl group-substituted phenyl group; a lower alkoxy group being substituted by a carboxy-substituted phenyl group; and an isoquinolyl-lower alkoxy group), and Ring B is a benzene ring of the formula:

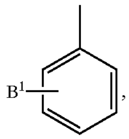,
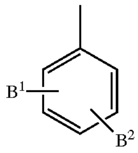
or
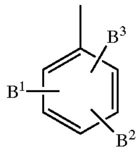

($B^1$, $B^2$ and $B^3$ are the same or different and each a member selected from a halogen atom, a lower alkyl group, and a lower alkoxy group), and $R^1$ is a phenyl group optionally being substituted by a protected or unprotected amino group, or a pyridyl group optionally being substituted by a protected or unprotected amino group, or a morpholino group, and $R^2$ is a lower alkoxycarbonyl group or a phenyl-lower alkoxycarbonyl group.

Among the desired compounds (I) of the present invention, more preferable compounds are compounds of the formula (I) wherein Ring A is a benzene ring of the formula:

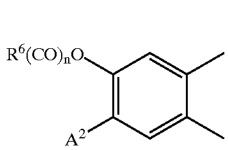
or
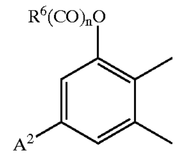

and Ring B is a benzene ring of the formula:

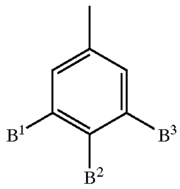

($R^6$ is (1) a lower alkyl group which may optionally be substituted by a group selected from a pyrrolyl group optionally being substituted by a lower alkyl group or a lower alkoxycarbonyl group; a pyridyl group optionally being substituted by a hydroxy-lower alkyl group; a thienyl group; an N-oxopyridyl group; a pyrazinyl group; a phenyl group optionally being substituted by 1 to 3 groups being the same or different, and selected from a carboxyl group, a lower alkoxycarbonyl group, a nitro group, an amino group, a mono- or di-lower alkylamino group, a phenyl group, a halogen atom, a lower alkoxy group, a hydroxy-substituted lower alkyl group and a lower alkyl group, a naphthyl group; a quinolyl group; an isoquinolyl group; a benzimidazolyl group; and a cyclo-lower alkyl group, or (2) a pyrrolyl group optionally being substituted by a group selected from a lower alkyl group and a nitro group, $A^2$ is a hydrogen atom or a lower alkoxy group, $B^1$, $B^2$ and $B^3$ are the same or different and each a halogen atom, a lower alkyl group, or a lower alkoxy group, and n is 0 or 1), and $R^1$ is a phenyl group, a phenyl group being substituted by a protected or unprotected amino group, or a morpholino group.

Other preferable compounds of the present invention are compounds of the formula (I) wherein Ring A is a benzene ring of the formula:

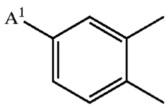
or
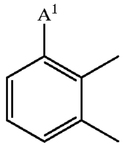

and Ring B is a benzene ring of the formula:

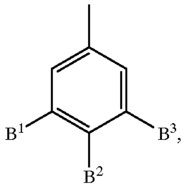, ($A^1$ is a protected or unprotected hydroxy group, or a lower alkoxy group being substituted by a group selected from a pyridyl group, a hydroxy-lower alkyl group-substituted pyridyl group, an N-oxopyridyl group, a pyrazinyl group, an amino-substituted phenyl group, a mono- or di-lower alkylamino-substituted phenyl group, a lower alkoxy-substituted phenyl group, a hydroxy-lower alkyl group-substituted phenyl group, an isoquinolyl group and a quinolyl group, $B^1$, $B^2$ and $B^3$ are the same or different and each a halogen atom, a lower alkyl group and a lower alkoxy group), and $R^1$ is a phenyl group being substituted by a protected or unprotected amino group.

Among the desired compounds (I) of the present invention, pharmaceutically preferable compounds are compounds of the formula (I-A):

(I-A)

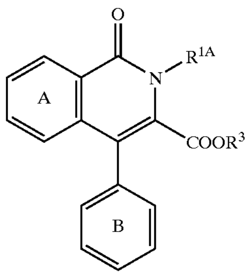

wherein Ring A and Ring B are the same or different and each a substituted or unsubstituted benzene ring, $R^{1A}$ is a substituted or unsubstituted aryl group or substituted or unsubstituted heterocyclic group, and $R^3$ is a hydrogen atom or an ester residue, or a pharmaceutically acceptable salt thereof.

Examples of the above compounds are compounds of the formula (I-A) wherein Ring A and Ring B are the same or different and each a benzene ring having optionally 1 to 4 substituents selected from (i) a hydroxy group;

(ii) a halogen atom;

(iii) a lower alkyl group;

(iv) a cyclo-lower alkoxy group;

(v) a lower alkylenedioxy group;

(vi) a lower alkoxy group;

(vii) a lower alkoxy group having 1 to 3 substituents selected from a hydroxy group, a benzoyl group, a lower alkoxycarbonyl group, a carboxyl group, a mono- or di-lower alkylamino group, a lower alkoxy-lower alkoxy group, a lower alkoxy group, a phenyl group, a naphthyl group and a phenyl group having 1 to 3 substituents selected from a nitro group, a halogen atom, a phenyl group, a carboxyl group, a lower alkoxycarbonyl group, a lower alkyl group, a lower alkoxy group, an amino group, a mono- or di-lower alkylamino group and a hydroxy-lower alkyl group; and (viii) a lower alkoxy group being substituted by a 5- to 10-membered heterocyclic group having 1 to 4 heteroatoms selected from a nitrogen atom, an oxygen atom and a sulfur atom, and optionally 1 to 3 substituents selected from a carboxyl group, a lower alkoxycarbonyl group, a lower alkyl group, a hydroxy-substituted lower alkyl group, a nitro group and an oxo group, $R^{1A}$ is a phenyl group; a phenyl group having 1 to 4 substituents selected from a protected or unprotected amino group, a halogen atom, a mono- or di-lower alkylamino group, a morpholino group, a lower alkyl-substituted pyrimidinyl group, a lower alkyl-substituted pyrazolyl group, a hydroxy-substituted lower alkyl group, a lower alkanoyl-substituted amino group, a lower alkoxy group, a lower alkyl group, a protected or unprotected hydroxy group, a carboxyl-substituted lower alkyl group, a lower alkoxycarbonyl-substituted lower alkyl group, a lower alkoxycarbonyl-substituted lower alkoxy group, a carbamoyl group, a carboxyl group, a lower alkylthio group, a lower alkoxycarbonyl group, a nitro group, a trihalogeno-lower alkyl group, a morpholinocarbonyl group, a carboxyl-substituted lower alkoxy group, a di-lower alkylsulfonyl-substituted amino group, a morpholino-lower alkylcarbamoyl-substituted lower alkoxy group, an amino group being substituted by a lower alkyl group and a protecting group for amino group, a lower alkylenedioxy group, a carbamoyl group being substituted by a protected or unprotected amino group, a lower alkylsulfinyl group and a lower alkylsulfonyl group; or a 5- to 10-membered heterocyclic group having 1 to 4 heteroatoms selected from a nitrogen atom, an oxygen atom and a sulfur atom, said heterocyclic group having 1 to 4 substituents selected from a hydroxy group, a halogen atom, a lower alkyl group, a phenyl-substituted lower alkyl group, a hydroxy-substituted lower alkyl group, an oxo group, a lower alkoxy group, a protected or unprotected amino group, a mono- or di-lower alkylamino group, a phenyl-substituted lower alkoxycarbonyl group, a lower alkoxycarbonyl group, a carboxyl group and a carbamoyl group, and $R^3$ is a hydrogen atom or a lower alkyl group.

Another embodiment of the compounds useful in the practice of the present invention is an isoquinolinone derivative of the formula (I-B):

(I-B)

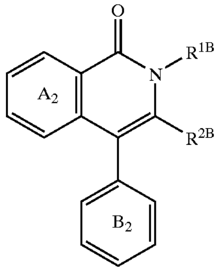

wherein Ring $A_2$ and Ring $B_2$ are the same or different and each a benzene ring which may optionally be substituted by 1 to 4 groups selected from the group consisting of a protected or unprotected hydroxyl group; a lower alkylenedioxy group; a halogen atom; a lower alkyl group; a mono- or di-lower alkylcarbamoyloxy group; and a group of the formula:

$R^{6B}$—$(CO)_n$—O in which $R^{6B}$ is (i) a lower alkyl group which may optionally have 1 or 2 substituents selected from the group consisting of a 5- to 12-membered heteromonocyclic or heterobicyclic group having optionally 1 to 4 substituents selected from the group consisting of a hydroxy-substituted lower alkyl group, a lower alkyl group, an oxo group and a lower alkoxycarbonyl group; a phenyl or naphthyl group having optionally 1 to 4 substituents selected from the group consisting of a protected or unprotected amino group, a lower alkylenedioxy group, a carboxyl group, a lower alkoxycarbonyl group, a lower alkoxy group, a sulfamoyl group, a carbamoyl group, a nitro group, a phenyl group, a halogen atom, a mono-lower alkylamino group, a di-lower alkylamino group, a lower alkylpiperazinocarbonyl group, a hydroxy-substituted lower alkyl group and a lower alkyl group; a cyano group; a carboxyl group; a mono or di-lower alkylamino group; a lower alkoxy-substituted lower alkoxy group; a lower alkoxy group; a hydroxy group; a carbamoyl group; a lower alkoxycarbonyl group; a cyclo-lower alkyl group; and a benzoyl group, (ii) a 5- to 12-membered heteromonocyclic or heterobicyclic group having optionally 1 to 4 substituents selected from the group consisting of a lower alkyl group, a cyano group, a carboxyl group, a mono- or di-lower alkylamino group, a lower alkoxy-substituted lower alkyl group, a hydroxy group, a lower alkoxy group, a carbamoyl group, a lower alkoxycarbonyl group and a nitro group, (iii) a cyclo-lower alkyl group, (iv) a lower alkenyl group, or (v) a lower alkyl-substituted or unsubstituted phenylsulfonyl group, n is an integer of 0 or 1, $R^{1B}$ is (i) a hydrogen atom, (ii) a lower alkyl group having optionally 1 to 3 substituents selected from the group consisting of a piperidyl group, a pyridyl group, an imidazolyl group, a lower alkyl-substituted piperidyl group, a furyl group, a morpholino group, a tetrahydrofuryl group, a dihydropyridyl group being substituted by a lower alkyl group and an oxo group, a piperazinyl group, a lower alkoxycarbonyl substituted-piperazinyl group, a cyclo-lower alkyl group, a phenyl group, a lower alkylenedioxyphenyl group, a lower alkoxycarbonyl group, a hydroxyl group, a hydroxy-substituted lower alkoxy group, a carboxyl group, a lower alkoxy group, a protected or unprotected amino group, a carbamoyl group, a di-lower alkylamino group and a pyridylcarbonyloxy group, (iii) a cyclo-lower alkyl group having optionally 1 to 3 substituents selected from the group consisting of a lower alkoxycarbonyl group, a hydroxy group, a carboxyl group, a lower alkyl group, a lower alkoxy group, a hydroxy-substituted lower alkoxy group and a protected or unprotected amino group, (iv) an unsaturated or partially saturated 6- to 14-membered monocyclic, bicyclic or tricyclic aryl group having optionally 1 to 4 substituents selected from the group consisting of a halogen atom, a mono- or di-lower alkylamino group, a morpholino group, a lower alkyl-substituted pyrimidinyl group, a lower alkyl-substituted pyrazolyl group, a hydroxy-substituted lower alkyl group, a protected or unprotected amino group, a lower alkanoyl-substituted amino group, a lower alkoxy group, a lower alkyl group, a protected or unprotected hydroxy group, a carboxy-substituted lower alkyl group, a lower alkoxycarbonyl-substituted lower alkyl group, a lower alkoxycarbonyl-substituted lower alkoxy group, a carbamoyl group, a carboxyl group, a lower alkylthio group, a lower alkoxycarbonyl group, a nitro group, a trihalogeno-lower alkyl group, a morpholinocarbonyl group, a carboxy-substituted lower alkoxy group, a di-lower alkylsulfonylamino group, a morpholino-lower alkyl carbamoylsubstituted lower alkyl group, a sulfamoyl group, a carbamoyl group being optionally substituted by a protected or unprotected amino group, a lower alkylsulfinyl group and a lower alkylsulfonyl group, (v) a 5- to 12-membered aromatic or aliphatic heteromonocyclic or heterobicyclic group having 1 to 4 substituents selected from the group consisting of a hydroxy group, a halogen atom, a phenyl-substituted lower alkyl group, a hydroxy-substituted lower alkyl group, an oxo group, a lower alkoxy group, a protected or unprotected amino group, a mono- or di-lower alkylamino group, a phenyl-lower alkoxycarbonyl group, a lower alkoxycarbonyl group, a carboxyl group and a carbamoyl group, or (vi) an amino group having optionally 1 or 2 substituents selected from the group consisting of a protecting group for amino group, a pyridyl group, a lower alkanoyl group, a lower alkoxy group, a hydroxy-substituted lower alkyl group, a phenyl group, a lower alkanoyloxy-substituted lower alkyl group and a trihalogeno-lower alkanoyl group, $R^{2B}$ is a group of the formula: —$COOR^{3B}$ or a group of the formula: —CON$(R^{4B})(R^{5B})$ $R^{3B}$ is a hydrogen atom, a lower alkyl group, a tri-lower alkylsilyl group or a phenyl-lower alkyl group, and a group of the formula: —N$(R^{4B})(R^{5B})$ is a hydroxy-lower alkyl-substituted piperazinyl group, a morpholino group, a pyrrolidinyl group, an imidazolyl-substituted lower alkylamino group or a mono, or di-lower alkylamino group, provided that when $R^{1B}$ is one of the groups of the above-mentioned (i) or (ii), then at least one of Ring $A_2$ and Ring $B_2$ is a benzene ring which is substituted by two or more lower alkoxy groups.

Examples of the pharmaceutically preferable compounds are as follows.

6-methoxy-3-methoxycarbonyl-2-morpholino-7-(4-pyridylmethyloxy)-4-(3,4,5-trimethoxyphenyl)-1(2H) isoquinolinone;

6-methoxy-3-methoxycarbonyl-2-morpholino-7-(3-pyridylmethyloxy)-4-(3,4,5-trimethoxyphenyl)-1(2H)-isoquinolinone;

6-methoxy-3-methoxycarbonyl-2-morpholino-7-(2-pyridylmethyloxy)-4-(3,4,5-trimethoxyphenyl)-1(2H)-isoquinolinone;

6-methoxy-3-methoxycarbonyl-2-phenyl-4-(3,4,5-trimethoxyphenyl)-7-(4-pyridylmethyloxy)-1(2H)-isoquinolinone;

6-methoxy-3-methoxycarbonyl-2-phenyl-4-(3,4,5-trimethoxyphenyl)-7-(3-pyridylmethyloxy)-1(2H)-isoquinolinone; or 6-methoxy-3-methoxycarbonyl-2-phenyl-4-(3,4,5-trimethoxyphenyl)-7-(2-pyridylmethyloxy)-1(2H)-isoquinolinone.

Among the desired compounds (I) of the present invention, other pharmaceutically preferable compounds are as follows.

2-(4-aminophenyl)-6-methoxy-3-methoxycarbonyl-7-(2-pyridylmethyloxy)-4-(3,4,5-trimethoxyphenyl)-1(2H)-isoquinolinone;

2-(4-aminophenyl)-7-(3-aminobenzyloxy)-6-methoxy-3-methoxycarbonyl-4-(3,4,5-trimethoxyphenyl)-1(2H)-isoquinolinone;

2-(4-aminophenyl)-6-methoxy-3-methoxycarbonyl-7-(4-pyridylmethyl-oxy)-4-(3,4,5-trimethoxyphenyl)-1 (2H)-isoquinolinone;

2-(4-aminophenyl)-7-(2-benzimidazolylmethyloxy)-6-methoxy-3-methoxycarbonyl-4-(3,4,5-trimethoxy-phenyl-1(2H)-isoquinolinone;

2-(4-aminophenyl)-7-(3,5-diaminobenzyloxy)-6-methoxy-3-methoxycarbonyl-4-(3,4,5-trimethoxy-phenyl)-1(2H)-isoquinolinone;

2-(4-aminophenyl)-4(4-bromo-3,5-dimethoxyphenyl)-6-methoxy-3-methoxycarbonyl-7-(2-pyridylmethyloxy)-1(2H)-isoquinolinone;

2-(4-aminophenyl)-4-(4-bromo-3,5-dimethoxyphenyl)-6-methoxy-3-methoxycarbonyl-7-(3-pyridylmethyloxy)-1(2H)-isoquinolinone;

2-(4-aminophenyl)-4(4-bromo-3,5-dimethoxyphenyl)-6-methoxy-3-methoxycarbonyl-7-(4-pyridylmethyloxy)-1(2H)-isoquinolinone;

2-(4-aminophenyl)-3-methoxycarbonyl-7-(2-pyridylmethyloxy)-4-(3,4,5-methoxyphenyl)-1(2H)-isoquinolinone;

2-(4-aminophenyl)-3-methoxycarbonyl-7-(3-pyridylmethyloxy)-4-(3,4,5-trimethoxyphenyl)-1(2H)-isoquinolinone;

2-(4-aminophenyl)-3-methoxycarbonyl-7-(4-pyridylmethyloxy)-4-(3,4,5-trimethoxyphenyl)-1(2H)-isoquinolinone;

2-(4-aminophenyl)-7-(2,5-methoxybenzyloxy)-3-methoxycarbonyl-4-(3,4,5-trimethoxyphenyl)-1(2H)-isoquinolinone;

2-(4-aminophenyl)-7-(3,5-dimethoxybenzyloxy)-3-methoxycarbonyl-4-(3,4,5-trimethoxyphenyl)-1(2H)-isoquinolinone;

2-(4-aminophenyl)-4-(4-bromo-3,5-dimethoxyphenyl)-3-methoxycarbonyl-7-(2-pyridylmethyloxy)-1(2H)-isoquinolinone;

2-(4-aminophenyl)-4-(4-bromo-3,5-dimethoxyphenyl)-3-methoxycarbonyl-7-(3-pyridylmethyloxy)-1(2H)-isoquinolinone;

2-(4-aminophenyl)-4-(4-bromo-3,5-dimethoxyphenyl)-3-methoxycarbonyl-7-(4-pyridylmethyloxy)-1(2H)-isoquinolinone;

2-(4-aminophenyl)-7-(3-aminobenzyloxy)-4-(4-bromo-3,5-dimethoxy-phenyl)-3-methoxycarbonyl-1(2H)-isoquinolinone;

2-(4-aminophenyl)-4-(4-chloro-3,5-dimethoxyphenyl)-3-methoxy-carbonyl-7-(2-pyridylmethyloxy)-1(2H)-isoquinolinone;

2-(4-aminophenyl)-4-(4-chloro-3,5-dimethoxyphenyl)-3-methoxy-carbonyl-7-(3-pyridylmethyloxy)-1(2H)-isoquinolinone;

2-(4-aminophenyl)-7-(3-dimethylaminobenzyloxy)-3-methoxycarbonyl-4-(3,4,5-trimethoxyphenyl)-1(2H)-isoquinolinone;

2-(4-aminophenyl)-3-methoxycarbonyl-7-pyrazinylmethyloxy-4-(3,4,5-trimethoxyphenyl)-1(2H)-isoquinolinone;

2-(4-aminophenyl)-4-(4-chloro-3,5-dimethoxyphenyl)-3-methoxy-carbonyl-7-(4-pyridylmethyloxy)-1(2H)-isoquinolinone;

2-(4-aminophenyl)-7-(3,5-diaminobenzyloxy)-3-methoxycarbonyl-4-(3,4,5-trimethoxyphenyl)-1(2H)-isoquinolinone;

2(4-aminophenyl)-7-(6-hydroxymethyl-2-pyridyimethyloxy)-3-methoxy-carbonyl-4-(3,4,5-trimethoxyphenyl)-1(2H)-isoquinolinone;

2-(4-aminophenyl)-7-(4-carboxybenzyloxy)-3-methoxycarbonyl-4-(3,4,5-trimethoxyphenyl)-1(2H)-isoquinolinone;

2-(4-aminophenyl)-7-(3-carboxybenzyloxy)-3-methoxycarbonyl-4-(3,4,5-trimethoxyphenyl)-1(2H)-isoquinolinone;

2-(4-aminophenyl)-3-methoxycarbonyl-7-[4-(4-methylpiperazinylcarbonyl)benzyloxy]-4-(3,4,5-trimethoxyphenyl)-1(2H)-isoquinolinone;

2-(4-aminophenyl)-3-methoxycarbonyl-7-[3-(4-methylpiperazinylcarbonyl)benzyloxy]-4-(3,4,5-trimethoxyphenyl)-1(2H-isoquinolinone;

2-(4-aminophenyl)-3-methoxycarbonyl-7-[3-(methylamino)benzyloxy]-4-(3,4,5-trimethoxy-phenyl)-1(2H)-isoquinolinone;

2-(4-aminophenyl)-7-(2-hydroxymethylbenzyloxy)-3-methoxycarbonyl-4-(3,4,5-trimethoxyphenyl)-1(2H)-isoquinolinone;

2-(4-aminophenyl)-3-methoxycarbonyl-7-(N-oxo-2-pyridylmethyloxy)-4-(3,4,5-trimethoxyphenyl)-1(2H)-isoquinolinone;

2-(4-aminophenyl)-3-methoxycabonyl-8-(2-pyridylmethyloxy)-4-(3,4,5-trimethoxyphenyl)-1(2H)-isoquinolinone;

2-(4-aminophenyl)-3-methoxycarbonyl-8-(3-pyridylmethyloxy)-4-(3,4,5-trimethoxyphenyl)-1(2H)-isoquinolinone;

2-(4-aminophenyl)-3-methoxycarbonyl-8-(4-pyridylmethyloxy)-4-(3,4,5-trimethoxyphenyl)-1(2H)-isoquinolinone;

2-(4-aminophenyl)-4-(4-chloro-3,5-dimethoxyphenyl)-7-(6-hydroxymethyl-2-pyridylmethyloxy)-3-methoxycarbonyl-1(2H)-isoquinolinone;

2-(4-aminophenyl)-4-(4-chloro-3,5-dimethoxyphenyl)-3-methoxycarbonyl-7-pyrazinylmethyloxy)-1(2H)-isoquinolinone;

2-(4-aminophenyl)-3-methoxycarbonyl-4-(3,5-dimethoxy-4-methylphenyl)-7-(4-pyridylmethyloxy)-1(2H)-isoquinolinone;

2-(4-aminophenyl)-3-methoxycarbonyl-4-(3,5-dimethoxy-4-methylphenyl)-7-(3-pyridylmethyloxy)-1(2H)-isoquinolinone;

2-(4-aminophenyl)-3-methoxycarbonyl-4-(3,5-dimethoxy-4-methyl-phenyl)-7-(2-pyridylmethyloxy)-1(2H)-isoquinolinone;

2-(4-aminophenyl)-7-(3,5-diaminobenzyloxy)-3-methoxycarbonyl-4-(3,5-dimethoxy-4-methylphenyl)-1(2H)-isoquinolinone;

2-(4-aminophenyl)-7-(6-hydroxymethyl-2-pyridylmethyloxy)-3-methoxycarbonyl-4-(3,5-dimethoxy-4-methylphenyl)-1(2H)-isoquinolinone;

2-(4-aminophenyl)-7-(3-methylaminobenzyloxy)-3-methoxycarbonyl-4-(3,5-dimethoxy-4-methylphenyl)-1(2H)-isoquinolinone;

2-(4-aminophenyl)-7-(2-hydroxymethylaminobenzyloxy)-3-methoxycarbonyl-4-(3,5-dimethoxy-4-methylphenyl)-1(2H)-isoquinolinone; or 2-(4-aminophenyl)-3-methoxycarbonyl-4-(3,5-dimethoxy-4-methylphenyl)-7-(2-pyrazinylmethyloxy)-1(2H)-isoquinolinone.

When the desired compound (I) of the present invention has an asymmetric carbon atom at the substituents of Ring A and Ring B and/or at $R^1$, it may exist in the form of an optically active isomer thereof owing to said asymmetric carbon atom thereof, and the present invention also includes these optical isomers and a mixture thereof.

The present compounds (I) can clinically be used either in the free form or in the form of a pharmaceutically acceptable salt thereof. The pharmaceutically acceptable salt includes a salt with an inorganic acid such as hydrochloride, sulfate or hydrobromide, or a salt with an organic acid such as acetate, fumarate, oxalate, citrate, methanesulfonate, tosylate, or maleate. The compounds (I) having a substituent such as a carboxyl group may clinically be used in the form of a salt with a base such as an alkali metal salt (e.g., sodium salt, potassium salt) or an alkaline earth metal salt (e.g., calcium salt) as well.

The desired compound (I) or a salt thereof includes either intramolecular salt or an additive thereof, and solvates or hydrates thereof.

Compounds of Formula I may be prepared by any suitable method known in the art or by the following processes that are set forth in PCT/JP98/00715. In the methods below, $R^1$, $R^2$ etc. are as defined in Formula I above, unless otherwise indicated.

The desired compounds (I) useful in the present invention may be prepared by the following Processes A, B, and C.

Process A

The desired compounds (I) useful in the present invention can be prepared by reacting an isocoumarin derivative of the formula (II):

(II)

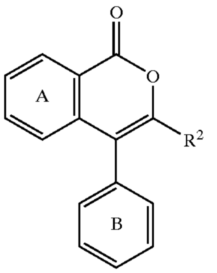

wherein the symbols are the same as defined above, or a salt thereof, with an amine compound of the formula (III):

$R^1$—$NH_2$ wherein the symbol is the same as defined above, or a salt thereof.

Process B

The desired compounds (I) useful in the present invention can be prepared by subjecting an isocoumarin derivative of the formula (II)

(II)

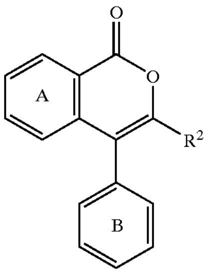

wherein the symbols are the same as defined above, or a salt thereof, to hydrolysis to give a compound of the formula (IV):

(IV)

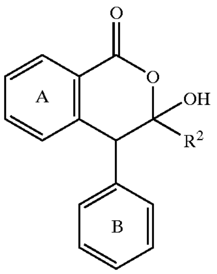

wherein the symbols are the same as defined above, and reacting the compound (IV) with an amine compound of the formula (III):

$R^1$—$NH_2$ wherein the symbol is the same as defined above, or a salt thereof. The compound of the formula (IV) may exist in a solution in equilibration as follows.

(IV)

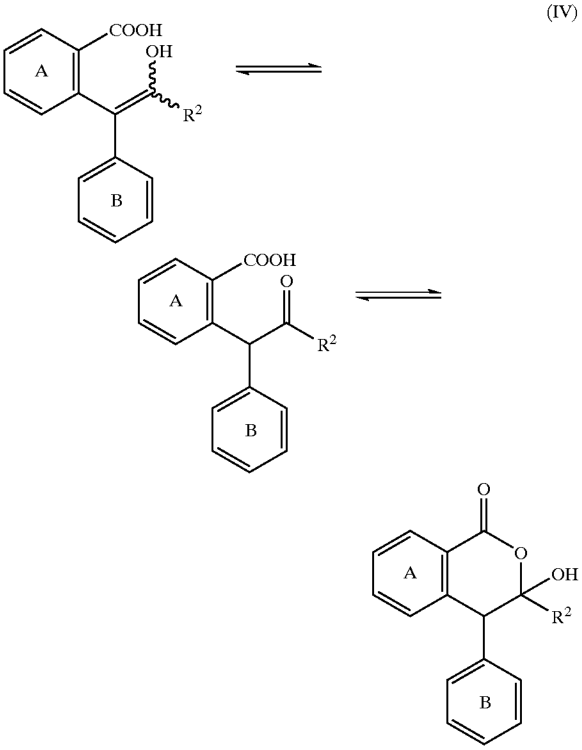

Process C

The desired compounds (I) useful in the present invention can be prepared subjecting a benzoylbenzamide, compound of the formula (V):

(V)

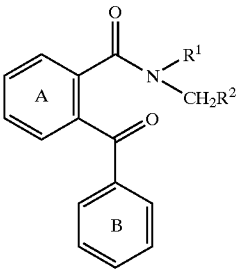

wherein the symbols are the same as defined above, or a salt thereof, to intramolecular cyclization reaction, to give a compound of the formula (VI):

(VI)

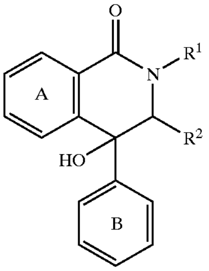

wherein the symbols are the same as defined above, and subjecting the compound (VI) to dehydration reaction.

The compound (I) obtained by Process A, B or C may, if necessary, be converted into a pharmaceutically acceptable salt thereof.

The above Processes A, B and C can be carried out as follows.

Process A

The reaction between the isocoumarin derivative (II) and the amine compound (III) or a salt thereof is carried out in a solvent or without a solvent. The solvent includes, for example, 1,3-dimethyl-2-imidazolidinone (DMI), dimethylformamide, dimethylsulfoxide, ethylene glycol, N-methylpyrrolidone, xylene, dichloroethane, etc. The reaction is carried out at 20–150° C., preferably at 40–130° C.

Process B

The hydrolysis of the isocoumarin derivative (II) is carried out in the presence of a strong base in a solvent. The strong base includes, for example, an alkali metal hydroxide (e.g., sodium hydroxide, potassium hydroxide, lithium hydroxide, etc.), an alkali metal carbonate (e.g., sodium carbonate, potassium carbonate, etc.), etc. The solvent includes, for example, water, or a mixture of water and methanol, ethanol, tetrahydrofuran, dioxane, dimethylformamide, etc. The reaction is carried out at 0–80° C., preferably at 5–60° C.

The reaction between the compound (IV) and the amine compound (III) is carried out in the presence or absence of an acid acceptor in a suitable solvent or without a solvent. The acid acceptor includes N-methylmorpholine, triethylamine, pyridine, sodium carbonate, potassium carbonate, sodium hydrogen carbonate, etc. The solvent may be any solvents used in the above Process A which does not disturb the reaction. The reaction is carried out at 20–140° C., preferably at 30–100° C.

Process C

The intramolecular cyclization reaction of the benzoylbenzamide compound (V) is carried out in the presence or absence of a base in a solvent. The base includes, for example, an organic base (e.g., 1,5-diazabicyclo[4.3.0]-non-5-ene (DBN), 1,8-diazabicyclo[5.4.0]undec-7-ene (DBU), etc.), or an organic base (e.g., sodium methoxide, potassium tert-butoxide, sodium hydride, n-butyl lithium, lithium diisopropyl amide, etc.), and these bases are usually used in an amount of 0.5–5 equivalents, preferably in an amount of 1–2 equivalents, to 1 equivalent of the compound (V). The solvent includes tetrahydrofuran, dimethylformamide, dioxane, dimethoxyethane, benzene, toluene, pyridine, etc., but may be any solvent used in the above Process A which does not disturb the reaction. The reaction is carried out at −50–100° C., preferably at −20–80° C.

The dehydration reaction of the compound (VI) is carried out in the presence of an acidic catalyst in a solvent. The acidic catalyst includes a sulfonic acid compound (e.g., p-toluenesulfonic acid, methanesulfonic acid, etc.), a carboxylic acid compound (e.g., acetic acid, trifluoroacetic acid, etc.), an inorganic acid compound (e.g., hydrogen chloride, hydrogen bromide, sulfuric acid, etc.), and a Lewis acid (e.g., boron trifluoride ethyl ether, aluminum chloride, etc.), and these acidic catalysts are usually used in an amount of 0.1–5 equivalent, preferably in an amount of 0.2–2 equivalents, to the amount of the compound (VI). The solvent includes, for example, chloroform, dioxane, benzene, toluene, methylene chloride, etc., but may be any solvent used in the above Process A which does not disturb the reaction. The reaction is carried out at 0–150° C., preferably at 20–110° C.

When $R^1$ of the amine compound (III) used in the above Processes A and B is an amino group, or a group containing an amino group, these Processes A and B are preferably carried out after introducing a protecting group such as a substituted or unsubstituted lower alkoxycarbonyl group (e.g., tert-butoxycarbonyl group, benzyloxycarbonyl group, etc.), and a lower alkanoyl group (e.g., formyl group, acetyl group, propionyl group, etc.) into said amino group.

The compound of formula (I) obtained in the above Processes A, B and C wherein the group —$COOR^3$ is a carboxyl group, i.e., a compound of the formula (I-a):

(I-a)

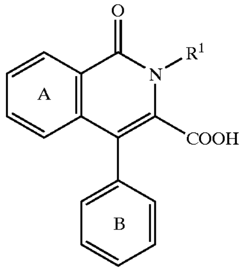

wherein the symbols are the same as defined above, is converted into a compound of the formula (I-b):

(I-b)

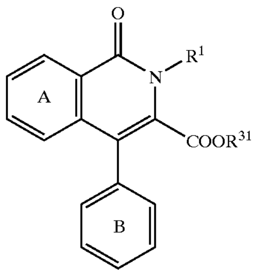

wherein $R^{31}$ is an ester residue and the other symbols are the same as defined above, by esterification reaction in a conventional manner. For example, the compound (I-b) is prepared by reacting the compound (I-a) with an esterifying agent in the presence or absence of an acid acceptor in a solvent. The acid acceptor includes, for example, an inorganic base (e.g., an alkali metal hydroxide, an alkali metal carbonate, etc.), and an organic base (e.g., N-methylmorpholine, triethylamine, pyridine, 1,5-diazabicyclo[4.3.0]non-5-ene (DBN), 1,8-diaza-bicyclo[5.4.0]undec-7-ene (DBU), etc.). The esterifying agent includes, for example, a diazoalkane (e.g., diazomethane, diazoethane, etc.), a dialkyl sulfate (e.g., dimethyl sulfate, diethyl sulfate, etc.), an alkyl halide (e.g., methyl iodide, methyl bromide, ethyl bromide, etc.), a tri-lower alkylsilyl-diazoalkane (e.g., trimethylsilyldiazomethane, etc.), an aryl-lower alkyl halide (e.g., benzyl chloride, benzyl bromide, etc.), etc. When a dialkyl sulfate, an alkyl halide or an aryl-lower alkyl halide is used as an esterifying agent, the acid acceptor is usually used in an amount of 1–5 equivalents, preferably in an amount of 1–2 equivalents, to 1 equivalent of the compound (1-a). The reaction is carried out at 0–60° C., preferably at 5–40° C. When a diazoalkane is used as an esterifying agent, the acid acceptor is usually used in an amount of 1–5 equivalents, preferably in an amount of 1–2 equivalents, to 1 equivalent of the compound (I-a). The reaction is carried out at 0–50° C., preferably at 5–30° C. The compound of the formula (1-a) wherein the group —$COOR^3$ is a methoxycarbonyl group is prepared under moderate conditions by using trimethylsilyldiazomethane as an esterifying agent in the above reaction. The solvent includes, for example, water, an alcohol (e.g., methanol, ethanol, isopropyl alcohol, etc.), an ether (e.g., diethyl ether, tetrahydrofuran, dioxane, etc.), a ketone (e.g., acetone, methyl ethyl ketone, etc.), as ester (e.g., ethyl acetate, etc.), an aromatic hydrocarbon (e.g., benzene, toluene, etc.), a halogenated hydrocarbon (e.g., methylene chloride, chloroform, etc.), an amide (e.g., N,N-dimethylformamide, N,N-dimethylacetamide, etc.), a sulfoxide (e.g., dimethylsulfoxide, etch), or a mixture of these solvents.

In addition, the compound (I-b) is prepared by reacting the compound (I-a) with a lower alcohol (e.g., methanol, ethanol, propanol, butanol, etc.), or an aryl-lower alcohol (e.g., benzyl alcohol, phenethyl alcohol, etc.), under acidic conditions. The acid includes, for example, sulfuric acid, hydrogen chloride, p-toluenesulfonic acid, etc., which is usually used in an amount of 0.01–20 equivalents, preferably in an amount of 0.1–10 equivalents, to 1 equivalent of the compound (1-a). The reaction is preferably carried out in said alcohol with heating under reflux.

When the above-mentioned compound (I-a) has one or more carboxyl group or a mono-substituted or unsubstituted amino group except the 3-carboxyl group (=$R^2$), said compound (I-a) can be converted into a corresponding compound of the formula (I-a) wherein said carboxyl group is esterified, or said amino group is converted into a mono- or di-lower alkylamino group, by reacting with the above-mentioned esterifying agent.

Besides, the compound (I) wherein the substituent $R^2$ is a group of the formula —CON($R^4$)($R^5$), i.e., a compound of the formula (1-c):

(I-c)

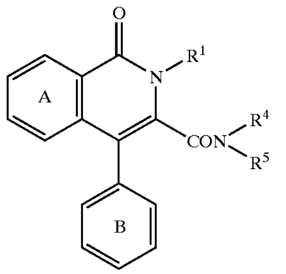

wherein a group of the formula —N($R^4$)($R^5$) is a substituted or unsubstituted nitrogen-containing aliphatic heterocyclic group, or a substituted or unsubstituted amino group, and the other symbols are the same as defined above, is prepared by reacting the compound of the formula (I-a) with an amine compound of the formula (VII):

(VII)

wherein the symbols are the same as defined above, in the presence of an condensing agent, or reacting a reactive derivative (e.g., an acid halide, an active amide, an active ester, a mixed acid anhydride, etc.) of the compound (I-a) with the amide compound (VII) in the presence or absence of a base in a solvent. The base includes an organic base (e.g., pyridine, 4-dimethylaminopyridine, N-methylmorpholine, triethylamine, N,N-dimethylaniline, N,N-diethylaniline, 1,8-diazabicyclo[5.4.0]undec-7-ene, etc., and an inorganic base (e.g., sodium hydrogen carbonate, potassium hydrogen carbonate, sodium carbonate, etc.). The condensing agent includes, for example, 1,3-dicyclohexylcarbodiimide (DCC), 1-ethyl-3-(3-dimethylaminopropyl)carbodiimide hydrochloride (WSCI), propanephosphonic anhydride (PPA), etc. The solvent includes, for example, dimethylformamide, methylene chloride, tetrahydrofuran, dioxane, ethyl acetate, and 1,3-dimethyl-2-imidazolidinone, but may be any solvent used in the above Process A that does not disturb the reaction. The reaction is carried out at −20–60° C., preferably at 5–40° C.

The active ester of the compound (I-a) is preferably an ester of the compound (I-a) with N-hydroxysuccinmide, N-hydroxyphthalimide, 1-hydroxybenzotriazole, or p-nitrophenol.

The acid halide of the compound (I-a) is preferably an acid chloride, an acid bromide, etc.

The active amide of the compound (I-a) is preferably an amide of the compound (1-a) with imidazole, etc.

In the preparation of the desired compound (a), the starting compounds (I-a), (I-d), (I-f), (1-h), (II), (III), (IV), (V), (VI) and (VII) in the above Processes A to C as well as to Steps (a) to (d) disclosed hereinafter can be used as well as in the form of a salt thereof. The salt may be, for example, a salt with an alkali metal (e.g., sodium, potassium, lithium, etc.), a salt with an organic base (e.g., pyridine, triethylamine, N-methylmorpholine, etc.), a salt with an inorganic acid (e.g., hydrogen chloride, hydrogen bromide, sulfuric acid, etc.), or a salt with an organic acid (e.g., acetic acid, formic acid, oxalic acid, citric acid, malonic acid, etc.).

The desired compound (I) of the present invention can also be prepared by converting the substituents of Ring A and/or Ring B, or the substituents $R^1$ and/or $R^2$ into other substituents. The method for conversion reaction of these substituents; is selected in accordance with the kinds of the substituents to be required, and may be the following steps (a) to (t).

Step (a)

The compound of the formula (I-e):

(I-e)

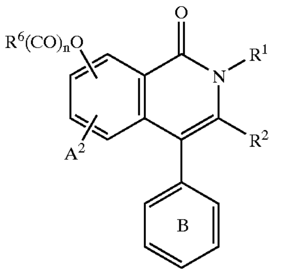

wherein the symbols are the same as defined above, is prepared by reacting a compound of the formula (I-d):

(I-d)

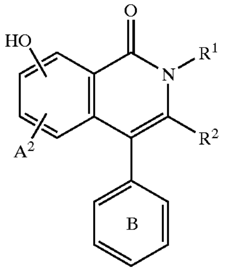

wherein the symbols are the same as defined above, or a salt thereof, with a compound of the formula (VIII-a):

$R^6$—COOH wherein $R^6$ is the same as defined above, or a reactive derivative thereof, or with a compound of the formula (VIII-b):

$R^6$—X wherein X is a leaving group, and $R^6$ is the same as defined above.

The leaving group (X) of the compound (VIII-b) is, for example, a hydroxy group, a tifluoromethanesulfonyloxy group, a p-tosyloxy group, a methanesulfonyloxy group, or a halogen atom such as chlorine, bromine, iodine, etc.

The reaction between the compound (I-d) and the compound (VIII-a) is carried out in the presence of a condensing agent (e.g., 1,3-dicyclohexylcarbodiimide, 1-ethyl-3-(3-dimethylaminopropyl)carbodiimide hydrochloride, diethylphosphonic cyanide, diphenylphosphonic azide, etc.). The reaction between a reactive derivative of the compound (VIII-a) (e.g., an active ester such as N hydroxysuccinimide ester, N-hydroxyphthalimide ester, 1-hydroxybenzotriazole ester, or an acid halide such as acid chloride, acid bromide, etc.) and the compound (1-d) is carried out in the presence of an acid acceptor such as an alkali metal hydroxide (e.g., sodium hydrochloride), an alkali metal hydrogen carbonate (e.g., sodium hydrogen carbonate), an alkali metal carbonate (e.g., sodium carbonate), or an organic base (e.g., triethylamine, pyridine, etc.), and if necessary, 4-dimethylaminopyridine (DMAP), etc. may be added to the reaction mixture in a catalytic amount. The reaction is carried out at 0–80° C., preferably at 5–60° C.

The reaction between the compound (I-d) and the compound (VIII-b) is carried out, for example, according to the method disclosed in Mitsunobu, et al. (cf., Synthesis, pp. 1–28, 1981), when the leaving group X is a hydroxy group. That is, the compound (I-d) and the compound (VIII-b) are reacted in the presence of diethyl azodicarboxylate (DEAD) and triphenylphosphine in a solvent such as tetrahydrofuran, dioxane, ethyl acetate, dimethylformamide, chloroform, methylene chloride, benzene, toluene, dimethoxyethane, etc. The reaction is carried out at 0–60° C., preferably at 5–40° C.

When the leaving group X of the compound (VIII-b) is a trifluoromethanesulfonyloxy group, p-tosyloxy group, methanesulfonyloxy group, or a halogen atom such as chlorine, bromine, iodine, etc., the reaction between the compound (I-d) and the compound (VIII-b) is carried out in the presence of a base. The reaction may also be carried out in the presence or absence of a base and/or a copper catalyst, The base includes, for example, an inorganic base such as an alkali metal hydride (e.g., sodium hydride), an alkali metal amide (e.g., sodium amide), an alkali metal alkoxide (e.g., sodium methoxide, potassium tert-butoxide), an alkali metal hydroxide (e.g., sodium hydroxide), an alkali metal carbonate (e.g., sodium carbonate), and an organic base such as N-methylmorpholine, triethylamine, pyridine, etc. The base is usually used in an amount of 1 to 5 equivalents, preferably in an amount of 1 to 2 equivalents, to 1 equivalent of the compound (I-d). When the substituent $R^1$ is an amino group optionally having one substituent, or a substituent containing an amino group optionally having one substituent, it is preferable to carry out the reaction after introducing a protecting group such as a lower alkoxycarbonyl group (e.g., tert-butoxycarbonyl group), an aryl-lower alkoxycaTbonyl group (e.g., benzyloxycarbonyl group), or a lower alkanoyl group (e.g., formyl group, acetyl group, propionyl group) into said amino group.

The copper catalyst may be copper(I) iodide, copper(II) bromide, copper(0) powder, copper(1) oxide, copper(II) bromide, etc. The reaction is carried out at 10–160° C., preferably at 20–120° C.

The desired compound (I) wherein Ring A is a benzene ring being substituted by a group selected from a lower alkyl-substituted piperazinylcarbonyloxy group, and a mono. or di-lower alkylcarbamoyloxy group is prepared by reacting the compound (I-d) with phosgene or triphosgene, followed by reacting the resulting corresponding product (chloroformate compound) with a lower alkyl-substituted piperazine or a mono- or di-lower alkylamine in the presence or absence of a base (e.g., triethylamine, N-methylmorpholine, pyridine, 4-dimethylaminopyridine, 1,8-diazabicyclo[5.4.0]undec-7-ene (DBU), etc.). The reaction is carried out at 0–80° C., preferably at 10–40° C.

Step (b)

The compound of the formula (I-g):

(I-g)

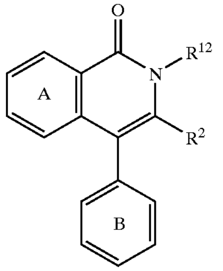

wherein $R^{12}$ is an amino-substituted lower alkyl group, an amino-substituted cyclo-lower alkyl group, an amino-substituted aryl group, an amino-substituted heterocyclic group, or an amino group, and the other symbols are the same as defined above, is prepared by removing a protecting group for amino group from a compound of the formula (I-f):

(I-f)

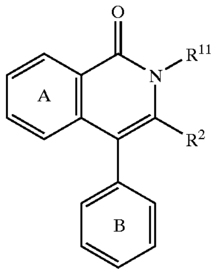

wherein $R^{11}$ is a lower alkyl group being substituted by a protected amino group, a cyclo-lower alkyl group being substituted by a protected amino group, an aryl group being substituted by a protected amino group, a heterocyclic group being substituted by a protected amino group, or a protected amino group, and the other symbols are the same as defined above, or a salt thereof.

The removal of the protecting group is carried out by a conventional method such as acid-treatment, base-treatment, catalytic reduction, etc., which is selected according to the kinds of the protecting group to be removed. The reaction is carried out at 0–150° C., preferably at 5–110° C.

Step (c)

The compound of the formula (I-i):

(I-i)

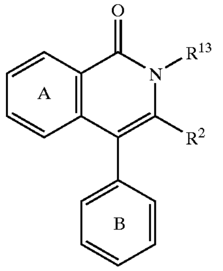

wherein $R^{13}$ is a substituted or unsubstituted lower alkyl group, and the other symbols are the same as defined above, is prepared by reacting a compound of 10 the formula (1-h):

(I-h)

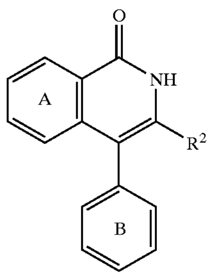

wherein the symbols are the same as defined above, or a salt thereof, with a compound of the formula (IX):

$R^{13}—X^1$ wherein $X^1$ is a halogen atom, and $R^{13}$ is the same as defined above.

The reaction between the compound (I-h) and the compound (IX) is carried out in the presence of an acid acceptor. The acid acceptor is, for example, an alkali metal hydroxide (e.g., sodium hydroxide), an alkali metal hydrogen carbonate (e.g., sodium hydrogen carbonate), an alkali metal carbonate (e.g., sodium carbonate), an alkali metal hydride (e.g., sodium hydride), or an organic base (e.g., triethylamine, pyridine, 1,8-diazabicyclo[5.4.0]-undec-7-ene, etc.). The reaction is carried out at 0–100° C., preferably at 20–80° C., Step (d)

The desired compound (I) wherein the substituent of Ring A and/or the substituent $R^1$ are a substituent containing an esterified carboxyl group (e.g., a lower alkoxycarbonyl-substituted aryl group, a lower alkoxycarbonyl-substituted-lower alkyl group, a lower alkoxycarbonyl-substituted cyclo-lower alkyl group, a lower alkoxycarbonyl-substituted lower alkyl-substituted aryl group, a lower alkoxycarbonyl-substituted lower alkoxy-substituted aryl group, etc.) is prepared by subjecting a corresponding compound of the formula (I) wherein the substituent of Ring A and/or the substituent $R^1$ are a substituent containing a free carboxyl group, to esterification reaction. The reaction is carried out in the same manner as in the esterification reaction of the compound (1-a) as mentioned above.

The Step (e)

The desired compound (I) wherein the substituent of Ring A and/or the substituent $R^1$ are a substituent containing a free carboxyl group (e.g., a carboxy-substituted aryl group, a carboxy-substituted cyclo-lower alkyl group, a carboxy-lower alkyl-substituted aryl group, a carboxy-lower alkyl group, a carboxy-lower alkoxy-substituted aryl group, a carboxy-substituted lower alkoxy group, a carboxy-aryl-substituted lower alkyl group, etc.) is prepared by subjecting a corresponding compound of the formula (I) wherein the substituent of Ring A and/or the substituent $R^1$ are a substituent containing an esterified carboxyl group, to desterification reaction, for example, hydrolysis with a base (e.g., sodium hydroxide), an acid-treatment with a trifluoroacetic acid, hydrogen chloride, hydrogen bromide, etc., or reduction under hydrogen atmosphere with palladium-black, or palladium-carbon, which is selected according to the kinds of the ester residue to be removed. Among these de-esterification reactions, the hydrolysis with a base is carried out at 5–70° C., the acid-treatment is carried out at 5–80° C., and the reduction is carried out at 10–40° C.

Step (f)

The desired compound (I) wherein $R^1$ is an aryl group being substituted by a protected or unprotected amino-substituted carbamoyl group, or an aryl group being substituted by a morpholinocarbonyl group is prepared by reacting a corresponding compound of the formula (I) wherein $R^1$ is carboxy-substituted aryl group with an amine compound of the formula:

$HN(R^a)(R^b)$ wherein one of $R^a$ and $R^b$ is a hydrogen atom, and the other is a protected or unprotected amino group, or both combine at their termini together with the adjacent nitrogen atom to form a morpholino group, in the presence of a condensing agent. The condensing agent includes a conventional one which is usually used in the amido-bond formation reaction between a carboxylic acid and an amine, for example, 1,1-carbonyldiimidazole (CDI), DCC, WSCI, isobutyl chloroformate and N-methylmorpholine, etc. The reaction is carried out at 0–50° C. When $R^a$ or $R^b$ of the product is a protected amino group, if necessary, said protecting group may be removed by a conventional method.

The desired compound (I) wherein the group $R^1$ is an aryl group being substituted by a morpholino-lower alkylcarbamoyl-substituted lower alkoxy group is prepared by reacting a corresponding compound of the formula (I) wherein $R^1$ is an aryl group being substituted by a carboxyl-substituted lower alkoxy group with a morpholino-lower alkylamine in the same manner as above.

The desired compound (I) wherein Ring A is a lower alkoxy-substituted benzene ring being substituted by a carbamoyl group is prepared by reacting a corresponding compound (I) wherein Ring A is a benzene ring being substituted by a carboxyl-substituted lower alkoxy group with ammonia in the same manner as above.

Step (g)

The desired compound (I) wherein the substituent of Ring A and/or the group $R^1$ is a substituent containing an amino group (e.g., an amino-lower alkyl-substituted aryl group, an amino-substituted aryl-substituted lower alkyl group, etc.) is prepared by removing a lower alkanoyl group or a protecting group for amino group from a corresponding compound of the formula (I) wherein the substituent of Ring A and/or the group $R^1$ is a substituent containing a mono-or di-lower alkanoylamino group or a protected amino group. The removal of said protecting group for amino group or said lower alkanoyl group is carried out by a conventional method (e.g., acid-treatment, base-treatment, catalytic reduction, etc.). The acid-treatment is carried out at 5–120° C., the base-treatment is carried out at 5–40° C., and the catalytic reduction is carried out at 10–40° C.

Step (h)

The desired compound (I) wherein the substituent of Ring A and/or the group $R^1$ is a substituent containing a heterocyclic group (e.g., piperazinyl group, piperidinyl group, or pyrrolidinyl group) is prepared by removing the N-substituent (i.e., a lower alkoxycarbonyl group, or an aryl-lower alkoxycarbonyl group) from a corresponding compound of the formula (I) wherein the substituent of Ring A and/or the group $R^1$ is a substituent containing a heterocyclic group having a substituent at the N-position selected from a lower alkoxycarbonyl group and an aryl-lower alkoxycarbonyl group (e.g., fluorenyl-lower alkoxycarbonyl group, phenyl-lower alkoxycarbonyl group, etc.). The removal of these groups is carried out by the same method as in the above Step (g).

Step (i)

The desired compound (I) wherein the group $R^1$ is a mono-lower alkanoylamino group, a di-lower alkanoylamino group or a mono- or di-lower alkanoylamino-substituted aryl group is prepared by reacting a corresponding compound of the formula (I) wherein the group $R^1$ is an amino group or an aryl group being substituted by an amino group with a lower alkanoic aid or a reactive derivative thereof. The lower alkanoic acid includes, for example, an alkanoic acid having 1 to 6 carbon atoms (e.g., formic acid, acetic acid, propionic acid, etc.). The reactive derivative of alkanoic acid is, for example, an acid halide (e.g., acid chloride, acid bromide, etc.), an acid anhydride, or a mixed acid anhydride. When a free lower alkanoic acid is used, the reaction is carried out in the presence of a condensing agent (e.g., 1,3-dicyclohexylcarbodiimide, 1-ethyl-3-(3-dimethylaminopropyl)carbodiimide hydrochloride, diethylphosphoric cyanide, diphenylphosphoric azide). When a reactive derivative of the above alkanoic acid is used, the reaction is carried out in the presence of an acid acceptor such as an organic base (e.g., triethylamine, pyridine, etc.), an alkali metal hydroxide, an alkali metal hydrogen carbonate, an alkali metal carbonate, etc. In the reaction, the conversion from the compound (I) wherein $R^1$ is an amino group into the corresponding compound (I) wherein $R^1$ is a mono-lower alkanoylamino group is carried out by controlling the amount of the lower alkanoic aid or a reactive derivative thereof in 0.8–1 equivalent to the amount of the starting compound. The conversion from the compound (I) wherein $R^1$ is an amino group into the corresponding compound (I) wherein $R^1$ is a di-lower alkanoylamino group is carried out by controlling the amount of the lower alkanoic aid or a reactive derivative thereof in 2–3 equivalents to the amount of the starting compound. The reaction is carried out at −30–80° C., preferably at −20–50° C.

Step (j)

The desired compound (I) wherein the group $R^1$ is an amino group being substituted by one or two groups selected from a lower alkyl group and a hydroxy-substituted lower alkyl group is prepared by reacting a corresponding compound of the formula (I) wherein the group $R^1$ is a mono-substituted or unsubstituted amino group with an allylating agent such as a lower alkyl halide (e.g., a lower alkyl chloride, a lower alkyl bromide, a hydroxy-lower alkyl chloride, a hydroxy-lower alkyl bromide, etc.) wherein the alkyl moiety may optionally be substituted by a hydroxy group, or a lower alkyl-lower alkane-sulfonate (e.g., a lower alkyl methanesulfonate, etc.), lower alkyl arylsulfonate (e.g., a lower alkyl p-toluenesulfonate) wherein the alkyl moiety may optionally be substituted by a hydroxy group in the presence or absence of an acid acceptor. The acid acceptor is, for example, an alkali metal hydroxide (e.g., sodium hydroxide), an alkali metal hydrogen carbonate (e.g., sodium hydrogen carbonate), an alkali metal carbonate (e.g., sodium carbonate), or an organic base (e.g., triethylamine, pyridine, etc.). The desired compound (I) wherein the group $R^1$ is an amino group being substituted by one group selected from a lower alkyl group and a hydroxy-substituted lower alkyl group is prepared by reacting a corresponding compound of the formula (I) wherein the group $R^1$ is unsubstituted amino group with a lower alkyl aldehyde wherein the alkyl moiety may optionally be substituted by a hydroxy group, and subjecting the product to reduction. The reducing agent is preferably sodium cyanoborohydride, sodium borohydride, sodium triacetoxyborohydride, formic acid, etc. The solvent may be, for example, water, acetic acid, tetrahydrofuran, dioxane, chloroform methylene chloride, methanol, ethanol, etc., or a mixture of these solvents. The reaction is carried out at 0–70° C., preferably at 5–50° C. The compound (a) wherein the group $R^1$ is an amino group being substituted by a lower alkanoyloxy-lower alkyl group is prepared in the same esterification reaction as in the preparation of the compound [I-b] from the compound [I-a], but preferably prepared by reacting a corresponding compound of the formula (I) wherein the group $R^1$ is an amino group being substituted by a hydroxy-substituted lower alkyl group with a lower alkanoic acid in the presence of a condensing agent (e.g., 1,3-dicyclohexylcarbodiimide, ethyl-3-(3-dimethylaminopropyl)carbodiimide hydrochloride, diethyl phosphoric cyanide, diphenyl-phosphoric azide, etc.), or with a reactive derivative of the above lower alkanoic acid such as an active ester (e.g., N-hydroxysuccinimide ester, N-hydroxyphthalimide ester, 1-hydroxybenzotriazol ester, etc.), a corresponding acid halide, a corresponding mixed acid anhydride, in the presence of an acid acceptor such as an alkali metal hydroxide (e.g., sodium hydroxide, etc.), an alkali metal hydrogen carbonate (e.g., sodium hydrogen carbonate, etc.), an alkali metal carbonate (e.g., sodium carbonate, etc.), or an organic base (e.g., triethylamine, pyridine, etc.). The reaction is carried out at −30–80° C., preferably at −20–50° C.

Step (k)

The desired compound (I) wherein the group $R^1$ is an aryl group being substituted by a di-(lower alkylsulfonyl) amino group is prepared by reacting a corresponding compound of the formula (I) wherein the group $R^1$ is an amino-substituted aryl group with a lower alkyl sulfonyl halide (e.g., a lower alkyl sulfonyl chloride, a lower alkyl sulfonyl bromide, etc.) in the presence of the same acid acceptor as those used in the above Step (j), i.e., an organic base (e.g., triethylamine, pyridine, etc.). The reaction is carried out at 0–80° C., preferably at 10–60° C.

Step (l)

The desired compound (I) wherein the group $R^1$ is a hydroxy-substituted aryl group, or the desired compound (I) wherein the substituent of Ring A and/or Ring B is a hydroxy group is prepared by removing the protecting groups from a corresponding compound of the formula (I) wherein the group $R^1$ is a protected hydroxy-substituted aryl group, or a corresponding compound of the formula (I) wherein the substituent of Ring A and/or Ring B is a protected hydroxy group. The removal of the protecting group is carried out by a conventional method such as acid-treatment, base-treatment, catalytic reduction, etc. which should be selected according to the kinds of the protecting groups to be removed. The reaction is carried out at 0–80° C., preferably at 5–50° C.

Step (m)

The desired compound (I) wherein the group $B^2$ of Ring B is a hydroxy group is prepared by treating a corresponding compound of the formula (I) wherein $B^2$ is a lower alkoxy group by a conventional method, such as acid-treatment. The reaction is carried out at 10–150° C., preferably at 20–120° C.

Step (n)

The desired compound (I) wherein the group $R^1$ is an aryl group being substituted by a group selected from a lower alkylsulfinyl group and a lower alkylsulfonyl group is prepared by oxidizing a corresponding compound of the formula (I) wherein $R^1$ is an aryl group being substituted by a lower alkylthio group. The oxidization reaction is carried out by using an oxidizing agent. The oxidizing agent is, for example, a peroxide compound such as 3-chloroperbenzoic acid, peracetic acid, hydrogen peroxide, trifluoroperacetic acid, etc., sodium periodate, osmium tetraoxide, sodium bromite, etc. When an oxidizing agent is used in an amount of 0.8–1 equivalent to 1 equivalent of the starting compound, there is obtained the compound of the formula (I) wherein $R^1$ is an aryl group being substituted by a lower alkylsulfinyl group. When an oxidizing agent is used in an amount of 2–3 equivalents to 1 equivalent of the starting compound, there is obtained the compound of the formula (I) wherein $R^1$ is an aryl group being substituted by a lower alkylsulfonyl group. The reaction is carried out at −10–60° C., preferably at 5–40° C.

Step (o)

The desired compound (I) wherein the group $R^1$ is a heterocyclic group being substituted by one or two oxo groups (e.g., a thiomorpholino group being substituted by one or two oxo groups) is prepared by treating a corresponding compound of the formula (I) wherein $R^1$ is a heterocyclic group in the same manner as in the above Step (n).

Step (p)

The desired compound (I) wherein the group $R^1$ is an aryl group being substituted by a mono- or di-lower alkylamino group, or a lower alkyl group being substituted by a mono- or di-lower alkylamino group is prepared in the same manner as in the above Step (j) but is prepared by reacting a corresponding compound of the formula (I) wherein $R^1$ is an amino-substituted aryl group or an amino-substituted lower alkyl group in the presence or absence of an acid acceptor with a lower alkyl halide (e.g., a lower alkyl chloride, a lower alkyl bromide, etc.). The acid acceptor is, for example, an alkali metal hydroxide, an alkali metal hydrogen carbonate, an alkali metal carbonate, an organic base (e.g., triethylamine, pyridine, etc.). When an alkylating agent is used in an amount of 0.8–1 equivalent to 1 equivalent of the starting compound, there is obtained the compound (I) wherein the group $R^1$ is an aryl group (or a lower alkyl group) substituted by a mono-lower alkylamino group. When an alkylating agent is used in an amount of 2–3 equivalents to 1 equivalent of the starting compound, there is obtained the compound (I) wherein the group $R^1$ is an aryl group (or a lower alkyl group) being substituted by a di-lower alkylamino group. The reaction is carried out at 0–60° C., preferably at 5–40° C. The desired compound (I) wherein the group $R^1$ is an aryl group being substituted by an amino group being substituted by a lower alkyl group and a protecting group for amino group is prepared by treating a corresponding compound of the formula (I) wherein $R^1$ is an aryl group substituted by an amino group being substituted by one protecting group for amino group in the same manner as above. Moreover, the compound (I) wherein the group $R^1$ is a mono-lower alkylamino-substituted aryl group is obtained by removing a protecting group from a corresponding compound of the formula (I) wherein $R^1$ is an aryl group being substituted by an amino group being substituted by a lower alkyl group and a protecting group for amino group by a conventional method.

Step (q)

The compound (I) wherein the group $R^1$ is a pyridylcarbonyloxy-lower alkyl group is prepared by reacting a corresponding compound of the formula (I) wherein $R^1$ is a hydroxy-substituted lower alkyl group with a pyridinecarboxylic acid in the presence of a condensing agent (e.g., 1,3-dicyclohexylcarbodiimide, 1-ethyl-3-(3-dimethylaminopropyl)carbodiimide hydrochloride, diethyl phosphoric cyanide, diphenylphosphoric azide, etc.), or with a reactive derivative of a pyridinecarboxylic acid (e.g., active ester such as N-hydroxysuccinimide ester, N-hydroxyphthalimide ester, 1-hydroxybenzotriazole ester, etc., pyridinecarboxylic halide) in the presence of an acid acceptor such as an alkali metal hydroxide (e.g., sodium hydroxide, etc.), an alkali metal hydrogen carbonate (e.g., sodium hydrogen carbonate, etc.), an alkali metal carbonate (e.g., sodium carbonate, etc.), an alkali metal hydride (e.g., sodium hydride, etc.), or an organic base (e.g., triethylamine, pyridine, etc.). The reaction is carried out at 0–60° C., preferably at 5–40° C.

Step (r)

The compound (I) wherein Ring A is a benzene ring being substituted by a tetrazolyl-lower alkoxy group is prepared by reacting a corresponding compound of the formula (I) wherein Ring A is a benzene ring being substituted by a cyano-lower alkoxy group, with a metal azide such as sodium azide, tributyltin azide. The reaction is carried out at 30–120° C., preferably at 50–100° C.

Step (s)

The compound (I) wherein the substituent of Ring A is a group containing a heterocyclic group substituted by an oxo group (e.g., an oxo-substituted pyridyl-substituted lower alkyl group) is prepared by treating a corresponding compound of the formula (I) wherein the substituent of Ring A is a group containing a heterocyclic group with an oxidizing agent (e.g., 3-chloroperbenzoic acid, hydrogen peroxide, peracetic acid, etc.). The reaction is carried out in the same manner as in the above Step (n).

Step (t)

The compound (I) wherein the group $R^1$ is a heterocyclic group (e.g., piperazinyl group) having a hydroxy-lower alkyl group at the N-position is prepared by reacting a corresponding compound of the formula (I) wherein the group $R^1$ is a heterocyclic group with a lower alkyl halide (e.g., hydroxy-lower alkyl chloride, hydroxy-lower alkyl bromide, etc.) wherein the alkyl moiety is substituted by a hydroxy group, in the presence or absence of the same acid acceptor (e.g., an alkali metal carbonate such as sodium carbonate) as those used in the above Step (j). The reaction is carried out at 40–120° C., preferably at 50–100° C.

The solvent used in the above Steps (a) to (t) may be any one which does not disturb the reaction, for example, dioxane, ethylene glycol dimethyl ether, dimethyl acetamide, dimethylfonnamide, hexamethylphosphoramide, benzene, tetrahydrofuran, toluene, ethyl acetate, a lower alcohol, methylene chloride, chloroform, carbon tetrachloride, 1,3-dimethyl-2-imidazolidinone, acetic acid, diethyl ether, dimethoxyethane, dimethylsulfoxide, water, or a mixture of these solvents.

The starting compound (II) is prepared, for example, by reacting a benzoylbenzoic acid compound of the formula (i):

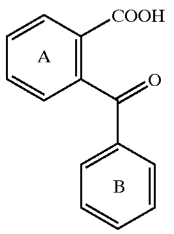

(i)

wherein the symbols are the same as defined above, with a malonic acid compound of the formula (ii):

$$X^2—CH(COOZ^1)_2$$

wherein $X^2$ is a leaving group, and $Z^1$ is a protecting group for carboxyl group, in the presence of a base, removing the protecting group from the product to give a compound of the formula (iii):

(iii)

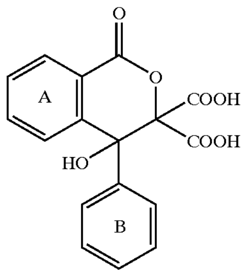

wherein the symbols are the same as defined above;

subjecting the compound (iii) to decarboxylation reaction and dehydration reaction in the presence or absence of an acid to give a compound of the formula (iv):

(iv)

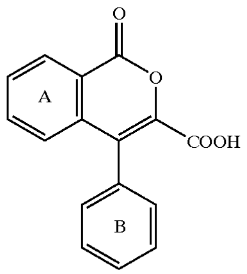

wherein the symbols are the same as defined above;

if necessary, followed by converting the 3-carboxyl group of the compound (iv) into the substituent $R^2$ by esterification or amidation by a conventional method.

The starting compound (V) is prepared, for example, by condensing the compound of the above formula (i) with a compound of the formula (v):

(v)

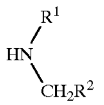

wherein the symbols are the same as defined above, in the same manner as in the condensation reaction between the compound (I-a) and the amine compound (VIII).

The benzoyl benzoic acid compound (i) is prepared by a conventional method, for example, by treating a benzaldehyde compound of the formula (vi):

(vi)

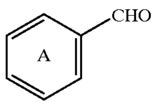

wherein Ring A is the same as defined above, with a halogen (bromide, etc.), reacting the resulting o-halogeno benzaldehyde compound with an acetalization agent, for example, with a lower alkyl orthoformate (e.g., methyl orthoformate, etc.), in the presence of an acidic catalyst (e.g., a strong acidic resin, etc.) to protect the formyl group, reacting the product with an aldehyde compound of the formula (vii):

(vii)

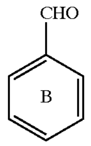

wherein Ring B is the same as defined above, oxidizing the product, i.e., treating with an oxidizing agent such as manganese dioxide, etc., to give a compound of the formula (viii):

(viii)

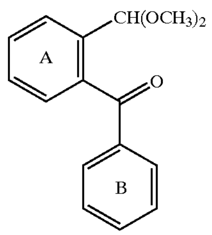

wherein the symbols are the same as defined above, subjecting the compound (viii) to deacetalization by treating with an acid (e.g., hydrochloric acid, trifluoroacetic acid, a strong acidic resin), followed by treating with an oxidizing agent (e.g., sodium chlorite).

Besides, in the preparation of the compound (i) as mentioned above benzoic acid compound of the following formula (ix) is also used instead compound (vii).

(ix)

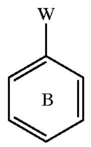

wherein W is a di-lower alkyl-substituted carbamoyl group, a lower alkoxycarbonyl group, or a carboxyl group forming a salt with an alkali metal (e.g., sodium, potassium, etc.), and Ring B is the same as defined above.

Moreover, the starting compound (i) of the present invention is prepared by reacting a compound of the formula (x):

(x)

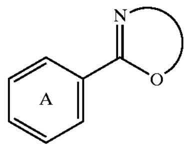

wherein a group of the formula: is a heterocyclic group which may optionally be substituted by a lower alkyl etc., and Ring A is the same as defined above, with the compound (vii) in the presence of a base (e.g., n-butyl lithium, etc.) to give a compound of the formula (xi):

(xi)

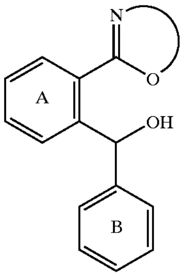

wherein the symbols are the same as defined above;

heating the compound (xi) in the presence of an acid (e.g., an inorganic acid such as hydrochloric acid, hydrobromic acid, sulfuric acid, etc.) to give a compound of the formula (xii):

(xii)

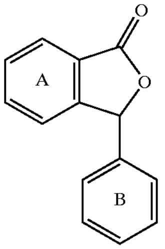

wherein the symbols are the same as defined above;

subjecting the compound (vii) to hydrolysis with a base (e.g., an alkali metal hydroxide such as potassium hydroxide, sodium hydroxide, etc.);

then, followed by subjecting the product to oxidation.

The compound (xii) is prepared by reacting a compound of the formula (xiii):

(xiii)

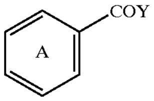

wherein Y is a mono- or di-lower alkylamino group, and Ring A is the same as defined above, with the compound (vii) in the presence of a base (e.g., sec-butyl lithium, etc.) to give a compound of the formula (xiv):

(xiv)

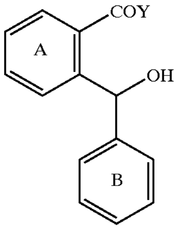

where the symbols are the same as defined above, followed by heating the compound (xiv) in the presence of an acid such as an inorganic acid (e.g., hydrochloric acid, hydrobromic acid, sulfuric acid, etc.).

Throughout the present description and the claims, the "alkyl group" means an alkyl group having 1 to 16 carbon atoms, and preferably a straight chain or branched chain alkyl group having 1 to 8 carbon atoms. The "lower all group", the "lower alkoxy group" and the "lower alkylene group" mean ones having 1 to 6 carbon atoms, respectively, and preferably ones having 1 to 4 carbon atoms. The "lower alkenyl group" and the "lower alkynyl group" mean ones having 2 to 7 carbon atoms, respectively, and preferably a straight chain or branched chain one having 2 to 5 carbon atoms. The "lower alkylenedioxy group" and the "alkanoyl group" mean ones having 1 to 7 carbon atoms, respectively, and preferably a straight chain or branched chain one having 1 to 5 carbon atoms. The "cyclo-lower alkyl group" means cycloalkyl groups having 3 to 8 carbon atoms, preferably ones having 3 to 6 carbon atoms.

The synthesis of the compounds of the invention and of the intermediates for use therein are illustrated by the following, non-limiting Examples from the aforesaid PCT application WO 98/38168. Representatives of compounds of formula (I) prepared by the above Processes are exemplified in Tables 1–46.

EXAMPLE 1

7-Benzyloxy-6-methoxy-4-(3,4,5-trimethoxyphenyl) isocoumarin-3-carboxylic acid (5.0 g) and 4-aminomorpholine (6.2 g) are dissolved in 1,3-dimethyl-2-imidazolidinone (20 ml), and the mixture is heated at 100° C. with stirring overnight. To the reaction mixture are added chloroform and water. The chloroform layer is separated, washed, dried, and concentrated under reduced pressure to give 7-benzyloxy-3-carboxy-6-methoxy-2-morpholino-4-(3,4,5-trimethoxyphenyl)-1(2H)isoquinolinone. The product thus obtained is dissolved in dimethylformamide (15 ml), and thereto are added potassium carbonate (2.1 g) and methyl iodide (1.27 ml). The mixture is stirred at room temperature for 30 minutes, and thereto are added ethyl acetate and water. The ethyl acetate layer is separated, washed, dried, and concentrated under reduced pressure. The residue is crystallized from diethyl ether to give 7-benzyloxy-6-methoxy-3-methoxycarbonyl-2-morpholino-4-(3,4,5-trimethoxyphenyl)-1(2H)isoquinolinone (3.4 g) as listed in Table 1.

EXAMPLE 2

To the compound obtained in Example 1 (2.8 g) are added methanol (100 ml), dimethylformamide (100 ml) and palladium-carbon (100 mg), and the mixture is stirred under hydrogen atmosphere (1 atm) at room temperature for 1.5 hour. The catalyst is removed by filtration, and the filtrate is concentrated. The precipitated crystals are collected by filtration, and washed with diethyl ether to give 7-hydroxy-6-methoxy-3-methoxycarbonyl-2-morpholino-4-(3,4,5-trimethoxyphenyl)-1(2H)-isoquinolinone (2.26 g) as listed in Table 1.

EXAMPLE 3

To a solution of the compound obtained in Example 2 (300 mg) in dimethylformamide (3 ml) are added 2-picolyl chloride hydrochloride (118 mg) and potassium carbonate (182 mg), and the mixture is stirred at 50° C. overnight. To the mixture are added ethyl acetate and water. The ethyl acetate layer is separated, washed, dried, and concentrated under reduced pressure. The residue (chemical name; 6-methoxy-3-methoxycarbonyl-2-morpholino-7-(2-pyridylmethyloxy)-4-(3,4,5-trimethoxyphenyl-1(2H)-isoquinolinone) is dissolved in ethyl acetate, and thereto is added a 4M solution of hydrogen chloride in ethyl acetate (150 μl). The mixture is stirred at room temperature for 30 minutes. The precipitated crystals are collected by filtration, and washed with ethyl acetate to give 6-methoxy-3-methoxycarbonyl-2-morpholino-7-(2-pyridylmethyloxy)-4-(3,4,5-trimethoxyphenyl)-1(2H)-isoquinolinone hydrochloride (279 mg) as listed in Table 1.

EXAMPLE 4

To 7-benzyloxy-3-hydroxymethoxy-4-(3,4,5-trimethoxyphenyl)-3,4-dihydroisocoumarin-3-carboxylic acid (the compound obtained in Reference Example 71) (12.8 g) are added 1,3-dimethyl-2-imidazolidinone (60 ml), N-methylmorpholine (415 ml) and N-tert-butoxycarbonyl-p-phenylenediamine (6.78 g), and the mixture is heated at 80° C. with stirring overnight. The reaction mixture is cooled to room temperature, and thereto are added a saturated aqueous citric acid solution and ethyl acetate. The ethyl acetate layer is separated, washed, dried, and concentrated under reduced pressure to give 7-benzyloxy-2-[4-(tert-butoxycarbonylamino)phenyl]-3-carboxy-6-methoxy-4-(3,4,5-trimethoxyphenyl)-1(2H)-isoqunolinone. The product is dissolved in dimethylformamide (60 ml), and thereto are added potassium carbonate (4.14 g) and methyl iodide (1.87 ml) under ice-cooling, and the mixture is stirred at room temperature overnight. To the mixture are added water and ethyl acetate. The ethyl acetate layer is separated, washed, dried, and concentrated under reduced pressure. The residue is crystallized from diethyl ether to give 7-benzyloxy-2-[4-(tert-butoxycarbonylamino) phenyl]-6-methoxy-3-methoxycarbonyl-4-(3,4,5-trimethoxyphenyl)-1(2H)-isoquinolinone (14.2 g) as listed in Table 2.

EXAMPLE 5

To a solution of the compound obtained in Example 4 (17.0 g) in a mixture of tetrahydrofuran (150 ml) and methanol (100 ml) is added palladium-carbon (1.0 g) under nitrogen atmosphere, and the mixture is subjected to catalytic reduction (3 atms) for one hour. The palladium-carbon is removed by filtration, and the filtrate is concentrated under reduced pressure. The residue is crystallized from diethyl ether to give 2-[4-(tert-butoxycarbonylamino)phenyl]-7-hydroxy-6-methoxy-3-methoxycarbonyl-4-(3,4,5-trimethoxyphenyl)-1(2H)-isoquinolinone (13.3 g) as listed in Table 2.

EXAMPLE 6

(1) The compound obtained in Example 5 (200 mg) is dissolved in dimethyl formamide (20 ml), and thereto are added potassium carbonate (92 mg), and 2-picolyl chloride hydrochloride (55 mg). The mixture is stirred at 60° C. overnight, and thereto are added water and ethyl acetate. The ethyl acetate layer is separated, washed, dried, and concentrated under reduced pressure. The residue is purified by silica gel column chromatography (solvent, hexane:ethyl acetate=1:2) to give 2-[4-(tert-butoxycarbonylamino) phenyl]-6-methoxy-3-methoxy-carbonyl-7-(2-pyridylmethyloxy)-4-(3,4,5-trimethoxyphenyl)-1(2H)-isoquinolinone (207 mg).

(2) The compound thus obtained is dissolved in chloroform (5 ml), and thereto is added a 4M solution of hydrogen chloride in ethyl acetate (8 ml), and the mixture is stirred at room temperature for 5 minutes. To the resulting suspension is added methanol (1 ml), and the mixture is stirred overnight. To the mixture is added diethyl ether, and the precipitated crystals are collected by filtration to give 2-(4-aminophenyl)-6-methoxy-3-methoxycarbonyl-7-(2-pyridylmethyloxy)-4-(3,4,5-trimethoxyphenyl)-1(2H)-isoquinolinone dihydrochloride (180 mg) as listed in Table 2.

EXAMPLE 7

(1) The compound obtained in Example 5 (250 mg), 3-hydroxymethyl-quinoline (98 mg) and triphenylphosphine (215 mg) are dissolved in THF (10 ml), and thereto is added diethyl azodicarboxylate (97.3 μl). The mixture is stirred at room temperature for 10 minutes, and concentrated under reduced pressure. The residue is purified by silica gel column chromatography (solvent; hexane:ethyl acetate=1:2) to give 2-[4-(tert-butoxycarbonylamino)phenyl]-6-methoxy-3-methoxycarbonyl-7-(3-quinolylmethyloxy)-4-(3,4,5-trimthoxyphenyl)-1-(2H)-isoquinolinone.

(2) The compound thus obtained is dissolved in chloroform (3 ml), and thereto is added a 4M solution of hydrogen chloride in ethyl acetate (5 ml), and the mixture is stirred at room temperature for 5 minutes. To the resulting suspension is added methanol (1 ml), and the mixture is stirred overnight To the reaction mixture is added diethyl ether, and the precipitated crystals are collected by filtration to give 2-(4-aminophenyl)-6-methoxy-3-methoxycarbonyl-7-(3-quinolylmethyloxy)-4-(3,4,5-trimethoxyphenyl)-1(2H)-isoquinolinone dihydrochloride (140 mg) as listed in Table 2.

EXAMPLE 8

(1) The compound obtained in Example 5 (10.0 g) is dissolved in chloroform (20 ml), and thereto are added a 4M solution of hydrogen chloride in ethyl acetate (60 ml). The mixture is stirred at room temperature overnight. The resulting suspension is neutralized with 2M aqueous sodium hydroxide solution (120 ml) under ice-cooling, and the mixture is extracted with ethyl acetate. The ethyl acetate layer is separated, washed, dried, and concentrated under reduced pressure. The residue is dissolved in a small amount of ethyl acetate, and crystallized from diethyl ether to give 2-(4-aminophenyl)-7-hydroxy-6-methoxy-3-methoxycarbonyl-4-(3,4,5-trimethoxyphenyl)-1(2H)-isoquinolinone (5.47 g).

(2) The compound thus obtained (5.47 g) is dissolved in a mixture of acetonitrile (50 ml) and 1,3-dimethyl-2-imidazolidinone (5 ml), and thereto is added 9-fluorenylmethyl chloroformate (2.8 g). The mixture is stirred at room temperature for 10 minutes. To the reaction mixture are added water and ethyl acetate. The ethyl acetate layer is washed, dried, and concentrated under reduced pressure. The residue is purified by silica gel column chromatography (solvent; hexane:ethyl acetate=1:2) to give 2-[4-(9-fluorenylmethyloxycarbonylamino)phenyl]-7-hydroxy-6-methoxy-3-methoxycarbonyl-4-(3,4,5-trimethoxyphenyl)-1(2H)-isoquinolinone (3.38 g) as listed in Table 2.

EXAMPLE 9

(1) The compound obtained in Example 8-(2) (418 mg), 2-hydroxymethylthiophene (97.6 μl), and triphenylphosphine (270 mg) are dissolved in tetrahydrofuran (10 ml), and thereto is added diethyl azodicarboxylate (162 μl). The mixture is stirred at room temperature for 10 minutes, and after the reaction is complete, the mixture is concentrated under reduced pressure. The residue is purified by silica gel column chromatography (solvent; hexane:ethyl acetate 1:1) to give 2-[4-(9-fluorenylmethyloxycarbonylamino)phenyl]-6-methoxy-3-methoxycarbonyl-7-(2-thienylmethyloxy)-4-(3,4,5-trimethoxyphenyl)-1(2H)-isoquinolinone.

(2) The compound thus obtained is dissolved in dimethylformamide (10 ml), and thereto is added piperidine (50 μl), and the mixture is stirred at room temperature overnight. To the mixture are added water and ethyl acetate. The ethyl acetate layer is separated, washed, dried, and concentrated under reduced pressure. The residue is purified by silica gel column chromatography (solvent; hexane:ethyl acetate=1:4) to give 2-(4-aminophenyl)-6-methoxy-3-methoxycarbonyl-7-(2-thienylmethyloxy)-4-(3,4,5-trimethoxyphenyl)-1(2H)-isoquinolinone (187 mg), m.p. 205–206° C.

(3) The compound thus obtained (155 mg) is dissolved in chloroform (5 ml), and thereto is added a 4M solution of hydrogen chloride in ethyl acetate (66 $\mu$l), and the mixture is stirred at room temperature for 30 minutes. To the mixture is diethyl ether, and the precipitated crystals are collected by filtration to give 2-(4-aminophenyl)-6-methoxy-3-methoxycarbonyl-7-(2-thienylmethyloxy)-4-(3,4,5-trimethoxyphenyl)-1(2H)-isoquinolinone hydrochloride (76 mg) as listed in Table 2.

EXAMPLE 10

(1) 6,7-Dimethoxy-4-(3,4,5-trimethoxyphenyl)isocoumarin-3-carboxylic acid (=the compound obtained in Reference Example 50) (2.0 g) and aniline (2.61 g) are dissolved in 1-methyl-2-pyrrolidinone (5 ml), and the mixture is heated with stirring at 120° C. overnight. To the reaction mixture are added ethyl acetate and water. The ethyl acetate layer is separated, washed, dried, and concentrated under reduced pressure to give 3-carboxy-2-phenyl-4-(3,4,5-trimethoxyphenyl)-1(2H)-isoquinolinone (1.98 g).

(2) The compound thus obtained (1.97 g) is dissolved in dimethylformamide (20 ml), and thereto are added potassium carbonate (1.16 g) and methyl iodide (1.59 g). The mixture is stirred at room temperature overnight, and thereto are added chloroform and water. The chloroform layer is separated, washed, dried, concentrated under reduced pressure, and the residue is crystallized from ethyl acetate to give 3-methoxycarbonyl-2-phenyl-4-(3,4,5-trimethoxyphenyl)-1(2H)-isoquinolinone (1.69 g) as listed in Table 3.

EXAMPLES 11–13, 11A–13A

The corresponding starting compounds are treated in the same manner as in Example 10-(2) to give the following compounds as listed in Table 3.

3-thoxycarbonyl-2-phenyl-4-(3,4,5-trimethoxyphenyl)-1(2H)-isoquinolinone (Example 11);

3-benzyloxycarbonyl-2-phenyl-4-(3,4,5-trimethoxyphenyl)-1(2H)-isoquinolinone (Example 12);

3-n-butoxycarbonyl-2-phenyl-4-(3,4,5-trimethoxyphenyl)-1(2H)-isoquinolinone (Example 13);

3-ethoxycarbonyl-4-(4-ethoxy-3,5-dimethoxyphenyl)-2-phenyl-1(2H)-isoquinolinone (Example 11a);

3-benzyloxycarbonyl-4-(4-benzyloxy-3,5-dimethoxyphenyl)-2-phenyl-1(2H)-isoquinolinone (Example 12a);

3-n-butoxycarbonyl-4-(4-n-butoxy-3,5-dimethoxyphenyl)-2-phenyl-1(2H)-isoquinolinone (Example 13a);

EXAMPLES 14–15

4-(3,4,5-Trimethoxyphenyl)isocoumarin-3-carboxylic acid (the compound obtained in Reference Example 51) and the corresponding starting compounds are treated in the same manner as in Example 1 to give the following compounds as listed in Table 4.

2-(2-chlorophenyl)-3-methoxycarbonyl-4-(3,4,5-trimethoxyphenyl)-1(2H)-isoquinolinone (Example 14);

3-methoxycarbonyl-2-(2-naphthyl)-4-(3,4,5-trimethoxyphenyl)-1(2H)-isoquinolinone (Example 15);

EXAMPLES 16–18

The compound obtained in Reference Example 51 and the corresponding starting compounds are treated in the same manner as in Example 4 to give the following compounds as listed in Table 4.

2-(4-n-butylphenyl)-3-methoxycarbonyl-4-(3,4,5-trimethoxyphenyl)-1(2H)-isoquinolinone (Example 16);

2-[3,5-bis(methoxycarbonyl)phenyl]-3-methoxycarbonyl-4-(3,4,5-trimethoxyphenyl)-1(2H)-isoquinolinone (Example 17);

3-methoxycarbonyl-2-(3-nitrophenyl)-4-(3,4,5-trimethoxyphenyl)-1(2H)-isoquinolinone (Example 18);

EXAMPLE 19

The compound obtained in Reference Example 51 and the corresponding starting compounds are treated in the same manner as in Example 1 to give 2-dimethylamino-3-methoxycarbonyl-4-(3,4,5-trimethoxyphenyl)-1(2H)-isoquinolinone as listed in Table 4.

EXAMPLE 20

The compound obtained in Reference Example 51 and the corresponding starting compounds are treated in the same manner as in Example 4 to give 3-methoxycarbonyl-2-(4-methoxycarbonylphenyl)-4-(3,4,5-trimethoxyphenyl)1(2H)-isoquinolinone as listed in Table 4.

EXAMPLE 21

(1) To the compound obtained in Example 20 (1.51 g) are added methanol (150 ml) and 1M aqueous sodium hydroxide solution (3 ml), and the mixture is stirred at 60° C. overnight. To the reaction solution is further added 1M aqueous sodium hydroxide solution (1.5 ml) which is divided to two portions, and the mixture is refluxed for 12 hours. The reaction mixture is allowed to stand for cooling, and thereto are added water and ethyl acetate. The aqueous layer is separated, and acidified with hydrochloric acid, and further extracted with ethyl acetate. The ethyl acetate layers are combined, washed, dried, and concentrated under reduced pressure. The residue is crystallized from diethyl ether to give 2-(4-carboxyphenyl)-3-methoxycarbonyl-4-(3,4,5-trimethoxyphenyl)-1(2H)-isoquinolinone (245 mg) as listed in Table 4.

(2) The compound thus obtained (245 mg) is dissolved with heating in 1M aqueous sodium hydroxide solution (0.50 ml). Water is removed by under reduced pressure from the mixture, and thereto is added diethyl ether. The precipitated crystals are collected by filtration to give 2-(4-carboxyphenyl)-3-methoxycarbonyl-4-(3,4,5-trimethoxyphenyl)-1(2H)-isoquinolinone sodium salt (245 mg) as listed in Table 4.

EXAMPLE 22

A solution of the compound obtained in Example 21 (200 mg), 1-hydroxybenzotriazole (69 mg) and 1-(3-dimethylaminopropyl)-3-ethyl-carbodiimide hydrochloride (86 mg) in methylene chloride (10 ml) is stirred at room temperature for 30 minutes. To the mixture is added a solution of morpholine (71 mg) in methylene chloride (2 ml), and the mixture is stirred at room temperature overnight. After the reaction is complete, to the mixture are added water and ethyl acetate. The ethyl acetate layer is separated, washed, dried, and concentrated under reduced pressure. The residue is crystallized from diethyl ether to give 3-methoxycarbonyl-2-[4-(morpholinocabonyl) phenyl]-4-(3,4,5-trimethoxyphenyl)-1(2H) isoquinolinone (210 mg) as listed in Table 4.

EXAMPLE 23

The compound obtained in Example 21 and tert-butyl carbazate are treated in the same manner as in Example 22 to give 2-[4-(tert-butoxycarbonylhydrazinocarbonyl) phenyl]-3-methoxycarbonyl-4-(3,4,5-trimethoxyphenyl)-1(2H)-isoquinolinone as listed in Table 4.

EXAMPLE 24

The compound obtained in Example 23 is dissolved in dioxane (2 ml), and thereto is added a 4M solution of hydrogen chloride in dioxane (5 ml), and the mixture is stirred at room temperature. To the reaction mixture is further added a 4M solution of hydrogen chloride in dioxane (5 ml), and the mixture is stirred for three hours. The reaction mixture is concentrated under reduced pressure, and the residue is purified by silica gel column chromatography (solvent; chloroform:methanol=30:1) to give 3-methoxycarbonyl-2-[4-(hydrazinocarbonyl)phenyl]-4-(3,4,5-trimethoxyphenyl)-1(2H)-isoquinolinone hydrochloride as listed in Table 4.

EXAMPLES 25–26

A solution of 3-hydroxy-4-(3,4,5-trimethoxyphenyl)-3,4-dihydro-isocoumarin-3-carboxylic acid (the compound obtained in Reference Example 75) (1.87 g), 1,4-diaminocyclohexane (1.14 g) and N-methylmorpholine (0.55 ml) in 1,3-dimethyl-2-imidazolidinone (10 ml) is heated with stirring at 100° C. for 30 minutes. The reaction mixture is cooled, and acidified with hydrochloric acid, and thereto is added ethyl acetate (20 ml). The pH value of the aqueous layer is adjusted to pH 9 with potassium carbonate, and thereto are added methanol (30 ml), tetrahydrofuran (100 ml) and di-tert-butyl dicarbonate (5.44 g), and the mixture is stirred at room temperature for 6 hours. The reaction mixture is acidified with 10% aqueous citric acid solution, and extracted with ethyl acetate. The extract is washed, dried, and concentrated under reduced pressure. To the residue are added methanol (50 ml), ethyl acetate (100 ml) and a 2M solution of trimethylsilyldiazomethane in hexane (2.5 ml), and the mixture is stirred at room temperature for one hour. The reaction mixture is concentrated under reduced pressure, and the residue is purified by silica gel column chromatography (solvent; chloroform:ethyl acetate=10:1) to give the following compounds as listed in Table 4.

2-[cis-4-(tert-butoxycarbonylamino)cyclohexyl]-3-methoxycarbonyl-4-(3,4,5-trimethoxyphenyl)-1(2H)-isoquinolinone (Example 25);

2-[trans-4-(tert-butoxycarbonylamino)cyclohexyl]-3-methoxycarbonyl-4-(3,4,5-trimethoxyphenyl)-1(2H)-isoquinolinone (Example 26);

EXAMPLES 27–28

The compounds obtained in Examples 25–26 are treated in the same manner as in Example 24 to give the following compounds as listed in Table 4

2-(cis-4-aminocyclohexyl)-3-methoxycarbonyl-4-(3,4,5-trimethoxyphenyl)-1(2H)-isoquinolinone hydrochloride (Example 27);

2-(trans-4-aminocyclohexyl)-3-methoxycarbonyl-4-(3,4,5-trimethoxyphenyl)-1(2H)-isoquinolinone hydrochloride (Example 28);

EXAMPLE 29

3-Hydroxy-4-(3,4,5-trimethoxyphenyl)-3,4-dihydroisocoumarin-3-carboxylic acid (the compound obtained in Reference Example 75) and the corresponding starting compounds are treated in the same manner as in Example 25 to give 2-[3-(N-tert-butoxycarbonyl) pyrrolidinyl]-3-methoxycarbonyl-4-(3,4,5-trimethoxyphenyl)-1(2H)-isoquinolinone as listed in Table 4.

EXAMPLE 30

The compound obtained in Example 29 is treated in the same manner as in Example 24 to give 3-methoxycarbonyl-2-(3-pyrrolidinyl)-4-(3,4,5-trimethoxyphenyl)-1(2H)-isoquinolinone hydrochloride as listed in Table 4.

EXAMPLE 31

To 3-hydroxy-4-(3,4,5-trimethoxyphenyl)-3,4-dihydroisocoumarin-3-carboxylic acid (the compound obtained in Reference Example 75) (500 mg) are added 1,3-dimethyl-2-imidazolidinone (5 ml) and 4-aminobenzenesulfonamide (920 mg), and the mixture is heated with stirring at 90° C. with stirring for three hours, and then further heated with stirring at 120° C. overnight. The reaction mixture is allowed to stand for cooling, and thereto are added 5% aqueous potassium carbonate solution (20 ml) and ethyl acetate (10 ml). The aqueous layer is separated, acidified with 10% aqueous citric acid solution, and extracted with ethyl acetate. The ethyl acetate layers are combined, washed, dried, and concentrated under reduced pressure to give 2-(4-sulfamoylphenyl)-3-carboxy-4-(3,4,5-trimethoxyphenyl)-1(2H)-isoquinolinone, which is dissolved in a mixture of methanol (5 ml) and ethyl acetate (20 ml). To the mixture is added a 2M solution of trimethylsilyldiazomethane in hexane (0.67 ml), and the mixture is stirred at room temperature for 30 minutes. The mixture is concentrated under reduced pressure, and the residue is purified by silica gel column chromatography (solvent; chloroform:acetone=9:1) to give 2-(4-sulfamoylphenyl)-3-methoxycarbonyl-4-(3,4,5-trimethoxyphenyl)-1(2H)-isoquinolinone (88 mg) as listed in Table 4.

EXAMPLE 32

The compound obtained in Reference Example 75 and the corresponding starting compounds are treated in the same manner in Example 4 or 31 to give 3-methoxycarbonyl-2-[4-(N-tert-butoxycarbonyl)piperidyl]-4-(3,4,5-trimethoxyphenyl)-1(2H)-isoquinolinone as listed in Table 4.

EXAMPLE 33

(1) The compound obtained in Example 32 is treated in the same manner as in Example 24 to give 3-methoxycarbonyl-2-(4-piperidyl)-4-(3,4,5-trimethoxyphenyl)-1(2H)-isoquinolinone hydrochloride.

(2) To the compound thus obtained (1.10 g) are added 10% aqueous potassium carbonate solution and ethyl acetate. The ethyl acetate layer is separated, washed with water, dried, and concentrated under reduced pressure to give 3-methoxycarbonyl-2-(4-piperidyl)-4-(3,4,5-trimethoxyphenyl)-1(2H)-isoquinolinone as listed in Table 4.

EXAMPLE 34

The compound obtained in Reference Example 75 and the corresponding starting compounds are treated in the same manner as in Example 4 or 31 to give 2-[3-amino-5-(methoxycarbonyl)phenyl]-3-methoxycarbonyl-4-(3,4,5-trimethoxyphenyl)-1(2H)-isoquinolinone as listed in Table 4.

EXAMPLE 35

The compound obtained in Example 34 is treated in the same manner as in Example 21 to give 2-(3-amino-5-carboxyphenyl)-3-methoxycarbonyl-4-(3,4,5-trimethoxyphenyl)-1(2H)-isoquinolinone as listed in Table 4.

EXAMPLES 36–38

The compound obtained in Reference Example 51 and the corresponding starting compounds are treated in the same manner as in Example 1 to give the following compounds as listed in Table 4.

2-(2-indanyl)-3-methoxycarbonyl-4-(3,4,5-trimethoxyphenyl)-1(2H)-isoquinolinone (Example 36);

2-(5-indanyl)-3-methoxycarbonyl-4-(3,4,5-trimethoxyphenyl)-1(2H)-isoquinolinone (Example 37);

3-methoxycarbonyl-2-[N-methyl-4-piperidyl)methyl]-4-(3,4,5-trimethoxyphenyl)-1(2H)-isoquinolinone (Example 38);

EXAMPLE 39

(1) 4-(3,4,5-Trimethoxyphenyl)isocoumarin-3-carboxylic acid (the compound obtained in Reference Example 51) (1.42 g) and N-acetyl-p-phenylenediamine (1.80 g) are dissolved in 1,3-dimethyl-2-imidazolidinone (3 ml), and the mixture is heated with stirring at 130° C. for 4 hours. The pH value of the reaction mixture is adjusted to pH 2 with 0.1M hydrochloric acid under ice-cooling. The mixture is stirred under ice-cooling, and the precipitated crystals are collected by filtration. The crystals are washed successively with water and chloroform to give 2-(4-acetylaminophenyl)-3-carboxy-4-(3,4,5-trimethoxyphenyl)-1(2H)-isoquinolinone (1.02 g).

(2) The compound thus obtained (0.50 g) is dissolved in a mixture of methanol (10 ml) and chloroform (10 ml), and thereto is added a 2M solution of trimethylsilyldiazometae in hexane (2 ml). The mixture is stirred at room temperature for three hours, and concentrated under reduced pressure. To the residue are added water and chloroform. The chloroform layer is separated, washed with aqueous sodium hydrogen carbonate solution and a saturated aqueous sodium chloride solution, dried, and concentrated under reduced pressure. The residue is crystallized from diethyl ether to give 3-methoxycarbonyl-2-(4-acetylaminophenyl)-4-(3,4,5-trimethoxyphenyl)-1(2H)-isoquinolinone (440 mg) as listed in Table 4.

EXAMPLE 40

The compound obtained in Example 39-(1) (0.50 g) is added to 2M hydrochloric acid (10 ml), and the mixture is heated under reflux for 12 hours. To the reaction mixture are added 2M aqueous sodium hydroxide solution under ice-cooling and the pH value of the mixture is adjusted to pH 6–7. The precipitated crystals are collected by filtration, and washed with water to give 2(4-aminophenyl)-3-carboxy-4-(3,4,5-trimethoxyphenyl)-1(2H)-isoquinolinone (0.40 g), which is further treated in the same manner as in Example 39-(2) to give 2-(4-aminophenyl)-3-methoxycarbonyl-4-(3,4,5-trimethoxyphenyl)-1(2H)-isoquinolinone (0.30 g). The compound thus obtained is dissolved in chloroform, and thereto is added a 4M solution of hydrogen chloride in dioxane (0.16 ml). The mixture is concentrated, and the residue is crystallized from ethyl acetate to give 2-(4-amiophenyl)-3-methoxycarbonyl-4-(3,4,5-trimethoxyphenyl)-1(2H)-isoquinolinone hydrochloride (0.28 g) as listed in Table 4.

EXAMPLES 41–42

The compound obtained in Reference Example 51 and the corresponding starting compounds are treated in the same manner as in Example 1 or 39 to give the following compounds as listed in Table 4.

2-(3,4-dimethoxyphenyl)-3-methoxycarbonyl-4-(3,4,5-trimethoxyphenyl)-1(2H)-isoquinolinone (Example 41);

2-(3,5-dimethoxyphenyl)-3-methoxycarbonyl-4-(3,4,5-trimethoxyphenyl)-1(2H)-isoquinolinone (Example 42);

EXAMPLE 43

(1) The compound obtained in Reference Example 51 and the corresponding starting compounds are treated in the same manner as in Example 39 to give 2-(3-amino-4-methoxyphenyl)-3-methoxycarbonyl-4-(3,4,5-trimethoxyphenyl)-1(2H)-isoquinolinone.

(2) The compound thus obtained is dissolved in ethyl acetate, and thereto is added a 4M solution of hydrogen chloride in dioxane. The mixture is concentrated under reduced pressure, crystallized from ethyl acetate to give 2-(3-amino-4-methoxyphenyl)-3-methoxycarbonyl-4-(3,4,5-trimethoxyphenyl)-1(2H)-isoquinolinone hydrochloride as listed in Table 4.

EXAMPLES 44–45

The compound obtained in Reference Example 75 and the corresponding starting compounds are treated in the same manner as in Example 4 or 31 to give the following compounds as listed in Table 4.

3-methoxycarbonyl-2-[3-(2-oxotetrahydrofuryl)1-4-(3,4,5-trimethoxyphenyl)-1(2H)-isoquinolinone (Example 44);

3-methoxycarbonyl-2-[3-(2-oxopyrrolidinyl)-4-(3,4,5-trimethoxyphenyl)-1(2H)-isoquinolinone (Example 45);

EXAMPLE 46

(1) The compound obtained in Reference Example 75 and the corresponding starting compounds are treated in the same manner as in Example 4 or 31 to give 2-(6-indolinyl)-3-methoxycarbonyl-4-(3,4,5-trimethoxyphenyl)-1(2H)-isoquinolinone.

(2) The compound thus obtained is treated in the same manner as in Example 43-(2) to give 2-(6-indolinyl)-3-methoxycarbonyl-4-(3,4,5-trimethoxyphenyl)-1(2H)-isoquinolinone hydrochloride as listed in Table 4.

EXAMPLES 47–50

The compound obtained in Reference Example 75 and the corresponding starting compounds are treated in the same manner as in Example 4 or 31 to give the following compounds as listed in Table 4.

2-cyclopropyl-3-methoxycarbonyl-4-(3,4,5-trimethoxyphenyl)-1(2H)-isoquinolinone (Example 47);

2-(trans-4-hydroxycyclohexyl)-3-methoxycarbonyl-4-(3,4,5-trimethoxyphenyl)-1(2H)-isoquinolinone (Example 48);

2-ethyl-3-methoxycarbonyl-4-(3,4,5-trimethoxyphenyl)-1(2H)-isoquinolinone (Example 49);

2-[4-(1-benzyl)piperidyl]-3-methoxycarbonyl-4-(3,4,5-trimethoxyphenyl)-1(2H)-isoquinolinone (Example 50);

EXAMPLES 51–53

The compound obtained in Reference Example 51 and the corresponding starting compounds are treated in the same manner as in Example 1 or 39 to give the following compounds as listed in Table 4.

3-methoxycarbonyl-2-(3-trifluoromethylphenyl)-4-(3,4,5-trimethoxyphenyl)-1(2H)-isoquinolinone (Example 51);

2-(5(1H)-indazolyl)-3-methoxycarbonyl-4-(3,4,5-trimethoxyphenyl)-1(2H)-isoquinolinone (Example 52);

3-methoxycarbonyl-2-piperidino-4-(3,4,5-trimethoxyphenyl)-1(2H)-isoquinolinone (Example 53);

EXAMPLE 54

The compound obtained in Reference Example 75 and the corresponding starting compounds are treated in the same manner as in Example 4 or 31 to give 2-(3-hydroxy-n-propyl)-3-methoxycarbonyl-4-(3,4,5-trimethoxyphenyl)-1(2H)-isoquinolinone as listed in Table 4.

EXAMPLE 55

(1) The compound obtained in Reference Example 75 and the corresponding starting compounds are treated in the same manner as in Example 4 or 31 to give 2-[1-(4-benzyloxycarbonyl)piperazinyl]-3-methoxycarbonyl-4-(3,4,5-trimethoxyphenyl)-1(2H)-isoquinolinone, which is used in the subsequent reaction without further purification.

(2) The compound thus obtained (260 mg) is dissolved in a 25% solution of hydrogen bromide in acetic acid (3 ml), and the mixture is stirred at room temperature for 30 minutes. The reaction mixture is poured into a saturated aqueous sodium hydrogen carbonate solution, and the mixture is extracted with ethyl acetate. The extract is washed, dried, and concentrated under reduced pressure. To a solution of the residue in chloroform is added a 4M solution of hydrogen chloride in ethyl acetate (75 μl), and the precipitated crystals are collected by filtration to give 3-methoxycarbonyl-2-(1-piperazinyl)-4-(3,4,5-trimethoxyphenyl)-1(2H)-isoquinolinone hydrochloride (95 mg) as listed in Table 4.

EXAMPLES 56–58

The compound obtained in Reference Example 75 and the corresponding starting compounds are treated in the same manner as in Example 4 or 31 to give the following compounds as listed in Table 4.

3-methoxycarbonyl-2-morpholino-4-(3,4,5-trimethoxyphenyl)-1(2H)-isoquinolinone (Example 56);

3-methoxycarbonyl-2-(3-pyridyl)-4-(3,4,5-trimethoxyphenyl)-1(2H)-isoquinolinone (Example 57);

2-[4-(benzyloxycarbonylaminomethyl)phenyl]-3-methoxycarbonyl-4-(3,4,5-trimethoxyphenyl)-1(2H)-isoquinolinone (Example 58);

EXAMPLE 59

The compound obtained in Example 58 (300 mg) is dissolved in a 25% solution of hydrogen bromide in acetic acid (10 ml), and the mixture is stirred at room temperature overnight The precipitated crystals are collected by filtration, washed, and thereto are added chloroform and aqueous sodium hydrogen carbonate solution. The chloroform layer is washed, dried, and concentrated. The residue is dissolved in ethyl acetate (3 ml), and thereto is added a 4M solution of hydrogen chloride in ethyl acetate (150 μl). The precipitated crystals are collected by filtration to give 2-(4-aminomethylphenyl)-3-methoxycarbonyl-4-(3,4,5-trimethoxyphenyl)-1(2H)-isoquinolinone hydrochloride (215 mg) as listed in Table 4.

EXAMPLES 60–61

The compound obtained in Reference Example 75 and the corresponding starting compounds are treated in the same manner as in Example 4 or 31 to give the following compounds as listed in Table 4.

3-methoxycarbonyl-2-[(6-methyl-2-pyridinon-3-yl)methyl]-4-(3,4,5-trimethoxyphenyl)-1(2H)-isoquinolinone (Example 60);

3-methoxycarbonyl-2-(3,4-methylenedioxybenzyl)-4-(3,4,5-trimethoxyphenyl)-1(2H)-isoquinolinone (Example 61);

EXAMPLES 62–63

The compound obtained in Reference Example 75 and the corresponding starting compounds are treated in the same manner as in Example 46 to give the following compounds as listed in Table 4.

2-(3-dimethylaminophenyl)-3-methoxycarbonyl-4-(3,4,5-trimethoxyphenyl)-1(2H)-isoquinolinone hydrochloride (Example 62);

3-methoxycarbonyl-2-[3-(6-methoxy)pyridyl]-4-(3,4,5-trimethoxyphenyl)-1(2H)-isoquinolinone hydrochloride (Example 63);

EXAMPLE 64

The compound obtained in Reference Example 75 and the corresponding starting compounds are treated in the same manner as in Example 4 or 31 to give 3-methoxycarbonyl-2-(3-methoxycarbonylphenyl)-4-(3,4,5-trimethoxyphenyl)-1(2H)-isoquinolinone as listed in Table 4.

EXAMPLE 65

The compound obtained in Example 64 is treated in the same manner as in Example 21 to give 2-(3-carboxyphenyl)-3-methoxycarbonyl-4-(3,4,5-trimethoxyphenyl)-1(2H)-isoquinolinone as listed in Table 4.

EXAMPLE 66

The compound obtained in Reference Example 51 and the corresponding starting compounds are treated in the same manner as in Example 10-(1) to give 2-(tert-butoxycarbonylamino)-3-carboxy-4-(3,4,5-trimethoxyphenyl)-1(2H)-isoquinolinone as listed in Table 5.

EXAMPLE 67

The compound obtained in Example 66 (1.0 g), dimethylaminopyridine (26 mg) and 1-(3-dimethylaminopropyl)-3- ethylcarbodiimide hydrochloride (448 mg) are dissolved in a mixture of methylene chloride (20 ml) and methanol (340 ml). The mixture is stirred at room temperature for 10 minutes, and thereto are added 1-(3-dimethylaminopropyl)-3-ethylcarbodiimide hydrochloride (41 mg) and dimethylaminopyridine (26 mg), and the mixture is stirred at room temperature overnight. To the reaction mixture are added water and ethyl acetate, and the ethyl acetate layer is washed, dried, and concentrated under reduced pressure. The residue is purified by silica gel column chromatography (solvent; hexane:ethyl acetate=2:1) to give 2-(tert-butoxycarbonylamino)-3-methoxycarbonyl-4-(3,4,5-trimethoxyphenyl)-1(2H)-isoquinolinone (438 mg) as listed in Table 6.

EXAMPLE 68

To the compound obtained in Example 67 (200 mg) is added a 4M solution of hydrogen chloride in ethyl acetate (10 ml) and the mixture is allowed to stand at room temperature for one hour. The reaction mixture is concentrated under reduced pressure, and to the residue is added ethyl acetate. The mixture is washed with a saturated aqueous sodium hydrogen carbonate solution, dried, and concentrated under reduced pressure to give 2-amino-3-methoxycarbonyl-4-(3,4,5-trimethoxyphenyl)-1(2H)-isoquinolinone (146 mg) as listed in Table 6.

EXAMPLE 69

To a solution of the compound obtained in Example 68 (200 mg) and pyridine (120 mg) in tetrahydrofuran (15 ml) is added dropwise a solution of acetyl chloride (61.3 mg) in tetrahydrofuran (5 ml) under ice-cooling, and the mixture is stirred under ice-cooling for one hour, and further stirred at room temperature overnight. To the reaction mixture are added ethyl acetate and water, and the ethyl acetate layer is separated, washed, dried, and concentrated under reduced pressure. The residue is crystallized from a mixture of hexanediethyl ether to give 2-acetylamino-3-methoxycarbonyl-4-(3,4,5-trimethoxyphenyl)-1(2H)-isoquinolinone (116 mg) as listed in Table 6.

EXAMPLE 70

A solution of the compound obtained in Example 68 (200 mg) and triethylamine (145 μd) in tetrahydrofuran (15 ml) is cooled to −20° C., and thereto is added a solution of acetyl chloride (61 mg) in tetrahydrofuran (5 ml). The reaction mixture is stirred at the same temperature for one hour, and warmed to room temperature. To the reaction mixture are added acetyl chloride (122 mg) and triethylamine (290 μl), and the mixture is stirred at room temperature overnight. To the reaction mixture are added ethyl acetate and water, and the ethyl acetate layer is separated, washed, dried, and concentrated under reduced pressure. The residue is purified by silica gel column chromatography (solvent; hexane:ethyl acetate=2:1) to give 2-diacetylamino-3-methoxycarbonyl-4-(3,4,5-trimethoxyphenyl)-1(2H)-isoquinolinone (75 mg) as listed in Table 6.

EXAMPLE 71

The compound obtained in Example 67 (1.00 g) is dissolved in dimethylformamide (10 ml), and thereto are added potassium carbonate (382 mg) and methyl iodide (392 mg). The mixture is stirred at room temperature overnight, and thereto are added chloroform and water. The chloroform layer is separated, washed, dried, and concentrated under reduced pressure. The residue is crystallized from diethyl ether to give 3-methoxycarbonyl-2-(N-methyl-N-tert-butoxycarbonylamino)-4-(3,4,5-trimethoxyphenyl)-1(2H)-isoquinolinone as listed in Table 6, which is used as a starting compound in Example 72 without further purification.

EXAMPLE 72

The compound obtained in Example 71 is treated in the same manner as in Example 24 to give 3-methoxycarbonyl-2-(methylamino)-4-(3,4,5-trimethoxyphenyl)-1(2H)-isoquinolinone as listed in Table 6.

EXAMPLE 73

The compound obtained in Example 67 and the corresponding starting compounds are treated in the same manner as in Example 10-(2) to give 2-[N-tert-butoxycarbonyl-N-(2-hydroxyethyl)amino]-3-methoxycarbonyl-4-(3,4,5-trimethoxyphenyl)-1(2H)-isoquinolinone as listed in Table 6, which is used as a starting compound in Example 74 without further purification.

EXAMPLE 74

To a solution of the compound obtained in Example 73 (170 nig) in dioxane (1 ml) is added a 4M solution of hydrogen chloride in dioxane (10 ml), and the mixture is stirred at room temperature for three hours. The reaction mixture is concentrated under reduced pressure, and the residue is dissolved in ethyl acetate. The mixture is washed with water, dried, and concentrated under reduced pressure. The residue is purified by Chromatotron (solvent; chloroform:acetone=5:1), and crystallized from diethyl ether to give 2-[-(2-hydroxyethyl)amino]-3-methoxycarbonyl-4-(3,4,5-trimethoxyphenyl)-1(2H)-isoquinolinone as listed in Table 6.

EXAMPLE 75

To a solution of the compound obtained in Example 74 (210 mg) in ethyl acetate (10 ml) is added a 4M solution of hydrogen chloride in ethyl acetate (10 ml), and the mixture is stirred at room temperature for five hours. The reaction mixture is concentrated under reduced pressure, and the residue is dissolved in ethyl acetate. The solution is washed successively with a saturated aqueous sodium hydrogen carbonate solution and water, and dried. The solution is concentrated under reduced pressure, and the residue is purified by silica gel column chromatography (solvent; hexane:ethyl acetate=2:1), and crystallized from diethyl ether to give 2-(2-acetoxyethylamino)-3-methoxycarbonyl-4-(3,4,5-trimethoxyphenyl)-1(2H)-isoquinolinone as listed in Table 6.

EXAMPLE 76

(1) The compound obtained in Reference Example 51 and the corresponding starting compounds are treated in the same manner as in Example 10-(2) to give 2-(N-tert-butoxycarbonyl-N-n-propylamino)-3-methoxycarbonyl-4-(3,4,5-trimethoxyphenyl)-1(2H)-isoquinolinone, which is used in the subsequent reaction without further purification.
(2) The compound thus obtained is treated in the same manner as in Example 24 to give 3-methoxycarbonyl-2-n-propylamino-4-(3,4,5-trimethoxyphenyl)-1(2H)-isoquinolinone as listed in Table 6.

EXAMPLE 77

The compound obtained in Reference Example 51 and the corresponding starting compounds are treated in the same manner as in Example 76 to give 2-ethylamino-3-methoxycarbonyl-4-(3,4,5-trimethoxyphenyl)-1(2H)-isoquinolinone as listed in Table 6.

EXAMPLE 78

The compound obtained in Reference Example 75 and the corresponding starting compounds are treated in the same manner as in Example 4 or 31 to give 2-[(1S)-1-benzyloxycarbonyl-2-phenylethyl]-3-methoxy-carbonyl-4-(3,4,5-trimethoxyphenyl)-1(2H)-isoquinolinone as listed in Table 6, which is used as a starting compound in Example 79 without further purification.

EXAMPLE 79

The compound obtained in Example 78 is treated in the same manner as in Example 2 to give 2-[(1S)-1-carboxy-2-phenylethyl]-3-methoxycarbonyl-4-(3,4,5-trimethoxy-phenyl)-1(2H)-isoquinolinone as listed in Table 6.

EXAMPLE 80

The compound obtained in Reference Example 75 and the corresponding starting compounds are treated in the same manner as in Example 4 or 31 to give 2-(1H-1-methylbenztriazol-6-yl)-3-methoxycarbonyl-4-(3,4,5-trimethoxyphenyl)-1(2H)-isoquinolinone as listed in Table 6.

EXAMPLES 81–85

6,7-Dimethoxy-4-(3,4,5-trimethoxyphenyl)-3-carboxylic acid (the compound obtained in Reference Example 50) and the corresponding starting compounds are treated in the same manner as in Example 1 or 31 to give the following compounds as listed in Table 7.

6,7-dimethoxy-2-(4-fluorophenyl)-3-methoxycarbonyl-4-(3,4,5-trimethoxyphenyl)-1(2H)-isoquinolinone (Example 81);

6,7-dimethoxy-2-(3-methoxy-4-aminophenyl)-3-methoxycarbonyl-4-(3,4,5-trimethoxyphenyl)-1(2H)-isoquinolinone (Example 82);

6,7-dimethoxy-2-[4-(2-hydroxyethyl)phenyl]-3-methoxycarbonyl-4-(3,4,5-trimethoxyphenyl)-1(2H)-isoquinolinone (Example 83);

6,7-dimethoxy-2-(3-hydroxyphenyl)-3-methoxy-carbonyl-4-(3,4,5-trimethoxyphenyl)-1(2H)-isoquinolinone (Example 84);

2-(N-tert-butoxycarbonyl-N-methylamino)-6,7-dimethoxy-3-methoxy-carbonyl-4-(3,4,5-trimethoxyphenyl)-1(2H)-isoquinolinone (Example 85), which is used as a starting compound in Example 86 without further purification,

EXAMPLE 86

The compound obtained in Example 85 is treated in the same manner as in Example 24 to give 6,7-dimethoxy-3-methoxycarbonyl-2-methylamino-4-(3,4,5-trimethoxy-phenyl)-1(2H)-isoquinolinone as listed in Table 7.

EXAMPLE 87

The compound obtained in Reference Example 50 and the corresponding starting compounds are treated in the same manner as in Example 1 or 39 to give 6,7-dimethoxy-3-methoxycarbonyl-2-[cis-(4-methoxycarbonyl)cyclohexyl]-4-(3,4,5-trimethoxyphenyl)-1(2H)-isoquinolinone as listed in Table 7.

EXAMPLE 88

The compound obtained in Example 87 is treated in the same manner as in Example 21 to give 2-(4-carboxycyclohexyl)-6,7-dimethoxy-3-methoxycarbonyl-4-(3,4,5-trimethoxyphenyl)-1(2H)-isoquinolinone as listed in Table 7.

EXAMPLES 89–91

The compound obtained in Reference Example 50 and the corresponding starting compounds are treated in the same manner as in Example I or 39 to give the following compounds as listed in Table 7.

6,7-dimethoxy-2-(2-furylmethyl)-3-methoxycarbonyl-4-(3,4,5-trimethoxyphenyl)-1(2H)-isoquinolinone (Example 89);

6,7-dimethoxy-2-(2,3-dimethylphenyl)-3-methoxycarbonyl-4-(3,4,5-trimethoxyphenyl)-1(2H)-isoquinolinone (example 90);

6,7-dimethoxy-3-methoxycarbonyl-2-(3,4,5-trimethoxyphenyl)-4-(3,4,5-trimethoxyphenyl)-1(2H)-isoquinolinone (Example 91);

EXAMPLE 92

(1) The compound obtained in Reference Example 50 and the corresponding starting compounds are treated in the same manner as in Example 43 to give 2-(4-aminophenyl)-6,7-dimethoxy-3-methoxycarbonyl-4-(3,4,5-trimethoxyphenyl)-1(2H)-isoquinolinone as listed in Table 7.

(2) The compound thus obtained is treated in the same manner as in Example 9-(3) to give 2-(4-aminophenyl)-6,7-dimethoxy-3-methoxycarbonyl-4-(3,4,5-trimethoxy-phenyl)-1(2H)-isoquinolinone hydrochloride as listed in Table 7.

EXAMPLE 93

To a solution of the compound obtained in Example 92-(1) (156 mg) in methylene chloride (2 ml) are added dropwise triethylamine (0.138 ml) and methylsulfonyl chloride (78 $\mu$l), which are divided into three portions, under ice-cooling. The mixture is stirred for 15 minutes, and warmed to room temperature. To the mixture are added water and chloroform. The chloroform layer is washed, dried, and concentrated under reduced pressure. The residue is crystallized from ethyl acetate to give 6,7-dimethoxy-2-{4-[N,N-bis(methylsulfonyl)amino]phenyl}-3-methoxycarbonyl-4-(3,4,5-trimethoxyphenyl)-1(2H)-isoquinolinone as listed in Table 7.

EXAMPLE 94

To a solution of formic acid (34 $\mu$l) in methylene chloride (2 ml) is added acetic anhydride (85 gl) under ice-cooling, and the mixture is stirred for 30 minutes. To the reaction mixture is added dropwise a solution of the compound obtained in Example 92-(1) (312 mg) in methylene chloride (1 ml), and the mixture is stirred for two hours. The reaction is warmed to room temperature, and thereto are added water and methylene chloride. The methylene chloride layer is washed, dried, and concentrated under reduced pressure. The residue is crystallized from diethyl ether to give 2-(4-acetylaminophenyl)-6,7-dimethoxy-3-methoxycarbonyl-4-

(3,4,5-trimethoxyphenyl)-1(2H)-isoquinolinone (270 mg) as listed in Table 7.

EXAMPLE 95

To a solution of the compound obtained in Example 94 (260 mg) in tetrahydrofuran (3 ml) is added 60% sodium hydride (28 mg) under ice-cooling, and the mixture is stirred at room temperature for 30 minutes. To the reaction mixture is added dropwise methyl iodide (58 μl), and the mixture is stirred for five hours. To the reaction mixture are added dilute hydrochloric acid and chloroform. The chloroform layer is separated, washed, dried, and concentrated under reduced pressure. To the residue is added a mixture of methanol and 2M hydrochloric acid (1:1) (10 ml), and the mixture is heated under reflux for 16 hours. The reaction mixture is cooled to room temperature, and concentrated under reduced pressure to remove the methanol. To the resulting aqueous layer is added aqueous sodium hydrogen carbonate solution to adjust the pH value to pH 8. The mixture is extracted with chloroform. The extract is washed with water, dried, and concentrated under reduced pressure. The residue is crystallized from diethyl ether to give 6,7-dimethoxy-3-methoxycarbonyl-2-[4-(methylamino)phenyl]-4-(3,4,5-trimethoxyphenyl)-1(2H)-isoquinolinone (170 mg) as listed in Table 7.

EXAMPLES 96–98

The compound obtained in Reference Example 50 and the corresponding starting compounds are treated in the same manner as in Example 1 or 39 to give the following compounds as listed in Table 7.

6,7-dimethoxy-3-methoxycarbonyl-2-piperidino-4-(3,4,5-trimethoxyphenyl)-1(2H)-isoquinolinone (Example 96);

6,7-dimethoxy-3-methoxycarbonyl-2-(3,4-methylenedioxybenzyl)-4-(3,4,5-trimethoxyphenyl)-1(2H)-isoquinolinone (Example 97);

6,7-dimethoxy-3-methoxycarbonyl-2-(3,4-methylenedioxyphenyl)-4-(3,4,5-trimethoxyphenyl)-1(2H)-isoquinolinone (Example 98);

EXAMPLE 99

(1) A mixture of a solution of 6,7-dimethoxy-4-(3,4,5-trimethoxyphenyl)-isocoumarin-3-carboxylic acid (the compound obtained in Reference Example 50) (2.4 g) in methanol (50 ml) and a 5.5M solution of ammonia in methanol (50 ml) is stirred at room temperature overnight. The reaction solution is concentrated under reduced pressure to remove the ammonia, and further the solvent is distilled off. The residue thus obtained is extracted with chloroform, and the extract is washed with water, dried, and concentrated under reduced pressure. To the residue is added a 4M solution of hydrogen chloride in ethyl acetate (30 ml), and the mixture is stirred at room temperature overnight. The mixture is concentrated under reduced pressure, and the resulting residue is extracted with chloroform. The extract is washed with water, dried, and concentrated under reduced pressure to give 3-carboxy-6,7-dimethoxy-4-(3,4,5-trimethoxyphenyl)-1(2H)-isoquinolinone (1.89 g) as listed in Table 8.

(2) The compound thus obtained (1.50 g) is dissolved with heating in 2M aqueous sodium hydroxide solution (1.8 ml) and water (20 ml). The mixture is allowed to stand at room temperature, and the precipitated crystals are collected by filtration to give 3-carboxy-6,7-dimethoxy-4-(3,4,5-trimethoxyphenyl)-1(2H)-isoquinolinone sodium salt as listed in Table 8.

EXAMPLE 100

The compound obtained in Reference Example 50 and the corresponding starting compounds are treated in the same manner as in Example 99-(1) to give 3-carboxy-6,7-dimethoxy-2-(2-piperidinoethyl)-4-(3,4,5-trimethoxyphenyl)-1(2H)-isoquinolinone as listed in Table 8.

EXAMPLES 101–106

The compound obtained in Reference Example 50 and the corresponding starting compounds are treated in the same manner as in Example 1 or 39 to give the following compounds as listed in Table 9.

6,7-dimethoxy-3-methoxycarbonyl-2-(4-methyl-1-piperazinyl)-4-(3,4,5-trimethoxyphenyl)-1(2H)-isoquinolinone (Example 101);

6,7-dimethoxy-3-methoxycarbonyl-2-phenyl-4-(3,4,5-trimethoxyphenyl)-1(2H)-isoquinolinone (Example 102);

2-(4-chlorophenyl)-6,7-dimethoxy-3-methoxycarbonyl-4-(3,4,5-trimethoxyphenyl)-1(2H)-isoquinolinone (Example 103);

2-(3-chlorophenyl)-6,7-dimethoxy-3-methoxycarbonyl-4-(3,4,5-trimethoxyphenyl)-1(2H)-isoquinolinone (Example 104);

2-cyclopentyl-6,7-dimethoxy-3-methoxycarbonyl-4-(3,4,5-trimethoxyphenyl)-1(2H)-isoquinolinone (Example 105);

2-benzyl-6,7-dimethoxy-3-methoxycarbonyl-4-(3,4,5-trimethoxyphenyl)-1(2H)-isoquinolinone (Example 106);

EXAMPLES 107–108

The compound obtained in Reference Example 50 and the corresponding starting compounds are treated in the same manner as in Example 43 to give the following compounds as listed in Table 9.

6,7-dimethoxy-2-(4-dimethylaminophenyl)-3-methoxycarbonyl-4-(3,4,5-trimethoxyphenyl)-1(2H)-isoquinolinone hydrochloride (Example 107);

6,7-dimethoxy-3-methoxycarbonyl-2-(4-morpholinophenyl)-4-(3,4,5-trimethoxyphenyl)-1(2H)-isoquinolinone hydrochloride (Example 108);

EXAMPLES 109–111

The compound obtained in Reference Example 50 and the corresponding sing compounds are treated in the same manner as in Example 1 or 39 to give the following compounds as listed in Table 9.

6,7-dimethoxy-2-[3-(1-imidazolyl)propyl]-3-methoxycarbonyl-4-(3,4,5-trimethoxyphenyl)-1(2H)-isoquinolinone (Example 109);

6,7-dimethoxy-2-[3-(hydroxymethyl)phenyl]-3-methoxycarbonyl-4-(3,4,5-trimethoxyphenyl)-1(2H)-isoquinolinone (Example 110);

6,7-dimethoxy-3-methoxycarbonyl-2-[4-(methoxycarbonylmethyl)-phenyl]-4-(3,4,5-trimethoxyphenyl)-1(2H)-isoquinolinone (Example 111);

EXAMPLE 112

(1) The compound obtained in Example 111 is treated in the same manner as in Example 21 to give 2-[4-(carboxymethyl)

phenyl]-6,7-dimethoxy-3-methoxycarbonyl-4-(3,4,5-trimethoxyphenyl)-1(2H)-isoquinolinone.

(2) The compound thus obtained is treated in the same manner as in Example 99-(2) to give 2-[4-(carboxymethyl) phenyl]-6,7-dimethoxy-3-methoxycarbonyl-4-(3,4,5-trimethoxyphenyl)-1(2H)-isoquinolinone sodium salt as listed in Table 9.

EXAMPLE 113

The compound obtained in Example 99-(1) (2 g) is suspended in methanol (20 ml), and thereto is added conc. sulfuric acid (5 ml) at room temperature. The mixture is heated under reflux for 8 hours, and poured into an aqueous potassium carbonate solution under ice-cooling. The mixture is extracted with chloroform, and the extract is washed, dried, and concentrated under reduced pressure. The residue is purified by silica gel column chromatography (solvent; chloroform) to give 6,7-dimethoxy-3-methoxycarbonyl-4-10-(3,4,5-trimethoxyphenyl)-1(2H)-isoquinolinone (1.75 g) as listed in Table 9.

EXAMPLE 114

To a solution of the compound obtained in Example 113 (1.4 g) in dimethylformamide (15 ml) are added 4-picolyl chloride hydrochloride (588 mg) and potassium carbonate (1.13 g), and the mixture is stirred at 50° C. for two hours. After the reaction is complete, to the mixture are added ethyl acetate and water. The mixture is extracted with ethyl acetate, and the extract is washed, dried, and concentrated under reduced pressure. The residue is purified by silica gel column chromatography (solvent; chloroform:acetone=10:1). The residue is dissolved in ethyl acetate, and thereto is added a 4M solution of hydrogen chloride in ethyl acetate (1 ml). The precipitated crystals are collected by filtration, washed with ethyl acetate to give 6,7-dimethoxy-3-methoxycarbonyl-2-(4-pyridylmethyl)-4-(3,4,5-trimethoxyphenyl)-1(2H)-isoquinolinone hydrochloride (820 mg) as listed in Table 9.

EXAMPLE 115

To a solution of the compound obtained in Example 113 (1.4 g) in dimethylformamide (15 ml) are added cyclopropylmethyl bromide (484 mg) and potassium carbonate (1.13 g), and the mixture is stirred at 50° C. for one hour. To the mixture are added ethyl acetate and water, and the ethyl acetate layer is separated, washed, dried, and concentrated under reduced pressure. The residue is purified by silica gel column chromatography (solvent, chloroform:hexane:ethyl acetate=5:5:1) to give 2-cyclopropylmethyl-6,7-dimethoxy-3-methoxy-carbonyl-4-(3,4,5-trimethoxyphenyl)-1(2H)-isoquinolinone (840 mg) as listed in Table 9.

EXAMPLES 116–117

The compound obtained in Example 113 and the corresponding starting compounds are treated in the same manner as in Example 114 to give the following compounds as listed in Table 9.

6,7-dimethoxy-3-methoxycarbonyl-2-(3-pyridylmethyl)-4-(3,4,5-trimethoxyphenyl)-1(2H)-isoquinolinone hydrochloride (Example 116);

6,7-dimethoxy-3-methoxycarbonyl-2-(2-pyridylmethyl)-4-(3,4,5-trimethoxyphenyl)-1(2H)-isoquinolinone hydrochloride (Example 117);

EXAMPLE 118

The compound obtained in Reference Example 50 and the corresponding starting compounds are treated in the same manner as in Example 1 or 39 to give 6,7-dimethoxy-3-methoxycarbonyl-2-morpholino-4-(3,4,5-trimethoxyphenyl)-1(2H)-isoquinolinone as listed in Table 9.

EXAMPLE 119

A mixture of the compound obtained in Example 118 (1.3 g), conc.hydrochloric acid (15 ml) and dioxane (15 ml) is heated under reflux overnight. The reaction mixture is cooled to room temperature, and thereto are added water and chloroform. The extract is washed, dried, and concentrated under reduced pressure. The residue is purified by silica gel column chromatography (solvent; chloroform:acetone=50:1) to give 6,7-dimethoxy-4-(3,5-dimethoxy-4-hydroxyphenyl)-3-methoxycarbonyl-2-morpholino-1(2H)-isoquinolinone (530 mg) as listed in Table 10.

EXAMPLE 120

6,7-Dimethoxy-3-hydroxy-4-(3,4,5-trimethoxyphenyl)-3,4-dihydroisocoumarin-3-carboxylic acid (the compound obtained in Reference Example 74) and the corresponding starting compounds are treated in the same manner as in Example 46 to give 6,7-dimethoxy-3-methoxycarbonyl-2-[(2-pyridyl)amino]-4-(3,4,5-trimethoxyphenyl)-1(2H)-isoquinolinone hydrochloride as listed in Table 11.

EXAMPLE 121

The compound obtained in Reference Example 50 and the corresponding starting compounds are treated in the same manner as in Example 1 or 39 to give 6,7-dimethoxy-3-methoxycarbonyl-2-(3-methylthiophenyl)-4-(3,4,5-trimethoxyphenyl)-1(2H)-isoquinolinone as listed in Table 11.

EXAMPLE 122

To a solution of the compound obtained in Example 121 (200 mg) in chloroform (15 ml) is added dropwise a solution of m-chloroperbenzoic acid (164 mg) in chloroform (10 ml) at room temperature, and the mixture is stirred overnight. The reaction mixture is washed with a 5% aqueous sodium hydroxide solution, and concentrated under reduced pressure to give 6,7-dimethoxy-3-methoxycarbonyl-2-(3-methylsulfonylphenyl)-4-(3,4,5-trimethoxyphenyl)-1(2H)-isoquinolinone (150 mg) as listed in Table 11.

EXAMPLE 123

To a solution of the compound obtained in Example 121 (200 mg) in chloroform (15 ml) is added a solution of m-chloroperbenzoic acid (78 mg) in chloroform (10 ml) at room temperature, and the mixture is stirred for one hour. The reaction mixture is washed with a 5% aqueous sodium hydroxide solution, dried, and concentrated under reduced pressure to give 6,7-dimethoxy-3-methoxycarbonyl-2-(3-methylsulfinylphenyl)-4-(3,4,5-trimethoxyphenyl)-1(2H)-isoquinolinone (1750 mg) as listed in Table 11.

EXAMPLE 124

The compound obtained in Reference Example 50 and the corresponding starting compounds are treated in the same manner as in Example 1 or 39 to give 6,7-dimethoxy-2-(tetrahydro-4H-1,4-thiazin-4-yl)-3-methoxy carbonyl-4-(3,4,5-trimethoxyphenyl)-1(2H)-isoquinolinone as listed in Table 11.

EXAMPLE 125

The compound obtained in Example 124 is treated in the same manner as in Example 122 to give 6,7-dimethoxy-2-

(1,1-dioxo-tetrahydro-4H-1,4-thiazin-4-yl)-3-methoxycarbonyl]-4-(3,4,5-trimethoxyphenyl)-1(2H)-isoquinolinone as listed in Table 11.

EXAMPLE 126

The compound obtained in Example 124 is treated in the same manner as in Example 123 to give 6,7-dimethoxy-2-(1-oxo-tetrahydro-4H-1,4-thiazinyl)-3-methoxycarbonyl-4-(3,4,5-trimethoxyphenyl)-1(2H)-isoquinolinone as listed in Table 11.

EXAMPLE 127

(1) To a solution of 2-(3,4,5-trimethoxybenzoyl)-4,5-dimethoxybenzoic acid (the compound obtained in Reference Example 14) (10.0 g), sarcosine methyl ester (5.38 g) and 1-hydroxybenzotriazole (4.48 g) in dimethylformamide (100 ml) are added 1-(3-dimethylaminopropyl)-3-ethylcarbodiimide hydrochloride (5.60 g) and triethylamine (4.89 ml) under ice-cooling, and the mixture is stirred at room temperature overnight. To the reaction mixture are added water and ethyl acetate. The ethyl acetate layer is separated, washed, dried, and concentrated under reduced pressure. The resulting residue is crystallized from diethyl ether to give N-methoxycarbonylmethyl-N-methyl-2-(3,4,5-trimethoxybenzoyl)-4,5-dimethoxybenzene carboxamide (10.1 g).

(2) To a solution of the compound (5.70 g) in tetrahydrofuran (1.30 ml) is added potassium tert-butoxide (2.08 g) under ice-cooling, and the mixture is stirred at room temperature for 30 minutes. To the reaction mixture are added water and ethyl acetate, and the ethyl acetate layer is separated, washed, dried, and concentrated under reduced pressure. The precipitated crystals are dissolved in chloroform (100 ml), and thereto is added p-toluenesulfonic acid (4.70 g). The mixture is refluxed for two hours, and the reaction mixture is washed, dried, and concentrated under reduced pressure. The residue is purified by silica gel column chromatography (solvent; hexane:ethyl acetate 1:2) to give 6,7-dimethoxy-3-methoxycarbonyl-2-methyl-4-(3,4,5-trimethoxyphenyl)-1(2H)-isoquinolinone (2.46 g) as listed in Table 12.

EXAMPLE 128

The compound obtained in Example 127 is treated in the same manner as in Example 21 to give 3-carboxy-6,7-dimethoxy-2-methyl-4-(3,4,5-trimethoxyphenyl)-1(2H)-isoquinolinone as listed in Table 12.

EXAMPLE 129

A solution of the compound obtained in Example 128 (1.50 g), 1,3-dicyclohexylcarbodiimide (793 mg) and 1-hydroxybenzotriazole (588 mg) in dimethylformamide (30 ml) is stirred at room temperature for one hour, and thereto is added morpholine (335 mg), and the mixture is stirred for two hours. The mixture is further stirred at 50° C. for four hours. To the reaction mixture are added water and ethyl acetate. The ethyl acetate layer is separated, washed, dried, and concentrated under reduced pressure. The residue is crystallized from diethyl ether-ethyl acetate to give 6,7-dimethoxy-2-methyl-3-morphlino-carbonyl-4-(3,4,5-trimethoxyphenyl)-1(2H)-isoquinolinone (893 mg) as listed in Table 12.

EXAMPLE 130

To a mixture of methylene chloride (10 ml) and dimethylformamide (5 ml) are added the compound obtained in Example 128 (1.66 g), 1,3-dicyclohexyl carbodiimide (960 mg) and 1-hydroxybenzotriazole (710 mg), and the mixture is stirred at room temperature for 30 minutes. To the reaction mixture is added a solution of 4-(2-aminoethyl)imidazole (850 mg) and triethylamine (1.28 ml) in dimethylfomamide (5 ml), and the mixture is stirred for three hours, and then further stirred at 50° C. for 7 hours. To the reaction mixture are added water and ethyl acetate. The ethyl acetate layer is separated, washed, dried, and concentrated under reduced pressure. The residue is purified by silica gel column chromatography (solvent; chloroform:hexane=30:1) to give 6,7-dimethoxy-3-[2-(4-imidazolyl)ethylaminocarbonyl]-2-methyl-4-(3,4,5-trimethoxyphenyl)-1(2H)-isoquinolinone (1.0 g) as listed in Table 12.

EXAMPLE 131

The compound obtained in Example 128 and the corresponding starting compounds are treated in the same manner as in Example 130 to give 6,7-dimethoxy-3-[4-(2-hydroxyethyl)piperazinocarbonyl]-2-methyl-4-(3,4,5-trimethoxyphenyl)-1(2H)-isoquinolinone as listed in Table 12.

EXAMPLE 132

The compound obtained in Reference Example 50 and the corresponding starting compounds are treated in the same manner as in Example 39 to give 6,7-dimethoxy-2-(3-methoxy-4-aminophenyl)-4-(3,4,5-trimethoxyphenyl)-3-trimethylsilylmethyloxycarbonyl-1(2H)-isoquinolinone as listed in Table 12.

EXAMPLE 133

6,7-Diethoxy-4-(3,4,5-trimethoxyphenyl)isocoumarin-3-carboxylic acid (the compound obtained in Reference Example 54) and the corresponding starting compounds are treated in the same manner as in Example 1 or 39 to give 6,7-diethoxy-3-methoxycarbonyl-2-morpholino-4-(3,4,5-trimethoxyphenyl)-1(2H)-isoquinolinone as listed in Table 13.

EXAMPLES 134–135

6,7-Diethoxy-3-hydroxy-4-(3,4,5-trimethoxyphenyl)-3,4-dihydroisocoumarin-3-carboxylic acid (the compound obtained in Reference Example 76) and the corresponding starting compounds are treated in the same manner as in Example 4 or 31 to give the following compounds as listed in Table 13.

6,7-diethoxy-3-methoxycabonyl-2-(4-tetrahydropyranyl)-4-(3,4,5-trimethoxyphenyl)-1(2H)-isoquinolinone (Example 134);

2-[4-(tert-butoxycarbonylamino)phenyl]-6,7-diethoxy-3-methoxycarbonyl-4-(3,4,5-trimethoxyphenyl)-1(2H)-isoquinolinone (Example 135);

EXAMPLE 136

(1) The compound obtained in Example 135 is treated in the same manner as in Example 24 to give 2-(4-aminophenyl)-6,7-diethoxy-3-methoxycarbonyl-4-(3,4,5-trimethoxyphenyl)-1(2H)-isoquinolinone hydrochloride as listed in Table 13.

(2) The compound thus obtained is treated in the same manner as in Example 33-(2) to give 2-(4-aminophenyl)-6,7-diethoxy-3-methoxycarbonyl-4-(3,4,5-trimethoxyphenyl)-1(2H)-isoquinolinone as listed in Table 13.

EXAMPLE 137

The compound obtained in Example 135 is treated in the same manner as in Example 71 to give 6,7-diethoxy-3-methoxycarbonyl-2-[4-(N-methyl-N-tert-butoxycarbonyl-amino)phenyl]-4-(3,4,5-trimethoxyphenyl)-1(2H)-isoquinolinone as listed in Table 13.

EXAMPLE 138

The compound obtained in Example 137 is treated in the same manner as in Example 24 to give 6,7-diethoxy-3-methoxycarbonyl-2-[4-(methylamino)phenyl]-4-(3,4,5-trimethoxyphenyl)-1(2H)-isoquinolinone hydrochloride as listed in Table 13.

EXAMPLE 139

The compound obtained in Reference Example 76 and the corresponding starting compounds are treated in the same manner as in Example 4 or 31 to give 2-(4-benyloxyphenyl)-6,7-diethoxy-3-methoxycarbonyl-4-(3,4,5-trimethoxy-phenyl)-1(2H)-isoquinolinone as listed in Table 13.

EXAMPLE 140

The compound obtained in Example 139 is treated in the same manner as in Example 2 to give 6,7-diethoxy-2-(4-hydroxyphenyl)-3-methoxycarbonyl-4-(3,4,5-trimethoxyphenyl)-1(2H)-isoquinolinone as listed in Table 13.

EXAMPLES 141–147

5-Substituted, 6-substituted, 7-substituted or 6,7-disubstituted-4-(3,4,5 trimethoxyphenyl)isocoumarin-3-carboxylic acid compounds (the compounds obtained in Reference Example 58, 57, 53, 52, 56, 59 or 55) and the corresponding starting compounds are treated in the same manner as in Example 1 or 39 to give the following compounds as listed in Table 14.

3-methoxycarbonyl-6-methyl-2-phenyl-4-(3,4,5-trimethoxyphenyl)-1(2H)-isoquinolinone (Example 141);

6-chloro-3-methoxycarbonyl-2-phenyl-4-(3,4,5-trimethoxyphenyl)-1(2H)-isoquinolinone (Example 142);

3-methoxycarbonyl-6,7-methylenedioxy-2-phenyl-4-(3,4,5-trimethoxyphenyl)-1(2H)-isoquinolinone (Example 143);

7-methoxy-3-methoxycarbonyl-2-phenyl-4-(3,4,5-trimethoxyphenyl)-1(2H)-isoquinolinone (Example 144);

8-chloro-3-methoxycarbonyl-2-phenyl-4-(3,4,5-trimethoxyphenyl)-1(2H)-isoquinolinone (Example 145);

8-methoxy-3-methoxycarbonyl-2-phenyl-4-(3,4,5-trimethoxyphenyl)-1(2H)-isoquinolinone (Example 146);

6-methoxy-3-methoxycarbonyl-2-phenyl-4-(3,4,5-trimethoxyphenyl)-1(2H)-isoquinolinone (Example 147);

EXAMPLE 148

8-Chloro-3-hydroxy-4-(3,4,5-trimethoxyphenyl)-3,4-dihydroisocoumarin-3-carboxylic acid (the compound obtained in Reference Example 78) and the corresponding sting compounds are treated in the same manner as in Example 4 or 31 to give 2-[4-(tert-butoxycarbonylamino)phenyl]-8-chloro-3-methoxycarbonyl-4-(3,4,5-trimethoxyphenyl)-1(2H)-isoquinolinone as listed in Table 14.

EXAMPLE 149

The compound obtained in Example 148 is treated in the same manner as in Example 24 to give 2-(4-aminophenyl)-8-chloro-3-methoxycarbonyl-4-(3,4,5-trimethoxyphenyl)-1(2H)-isoquinolinone hydrochloride as listed in Table 14.

EXAMPLE 150

3-Hydroxy-4-(3,4,5-trimethoxyphenyl)-6-methoxy-3,4-dihydroisocoumarin-3-carboxylic acid (the compound obtained in Reference Example 77) and the corresponding starting compounds are treated in the same manner as in Example 4 or 31 to give 2-[4-tert-butoxycarbonylamino)phenyl]-6-methoxy-3-methoxycarbonyl-4-(3,4,5-trimethoxyphenyl)-1(2H)-isoquinolinone as listed in Table 14.

EXAMPLE 151

The compound obtained in Example 150 is treated in the same manner as in Example 8-(1) to give 2-(4-aminophenyl)-6-methoxy-3-methoxycarbonyl-4-(3,4,5-trimethoxyphenyl)-1(2H)-isoquinolinone as listed in Table 14.

EXAMPLE 152

4-(3-Bromo-4,5-dimethoxyphenyl)-6,7-dimethoxyisocoumarin-3-carboxylic acid (the compound obtained in Reference Example 60) and the corresponding starting compounds are treated in the same manner as in Example 10-(1) to give 4-(3-bromo-4,5-dimethoxyphenyl)-3-carboxy-6,7-dimethoxy-2-phenyl-1(2H)-isoquinolinone as listed in Table 15.

EXAMPLE 153

The corresponding starting compounds are treated in the same manner as in Example 10-(2) to give 4-(3-bromo-4,5-dimethoxyphenyl)-6,7-dimethoxy-3-methoxycarbonyl-2-phenyl-1(2H)-isoquinolinone as listed in Table 15.

EXAMPLES 154–155

The compound obtained in Example 152 and the corresponding starting compounds are treated in the same manner as in Example 129 to give the following compounds as listed in Table 15.

4-(3-bromo-4,5-dimethoxyphenyl)-3-carbamoyl-6,7-dimethoxy-2-phenyl-1(2H)-isoquinolinone (Example 154);

4-(3-bromo-4,5-dimethoxyphenyl)-6,7-dimethoxy-3-(N-methylcarbamoyl)-2-phenyl-1(2H)-isoquinolinone (Example 155);

EXAMPLE 156–160

4-(3-Bromo-4,5-dimethoxyphenyl)-3-hydroxy-6,7-dimethoxyisocoumarin-3-carboxylic acid (the compound obtained in Reference Example 80) and the corresponding starting compounds are treated in the same manner as in Example 4 or 31 to give the following compounds as listed in Table 16.

4-(3-bromo-4,5-dimethoxyphenyl)-2-(4-bromo-3-methylphenyl)-6,7-dimethoxy-3-methoxycarbonyl-1(2H)-isoquinolinone (Example 156);

4-(3-bromo-4,5-dimethoxyphenyl)-2-(4-carbamoylphenyl)-6,7-dimethoxy-3-methoxycarbonyl-1(2H)-isoquinolinone (Example 157);

4-(3-bromo-4,5-dimethoxyphenyl)-2-(3-carbamoylphenyl)-6,7-dimethoxy-3-methoxycarbonyl-1(2H)-isoquinolinone (Example 158);

4-(3-bromo-4,5-dimethoxyphenyl)-6,7-dimethoxy-3-methoxycarbonyl-2-methoxycarbonylmethyl-1(2H)-isoquinolinone (Example 159);

4-(3-bromo-4,5-dimethoxyphenyl)-6,7-dimethoxy-2-ethoxycarbonyl-methyl-3-methoxycarbonyl-1(2H)-isoquinolinone (Example 160);

EXAMPLE-161

The compound obtained in Example 159 is treated in the same manner as in Example 21 to give 4-(3-bromo-4,5-dimethoxyphenyl)-2-carboxymethyl-6,7-dimethoxy-3-methoxycarbonyl-1(2H)-isoquinolinone as listed in Table 16.

EXAMPLES 162–164

The compound obtained in Reference Example 80 and the corresponding starting compounds are treated in the same manner as in Example 4 or 31 to give the following compounds as listed in Table 16.

4-(3-bromo-4,5-dimethoxyphenyl)-6,7-dimethoxy-2-[2-(2-hydroxyethyloxy)ethyl]-3-methoxycarbonyl-1(2H)-isoquinolinone (Example 162);

4-(3-bromo-4,5-dimethoxyphenyl)-6,7-dimethoxy-3-methoxycarbonyl-2-(1-pyrrolyl)-1(2H)-isoquinolinone (Example 163);

4-(3-bromo-4,5-dimethoxyphenyl)-2-[2-(tert-butoxycarbonylamino)ethyl]-6,7-dimethoxy-3-methoxycarbonyl-1(2H)-isoquinolinone (Example 164);

EXAMPLE 165

The compound obtained in Example 164 is treated in the same manner as in Example 24 to give 2-(2-aminoethyl)-4-(3-bromo-4,5-dimethoxyphenyl)-6,7-dimethoxy-3-methoxycarbonyl-1(2H)-isoquinolinone hydrochloride as listed in Table 16.

EXAMPLE 166

The compound obtained in Reference Example 80 and the corresponding starting compounds are treated in the same manner as in Example 4 or 31 to give 4-(3-bromo-4,5-dimethoxyphenyl)-6,7-dimethoxy-3-methoxycarbonyl-2-(5-methylisoxazol-3-yl)-1(2H)-isoquinolinone as listed in Table 16.

EXAMPLE 167

4-(3-Bromo-4,5-dimethoxyphenyl)-6,7-dimethoxyisocoumarin-3-carboxylic acid (the compound obtained in Reference Example 60) and the corresponding starting compounds are treated in the same manner as in Example 1 or 39 to give 4-(3-bromo-4,5-dimethoxyphenyl)-6,7-dimethoxy-3-methoxy-carbonyl-2N-phenylamino)-1(2H)-isoquinolinone as listed in Table 16.

EXAMPLES 168–169

The compound obtained in Reference Example 80 and the corresponding starting compounds are treated in the same manner as in Example 4 or 31 to give the following compounds as listed in Table 16.

4-(3-bromo-4,5-dimethoxyphenyl)-6,7-dimethoxy-3-methoxycarbonyl-2-(3-nitrophenyl)-1(2H)-isoquinolinone Example 168);

4-(3-bromo-4,5-dimethoxyphenyl)-4,7-dimethoxy-3-methoxycarbonyl-2-(2-methoxyethyl)-1(2H)-isoquinolinone (Example 169);

EXAMPLE 170

(1) The compound obtained in Reference Example 80 and the corresponding starting compounds are treated in the same manner as in Example 4 or 31 to give 4-(3-bromo-4,5-dimethoxyphenyl)-6,7-dimethoxy-3-methoxy-carbonyl-2-(3-methoxycarbonylphenyl)-1(2H)-isoquinolinone.

(2) The compound thus obtained is treated in the same manner as in Example 21 to give 4-(3-bromo-4,5-dimethoxyphenyl)-2-(3-carboxyphenyl)-6,7-dimethoxy-3-methoxycarbonyl-1(2H)-isoquinolinone as listed in Table 16.

EXAMPLE 171

The compound obtained in Example 170 is treated in the same manner as in Example 129 to give 4-(3-bromo-4,5-dimethoxyphenyl)-2-{3-[2-(tert-butoxycarbonyl)hydrazinocarbonyl]phenyl}-6,7-dimethoxy-3-methoxycarbonyl-1(2H)-isoquinolinone as listed in Table 16.

EXAMPLE 172

The compound obtained in Example 171 is treated in the same manner as in Example 68 to give 4-(3-bromo-4,5-dimethoxyphenyl)-6,7-dimethoxy-2-[3-(hydrazinocarbonyl)phenyl]-3-methoxycarbonyl-1(2H)-isoquinolinone as listed in Table 16.

EXAMPLE 173

The compound obtained in Reference Example 80 and the corresponding starting compounds are treated in the same manner as in Example 4 or 31 to give 4-(3-bromo-4,5-dimethoxyphenyl)-6,7-dimethoxy-3-methoxycarbonyl-2-[3-(methoxycarbonylmethoxy)phenyl]-1(2H)-isoquinolinone as listed in Table 16.

EXAMPLE 174

The compound obtained in Example 173 is treated in the same manner as in Example 21 to give 4-(3-bromo-4,5-dimethoxyphenyl)-2-[3-(carboxymethoxy)phenyl]-6,7-dimethoxy-3-methoxycarbonyl-1(2H)-isoquinolinone as listed in Table 16.

EXAMPLE 175

The compound obtained in Example 174 is treated in the same manner as in Example 129 to give 4-(3-bromo-4,5-dimethoxyphenyl)-6,7-dimethoxy-3-methoxycarbonyl-2-{3-[N-(3-morpholinopropyl)carbamoylmethyloxy]phenyl}-1(2H)-isoquinolinone as listed in Table 16.

EXAMPLE 176

The compound obtained in Reference Example 80 and the corresponding starting compounds are treated in the same manner as in Example 4 or 31 to give 2-(3-aminophenyl)-4-(3-bromo-4,5-dimethoxyphenyl)-6,7-dimethoxy-3-methoxycarbonyl-1(2H)-isoquinolinone as listed in Table 16.

EXAMPLE 177

To formic acid (3 ml) is added acetic anhydride (3 ml), and the mixture is stirred at room temperature for four hours. To the reaction mixture is added the compound obtained in Example 176 (500 mg), and the mixture is stirred at room temperature overnight. The mixture is further stirred at 60° C. overnight. After the reaction is complete, to the reaction mixture are added water and ethyl acetate. The ethyl acetate layer is separated, washed with water, dried, and concentrated under reduced pressure. The residue is purified by silica gel column chromatography (solvent; chloroform:acetone=10:1) to give 6,7-dimethoxy-2-[3-(formylamino)phenyl]-4-(3-bromo-4,5-dimethoxyphenyl)-3-methoxycarbonyl-1(2H)-isoquinolinone as listed in Table 16.

EXAMPLES 178–180

The compound obtained in Reference Example 80 and the corresponding starting compounds are treated in the same manner as in Example 4 or 31 to give the following compounds as listed in Table 16.

- 4-(3-bromo-4,5-dimethoxyphenyl)-6,7-dimethoxy-3-methoxycarbonyl-2-[3-(2-methylpyrimidin-4-yl)phenyl]-1(2H)-isoquinolinone (Example 178);
- 4-(3-bromo-4,5-dimethoxyphenyl)-6,7-dimethoxy-3-methoxycarbonyl-2-[3-(1-methylpyrazol-3-yl)phenyl]-1(2H)-isoquinolinone (Example 179);
- 4-(3-bromo-4,5-dimethoxyphenyl)-2-{2-[4-(tert-butoxycarbonyl)piperazin-1-yl]-ethyl}-6,7-dimethoxy-3-methoxycarbonyl-1(2H)-isoquinolinone (Example 180);

EXAMPLE 181

The compound obtained in Example 180 is treated in the same manner as in Example 24 to give 4-(3-bromo-4,5-dimethoxyphenyl)-6,7-dimethoxy-2-(2-piperazinoethyl)-3-methoxycarbonyl-1(2H)-isoquinolinone dihydrochloride as listed in Table 16.

EXAMPLE 182

The compound obtained in Reference Example 60 and the corresponding starting compounds are treated in the same manner as in Example 39, and further treated in the same manner as in Example 43-(2) to give 4-(3-bromo-4,5-dimethoxyphenyl)-6,7-dimethoxy-3-methoxycarbonyl-2-(2-morpholinoethyl)-1(2H)-isoquinolinone hydrochloride as listed in Table 16.

EXAMPLE 183

The compound obtained in Reference Example 60 and the corresponding starting compounds are treated in the same manner as in Example 1 or 39 to give 2-amino-4-(3-bromo-4,5-dimethoxyphenyl)-6,7-dimethoxy-3-methoxycarbonyl-1(2H)-isoquinolinone as listed in Table 16.

EXAMPLE 184

The compound obtained in Reference Example 80 and the corresponding starting compounds are treated in the same manner as in Example 4 or 31 to give 4-(3-bromo-4,5-dimethoxyphenyl)-6,7-dimethoxy-2-(3-hydroxypropyl)-3-methoxycarbonyl-1(2H)-isoquinolinone as listed in Table 16.

EXAMPLE 185

To a solution of the compound obtained in Example 184 (190 mg) in dimethylformamide (3 ml) are added nicotinoyl chloride (69 mg) and triethylamine (0.11 ml), and the mixture is stirred at room temperature overnight To the reaction mixture are added nicotinoyl chloride (69 mg) and triethylamine (0.11 ml), and the mixture is stirred overnight. After the reaction is complete, to the mixture are added ethyl acetate and water. The ethyl acetate layer is separated, washed, dried, and concentrated under reduced pressure to give 4-(3-bromo-4,5-dimethoxyphenyl)-6,7-dimethoxy-3-methoxycarbonyl-2-[3-(nicotinoyloxy)propyl]-1(2H)-isoquinolinone (170 mg) as listed in Table 16.

EXAMPLES 186–198

The compound obtained in Reference Example 80 and the corresponding starting compounds are treated in the same manner as in Example 4 or 31 to give the following compounds as listed in Table 16.

- 2-n-butyl-4-(3-bromo-4,5-dimethoxyphenyl)-6,7-dimethoxy-3-methoxycarbonyl-1(2H)-isoquinolinone (Example 186);
- 4-(3-bromo-4,5-dimethoxyphenyl)-2-carbamoylmethyl-6,7-dimethoxy-3-methoxycarbonyl-1(2H)-isoquinolinone (Example 187);
- 4-(3-bromo-4,5-dimethoxyphenyl)-6,7-dimethoxy-3-methoxycarbonyl-2-(6-quinolyl)-1(2H)-isoquinolinone (Example 188);
- 4-(3-bromo-4,5-dimethoxyphenyl)-6,7-dimethoxy-3-methoxycarbonyl-2-(2-tetraydrofurylmethyl)-1(2H)-isoquinolinone (Example 189);
- 4-(3-bromo-4,5-dimethoxyphenyl)-6,7-dimethoxy-3-methoxycarbonyl-2-(3-quinolyl)-1(2H)-isoquinolinone (Example 190);
- 4-(3-bromo-4,5-dimethoxyphenyl)-6,7-dimethoxy-2-[(1-hydroxymethyl-2-hydroxy)ethyl]-3-methoxycarbonyl-1(2H)-isoquinolinone (Example 191);
- 4-(3-bromo-4,5-dimethoxyphenyl)-6,7-dimethoxy-2-(3-dimethylaminopropyl)-3-methoxycarbonyl-1(2H)-isoquinolinone (Example 192);
- 4-(3-bromo-4,5-dimethoxyphenyl)-2-[3-(tert butoxycarbonylamino)propyl]-6,7-dimethoxy-3-methoxycarbonyl-1(2H)-isoquinolinone (Example 193);
- 4-(3-bromo-4,5-dimethoxyphenyl)-6,7-dimethoxy-3-methoxycarbonyl-2-(3-methoxypropyl)-1(2H)-isoquinolinone (Example 194);
- 2-(N-benzylpiperidin-4-yl)-4-(3-bromo-4,5-dimethoxyphenyl)-6,7-dimethoxy-3-methoxycarbonyl-1(2H)-isoquinolinone (Example 195);
- 2-benzyl-4-(3-bromo-4,5-dimethoxyphenyl)-6,7-dimethoxy-3-methoxycarbonyl-1(2H)-isoquinolinone (Example 196);
- 4-(3-bromo-4,5-dimethoxyphenyl)-6,7-dimethoxy-3-methoxycarbonyl-2-propyl-1(2H)-isoquinolinone (Example 197);
- 2-[3-(6-amino)pyridyl]-4-(3-bromo-4,5-dimethoxyphenyl)-6,7-dimethoxy-3-methoxycarbonyl-1(2H)-isoquinolinone (Example 198);

EXAMPLES 199–201

The compound obtained in Reference Example 80 and the corresponding starting compounds are treated in the same manner as in Example 46 to give the following compounds as listed in Table 16.

2-(4-aminopropyl)-4-(3-bromo-4,5-dimethoxyphenyl)-6,7-dimethoxy-3-methoxycarbonyl-1(2H)-isoquinolinone hydrochloride (Example 199);

2-(cis-2-amino-1-hexyl)-4-(3-bromo-4,5-dimethoxyphenyl)-6,7-dimethoxy-3-methoxycarbonyl-1(2H)-isoquinolinone (Example 200);

2-(4-aminocyclohexyl)-4-(3-bromo-4,5-dimethoxyphenyl)-6,7-dimethoxy-3-methoxycarbonyl-1(2H)-isoquinolinone hydrochloride (Example 201);

EXAMPLE 202

The compound obtained in Reference Example 60 and the corresponding starting compounds are treated in the same manner as in Example 1 or 39 to give 2-(4-acetylaminophenyl)-4-(3-bromo-4,5-dimethoxyphenyl)-6,7-dimethoxy-3-methoxycarbonyl-1(2H)-isoquinolinone as listed in Table 16.

EXAMPLES 203–204

The compound obtained in Reference Example 60 and the corresponding starting compounds are treated in the same manner as in Example 1 or 39 to give the following compounds as listed in Table 16.

4-(3-bromo-4,5-dimethoxyphenyl)-6,7-dimethoxy-3-methoxycarbonyl-2-morpholino-1(2H)-isoquinolinone (Example 203);

2-[(4-benzyloxycarbonyl)piperazin-1-yl]-4-(3-bromo-4,5-dimethoxyphenyl)-6,7-dimethoxy-3-methoxycarbonyl-1(2H)-isoquinolinone (Example 204);

EXAMPLES 205–206

The compound obtained in Example 204 (550 mg) is dissolved in a 25% solution of hydrogen bromide in acetic acid (2.5 ml), and the mixture is stirred at room temperature for 15 minutes. To the reaction mixture are added ethyl acetate and a saturated aqueous sodium hydrogen carbonate solution. The ethyl acetate layer is separated, washed, dried, and concentrated under reduced pressure. The resulting residue is dissolved in acetonitrile (3 ml), and thereto are added 2-bromoethanol (99 mg) and potassium carbonate (65 mg). The reaction mixture is heated under reflux for three hours. The reaction solution is warmed to room temperature, and thereto are added ethyl acetate and a saturated aqueous sodium hydrogen carbonate solution. The ethyl acetate layer is separated, washed, dried, and concentrated under reduced pressure. The residue is purified by silica gel column chromatography (solvent; chloroform:methanol=20:1) to give 4-(3-bromo-4,5-dimethoxyphenyl)-6,7-dimethoxy-2-[4-(2-hydroxyethyl)piperazin-1-yl]-3-methoxycarbonyl-1(2H)-isoquinolinone as listed in Table 16. The compound thus obtained is dissolved in chloroform (3 ml), and thereto is added a 4M solution of hydrogen chloride in ethyl acetate (50 $\mu$l). The reaction mixture is concentrated under reduced pressure, and to the residue is added diethyl ether. The resulting crystals are collected by filtration to give 4-(3-bromo-4,5-dimethoxyphenyl)-6,7-dimethoxy-2-[4-(2-hydroxyethyl)piperazin-1-yl]-3-methoxycarbonyl-1(2H)-isoquinolinone hydrochloride (Example 205) as listed in Table 16. During the above reaction (the reaction of the compound obtained in Example 204 with 2-bromoethanol), 2-(4-benzylpiperazin-1-yl)-4-(3-bromo-4,5-dimethoxyphenyl)-6,7-dimethoxy-3-methoxycarbonyl-1(2H)-isoquinolinone (Example 206) as listed in Table 16 is obtained as a by-product.

EXAMPLE 207

The compound obtained in Example 193 is treated in the same manner as in Example 24 to give 2-(4-aminopropyl)-4-(3-bromo-4,5-dimethoxyphenyl)-6,7-dimethoxy-3-methoxycarbonyl-1(2H)-isoquinolinone hydrochloride as listed in Table 16.

EXAMPLE 208

4-(4-Bromo-3,5-dimethoxyphenyl)-3-hydroxy-6,7-dimethoxy-3,4-dihydroisocoumarin-3-carboxylic acid (the compound obtained in Reference Example 81) and the corresponding starting compounds are treated in the same manner as in Example 4 or 31 to 2-[4-(tert-butoxycarbonylamino)phenyl]-4-(4-bromo-3,5-dimethoxyphenyl)-6,7-dimethoxy-3-methoxycarbonyl-1(2H)-isoquinolinone, which is further treated in the same manner as in Example 24 to give 2-(4-aminophenyl)-4-(4-bromo-3,5-dimethoxyphenyl)-6,7-dimethoxy-3-methoxycarbonyl-1(2H)-isoquinolinone hydrochloride as listed in Table 17.

EXAMPLE 209

4-(3,5-Dimethoxyphenyl)-3-hydroxy-6,7-dimethoxy-3,4-dihydroisocoumarin-3-carboxylic acid (the compound obtained in Reference Example 83) and the corresponding starting compounds are treated in the same manner as in Example 4 or 31 to 2-[4-(tert-butoxycarbonylamino)phenyl]-6,7-dimethoxy-4-(3,5-dimethoxyphenyl)-3-methoxycarbonyl-1(2H)-isoquinolinone, which is further treated in the same manner as in Example 24 to give 2-(4-aminophenyl)-6,7-dimethoxy-4-(3,5-dimethoxyphenyl)-3-methoxycarbonyl-1(2H)-isoquinolinone hydrochloride as listed in Table 17.

EXAMPLES 210–211

The corresponding 6,7-dimethoxyisocoumarin-3-carboxylic acid compounds (the compounds obtained in Reference Example 61 or 63) and the corresponding starting compounds are treated in the same manner as in Example 1 or 39 to give the following compounds as listed in Table 17.

4-(4-bromo-3,5-dimethoxyphenyl)-6,7-dimethoxy-3-methoxycarbonyl-2-morpholino-1(2H)-isoquinolinone (Example 210);

6,7-dimethoxy-4-(3,5-dimethoxyphenyl)-3-methoxycarbonyl-2-morpholino-1(2H)-isoquinolinone (Example 211);

EXAMPLE 212

6,7-Dimethoxy-4-(2,3,4-trimethoxyphenyl)isocoumarin-3-carboxylic acid (the compound obtained in Reference Example 64) and the corresponding stating compounds are treated in the same manner as in Example 1 or 39 to give 6,7-dimethoxy-3-methoxycarbonyl-2-phenyl-4-(2,3,4-trimethoxyphenyl)-1(2H)-isoquinolinone as listed in Table 17,

EXAMPLE 213

7-Benzyloxy-3-hydroxymethoxy-4-(3,4,5-trimethoxyphenyl)-3,4-dihydroisocoumarin-3-carboxylic acid (the compound obtained in Reference Example 71) and the corresponding starting compounds are treated in the same manner as in Example 4 or 31 to give 7-benzyloxy-6-methoxy-3-methoxy-carbonyl-2-phenyl-4-(3,4,5-trimethoxyphenyl)-1(2H)-isoquinolinone as listed in Table 18.

EXAMPLE 214

The compound obtained in Example 213 treated in the same manner as in Example 2 to give 7-hydroxy-6-methoxy-3-methoxycarbonyl-2-phenyl-4-(3,4,5-trimethoxyphenyl)-1(2H)-isoquinolinone as listed in Table 18.

EXAMPLES 215–217

The compound obtained in Example 214 is treated in the same manner as in Example 3 to give the following compounds as listed in Table 18.

6-methoxy-3-methoxycarbonyl-2-phenyl-4-(3,4,5-trimethoxyphenyl)-7-(4-pyridylmethyloxy)-1(2H)-isoquinolinone hydrochloride (Example 215);

6-methoxy-3-methoxycarbonyl-2-phenyl-4-(3,4,5-trimethoxyphenyl)-7-(3-pyridylmethyloxy)-1(2H)-isoquinolinone hydrochloride (Example 216);

6-methoxy-3-methoxycarbonyl-2-phenyl-4-(3,4,5-trimethoxyphenyl)-7-(2-pyridylmethyloxy)-1(2H)-isoquinolinone hydrochloride (Example 217);

EXAMPLE 218

Pyrrol-2-carboxylic acid (38.4 mg) and 1-hydroxybenzotriazole monohydrate (53 mg) are dissolved in acetonitrile (10 ml), and thereto is added 1-(3-dimethylaminopropyl)-3-ethylcarbodiimide hydrochloride (66.3 mg), and the mixture is stirred at room temperature for 30 minutes. The reaction mixture is added to a solution of the compound obtained in Example 214 (162 mg) and potassium carbonate (48 mg) in dimethylformamide (10 ml), and the mixture is stirred at room temperature for 30 minutes. Water and ethyl acetate are added to the reaction mixture. The ethyl acetate layer is separated, washed, dried, and concentrated under reduced pressure. The residue is crystallized from diethyl ether to give 6-methoxy-3-methoxycarbonyl-2-phenyl-7-(2-pyrrolylcarbonyloxy)-4-(3,4,5-trimethoxyphenyl)-1(2H)-isoquinolinone (145 mg) as listed in Table 18.

EXAMPLES 219–220

The compound obtained in Example 214 is treated in the same manner as in Example 7-(1) to give the compounds as listed in Table 18.

6-methoxy-3-methoxycarbonyl-2-phenyl-7-(2-thienylmethyloxy)-4-(3,4,5-trimethoxyphenyl)-1(2H)-isoquinolinone (Example 219);

6-methoxy-3-methoxycarbonyl-7-{[(1-methyl-2-methoxycarbonyl)-pyrrol-4-yl]methyloxy}-2-phenyl-4-(3,4,5-trimethoxyphenyl)-1(2H)-isoquinolinone (Example 220);

EXAMPLE 221

7-Benzyloxy-3-hydroxy-4-(3,4,5-trimethoxyphenyl)-3,4-dihydroisocoumarin-3-carboxylic acid (the compound obtained in Reference Example 73) and the corresponding starting compounds are treated in the same manner as in Example 4 or 31 to give 2-[4-(tert-butoxycarbonylamino)phenyl]-7-benzyloxy-3-methoxycarbonyl-4-(3,4,5-trimethoxyphenyl)-1(2H)-isoquinolipone as listed in Table 19.

EXAMPLE 222

The compound obtained in Example 221 is treated in the same manner as in Example 24 to give 2-(4-aminophenyl)-7-benzyloxy-3-methoxycarbonyl-4-(3,4,5-trimethoxyphenyl)-1(2H)-isoquinolinone hydrochloride as listed in Table 19.

EXAMPLE 223

The compound obtained in Example 221 is treated in the same manner as in Example 5 to give 2-[4-(tert-butoxycarbonylaminophenyl]-7-hydroxy-3-methoxycarbonyl-4(3,4,5-trimethoxyphenyl)-1(2H)-isoquinolinone as listed in Table 19.

EXAMPLE 224

The compound obtained in Example 223 is treated in the same manner as in Example 24 to give 2-(4-aminophenyl)-7-hydroxy-3-methoxycarbonyl-4-(3,4,5-trimethoxyphenyl)-1(2H)-isoquinolinone hydrochloride as listed in Table 19.

EXAMPLE 225

The compound obtained in Example 223 is treated in the sa me manner as in Example 6 or 7 to give 2-(4-aminophenyl)-3-methoxycarbonyl-7-(2-quinolylmethyloxy)-4-(3,4,5-trimethoxyphenyl)-1(2H)-isoquinolinone dihydrochloride as listed in Table 19.

EXAMPLES 226–227

The compound obtained in Example 223 is treated in the same manner as in Example 6 or 7 to give the following compounds as listed in Table 19.

2-(4-aminophenyl)-3-methoxycarbonyl-7-(4-quinolylmethyloxy)-4-(3,4,5-trimethoxyphenyl)-1(2H)-isoquinolinone dihydrochloride (Example 226);

2-(4-aminophenyl)-3-methoxycarbonyl-7-(3-quinolylmethyloxy)-4-(3,4,5-trimethoxyphenyl)-1(2H)-isoquinolinone dihydrochloride (Example 227);

EXAMPLE 228

The compound obtained in Example 4 is treated in the same manner as in Example 6-(2) to give 2-(4-aminophenyl)-7-benzyloxy-6-methoxy-3-methoxycarbonyl-4-(3,4,5-trimethoxyphenyl)-1(2H)-isoquinolinone hydrochloride as listed in Table 20.

EXAMPLE 229

The compound obtained in Example 5 is treated in the same manner as in Example 6-(2) to give 2-(4-aminophenyl)-7-hydroxy-6-methoxy-3-methoxycarbonyl-4-(3,4,5-trimethoxyphenyl)-1(2H)-isoquinolinone hydrochloride as listed in Table 20.

EXAMPLES 230–238

The compound obtained in Example 5 and the corresponding starting compounds are treated in the same manner as in Example 6 to give the following compounds as listed in Table 20.

2-[4-(tert-butoxycarbonylamino)phenyl]-7-(tert-butoxycarbonylmethyoxy)-6-methoxy-3-methoxycarbonyl-4-(3,4,5-trimethoxyphenyl)-1(2H)-isoquinolinone (Example 230 (1));

2-(4-aminophenyl)-7-(carboxymethyloxy)-6-methoxy-3-methoxycarbonyl-4-(3,4,5-trimethoxyphenyl)-1(2H)-isoquinolinone hydrochloride (Example 230 (2));

2-[4-(tert-butoxycarbonylamino)phenyl]-7-cyclopentyloxymethoxy-3-methoxycarbonyl-4-(3,4,5-trimethoxyphenyl)-1(2H)-isoquinolinone (Example 231(1));

2-(4-aminophenyl)-7-cyclopentyloxy-6-methoxy-3-methoxycarbonyl-4-(3,4,5-trimethoxyphenyl)-1(2H)-isoquinolinone hydrochloride (Example 231 (2));

2-[4-(tert-butoxycarbonylamino)phenyl]-7-[2-(N,N-dimethylamino)ethyloxy]-6-methoxy-3-methoxycarbonyl-4-(3,4,5-trimethoxyphenyl)-1(2H)-isoquinolinone (Example 232 (1));

2-(4-aminophenyl)-7-[2-(N,N-dimethylamino)ethyloxy]-6-methoxy-3-methoxycarbonyl-4-(3,4,5-trimethoxyphenyl)-1(2H)-isoquinolinone dihydrochloride (Example 232 (2));

2-[4-(tert-butoxycarbonylamino)phenyl]-methoxy-3-methoxycarbonyl-7-[2-(2-methoxyethyloxy)ethyloxy]-4-(3,4,5-trimethoxyphenyl)-1(2H)-isoquinolinone (Example 233 (1));

2-(4-aminophenyl)-6-methoxy-3-methoxycarbonyl-7-[2-(2-methoxyethyloxy) ethyloxy]-4-(3,4,5-trimethoxyphenyl)-1(2H)-isoquinolinone hydrochloride (Example 233 (2));

7-ethoxy-2-[4-(tert-butoxycarbonylamino)phenyl]-6-methoxy-3-methoxycarbonyl-4-(3,4,5-trimethoxyphenyl)-1(2H)-isoquinolinone (Example 234(1));

2-(4-aminophenyl)-7-ethoxy-6-methoxy-3-methoxycarbonyl-4-(3,4,5-trimethoxyphenyl)-1(2H)-isoquinolinone hydrochloride (Example 234 (2));

2-[4-(tert-butoxycarbonylamino)phenyl]-6-methoxy-3-methoxycarbonyl-7-(2-methoxyethyloxy)-4-(3,4,5-trimethoxyphenyl)-1(2H)-isoquinolinone (Example 235 (1));

2-(4-aminophenyl)-6-methoxy-3-methoxycarbonyl-7-(2-methoxyethyloxy)-4-(3,4,5-trimethoxyphenyl)-1(2H)-isoquinolinone hydrochloride (Example 23 5 (2));

2-[4-(tert-butoxycarbonylamino)phenyl]-6-methoxy-3-methoxycarbonyl-7-(4-pyridylmethyloxy)-4-(3,4,5-trimethoxyphenyl)-1(2H)-isoquinolinone (Example 236 (1));

2-(4-aminophenyl)-6-methoxy-3-methoxycarbonyl-7-(4-pyridylmethyloxy)-4-(3,4,5-trimethoxyphenyl)-1(2H)-isoquinolinone dihydrochloride (Example 236 (2));

2-[4-(tert-butoxycarbonylamino)phenyl-6-methoxy-3-methoxycarbonyl-7-(3-pyridylmethyloxy)-4-(3,4,5-trimethoxyphenyl)-1(2H)-isoquinolinone (Example 237 (1));

2-(4-aminophenyl)-6-methoxy-3-methoxycarbonyl-7-(3-pyridylmethyloxy)-4-(3,4,5-trimethoxyphenyl)-1(2H)-isoquinolinone dihydrochloride (Example 237 (2));

2-[4-(tert-butoxycarbonylamino)phenyl]-6-methoxy-3-methoxycarbonyl-7-(2-quinolylmethyloxy)-4-(3,4,5-trimethoxyphenyl)-1(2H)-isoquinolinone (Example 238 (1));

2-(4-aminophenyl)-6-methoxy-3-methoxycarbonyl-7-(2-quinolylmethyloxy)-4-(3,4,5-trimethoxyphenyl)-1 (214)-isoquinolinone dihydrochloride (Example 238 (2));

EXAMPLE 239

(1) The compound obtained in Example 5 and the corresponding starting compounds are treated in the same manner as in Example 6-(1) to give 2-[4-(tert-butoxycarbonylamino) phenyl]-7-(2-hydroxyethyloxy)-6-methoxy-3-methoxycarbonyl-4-(3,4,5-trimethoxyphenyl)-1(2H)-isoquinolinone as listed in Table 20.

(2) The compound thus obtained is treated in the same manner as in Example 24 to give 2-(4-aminophenyl)-7-(2-hydroxyethyloxy)-6-methoxy-3-methoxycarbonyl-4-(3,4,5-trimethoxyphenyl)-1(2H)-isoquinolinone hydrochloride as listed in Table 20.

EXAMPLES 240–253

The compound obtained in Example 5 and the corresponding starting compounds are treated in the same manner as in Example 6 to give the following compounds as listed in Table 20.

2-[4-(tert-butoxycarbonylamino)phenyl]-6-methoxy-3-methoxy-carbonyl-7-(2-phenylethyloxy)-4-(3,4,5-trimethoxyphenyl)-1(2H)-isoquinolinone (Example 240 (1));

2-(4-aminophenyl)-6-methoxy-3-methoxycarbonyl-72-phenylethyloxy)-4-(3,4,5-trimethoxyphenyl)-1(2H)-isoquinolinone hydrochloride (Example 240 (2));

7-benzoylmethyloxy-2-[4-(tert-butoxycarbonylamino) phenyl-6-methoxy-3-methoxycarbonyl-4-(3,4,5-trimethoxyphenyl) 1(2H)-isoquinolinone (Example 241 (1));

2-(4-aminophenyl)-7-benzoylmethyloxy-6-methoxy-3-methoxycarbonyl-4-(3,4,5-trimethoxyphenyl)-1(2H)-isoquinolinone hydrochloride (Example 241 (2));

2-[4-(tert-butoxycarbonylamino)phenyl]-6-methoxy-3-methoxycarbonyl-7-(2-nitrobenzyloxy)-4-(3,4,5-trimethoxyphenyl)-1(2H)-isoquinolinone (Example 242 (1));

2-(4-aminophenyl)-6-methoxy-3-methoxycarbonyl-7-(2-nitrobenzyloxy)-4-(3,4,5-trimethoxyphenyl)-1(2H)-isoquinolinone hydrochloride (example 242 (2));

2-[4-(tert-butoxycarbonylamino)phenyl]-6-methoxy-3-methoxycarbonyl-7-(3-nitrobenzyloxy)-4-(3,4,5-trimethoxyphenyl)-1(2H)-isoquinolinone (Example 243 (1));

2-(4-aminophenyl)-6-methoxy-3-methoxycarbonyl-7-(3-nitrobenzyloxy)-4-(3,4,5-trimethoxyphenyl)-1(2H)-isoquinolinone hydrochloride (Example 243 (2));

2-[4-(tert-butoxycarbonylamino)phenyl]-7-cyclohexylmethyloxy-6-methoxy-3-methoxycarbonyl-4-(3,4,5-trimethoxyphenyl)-1(2H)-isoquinolinone (Example 244 (1));

2-(4-aminophenyl)-7-cyclohexylmethyloxy-6-methoxy-3-methoxycarbonyl-4-(3,4,5-trimethoxyphenyl)-1 (2H)-isoquinolinone hydrochloride (Example 244 (2));

2-[4-(tert-butoxycarbonylamino)phenyl]-6-methoxy-3-methoxycarbonyl-7-(methoxycarbonylmethyloxy)-4-(3,4,5-trimethoxyphenyl)-1(2H)-isoquinolinone (Example 245 (1));

2-(4-aminophenyl)-6-methoxy-3-methoxycarbonyl-7-(methoxycarbonylmethyloxy)-4-(3,4,5-trimethoxyphenyl)-1(2H)-isoquinolinone hydrochloride (Example 245 (2));

2-(4-(tert-butoxycarbonylamino)phenyl]-7-(3,4-dichlorobenzyloxy)-6-methoxy-3-methoxycarbonyl-4-(3,4,5-trimethoxyphenyl)-1(2H)-isoquinolinone (Example 246 (1));

2-(4-aminophenyl)-7-(3,4-dichlorobenzyloxy)-6-methoxy-3-methoxycarbonyl-4-(3,4,5-trimethoxyphenyl)-1(2H)-isoquinolinone hydrochloride (Example 246 (2));

2-[4-(tert-butoxycarbonylamino)phenyl]-6-methoxy-3-methoxycarbonyl-7-(4-nitrobenzyloxy)-4-(3,4,5-trimethoxyphenyl)-1(2H)-isoquinolinone (Example 247 (1));

2-(4-aminophenyl)-6-methoxy-3-methoxycarbony-7-(4-nitrobenzyoxy)-4-(3,4,5-trimethoxyphenyl)-1(2H)-isoquinolinone hydrochloride (Example 247 (2));

2-[4-(tert-butoxycarbonylamino)phenyl]-6-methoxy-3-methoxy-carbonyl-7-(4-phenylbenzyloxy)-4-(3,4,5-trimethoxyphenyl)-1(2H)-isoquinolinone (Example 248 (1));

2-(4-aminophenyl)-6-methoxy-3-methoxycarbonyl-7-(4-phenylbenzyloxy)-4-(3,4,5-trimethoxyphenyl)-1(2H)-isoquinolinone hydrochloride (Example 248 (2));

2-[4-(tert-butoxycarbonylamino)phenyl]-6-methoxy-3-methoxycarbonyl-7-(3-methoxycarbonylbenzyloxy)-4-(3,4,5-trimethoxyphenyl)-1(2H)-isoquinolinone (Example 249 (1));

2-(4-aminophenyl)-6-methoxy-3-methoxycarbonyl-7-(3-methoxycarbonylbenzyloxy)-4-(3,4,5-trimethoxyphenyl)-1(2H)-isoquinolinone hydrochloride (Example 249 (2));

2-[4-(tert-butoxycarbonylamino)phenyl]-7-(2-fluorobenzyloxy)-6-methoxy-3-methoxycarbonyl-4-(3,4,5-trimethoxyphenyl)-1(2H)-isoquinolinone (Example 250 (1));

2-(4-aminophenyl)-7-(2-fluorobenzyloxy)-6-methoxy-3-methoxycarbonyl-4-(3,4,5-trimethoxyphenyl)-1(2H)-isoquinolinone hydrochloride Example 250 (2));

2-[4-(tert-butoxycarbonylamino)phenyl]-6-methoxy-3-methoxycarbonyl-7-(1-naphthylmethyloxy)-4-(3,4,5-trimethoxyphenyl)-1(2H)-isoquinolinone (Example 251 (1));

2-(4-aminophenyl)-6-methoxy-3-methoxycarbonyl-7-(1-naphthylmethyloxy)-4-(3,4,5-trimethoxyphenyl)-1(2H)-isoquinolinone hydrochloride (Example 251 (2));

2-[4-(tert-butoxycarbonylamino)phenyl]-6-methoxy-3-methoxycarbonyl-7-(2-naphthylmethyloxy)-4-(3,4,5-trimethoxyphenyl)-1(2H)-isoquinolinone (Example 252 (1));

2-(4-aminophenyl)methoxy-3-methoxycarbonyl-7-(2-naphthylmethyloxy)-4-(3,4,5-trimethoxyphenyl)-1(2H)-isoquinolinone hydrochloride (Example 252 (2));

7-allyloxy-2-[4-(tert-butoxycarbonylamino)phenyl]-methoxy-3-methoxycarbonyl-4-(3,4,5-trimethoxyphenyl)-1(2H)-isoquinolinone (Example 253 (1));

7-allyloxy-2-(4-aminophenyl)-6-methoxy-3-methoxycarbonyl-4-(3,4,5-trimethoxyphenyl)-1(2H)-isoquinolinone hydrochloride (Example 253 (2));

EXAMPLE 254

(1) The compound obtained in Example 5 and the corresponding starting compounds are treated in the same manner as in Example 6-(1) to give 2-[4-(tert-butoxycarbonylamino)phenyl]-6-methoxy-3-methoxycarbonyl-7-(4-methoxycarbonylbenzyloxy)-4-(3,4,5-trimethoxyphenyl)-1(2H)-isoquinolinone. m.p. 197–199° C.

(2) The compound thus obtained is treated in the same manner as in Example 21 to give 2-(4-aminophenyl)-7-(4-carboxybenzyloxy)-6-methoxy-3-methoxycarbonyl-4-(3,4,5-trimethoxyphenyl)-1(2H)-isoquinolinone hydrochloride as listed in Table 20.

(3) The compound thus obtained is treated in the same manner as in Example 6-(2) to give 2-(4-aminophenyl)-6-methoxy-3-methoxycarbonyl-7-(4-methoxycarbonylbenzyloxy)-4-(3,4,5-trimethoxyphenyl)-1(2H)-isoquinolinone hydrochloride as listed in Table 20.

EXAMPLE 255

(1) A suspension of the compound obtained in Example 5 (300 mg), 2-bromopyridine (57 μl), copper iodide (113 mg) and potassium carbonate (82 mg) in dimethylformamide (5 μl) is heated with stirring at 80° C. for five hours. After the reaction is complete, the reaction mixture is extracted with ethyl acetate. The extract is washed with aqueous ammonia, and further washed with water, dried, and concentrated under reduced pressure. The residue is purified by Chromatotron (solvent; hexane:ethyl acetate=1:1) to give 2-[4-(tert-butoxycarbonylamino)phenyl]-6-methoxy-3-methoxycarbonyl-7-(2-pyridyloxy)-4-(3,4,5-trimethoxyphenyl)-1(2H)-isoquinolinone (40 rag) as listed in Table 20.

(2) The compound thus obtained is treated in the same manner as in Example 24 to give 2-(4-aminophenyl)-6-methoxy-3-methoxycarbonyl-7-(2-pyridyloxy)-4-(3,4,5-trimethoxyphenyl)-1(2H)-isoquinolinone dihydrochloride as listed in Table 20.

EXAMPLE 256

(1) The compound obtained in Example 5 and the corresponding starting compounds are treated in the same manner as in Example 218 to give 2-[4-(tertbutoxycarbonylamino)phenyl]-methoxy-3-methoxycarbonyl-7-[(1-methyl-4-nitro)pyrrol-2-yl-carbonyloxy]-4-(3,4,5-trimethoxyphenyl)-1(2H)-isoquinolinone as listed in Table 20.

(2) The compound thus obtained is treated in the same manner as in Example 6-(2) to give 2-(4-aminophenyl)-6-methoxy-3-methoxycarbonyl-7-[(1-methyl-4-nitro)pyrrol-2-yl-carbonyloxy]-4-(3,4,5-trimethoxyphenyl)-1(2H)-isoquinolinone hydrochloride as listed in Table 20.

EXAMPLE 257

(1) The compound obtained in Example 5 (200 mg) is dissolved in dimethylformamide (10 ml), and thereto are added benzochloride (40 μl), triethylamine (48 μl) and 4-dimethylaminopyridine (5 mg), and the mixture is stirred at room temperature overnight. After the reaction is complete, to the mixture is added a saturated aqueous sodium hydrogen carbonate solution, and the mixture is extracted with ethyl acetate. The extract is washed, dried, and concentrated under reduced pressure. The residue is purified by silica gel column chromatography (solvent; hexane:ethyl acetate=1:1) to give 7-benzoyloxy-2-[4-(tert-butoxycarbonylamino)phenyl]-6-methoxy-3-methoxycarbonyl-4-(3,4,5-trimethoxyphenyl)-1(2H)-isoquinolinone as listed in Table 20.

(2) The compound thus obtained is treated in the same manner as in Example 6-(2) to give 2-(4-aminophenyl)-7-benzoyloxy6-methoxy-3-methoxycarbonyl-4-(3,4,5-trimethoxyphenyl)-1(2H)-isoquinolinone hydrochloride as listed in Table 20.

EXAMPLE 258

(1) The compound obtained in Example 5 and the corresponding starting compounds are treated in the same manner as in Example 218 to give 2-[4-(tertbutoxycarbonylamino)phenyl]-6-methoxy-3-methoxycarbonyl-7-(2-pyrrolylcarbonyloxy)-4-(3,4,5-trimethoxyphenyl)-1(2H)-isoquinolinone as listed in Table 20, which is used in the subsequent reaction without further purification.

(2) The compound thus obtained is treated in the same manner as in Example 6-(2) to give 2-(4-aminophenyl)-6- methoxy-3-methoxycarbonyl-7-(2-pyrrolyl-carbonyloxy)-4-(3,4,5-trimethoxyphenyl)-1(2H)-isoquinolinone hydrochloride as listed in Table 20.

EXAMPLES 259–268

The compound obtained in Example 5 and the corresponding starting compounds are treated in the same manner as in Example 7 to give the following compounds as listed in Table 20.

2-[4-(tert-butoxycarbonylamino)phenyl]-6-methoxy-3-methoxycarbonyl-7-[2-(2-pyridyl)ethyloxy]-4-(3,4,5-trimethoxyphenyl))-1(2H)-isoquinolinone (Example 259 (1));

2-(4-aminophenyl)-6-methoxy-3-methoxycarbonyl-7-[2-(2-pyridylethyloxy]-4-(3,4,5-trimethoxyphenyl)-1 (2H)-isoquinolinone dihydrochloride (Example 259 (2));

2-[4-(tert-butoxycarbonylamino)phenyl]-6-methoxy-3-methoxycarbonyl-4-(3,4,5-trimethoxyphenyl)-7-(3-thienylmethyloxy)-1(2H)-isoquinolinone (Example 260 (1));

2-(4-aminophenyl)-6-methoxy-3-methoxycarbonyl-4-(3,4,5-trimethoxyphenyl)-7-(3-thienylmethyloxy)-1(2H)-isoquinolinone hydrochloride (Example 260 (2));

2-[4-(tert-butoxycarbonylamino)phenyl-6-methoxy-3-methoxycarbonyl-4-(3,4,5-trimethoxyphenyl)-7-(4-quinolylmethyloxy)-1(2H)-isoquinolinone (Example 261 (1));

2-(4-aminophenyl)-6-methoxy-3-methoxycarbonyl-7-(4-quinolylmethyloxy)-4-(3,4,5-trimethoxyphenyl)-1 (2H)-isoquinolinone dihydrochloride (Example 261 (2));

2-[4-(tert-butoxycarbonylamino)phenyl]-6-methoxy-3-methoxycarbonyl-7-(3-methylbenzyloxy)-4-(3,4,5-trimethoxyphenyl)-1(2H)-isoquinolinone (Example 262 (1));

2-(4-aminophenyl)-6-methoxy-3-methoxycarbonyl-7-(3-methylbenzyloxy)-4-(3,4,5-trimethoxyphenyl)-1(2H)-isoquinolinone hydrochloride (Example 262 (2));

2-[4-(tert-butoxycarbonylamino)phenyl]-7-[(2-chloro-5-nitro)benzyloxy]-6-methoxy-3-methoxycarbonyl-4-(3,4,5-trimethoxyphenyl)-1 (2H)-isoquinolinone (Example 263 (1));

2-(4-aminophenyl)-7-[(2-chloro-5-nitro)benzyloxy]-6-methoxy-3-methoxycarbonyl-4-(3,4,5-trimethoxy-phenyl)-1(2H)-isoquinolinone hydrochloride (Example 263 (2));

2-[4-(tert-butoxycarbonylamino)phenyl]-6-methoxy-7-(3-methoxybenzyloxy)-3-methoxycarbonyl-4-(3,4,5-trimethoxyphenyl)-1(2H)-isoquinolinone (Example 264 (1)), which is used in the subsequent reaction without further purification;

2-(4-aminophenyl)-6-methoxy-7-(3-methoxybenzyloxy)-3-methoxycarbonyl-4-(3,4,5-trimethoxyphenyl)-1 (2H)-isoquinolinone hydrochloride (Example 264 (2));

7-[3-(tert-butoxycarbonylamino)benzyloxy]-2-[4-(tert-butoxycarbonylamino) phenyl]-6-methoxy-3-methoxycarbonyl-4-(3,4,5-trimethoxyphenyl-1(2H)-isoquinolinone (Example 265 (1)), which is used in the subsequent reaction without further purification;

7-(3-aminobenzloxy)-2-(4-aminophenyl)-6-methoxy-3-methoxycarbonyl-4-(3,4,5-trimethoxyphenyl)-1(2H)-isoquinolinone dihydrochloride (Example 265 (2));

2-[4-(tert-butoxycarbonylamino)phenyl]-7-cyclopentylmethyloxy-6-methoxy-3-methoxycarbonyl4-(3,4,5-trimethoxyphenyl)-1(2H)-isoquinolinone (Example 266 (1)), which is used in the subsequent reaction without further purification;

2-(4-aminophenyl)-7-cyclopentylmethyloxy6-methoxy-3-methoxycarbonyl-4-(3,4,5-trimethoxyphenyl)-1 (2H)-isoquinolinone hydrochloride (Example 266 (2));

2-[4-(tert-butoxycarbonylamino)phenyl]-7-[4-(1-tert-butoxycarbonyl)piperidylmethyloxy]-6-methoxy-3-methoxycarbonyl-4-(3,4,5-trimethoxy-phenyl)-1(2H)-isoquinolinone (Example 267 (1));

2-(4-aminophenyl)-6-methoxy-3-methoxycarbonyl-7-(4-piperidylmethyloxy)-4-(3,4,5-trimethoxyphenyl)-1 (2H)-isoquinolinone dihydrochloride (Example 267 (2));

2-[4-(tert-butoxycarbonylamino)phenyl]-6-methoxy-3-methoxycarbonyl-7-(2-piperidinoethyloxy)-4-(3,4,5-trimethoxyphenyl)-1(2H)-isoquinolinone (Example 268 (1));

2-(4-aminophenyl)-6-methoxy-3-methoxycarbonyl-7-(2-piperidinoethyloxy)-4-(3,4,5-trimethoxyphenyl)-1 (2H)-isoquinolinone dihydrochloride (Example 268 (2));

EXAMPLE 269

(I) A solution of the compound obtained in Example 5 (100 mg) and triethylamine (50 mg) in chloroform (10 ml) is cooled to −10° C., and thereto is added dropwise a solution of triphosgene (49 mg) in chloroform. The mixture is warmed to room temperature, and the mixture is stirred for 30 minutes. To the mixture is added a solution of N-methylpiperazine (50 mg) and triethylamine (17 mg) in chloroform, and the mixture is further stirred for two hours. After the reaction is complete, the reaction mixture is washed, dried, and concentrated under reduced pressure. The residue is crystallized from diethyl ether to give 2[4-(tert-butoxycarbonylamino)phenyl]-6-methoxy-3-methoxycarbonyl-7-(4-methylpiperazinylcarbonyloxy)-4-(3,4,5-trimethoxyphenyl)-1(2H)-isoquinolinone (73 mg) as listed in Table 20.

(2) The compound thus obtained is treated in the same manner as in Example 24 to give 2-(4-aminophenyl)-7-(4-methylpiperazinylcarbonyloxy)-6-methoxy-3-methoxycarbonyl-4-(3,4,5-trimethoxyphenyl)-1(2H)-isoquinolinone dihydrochloride as listed in Table 20.

EXAMPLE 270

(1) The compound obtained in Example 5 and the corresponding starting compounds are treated in the same manner as in Example 269-(1) to give 2-[4-(tert-butoxy carbonylamino)phenyl]-7-diethylaminocarbonyloxy-6-methoxy-3-methoxycarbonyl-4-(3,4,5-trimethoxyphenyl)-1 (2H)-isoquinolinone as listed in Table 20.

(2) The compound thus obtained is treated in the same manner as in Example 269-(2) to give 2-(4-aminophenyl)-7-diethylaminocarbonyloxy-6-methoxy-3-methoxycarbonyl-4-(3,4,5-trimethoxyphenyl)-1(2H)-isoquinolinone hydrochloride as listed in Table 20.

EXAMPLE 271

(1) The compound obtained in Example 5 and the corresponding starting compounds are treated in the same manner as in Example 269-(1) to give 2-[4-(tert-butoxycarbonylamino)phenyl]-6-methoxy-3-methoxycarbonyl-7-morpholinocarbonyloxy-4-(3,4,5-trimethoxyphenyl)-1(2H)-isoquinolinone as listed in Table 20.

(2) The compound thus obtained is treated in the same manner as in Example 269-(2) to give 2-(4-aminophenyl)-

6-methoxy-3-methoxycarbonyl-7-morpholinocarbonyloxy-4-(3,4,5-trimethoxyphenyl)-1(2H)-isoquinolinone hydrochloride as listed in Table 20.

EXAMPLE 272

(1) The compound obtained in Example 5 and the corresponding starting compounds are treated in the same manner as in Example 6-(1) to give 2-[4-(tert-butoxycarbonylamino)phenyl]-7-cyanomethyl-6-methoxy-3-methoxycarbonyl-4-(3,4,5-trimethoxyphenyl)-1(2H)-isoquinolinone. m.p. 136–138° C.

(2) A solution of the compound thus obtained (310 mg), sodium azide (156 mg) and ammonium chloride (128 mg) in dimethylformamide (30 ml) is heated with stirring at 70° C. for 48 hours. To the mixture is added water, and the mixture is extracted with ethyl acetate. The extract is washed, dried, and concentrated under reduced pressure. The residue is crystallized from a mixture of ethyl acetate and diethyl ether to give 2-[4-(tert-butoxycarbonylamino)phenyl]-6-methoxy-3-methoxycarbonyl-7-(5-tetrazolylmethyloxy)-4-(3,4,5-trimethoxyphenyl)-1(2H)-isoquinolinone (178 mg) as listed in Table 20.

(3) The compound thus obtained is treated in the same manner as in Example 6-(2) to give 2-(4-aminophenyl)-6-methoxy-3-methoxycarbonyl-7-(5-tetrazolymethyloxy)-4-(3,4,5-trimethoxyphenyl)-1(2H)-isoquinolinone hydrochloride as listed in Table 20.

EXAMPLES 273–275

(1) The compound obtained in Example 6 (1), 236 (1) or 237 (1) is treated with m-chloroperbenzoic acid to give the following compounds as listed in Table 20.

2-[4-(tert-butoxycarbonylamino)phenyl]-6-methoxy-3-methoxycarbonyl-7-(N-oxo-4-pyridylmethyloxy)-4-(3,4,5-trimethoxyphenyl)-1(2H)-isoquinolinone (Example 273 (1));

2-[4-(tert-butoxycarbonylamino)phenyl]-6-methoxy-3-methoxycarbonyl-7-(N-oxo-3-pyridylmethyloxy)-4-(3,4,5-trimethoxyphenyl)-1(2H)-isoquinolinone (Example 274 (1));

2-[4-(tert-butoxycarbonylamino)phenyl]-6-methoxy-3-methoxycarbonyl-7-(N-oxo-2-pyridylmethyloxy)-4-(3,4,5-trimethoxyphenyl)-1(2H)-isoquinolinone (Example 275

(2) The compounds thus obtained are treated in the same manner as in Example 6-(2) to give the following compounds as listed in Table 20.

2-(4-aminophenyl)-6-methoxy-3-methoxycarbonyl-7-N-oxo-4-pyridyl-methyloxy)-4-(3,4,5-trimethoxyphenyl)-1(2H)-isoquinolinone hydrochloride (Example 273 (2));

2-(4-aminophenyl)-6-methoxy-3-methoxycarbonyl-7N-oxo-3-pyridylmethyloxy)-4-(3,4,5-trimethoxyphenyl)-1(2H)-isoquinolinone hydrochloride (Example 274 (2));

2-(4-aminophenyl)-6-methoxy-3-methoxycarbonyl-7-(N-oxo-2-pyridyl-methyloxy)-4-(3,4,5-trimethoxyphenyl)-1(2H)-isoquinolinone hydrochloride (Example 275 (2));

EXAMPLE 276

(1) The compound obtained in Example 245-(1) is treated in the same manner as in Example 21 to give 2-[4-(tert-butoxycarbonylamino)phenyl]-7-(carboxymethyloxy)-6-methoxy-3-methoxycarbony-4-(3,4,5-trimethoxyphenyl)-1(2H)-isoquinolinone. The compound thus obtained (150 mg) is dissolved in dimethylformamide (5 ml), and thereto is added carbonyl diimidazole (40 mg) under ice-cooling. The mixture is stirred at room temperature for 30 minutes, and thereto is added conc. aqueous ammonia (0.5 ml), and the mixture is stirred at room temperature for one hour. After the reaction is complete, water is added to the mixture, and the mixture is extracted with ethyl acetate. The extract is washed, dried, and concentrated under reduced pressure. The residue is crystallized from diethyl ether to give 2-[4-(tert-butoxycarbonylamino)phenyl]-7-carbamoylmethyloxy)-6-methoxy-3-methoxycarbonyl-4-(3,4,5-trimethoxyphenyl)-1(2H)-isoquinolinone (141 mg) as listed in Table 20.

(2) The compound thus obtained is treated in the same manner as in Example 24 to give 2-(4-aminophenyl)-7-carbamoylmethyloxy-6-methoxy-3-methoxy-carbonyl-4-(3,4,5-trimethoxyphenyl)-1(2H)-isoquinolinone hydrochloride as listed in Table 20.

EXAMPLE 277

(1) The compound obtained in Example 249-(1) is treated in the same manner as in Example 21 to give 2-[4-(tert-butoxycarbonylamino)phenyl]-7-(3-carboxybenzyloxy)-6-methoxy-3-methoxycarbonyl-4-(3,4,5-trimethoxyphenyl)-1(2H)-isoquinolinone as listed in Table 20, which is used in the subsequent reaction without further purification.

(2) The compound thus obtained is treated in the same manner as in Example 24 to give 2-(4-aminophenyl)-7-(3-carboxybenzyloxy)-methoxy-3-methoxycarbonyl-4-(3,4,5-trimethoxyphenyl)-1(2H)-isoquinolinone hydrochloride as listed in Table 20.

EXAMPLES 278–279

The compound obtained in Example 2 and the corresponding starting compounds are treated in the same manner as in Example 3 to give the following compounds as listed in Table 21.

6-methoxy-3-methoxycarbonyl-2-morpholino-7-(4-pyridylmethyloxy)-4-(3,4,5-trimethoxyphenyl)-1(2H)-isoquinolinone hydrochloride (Example 278);

6-methoxy-3-methoxycarbonyl-2-morpholino-7-(3-pyridylmethyloxy)-4-(3,4,5-trimethoxyphenyl)-1(2H)-isoquinolinone hydrochloride (example 279);

EXAMPLE 280

6-Benzyloxy-3-hydroxy-7-methoxy-4-(3,4,5-trimethoxyphenyl)-3-carboxylic acid (the compound obtained in Reference Example 72) and the corresponding starting compounds are treated in the same manner as in Example 4 or 31 to give 6-benzyloxy-2-[4-(tert-butoxycarbonylamino)phenyl]-7-methoxy-3-methoxycarbonyl-4-(3,4,5-trimethoxyphenyl)-1(2H)-isoquinolinone as listed in Table 22.

EXAMPLE 281

The compound obtained in Example 280 is treated in the same manner as in Example 5 to give 2-[4-(tert-butoxycarbonylamino)phenyl]-6-hydroxy-7-methoxy-3-methoxycarbonyl-4-(3,4,5-trimethoxyphenyl)-1(2H)-isoquinolinone as listed in Table 22.

EXAMPLES 282–283

The compounds obtained in Example 280–281 are treated in the same manner as in Example 6-(2) to give the following compounds as listed in Table 22.

2-(4-aminophenyl)-6-benzyloxy-7-methoxy-3-methoxycarbonyl-4-(3,4,5-trimethoxyphenyl)-1(2H)-isoquinolinone hydrochloride (Example 282);

2-(4-aminophenyl)-6-hydroxy-7-methoxy-3-methoxycarbonyl-4-(3,4,5-trimethoxyphenyl)-1(2H)-isoquinolinone hydrochloride (Example 283);

EXAMPLES 284–291

The compound obtained in Example 281 and the corresponding starting compounds are treated in the same manner as in Example 6 to give the following compounds as listed in Table 22.

2-[4-(tert-butoxycarbonylamino)phenyl]-7-methoxy-3-methoxycarbonyl-6-[2-(2-methoxyethyloxy)ethyloxy]-4-(3,4,5-trimethoxyphenyl)-1(2H)-isoquinolinone (Example 284 (1));

2-(4-aminophenyl)-7-methoxy-3-methoxycarbonyl-6-[2-(2-methoxyethyloxy)ethyloxy]-4-(3,4,5-trimethoxyphenyl)-1(2H)-isoquinolinone hydrochloride (Example 284 (2));

2-[4-tert-butoxycarbonylamino)phenyl]-6-ethoxy-7-methoxy-3-methoxycarbonyl-4-(3,4,5-trimethoxyphenyl)-1(2H)-isoquinolinone (Example 285 (1));

2-(4-aminophenyl)-6-ethoxy-7-methoxy-3-methoxycarbonyl-4-(3,4,5-trimethoxyphenyl)-1(2H)-isoquinolinone hydrochloride (Example 285 (2));

2-[4-(tert-butoxycarbonylamino)phenyl]-7-methoxy-3-methoxycarbonyl-6-(2-methoxyethyloxy)-4-(3,4,5-trimethoxyphenyl)-1(2H)-isoquinolinone (Example 286 (1));

2-(4-aminophenyl)-7-methoxy-3-methoxycarbonyl-6-(2-methoxyethyloxy)-4-(3,4,5-trimethoxyphenyl)-1(2H)-isoquinolinone hydrochloride (Example 286 (2));

2-[4-(tert-butoxycarbonylamino)phenyl]-6-(2-hydroxyethyloxy)-7-methoxy-3-methoxycarbonyl-4-(3,4,5-trimethoxyphenyl)-1(2H)-isoquinolinone (Example 287 (1));

2-(4-aminophenyl)-6-(2-hydroxyethyloxy)-7-methoxy-3-methoxycarbonyl-4-(3,4,5-trimethoxyphenyl)-1(2H)-isoquinolinone hydrochloride (Example 287 (2));

2-[4-(tert-butoxycarbonylamino)phenyl]-7-methoxy-3-methoxycarbonyl-6-(4-pyridylmethyloxy)-4-(3,4,5-trimethoxyphenyl)-1(2H)-isoquinolinone (Example 288 (1));

2-(4-aminophenyl)-7-methoxy-3-methoxycarbonyl-6-(4-pyridylmethyloxy)-4-(3,4,5-trimethoxyphenyl)-1(2H)-isoquinolinone dihydrochloride (Example 288 (2));

2-[4-(tert-butoxycarbonylamino)phenyl]-7-methoxy-3-methoxycarbonyl-6-(3-pyridylmethyloxy-4-(3,4,5-trimethoxyphenyl)-1(2H)-isoquinolinone (Example 289 (1));

2-(4-aminophenyl)-7-methoxy-3-methoxycarbonyl-6-(3-pyridylmethyloxy)-4-(3,4,5-trimethoxyphenyl)-1(2H)-isoquinolinone dihydrochloride (Example 289 (2));

2-[4-(tert-butoxycarbonylamino)phenyl]-7-methoxy-3-methoxycarbonyl-6-(2-pyridylmethyloxy)-4-(3,4,5-trimethoxyphenyl)-1(2H)-isoquinolinone (Example 290 (1));

2-(4-aminophenyl)-7-methoxy-3-methoxycarbonyl-6-(2-pyridylmethyloxy)-4-(3,4,5-trimethoxyphenyl)-1(2H)-isoquinolinone dihydrochloride (Example 290 (2));

2-[4-(tert-butoxycarbonylamino)phenyl]-6-cyclopentyloxy-7-methoxy-3-methoxycarbonyl-4-(3,4,5-trimethoxyphenyl)-1(2H)-isoquinolinone (Example 291 (1));

2-(4-aminophenyl)-6-cyclopentyloxy-7-methoxy-3-methoxycarbonyl-4-(3,4,5-trimethoxyphenyl)-1(2H)-isoquinolinone hydrochloride (Example 291 (2));

EXAMPLE 292

(1) The compound obtained in Example 281 and the corresponding starting compounds are treated in the same manner as in Example 7-(1) to give 2-[4-(tert-butoxycarbonylamino)phenyl]-7-methoxy-3-methoxycarbonyl-6-[(2-(2-pyridyl)ethyloxy]-4-(3,4,5-trimethoxyphenyl)-1(2H)-isoquinolinone as listed in Table 22.

(2) The compound thus obtained is treated in the same manner as in Example 7-(2) to give 2-(4-aminophenyl)-7-methoxy-3-methoxycarbonyl-6-[(2-(2-pyridyl)ethyloxy]-4-(3,4,5-trimethoxyphenyl)-1(2H)-isoquinolinone dihydrochloride as listed in Table 22.

EXAMPLES 293–294

6,7-Dimethoxy-4-(3,4-methylenedioxyphenyl)isocoumarin-3-carboxylic acid (the compound obtained in Reference Example 65) or 4-(3,4-dichlorophenyl)-6,7-dimethoxyisocoumarin-3-carboxylic acid (the compound obtained in Reference Example 62), and the corresponding starting compounds are treated in the same manner as in Example or 39 to give the following compounds as listed in Table 23.

6,7-dimethoxy-3-methoxycarbonyl-4-(3,4-methylenedioxyphenyl)-2-phenyl-1(2H)-isoquinolinone (Example 293);

4-(3,4-dichlorophenyl)-6,7-dimethoxy-3-methoxycarbonyl-2-phenyl-1(2H)-isoquinolinone Example 294);

EXAMPLE 295

The compound obtained in Example 202 is treated in the same manner as in Example 40 to give 2-(4-aminophenyl)-4-(3-bromo-4,5-dimethoxyphenyl)-6,7-dimethoxy-3-methoxycarbonyl-1(2H)-isoquinolinone hydrochloride as listed in Table 24.

EXAMPLE 296

4-(3-Bromo-4,5-dimethoxyphenyl)-6,7-dimethoxyisocoumarin-3-carboxylic acid (the compound obtained in Reference Example 60) and the corresponding starting compounds are treated in the same manner as in Example 1 or 39 to give 4-(3-bromo-4,5-dimethoxyphenyl)-6,7-dimethoxy-2-(6-1H-indazolyl)-3-methoxycarbonyl-1(2H)-isoquinolinone as listed in Table 24.

EXAMPLE 297

3-Hydroxy-4-(3,4,5-trimethoxyphenyl)-3,4-dihydroisocoumarin-3-carboxylic acid (the compound obtained in Reference Example 75) and the corresponding starting compounds are treated in the same manner as in Example 4 or 31 to give 2-(1-indolyl)-3-methoxycarbonyl-4-(3,4,5-trimethoxyphenyl)-1(2H)-isoquinolinone as listed in Table 24.

EXAMPLE 298

To a solution of the compound obtained in Example 67 (5.60 g) in methylene chloride (15 ml) is added trifluoroacetic acid (15 ml), and the mixture is allowed to stand at room temperature for three hours. After the reaction is complete, the reaction mixture is concentrated under reduced pressure. The resulting residue is dissolved in ethyl acetate, and extracted. The extract is washed, dried, and concentrated under reduced pressure. The resulting residue is crystallized from ethyl acetate to give 3-methoxycarbonyl-2-(trifluoroacetyl-amino)-4-(3,4,5-trimethoxyphenyl)-1(2H)-isoquinolinone as listed in Table 24.

EXAMPLE 299

4-(3,5-Dibromo-4-methoxyphenyl)-6,7-dimethoxy-3-hydroxy-3,4-dihydroisocoumarin-3-carboxylic acid (the compound obtained in Reference Example 86) and the corresponding starting compounds are treated in the same manner as in Example 4 or 31 to give 4-(3,5-dibromo-4-methoxyphenyl)-6,7-dimethoxy-3-methoxycarbonyl-2-phenyl-1(2H)-isoquinolinone as listed in Table 24.

EXAMPLES 300–308

The compound obtained in Example 8-(2) and the corresponding starting compounds are treated in the same manner as in Example 9 to give the following compounds as listed in Table 25.

2-(4-aminophenyl)-7-(4-aminobenzyloxy)-6-methoxy-3-methoxycarbonyl-4-(3,4,5-trimethoxyphenyl)-1(2H)-isoquinolinone dihydrochloride (Example 300);

2-(4-aminophenyl)-6-methoxy-3-methoxycarbonyl-7-(3,4-methylenedioxybenzyloxy)-4-(3,4,5-trimethoxyphenyl)-1(2H)-isoquinolinone hydrochloride (Example 301);

2-(4-aminophenyl)-7-(2,4-dimethoxybenzyloxy)-6-methoxy-3-methoxycarbonyl-4-(3,4,5-trimethoxyphenyl)-1(2H)-isoquinolinone hydrochloride (Example 302);

2-(4-aminophenyl)-7-(2,5-dimethoxybenzyloxy)-6-methoxy-3-methoxycarbonyl-4-(3,4,5-trimethoxyphenyl)-1(2H)-isoquinolinone hydrochloride (Example 303);

2-(4-aminophenyl)-7-(3,5-dimethoxybenzyloxy)-6-methoxy-3-methoxycarbonyl-4-(3,4,5-trimethoxyphenyl)-1(2H)-isoquinolinone hydrochloride (Example 304);

2-(4-aminophenyl)-7-(3,4-dimethoxybenzyloxy)-6-methoxy-3-methoxycarbonyl-4-(3,4,5-trimethoxyphenyl)-1(2H)-isoquinolinone hydrochloride (Example 305);

2-(4-aminophenyl)-7-(2,3-dimethoxybenzyloxy)-6-methoxy-3-methoxycarbonyl-4-(3,4,5-trimethoxyphenyl)-1(2H)-isoquinolinone hydrochloride (Example 306);

2-(4-aminophenyl)-6-methoxy-3-methoxycarbonyl-7(-methoxybenzyloxy)-4-(3,4,5-trimethoxyphenyl)-1(2H)-isoquinolinone hydrochloride (Example 307);

2-(4-aminophenyl)-6-methoxy-3-methoxycarbonyl-7-(4-methoxybenzyloxyl-4-(3,4,5-trimethoxyphenyl)-1(2H)-isoquinolinone hydrochloride (Example 308);

EXAMPLES 309–316

The compound obtained in Example 223 and the corresponding starting compounds are treated in the same manner as in Example 6 or 7 to give the following compounds as listed in Table 26.

2-(4-aminophenyl)-7-(2-benzimidazolylmethyloxy)-3-methoxycarbonyl-4-(3,4,5-trimethoxyphenyl)-1(2H)-isoquinolinone dihydrochloride (Example 309);

2-(4-aminophenyl)-3-methoxycarbonyl-7-(4-methylphenylsulfonyloxy)-4-(3,4,5-trimethoxyphenyl)-1(2H)-isoquinolinone hydrochloride (Example 310);

2-[4-(tert-butoxycarbonylamino)phenyl]-3-methoxycarbonyl-7-(4-pyridylmethyloxy)-4-(3,4,5-trimethoxyphenyl)-1(2H)-isoquinolinone (Example 311 (1));

2-(4-aminophenyl)-3-methoxycarbonyl-7-(4-pyridylmethyloxy)-4-(3,4,5-trimethoxyphenyl)-1(2H)-isoquinolinone dihydrochloride (Example 311 (2));

2-[4-(tert-butoxycarbonylamino)phenyl]-3-methoxycarbonyl-7-(3-pyridylmethyloxy)-4-(3,4,5-trimethoxyphenyl)-1(2H)-isoquinolinone (Example 312 (1));

2-(4-aminophenyl)-3-methoxycarbonyl-7-(3-pyridylmethyoxy)-4-(3,4,5-trimethoxyphenyl)-1(2H)-isoquinolinone dihydrochloride (Example 312 (2));

2-[4-(tert-butoxycarbonylamino)phenyl]-3-methoxycarbonyl-7-(2-pyridylmethyloxy)-4-(3,4,5-trimethoxyphenyl)-1(2H)-isoquinolinone (Example 313 (1));

2-(4-aminophenyl)-3-methoxycarbonyl-7-(2-pyridylmethyloxy)-4-(3,4,5-trimethoxyphenyl)-1(2H)-isoquiolinone dihydrochloride (Example 313 (2));

2-(4-aminophenyl)-3-methoxycarbonyl-7-(4-nitrobenzyloxy)-4-(3,4,5-trimethoxyphenyl)-1(2H)-isoquinolinone hydrochloride (Example 314);

2-(4-aminophenyl)-3-methoxycarbonyl-7-(3-nitrobenzyloxy)-4-(3,4,5-trimethoxyphenyl)-1(2H)-isoquinolinone hydrochloride (Example 315);

2-(4-aminophenyl)-3-methoxycarbonyl-7-(2-nitrobenzyloxy)-4-(3,4,5-trimethoxyphenyl)-1(2H)-isoquinolinone hydrochloride (Example 316);

EXAMPLE 317

7-Benzyloxy-4-(4-bromo-3,5-dimethoxyphenyl)-6-methoxy-3,4-dihydroisocoumarin-3-carboxylic acid (the compound obtained in Reference Example 102) and the corresponding starting compounds are treated in the same manner as in Example 4 or 31 to give 7-benzyloxy4-(4-bromo-3,5-dimethoxyphenyl)-2-[4-(tert-butoxycarbonyl-amino)phenyl]-6-methoxy-3-methoxycarbonyl-1(2H)-isoquinolinone as listed in Table 27.

EXAMPLE 318

The compound obtained in Example 317 is treated in the same manner as in Example 24 to give 2-(4-aminophenyl)-7-benzyloxy-4-(4-bromo-3,5-dimethoxyphenyl)-6-methoxy-3-methoxycarbonyl-1(2H)-isoquinolinone hydrochloride as listed in Table 27.

EXAMPLE 319

(1) The compound obtained in Example 317 (3.66 g) is dissolved in 1,4-dioxane (45 ml), and thereto are added conc. hydrochloric acid (50 ml) and methanol (5 ml). The mixture is heated with stirring at 90° C. for 1.5 hour. To the mixture is added gradually a 2M aqueous sodium hydroxide solution (200 ml) under ice-cooling, and the mixture is neutralized with a saturated aqueous sodium hydrogen carbonate solution. The mixture is extracted with ethyl acetate, and the extract is washed, dried, and concentrated under reduced pressure. The residue is crystallized from diethyl ether to give 2-(4-aminophenyl)-4-(4-bromo-3,5-dimethoxyphenyl)-7-hydroxy-6-methoxy-3-methoxycarbonyl-1(2H)-isoquinolinone (2.54 g) as listed in Table 27.

(2) The compound thus obtained is reacted in the same manner as in Example 9-(3) to give 2-(4-aminophenyl)-4-(4-bromo-3,5-dimethoxyphenyl)-7-hydroxy-6-methoxy-3-methoxycarbonyl-1(2H)-isoquinolinone hydrochloride as listed in Table 27.

EXAMPLE 320

A mixture of the compound obtained in Example 319-(1) (400 mg), 4-picolyl chloride hydrochloride (120 mg) and potassium carbonate (252 mg) in dimethylformamide (15 ml) is heated with stirring at 60° C. for three hours. To the mixture is added water, and the mixture is extracted with ethyl acetate. The ethyl acetate layer is washed, dried, and concentrated under reduced pressure. The residue is crystallized from ethyl acetate, and the resulting crystals are dissolved in a mixture of chloroform (20 ml) and methanol (5 ml). To the mixture is added a 4M solution of hydrogen chloride in ethyl acetate (5 ml), and the mixture is crystallized from diethyl ether to give 2-(4-aminophenyl)-4-(4-bromo-3,5-dimethoxyphenyl)-6-ethoxy-3-ethoxycarbonyl-7-(4-pyridylmethyloxy)-1(2H)-isoquinolinone dihydrochloride (328 mg) as listed in Table 27.

EXAMPLES-321–323

The compound obtained in Example 319-(1) and the corresponding starting compounds are treated in the same manner as in Example 320 to give the following compounds as listed in Table 27.

2-(4-aminophenyl)-4-(4-bromo-3,5-dimethoxyphenyl)-6-methoxy-3-methoxycarbonyl-7-(3-pyridylmethyloxy)-1(2H)-isoquinolinone dihydrochloride (Example 321);

2-(4-aminophenyl)-4-(4-bromo-3,5-dimethoxyphenyl)-6-methoxy-3-methoxycarbonyl-7-(2-pyridylmethyloxy)-1(2H)-isoquinolinone dihydrochloride (Example 322);

2-(4-aminophenyl)-4-(4-bromo-3,5-dimethoxyphenyl)-6-methoxy-3-methoxycarbonyl-7-(2-quinolylmethyloxy)-1(2H)-isoquinolinone dihydrochloride (Example 323);

EXAMPLE 324

7-Benzyloxy-4-(3,4,5-trimethoxyphenyl)isocoumarin-3-carboxylic acid (the compound obtained in Reference Example 67) and the corresponding starting compounds are treated in the same manner as in Example 1 or 39 to give 7-benzyloxy-3-methoxycarbonyl-2-morpholino-4-(3,4,5-trimethoxyphenyl)-1(2H)-isoquinolinone as listed in Table 28.

EXAMPLE 325

The compound obtained in Example 324 is treated in the same manner as in Example 2 to give 7-hydroxy-3-methoxycarbonyl-2-morpholino-4-(3,4,5-trimethoxyphenyl)-1(2H)-isoquinolinone as listed in Table 28.

EXAMPLES 326–328

The compound obtained in Example 325 and the corresponding starting compounds are treated in the same manner as in Example 6 or 7 to give the following compounds as listed in Table 28.

3-methoxycarbonyl-2-morpholino-7-(2-pyridylmethyloxy)-4-(3,4,5-trimethoxyphenyl)-1(2H)-isoquinolinone hydrochloride (Example 326);

3-methoxycarbonyl-2-morpholino-7-(3-pyridylmethyloxy)-4-(3,4,5-trimethoxyphenyl)-1(2H)-isoquinolinone hydrochloride (Example 327);

3-methoxycarbonyl-2-morpholino-7-(4-pyridylmethyloxy)-4-(3,4,5-trimethoxyphenyl)-1(2H)-isoqunolinone hydrochloride (Example 328);

EXAMPLES 329–333

The compound obtained in Example 5 and the corresponding starting compounds are treated in the same manner as in Example 6 or 7 to give the following compounds as listed in Table 29.

2-(4-aminophenyl)-6-methoxy-3-methoxycarbonyl-7-[(4-methyl)-imidazol-5-yl-methyloxy]-4-(3,4,5-trimethoxyphenyl)-1(2H)-isoquinolinone (Example 329);

2-[4-(tert-butoxycarbonylamino)phenyl]-7-cyclopropylmethyloxy-6-methoxy-3-methoxycarbonyl-4-(3,4,5-trimethoxyphenyl)-1(2H)-isoquinolinone (Example 330-(1));

2-(4-aminophenyl)-7-cyclopropylmethyloxy-6-methoxy-3-methoxycarbonyl-4-(3,4,5-trimethoxyphenyl)-1(2H)-isoquinolinone hydrochloride 5 (Example 330-(2));

2-(4-aminophenyl)-7-[(2-hydroxymethyl)pyridin-6-ylmethyloxy]-6-methoxy-3-methoxycarbonyl-4-(3,4,5-trimethoxyphenyl)-1(2H)-isoquinolinone dihydrochloride (Example 331);

2-(4-aminophenyl)-7-(3,5-diaminobenzyloxy)-6-methoxy-3-methoxycarbonyl-4-(3,4,5-trimethoxyphenyl)-1(2H)-isoquinolinone trihydrochloride (Example 332);

2-(4-aminophenyl)-7-(2-benzimidazolylmethyloxy)-6-methoxy-3-methoxycarbonyl-4-(3,4,5-trimethoxyphenyl)-1(2H)-isoquinolinone trihydrochloride (Example 333).

EXAMPLE 334

3-Hydroxy-4-(3,4,5-trimethoxyphenyl)-3,4-dihydroisocoumarin-3-carboxylic acid (the compound obtained in Reference Example 75) and the corresponding starting compounds are treated in the same manner as in Example 4 or 31 to give 2-[4-(2,6-dioxo)piperidyl]-3-methoxycarbonyl-4-(3,4,5-trimethoxyphenyl)-1(2H)-isoquinolinone as listed in Table 30.

EXAMPLE 335

8-Benzyloxy-3-hydroxy-4-(3,4,5-trimethoxyphenyl)-3,4-dihydroisocoumarin-3-carboxylic acid (the compound obtained in Reference Example 79) and the corresponding starting compounds are treated in the same manner as in Example 4 or 31 to give 8-benzyloxy-2-[4-(tert-butoxycarbonylamino)phenyl]-3-methoxycarbonyl-4-(3,4,5-trimethoxyphenyl)-1(2H)-isoquinolinone as listed in Table 30.

EXAMPLE 336

A solution of the compound obtained in Example 335 (53 mg) in chloroform (4 ml) is cooled to 0° C., and thereto is added a 4M solution of hydrogen chloride in ethyl acetate (2 ml). The mixture is stirred at 0° C. for two hours, and thereto is added a saturated aqueous sodium hydrogen carbonate solution, and the mixture is extracted with ethyl acetate. The extract is washed, dried, and concentrated under reduced pressure. The residue is purified by silica gel column chromatography (solvent; hexane:ethyl acetate=1:2) to give 2-(4-aminophenyl)-8-benzyloxy-3-methoxycarbonyl-4-(3,4,5-trimethoxyphenyl)-1(2H)-isoquinolinone (20 mg) as listed in Table 30.

EXAMPLE 337

The compound obtained in Example 336 is treated in the same manner as in Example 24 to give 2-(4-aminophenyl)-8-hydroxy-3-methoxycarbonyl-4-(3,4,5-trimethoxyphenyl)-1(2H)-isoquinolinone hydrochloride as listed in Table 30.

EXAMPLE 338

7-Benzyloxy-4-(4-bromo-3,5-dimethoxyphenyl)-3-hydroxy-3,4-dihydroisocoumarin-3-carboxylic acid (the compound obtained in Reference Example 104) and the corresponding starting compounds are treated in the same manner as in Example 4 or 31 to give 7-benzyloxy-2-[4-(tert-butoxycarbonylamino)phenyl]-4-(4-bromo-3,5-dimethoxyphenyl)-3-methoxycarbonyl-1(2H)-isoquinolinone as listed in Table 31.

EXAMPLE 339

The compound obtained in Example 338 is treated in the same manner as in Example 24 to give 2-(4-aminophenyl)-7-benzyloxy-4-(4-bromo-3,5-dimethoxyphenyl)-3-methoxycarbonyl-1(2H)-isoquinolinone hydrochloride as listed in Table 31.

EXAMPLE 340

(1) The compound obtained in Example 338 is treated in the same manner as in Example 319-(1) to give 2-(4-aminophenyl)-4-(4-bromo-3,5-dimethoxyphenyl)-7-hydroxy-3-methoxycarbonyl-1(2H)-isoquinolinone as listed in Table 31.

(2) The compound thus obtained is treated in the same manner as in Example 319-(2) to give 2-(4-aminophenyl)-4-(4-bromo-3,5-dimethoxyphenyl)-7-hydroxy-3-methoxycarbonyl-1(2H)-isoquinolinone hydrochloride as listed in Table 31.

EXAMPLE 341

7-Benzyloxy-3-hydroxy-4-(3,4,5-trimethoxyphenyl)-3,4-dihydroisocoumarin-3-carboxylic acid (the compound obtained in Reference Example 73) and the corresponding starting compounds are treated in the same manner as in Example 4 or 31 to give 7-benzyloxy-3-methoxycarbonyl-2-phenyl-4-(3,4,5-trimethoxyphenyl)-1(2H)-isoquinolinone as listed in Table 32.

EXAMPLE 342

The compound obtained in Example 341 is treated in the same manner as, in Example 2 to give 7-hydroxy-3-methoxycarbonyl-2-phenyl-4-(3,4,5-trimethoxyphenyl)-1(2H)-isoquinolinone as listed in Table 32.

EXAMPLE 343–347

The compound obtained in Example 342 and the corresponding starting compounds are treated in the same manner as in Example 6 or 7 to give the following compounds as listed in Table 32.

3-methoxycarbonyl-2-phenyl-7-(2-quinolylmethyloxy)-4-(3,4,5-trimethoxyphenyl)-1(2H)-isoquinolinone hydrochloride (Example 343);

3-methoxycarbonyl-2-phenyl-7-(4-quinolylmethyloxy)-4-(3,4,5-trimethoxyphenyl)-1(2H)-isoquinolinone hydrochloride (Example 344);

3-methoxycarbonyl-2-phenyl-7-(4-pyridylmethyloxy)-4-(3,4,5-trimethoxyphenyl)-1(2H)-isoquinolinone hydrochloride (Example 345);

3-methoxycarbonyl-2-phenyl-7-(3-pyridylmethyloxy)-4-(3,4,5-trimethoxyphenyl)-1(2H)-isoquinolinone hydrochloride (Example 346);

3-methoxycarbonyl-2-phenyl-7-(2-pyridylmethyloxy)-4-(3,4,5-trimethoxyphenyl)-1(2H)-isoquinolinone hydrochloride (Example 347);

EXAMPLE-348

The corresponding starting compounds are treated in the same manner as in Example 3 to give 3-methoxycarbonyl-2-morpholino-7-(2-quinolylmethyloxy)-4-(3,4,5-trimethoxyphenyl)-1(2H)-isoquinolinone hydrochloride as listed in Table 33.

EXAMPLES 349–352

The corresponding staring compounds are treated in the same manner as in Example 9 to give the following compounds as listed in Table 34.

2-(4-aminophenyl)-7-(3-dimethylaminobenzyloxy)-3-methoxycarbonyl-4-(3,4,5-trimethoxyphenyl)-1(2H)-isoquinolinone dihydrochloride (Example 349);

2-(4-aminophenyl)-3-methoxycarbonyl-7-pyrazinylmethyloxy-4-(3,4,5-trimethoxyphenyl)-1(2H)-isoquinolinone dihydrochloride (Example 350);

2-(4-aminophenyl)-7-(3,5-dimethoxybenzyloxy)-3-methoxycarbonyl-4-(3,4,5-trimethoxyphenyl)-1(2H)-isoquinolinone hydrochloride (Example 351);

2-(4-aminophenyl)-7-(2,5-dimethoxybenzyloxy)-3-methoxycarbonyl-4-(3,4,5-trimethoxyphenyl)-1(2H)-isoquinolinone hydrochloride (Example 352);

EXAMPLE 353

7-Benzyloxy-4-(4-chloro-3,5-dimethoxyphenyl)-3-hydroxy-3,4-dihydroisocoumarin-3-carboxylic acid (the compound obtained in Reference Example 105) and the corresponding starting compounds are treated in the same manner as in Example 4 or 31 to give 7-benzyloxy-2-[4-(tert-butoxycarbonylamino)-phenyl]-4-(4-chloro-3,5-dimethoxyphenyl)-3-methoxycarbonyl-1(2H)-isoquinolinone, which is further treated in the same manner as in Example 24 to give 2-(4-aminophenyl)-7-benzyloxy-4-(4-chloro-3,5-dimethoxyphenyl)-3-methoxycarbonyl-1(2H)-isoquinolinone hydrochloride as listed in Table 35.

EXAMPLE 354

The compound obtained in Example 353 is treated in the same manner as in Example 319-(1) to give 2-(4-aminophenyl)-4-(4-chloro-3,5-dimethoxyphenyl)-7-hydroxy-3-methoxycarbonyl-1(2H)-isoquinolinone as listed in Table 35.

EXAMPLES 355–358

The compound obtained in Example 354 and the corresponding starting compounds are treated in the same manner as in Example 320 or Example 9 (1) and (3), to give the following compounds as listed in Table 35.

2-(4-aminophenyl)-4-(4-chloro-3,5-dimethoxyphenyl)-3-methoxycarbonyl-7-(2-pyridylmethyloxy)-1(2H)-isoquinolinone dihydrochloride (Example 355);

2-(4-aminophenyl)-4-(4-chloro-3,5-dimethoxyphenyl)-3-methoxycarbonyl-7-(3-pyridylmethyloxy)-1(2H)-isoquinolinone dihydrochloride (Example 356);

2-(4-aminophenyl)-4-(4-chloro-3,5-dimethoxyphenyl)-3-methoxycarbonyl-7-(4-pyridylmethyloxy)-1(2H)-isoquinolinone dihydrochloride (Example 357);

2-(4-aminophenyl)-4-(4-chloro-3,5-dimethoxyphenyl)-3-methoxycarbonyl-7-(2-quinolylmethyloxy)-1(2H)-isoquinolinone dihydrochloride (Example 358),

EXAMPLES 359–364

The compound obtained in Example 340 (1) and the corresponding starting compounds are treated in the same manner as in Example 320, or Example 9 (1) and (3), to give the following compounds as listed in Table 35.

2-(4-aminophenyl)-4-(4-bromo-3,5-dimethoxyphenyl)-3-methoxycarbonyl-7-(2-pyridylmethyloxy)-1(2H)-isoquinolinone dihydrochloride (Example 359);

2-(4-aminophenyl)-4-(4-bromo-3,5-dimethoxyphenyl)-3-methoxycarbonyl-7-(3-pyridylmethyloxy)-1(2H)-isoquinolinone dihydrochloride (Example 360);

2-(4-aminophenyl)-4-(4-bromo-3,5-dimethoxyphenyl)-3-methoxycarbonyl-7-(4-pyridylmethyloxy)-1(2H)-isoquinolinone dihydrochloride (Example 361);

2-(4-aminophenyl)-4-(4-bromo-3,5-dimethoxyphenyl)-3-methoxycarbonyl-7-(2-quinolylmethyloxy)-1(2H)-isoquinolinone dihydrochloride (Example 362);

2-(4-aminophenyl)-4-(4-bromo-3,5-dimethoxyphenyl)-7-(3,5-dimethoxybenzyloxy)-3-methoxycarbonyl-1(2H)-isoquinolinone hydrochloride (Example 363);

7-(3-aminobenzyloxy)-2-(4-aminophenyl)-4-(4-bromo-3,5-dimethoxyphenyl)-3-methoxycarbonyl-1(2H)-isoquinolinone dihydrochloride (Example 364);

EXAMPLES 365–366

The compound obtained in Example 319 (1) and the corresponding starting compounds are treated in the same manner as in Example 9 (1) and (3) to give the following compounds as listed in Table 37.

2-(4-aminophenyl)-4-(4-bromo-3,5-dimethoxyphenyl)-7-(3,5-dimethoxybenzyloxy)-6-methoxy-3-methoxycarbonyl-1(2H)-isoquinolinone hydrochloride (Example 365);

2-(4-aminophenyl)-4-(4-bromo-3,5-dimethoxyphenyl)-7-(2,5-dimethoxybenzyloxy)-6-methoxy-3-methoxycarbonyl-1(2H)-isoquinolinone hydrochloride (Example 366);

EXAMPLE 367

The compound obtained in Example 319 (1) and the corresponding starting compounds are treated in the same manner as in Example 320 to give 2-(4-aminophenyl)-4-(4-bromo-3,5-dimethoxyphenyl)-7-cyanomethyloxy-6-methoxy-3-methoxycarbonyl-1(2H)-isoquinolinone hydrochloride as listed in Table 37.

EXAMPLE 368

The compound obtained in Example 319 (1) and the corresponding starting compounds are treated in the same manner as in Example 9 (1) and (3) to give 2-(4-aminophenyl)-4-(4-bromo-3,5-dimethoxyphenyl)-7-(1-isoquinolylmethyloxy)-6-methoxy-3-methoxycarbonyl-1(2H)-isoquinolinone dihydrochloride as listed in Table 37.

EXAMPLE 369

A suspension of the compound obtained in Example 224 in chloroform is neutralized with a 2M aqueous sodium hydroxide solution under ice-cooling, and the mixture is extracted with ethyl acetate. The extract is washed, dried, and concentrated under reduced pressure. The residue is dissolved in a small amount of ethyl acetate, and the mixture is crystallized from diethyl ether to give 2-(4-aminophenyl)-7-hydroxy-3-methoxycarbonyl-4-(3,4,5-trimethoxyphenyl)-1(2H)-isoquinolinone as listed in Table 38.

EXAMPLE 370

The compound obtained in Example 369 is treated in the same manner as in Example 8-(2) to give 2-[4-(9-fluorenylmethyloxycarbonylamino)phenyl]-7-hydroxy-3-methoxycarbonyl-4-(3,4,5-trimethoxyphenyl)-1(2H)-isoquinolinone as listed in Table 38.

EXAMPLES 371–374

The compound obtained in Example 223 and the corresponding starting compounds are treated in the same manner as in Example 6 or 7 to give the following compounds as listed in Table 38.

2-(4-aminophenyl)-7-(3,5-diaminobenzyloxy)-3-methoxycarbonyl-4-(3,4,5-trimethoxyphenyl)-1(2H)-isoquinolinone trihydrochloride (Example 371);

2-(4-aminophenyl)-7-(6-hydroxymethyl-2-pyridylmethyloxy)-3-methoxycarbonyl-4-(3,4,5-trimethoxyphenyl)-1(2H)-isoquinolinone dihydrochloride (Example 372);

2-[4-(tert-butoxycarbonylamino)phenyl]-7-(4-methoxycarbonylbenzyloxy)-3-methoxycarbonyl-4-(3,4,5-trimethoxyphenyl)-1(2H)-isoquinolinone (Example 373-(1));

2-(4-aminophenyl)-7-(4-methoxycarbonylbenzyloxy)-3-methoxycarbonyl-4-(3,4,5-trimethoxyphenyl)-1(2H)-isoquinolinone hydrochloride (Example 373-(2));

2-[4-(tert-butoxycarbonylamino)phenyl]-7-(3-methoxycarbonylbenzyloxy)-3-methoxycarbonyl-4-(3,4,5-trimethoxyphenyl)-1(2H)-isoquinolinone (Example 374);

EXAMPLES 375–376

The compound obtained in Example 373-(1) or 374 is treated in the same manner as in Example 21-(1) and Example 6-(2) to give the following compounds as listed in Table 38.

2-[4-(tert-butoxycarbonylamino)phenyl]-7-(4-carboxybenzyloxy)-3-methoxycarbonyl-4-(3,4,5-trimethoxyphenyl)-1(2H)-isoquinolinone (Example 375-0));

2-(4-aminophenyl)-7-(4-carboxybenzyloxy)-3-methoxycarbonyl-4-(3,4,5-trimethoxyphenyl)-1(2H)-isoquinolinone hydrochloride (Example 375(2));

2-[4-(tert-butoxycarbonylamino)phenyl]-7-(3-carboxybenzyloxy)-3-methoxycarbonyl-4-(3,4,5-trimethoxyphenyl)-1(2H)-isoquinolinone (Example 376-(1));

2-(4-aminophenyl)-7-(3-carboxybenzyloxy)-3-methoxycarbonyl-4-(3,4,5-trimethoxyphenyl)-1(2H)-isoquinolinone hydrochloride (Example 376(2));

EXAMPLES 377–378

The compound obtained in Example 375-(1) or 376-(1), and the corresponding starting compounds are treated in the same manner as in Example 129 and 6 (2) to give the following compounds as listed in Table 39.

2-(4-aminophenyl)-3-methoxycarbonyl-7-[4-(4-methylpiperazinyl-carbonyl)benzyloxyl-4-(3,4,5-trimethoxyphenyl)-1(2H)-isoquinolinone dihydrochloride (Example 377);

2-(4-aminophenyl)-3-methoxycarbonyl-7-[3-(4-methylpiperazinyl-carbonyl)benzyloxyl-4-(3,4,5-trimethoxyphenyl)-1(2H)-isoquinolinone dihydrochloride (Example 378);

EXAMPLES 379–382

The compound obtained in Example 369 and the corresponding starting compounds are treated in the same manner as in Example 9-(1), and the product thus obtained is further treated in the same manner as in Example 943) to give the following compounds as listed in Table39.

2-(4-aminophenyl)-3-methoxycarbonyl-7-[3-(methylamino)benzyloxy]-4-(3,4,5-trimethoxy-phenyl)-1(2H)-isoquinolinone dihydrochloride (Example 379);

2-(4-aminophenyl)-7-(2-hydroxymethylbenzyloxy)-3-methoxycarbonyl-4-(3,4,5-trimethoxyphenyl)-1(2H)-isoquinolinone hydrochloride (Example 380);

2-(4-aminophenyl)-7-(3-hydroxymethylbenzyloxy)-3-methoxycarbonyl-4-(3,4,5-trimethoxyphenyl)-1(2H)-isoquinolinone hydrochloride (Example 381);

2-(4-aminophenyl)-7-(4-hydroxymethylbenzyloxy)-3methoxycarbonyl-4-(3,4,5-trimethoxyphenyl)-1(2H)-isoquinolinone hydrochloride (Example 382);

EXAMPLE 383

The compound obtained in Example 312-(2) is treated in the same manner as in Example 69 to give 2-[4-(acetylamino)phenyl]-3-methoxy-carbonyl-7-(2-pyridylmethyloxy)-4-(3,4,5-trimethoxyphenyl)-1(2H)-isoquinolinone as listed in Table 40.

EXAMPLE 384

(1) The compound obtained in Example 313-(1) is treated in the same manner as in Example 273 to give 2-[4-(tert-butoxycarbonylamino)phenyl]-3-methoxycarbonyl-7-(N-oxo-2-pyridylmethyloxy)-4-(3,4,5-trimethoxyphenyl)-1(2H)-isoquinolinone as listed in Table 40.

(2) The compound thus obtained is treated in the same manner as in Example 6-(2), and the product thus obtained is further treated in the same manner as in Example 369 to give 2-(4-aminophenyl)-3-methoxycarbonyl-7-(N-oxo-2-pyridylmethyloxy)-4-(3,4,5-trimethoxyphenyl)-1(2H)-isoquinolinone as listed in Table 40.

EXAMPLES 385–386

The compound obtained in Example 325 and the corresponding starting compounds are treated in the same manner as in Example 6 or 7 to give the following compounds as listed in Table 40.

7-(3-aminobenzyloxy)-3-methoxycarbonyl-2-morpholino-4-(3,4,5-trimethoxyphenyl)-1(2H)-isoquinolinone hydrochloride (Example 385);

7-(2-benzimidazolylmethyloxy)-3-methoxycarbonyl-2-morpholino-4-(3,4,5-trimethoxyphenyl)-1(2H)-isoquinolinone (Example 386);

EXAMPLE 387

The compound obtained in Example 335 is treated in the same manner as in Example 8-(1) to give 2-(4-aminophenyl)-8-hydroxy-3-methoxycarbonyl-4-(3,4,5-trimethoxyphenyl)-1(2H)-isoquinolinone as listed in Table 41.

EXAMPLES 388–392

The compound obtained in Example 387 is treated in the same manner as in Example 6 to give the following compounds as listed in Table 41.

2-(4-aminophenyl)-3-methoxycarbonyl-8-(2-pyridylmethyloxy)-4-(3,4,5-trimethoxyphenyl)1(2H)-isoquinolinone dihydrochloride (Example 388);

2-(4-aminophenyl)-3-methoxycarbonyl-8-(3-pyridylmethyloxy)-4-(3,4,5-trimethoxyphenyl)-1(2H)-isoquinolinone dihydrochloride (Example 389);

2-(4-aminophenyl)-3-methoxycarbonyl-8-(4-pyridylmethyloxy)-4-(3,4,5-trimethoxyphenyl)-1(2H)-isoquinolinone dihydrochloride (Example 390);

2-(4-aminophenyl)-3-methoxycarbonyl-8-(2-quinolylmethyloxy)-4-(3,4,5-trimethoxyphenyl)-1(2H)-isoquinolinone dihydrochloride (Example 391);

2-(4-aminophenyl)-3-methoxycarbonyl-8-(phenylethyloxy)-4-(3,4,5-trimethoxyphenyl)-1(2H)-isoquinolinone hydrochloride (Example 392);

EXAMPLE 393

The compound obtained in Example 369 and the corresponding starting compounds are treated in the same manner as in Example 7 to give 2-(4-aminophenyl)-7-(4-imidazolylmethyloxy)-3-methoxycarbonyl-4-(3,4,5-trimethoxy-phenyl)-1(2H)-isoquinolinone dihydrochloride as listed in Table 41.

EXAMPLE 394

The compound obtained in Example 382 (300 mg) and triethylamine (0.36 ml) is dissolved in dichloromethane (5 ml), and methanesulfonyl chloride (0.084 ml) is added dropwise thereto under ice-cooling After 12 hours, the reaction mixture is poured into water, and extracted with dichloromethane. The extract is washed, dried, and concentrated under reduced pressure. The residue is dissolved in dimethylformamide (5 ml) and thereto is added sodium bisformylamide (285 mg), and then the mixture is stirred for 12 hours at room temperature. The reaction mixture is poured into water, and extracted with ethyl acetate. The extract is washed, dried, and concentrated under reduced pressure. To the residue are added ethanol (5 ml) and conc. hydrochloric acid solution (1 ml), and the mixture is stirred for 12 hours at room temperature. The reaction mixture is poured into a saturated aqueous sodium hydrogen carbonate solution, and extracted with chloroform. The extract is washed, dried, and concentrated under reduced pressure. The residue is purified by silica gel column chromatography (solvent; chloroform:acetone=3:1) to give 7-(4-aminomethylbenzyloxy)-2-(4-methanesulfonylamino-phenyl)-3-methoxycarbonyl-4-(3,4,5-trimethoxyphenyl)-1(2H)-isoquinolinone (108 mg) as listed in Table 41.

EXAMPLES 395–398

The compound obtained in Example 354 and the corresponding staring compounds are treated in the same manner as in Example 320 or 9-(1), and the product thus obtained is further treated in the same manner as in Example 9-(3) to give the following compounds as listed in Table 42.

2-(4-aminophenyl)-7-(2-benzimidazolylmethyloxy)-4-(4-chloro-3,5-dimethoxyphenyl)-3-methoxycarbonyl)-1(2H)-isoquinolinone dihydrochloride (Example 395);

2-(4-aminophenyl)-4-(4-chloro-3,5-dimethoxyphenyl)-7-(3,5-dimethoxy-benzyloxy)-3-methoxycarbonyl-1(2H)-isoquinolinone hydrochloride (Example 396);

2-(4-aminophenyl)-4-(4-chloro-3,5-dimethoxyphenyl)-7-(6-hydroxy-methyl-2-pyridylmethyloxy)-3-methoxycarbonyl-1(2H)-isoquinolinone dihydrochloride (Example 397);

2-(4-aminophenyl)-4-(4-chloro-3,5-dimethoxyphenyl)-3-methoxycarbonyl-7-pyrazinylmethyloxy-1(2H)-isoquinolinone dihydrochloride (Example 398);

EXAMPLE 399

The compound obtained in Example 319-(1) and the corresponding starting compounds are treated in the same manner as in Example 9-(1), and the product thus obtained is further treated in the same manner as in Example 9-(3) to give 2-(4-aminophenyl)-4-(4-bromo-3,5-dimethoxyphenyl-7-(2-furylmethyl-oxy)-6-methoxy-3-methoxycarbonyl-1(2H)-isoquinolinone hydrochloride as listed in Table 43.

EXAMPLE 400

7-Benzyloxy-3-hydroxy-6-methoxy-4-(3,5-dimethoxy)-4-methyl-phenyl)-3,4-dihydroisocoumarin-3-carboxylic acid (the compound obtained in Reference Example 103) is treated in the same manner as in Example 4 to give 7-benzyloxy-2-[4-(tert-butoxycarbonylamino)phenyl]-methoxy-3-methoxy-carbonyl-4-(3,5-dimethoxy-4-methylphenyl)-1(2H)-isoquinolinone hydrochloride as listed in Table 43.

EXAMPLES 401

The compound obtained in Example 400 is treated in the same manner as in Example 6-(2) to give 2(4-aminophenyl)-7-benzyloxy-6-methoxy-3-methoxycarbonyl-4-(3,5-dimethoxy-4-methylphenyl)-1(2H)-isoquinolinone hydrochloride as listed in Table 43.

EXAMPLE 402

The compound obtained in Example 400 is treated in the same manner as in Example 6 to give 2-[4-(tert-butoxycarbonylamino)phenyl]-7-hydroxy-6methoxy-3-methoxycarbonyl-4-(3,5-dimethoxy-4-methylphenyl)-1(2H)-isoquinolinone as listed in Table 43.

EXAMPLE 403

The compound obtained in Example 402 is treated in the same manner as in Example 6-(2) to give 2-(4-aminophenyl)-7-hydroxy-6-methoxy-3-methoxycarbonyl-4-(3,5-dimethoxy-4-methylphenyl)-1(2H)-isoquinolinone hydrochloride as listed in Table 43.

EXAMPLES 404–407

The compound obtained in Example 402 and the corresponding starting compounds are treated in the same manner as in Example 6 to give the following compounds as listed in Table 43.

2-(4-aminophenyl)-6-methoxy-3-methoxycarbonyl-4-(3,5-dimethoxy-4-methylphenyl)-7-(4-pyridylmethyl-oxy)-1(2H)-isoquinolinone dihydrochloride (Examples 404);

2-(4-aminophenyl)-6-methoxy-3-methoxycarbonyl-4-(3,5-dimethoxy-4-methylphenyl)-7-(3-pyridylmethyl-oxy)-1(2H)-isoquinolinone dihydrochloride (Examples 405);

2-(4-aminophenyl)-6-methoxy-3-methoxycarbonyl-4-(3,5-dimethoxy-4-methylphenyl)-7-(2-pyridylmethyl-oxy)-1(2H)-isoquinolinone dihydrochloride (Examples 406);

2-(4-aminophenyl)-6-methoxy-3-methoxycarbonyl-4-(3,5-dimethoxy-4-methylphenyl)-7-(2-quinolylmethyl-oxy)-1(2H)-isoquinolinone dihydrochloride (Examples 407);

EXAMPLE 408

7-Benzyloxy-3-hydroxy-4-(3,5-dimethoxyphenyl-4-methylphenyl)-3,4-dihydroisocoumarin-3-carboxylic acid (the compound obtained in Reference Example 106) is treated in the same manner as in Example 4 to give 7-benzyloxy-2-[4-(tert-butoxycarbonylamino)phenyl]-3-methoxycarbonyl-(3,5-dimethoxy-4-methylphenyl)-1(2H)-isoquinolinone as listed in Table 44.

EXAMPLE 409

The compound obtained in Example 408 is treated in the same manner as in Example 6-(2) to give 2-(4-aminophenyl)-7-benzyloxy-3-methoxycarbonyl-4-(3,5-dimethoxy-4-methylphenyl)-1(2H)-isoquinolinone hydrochloride as listed in Table 44.

EXAMPLE 410

The compound obtained in Example 408 is treated in the same manner as in Example 5 to give 2-[4-(tert-butoxycarbonylamino)phenyl]-7-hydroxy-3-methoxycarbonyl-4-(3,5-dimethoxy-4-methylphenyl)-1(2H)-isoquinolinone as listed in Table 44.

EXAMPLE 411

The compound obtained in Example 410 is treated in the same manner as in Example 6-(2) to give 2-(4-aminophenyl)-7-hydroxy-3-methoxycarbonyl-4-(3,5-dimethoxy-4-methylphenyl)-1(2H)-isoquinolinone hydrochloride as listed in Table 44.

EXAMPLES 412–421

The compound obtained in Example 410 and the corresponding starting compounds are treated in the same manner as in Example 6 or 7 to give the following compounds as listed in Tables 44 and 45.

2-(4-aminophenyl)-3-methoxycarbonyl-4-(3,5-dimethoxy-4-methyl-phenyl)-7-(4-pyridylmethyloxy)-1(2H)-isoquinolinone dihydrochloride Examples 412);

2-(4-aminophenyl)-3-methoxycarbonyl-4-(3,5-dimethoxy-4-methyl-phenyl)-7-(3-pyridylmethyloxy)-1(2H)-isoquinolinone dihydrochloride Examples 413);

2-(4-aminophenyl)-3-methoxycarbonyl-4-(3-dimethoxy-4-methyl-phenyl)-7-(2-pyridylmethyloxy)-1(2H)-isoquinolinone dihydrochloride (Examples 414);

2-(4-aminophenyl)-3-methoxycarbonyl-4-(3,5-dimethoxy-4-methyl-phenyl)-7-(2-quinolylmethyl-oxy)-1(2H)-isoquinolinone dihydrochloride (Examples 415);

2-(4-aminophenyl)-7-(1-isoquinolylmethoxy)-3-methoxycarbonyl-4-(3,5-dimethoxy-4-methylphenyl)-1(2H)-isoquinolinone dihydrochloride Examples 416);

2-(4-aminophenyl)-7-(3,5-diaminobenzyloxy)-3-methoxycarbonyl-4-(3,5-dimethoxy-4-methylphenyl)-1(2H)-isoquinolinone trihydrochloride Examples 417);

2-(4-aminophenyl)-7-(6-hydroxymethyl-2-pyridylmethyloxy)-3-methoxy-carbonyl-4-(3,5-dimethoxy-4-methylphenyl)-1(2H)-isoquinolinone ihydrochloride (Examples 418);

2-(4-aminophenyl)-7-(3-methylaminobenzyloxy)-3-methoxycarbonyl-4-(3,5-dimethoxy-4-methylphenyl)-1(2H)-isoquinolinone dihydrochloride (Examples 419);

2-(4-aminophenyl)-7-(2-hydroxymethylbenzyloxy)-3-methoxycarbonyl-,4-(3,5-dimethoxy-4-methylphenyl)-1(2H)-isoquinolinone hydrochloride (Examples 420);

2-(4-aminophenyl)-3-methoxycarbonyl-4-(3,5-dimethoxy-4-methyl-phenyl)-7-(2-pyrazinylmethyl-oxy)-1(2H)-isoquinolinone dihydrochloride,(Examples 421);

EXAMPLE 422

(1) To a solution of the compound obtained in Example 311-(2) (12.2 g) in chloroform (200 ml) is added a saturated aqueous sodium hydrogen carbonate solution, and the mixture is stirred for one hour. The chloroform layer is separated, dried, and concentrated under reduced pressure. The residue is crystallized from ethyl acetate to give 2-(4-aminophenyl)-3-methoxycarbonyl-7-(4-pyridylmethyloxy)-4-(3,4,5-trimethoxyphenyl)-1(2H)-isoquinolinone (10.8 g) as listed in Table 46.

(2) The compound thus obtained (2.00 g) is dissolved in ethanol (150 ml) under warming at 80° C., and thereto is added dropwise a 1M aqueous sulfuric acid solution (3.53 ml). Then, the mixture is cooled to room temperature, and stirred overnight. The precipitated crystals are collected by filtration, and washed with cooled ethanol to give 2-(4-aminophenyl)-3-methoxycarbonyl-7-(4-pyridylmethyloxy)-4-(3,4,5-trimethoxyphenyl)-1(2H)-isoquinolinone sulfate (2.12 g) as listed in Table 46.

EXAMPLE 423

The compound obtained in Example 422-(1) (2.00 g) is dissolved in ethanol (150 ml) under warming at 80° C., and thereto is added methanesulfonic acid (0.48 ml). Then, the mixture is cooled to room temperature and stirred for three hours. The precipitated crystals are collected by filtration, and washed with cooled ethanol to give 2-(4-aminophenyl)-3-methoxycarbonyl-7-(4-pyridylmethyloxy)-4-(3,4,5-trimethoxyphenyl)-1 (2H)"-isoquinolinone dimethanesulfonate (2.65 g) as listed in Table 46.

EXAMPLES 424–425

The compound obtained in Example 313-(2) is treated in the same manner as in Example 422 or 423 to give the following compounds as listed in Table 46.

2-(4-aminophenyl)-3-methoxycarbonyl-7-(2-pyridylmethyloxy)-4-(3,4,5-trimethoxyphenyl)-1(2H)-isoquinolinone sulfate (Example 424);

2-(4-aminophenyl)-3-methoxycarbonyl-7-(2-pyridylmethyloxy)-4-(3,4,5-trimethoxyphenyl)-1(2H)-isoquinolinone dimethanesulfonate Example 425);

EXAMPLE 426

The compound obtained in Reference Example 80 and the corresponding starting compounds are treated in the same manner as in Example 99-(1) to give 4-(3-bromo-4,5-dimethoxyphenyl)-3-carboxy-6,7-dimethoxy-1(2H)-isoquinolinone as listed in Table 47.

EXAMPLE 427

The compound obtained in Example 429 and starting compounds are treated in the same manner as in Example 10-(2) to give 4-(3-bromo-4,5-dimethoxyphenyl)-6,7-dimethoxy-3-methoxycarbonyl-1(2H the corresponding)-isoquinolinone as listed in Table 47.

EXAMPLE 428

(1) The compound obtained in Reference Example 107-(5) and the corresponding starting compounds are treated in the same manner as in Example 4 or 31 to give 7-benzyloxy-2-[4-(tert-butoxycarbonylamino)phenyl]-4-(3,4-dimethoxy-5-methoxymethoxyphenyl)-3-methoxycarbonyl-1(2H)-isoquinolinone.

(2) The compound thus obtained (540 mg) is treated in the same manner as in Example 5 or 6-(1) to give 2-[4-(tert-butoxycarbonylamino)phenyl]-4-(3,4-dimethoxy-5-methoxymethoxyphenyl)-3-methoxycarbonyl-7-(2-pyridylmethyloxy)-1(2H)-isoquinolinone.

(3) To a solution of the compound thus obtained in chloroform is added a 4M solution of hydrogen chloride in ethyl acetate, and the mixture is stirred for one hour at room temperature. Ethanol is added thereto, and then the mixture is stirred for three hours at 40° C., The mixture is concentrated under reduced pressure, and ethyl acetate is added thereto. The precipitated crystals are collected by filtration to give 2-(4-aminophenyl)-4-(3,4-dimethoxyphenyl-5-hydroxy)-3-methoxycarbonyl-7-(2-pyridylmethyloxy)-1(2H)-isoquinolinone dihydrochloride as listed in Table 48.

EXAMPLE 429

To the compound obtained in Example 313-(2) (1.70 g) are added dioxane (30 ml) and conc. hydrochloric acid solution (30 ml), and the mixture is heated under reflux overnight. The reaction mixture is evaporated to remove dioxane, and the residual solution is neutralized with a 2M aqueous sodium hydroxide solution. The mixture is extracted with ethyl acetate, and the extract is washed, dried, and concentrated under reduced pressure. The residue is purified by silica gel column chromatography (solvent; chloroform:acetone 3:2) to give 2-(4-aminophenyl)-4-(3,5-dimethoxy-4-hydroxyphenyl)-3-methoxy-carbonyl-7-(2-pyridylmethyloxy)-1(2H)-isoquinolinone (920 mg) as listed in Table 48.

REFERENCE EXAMPLE 1

2-Bromo-4,5-dimethoxybenzaldehyde dimethyl acetal (74.0 g) is dissolved in tetrahydrofuran (400 ml), and the mixture is cooled to −78T under nitrogen atmosphere. To the mixture is added dropwise and gradually a 1.6M nbutyl lithium (191 ml), and then the mixture is stirred for 15 minutes. To the mixture is added dropwise a solution of N,N-dimethyP3A5-trimethoxybenzamide (61 g) in tetrahydrofuran, and the mixture is gradually warmed to −45° C. The reaction mixture is poured into water, and the mixture is extracted with ethyl acetate. The extract is washed with water and a saturated aqueous sodium chloride solution, dried, and concentrated under reduced pressure. The precipitated crystals are collected by filtration with diethyl ether to give 3,4-dimethoxy-6-(3,4,5-trimethoxybenzoyl)benzaldehyde dimethyl acetal (90.0 g) as listed in Table 49.

REFERENCE EXAMPLES 2–8

N,N-Dimethyl-3,4,5-trimethoxybenzamide and the corresponding bromobenzaldehyde dimethyl acetal are treated in the same manner as in Reference Example 1 to give the compounds as listed in Table 49.

REFERENCE EXAMPLE 9

2-Bromo-4,5-dimethoxybenzaldehyde dimethyl acetal (5.68 g) is dissolved in tetrahydrofuran (20 ml), and the mixture is cooled to −60T. To the mixture is added n-butyl lithium (12.8 ml) over a period of 30 minutes. To the mixture is added dropwise a solution of 4-bromo-3,5-dimethoxybenzaldehyde (4.78 g) in tetrahydrofuran over a period of 30 minutes. Acetic acid (1.06 ml) is added to the reaction mixture, and the mixture is poured into water. The resultant mixture is extracted with ethyl acetate. The extract is washed, dried, and concentrated under reduced pressure to give an alcohol compound (9.02 g) as an oily product. The alcohol compound thus obtained is dissolved in toluene (30 ml), and thereto is added solid manganese dioxide (26 g) in portions. The suspension is warmed to WC, and five hours thereafter, the insoluble materials are removed by filtration. The filtrate is concentrated under reduced pressure, and the precipitated crystals are collected by filtration to give 2-(4-(bromo-3,5-dimethoxybenzoyl)-4,5-dimethoxybenzaldehyde dimethyl acetal (3.68 g) as listed in Table 50.

REFERENCE EXAMPLES 10–13

The corresponding starting compounds are treated in the same manner as in Reference Example 9 to give the compounds as listed in Table 50.

REFERENCE EXAMPLE 14

4,5-Dimethoxy-2-(3,4,5-trimethoxybenzoyl) benzaldehyde dimethyl acetal (1.0 g) is dissolved with heating in a mixture of acetone (15 ml) and water (0.5 ml), and thereto is added an acidic ion-exchange resin (IRA-20) (50 nig). The mixture is stirred at room temperature for two hours. After the reaction is complete, the acidic resin is removed by filtration, and the filtrate is concentrated under reduced pressure. The residue is dissolved in dioxane (12 ml), and thereto are added resorcinol (456 nig) and acetate buffer (pH 3.8, 12 ml). To the mixture is added dropwise and gradually aqueous solution of sodium chlorite (374 mg), and the mixture is stirred at room temperature overnight. After the reaction is complete, the pH value of the mixture is adjusted to pH 1 with conc. hydrochloric acid, and the mixture is extracted with chloroform. The chloroform layer is washed, dried, and concentrated under reduced pressure. The precipitated crystals are collected by filtration with diethyl ether to give 4,5-dimethoxy-2-(3,4,5-trimethoxybenzoyl)benzoic acid (8 10 mg) as listed in Table 51.

REFERENCE EXAMPLES 15–26

The corresponding compounds are treated in the same manner as in Reference Example 14 to give the compounds as listed in Tables 51 and 52.

REFERENCE EXAMPLE 27

A solution of 2-bromo-4,5-dimethoxybenzaldehyde dimethyl acetal (14.8 g) in tetrahydrofuran (50 ml) is cooled to −70° C., and thereto is added dropwise a 1.6 M solution of n-butyl lithium in hexane (33.4 ml) under nitrogen atmosphere over a period of 20 minutes. The mixture is reacted at −60T for 30 minutes, and thereto is added dropwise a solution of 2,3,4-trimethoxybenz aldehyde (10.0 g) in tetrahydrofuran (30 ml) over a period of 10 minutes. After reaction for one hour, to the mixture are added water and ethyl acetate (200 ml). The ethyl acetate layer is separated, washed, dried, and thereto is added an acidic ion-exchange resin (IRA-120) (7.0 g). The mixture is allowed to stand at room temperature for one hour. The mixture is filtered, and the filtrate is concentrated under reduced pressure. To the resultant are added pyridine (150 ml), 1.8M aqueous potassium hydroxide solution (150 ml), and the mixture is warmed to 80T. To the mixture is added solid potassium permanganate (24.1 g) in portions, and the mixture is reacted at the same temperature for one hour. The insoluble materials are removed by filtration, and to the filtrate are added conc. hydrochloric acid (200 ml) and ethyl acetate (300 ml) under ice-cooling. The ethyl acetate layer is separated, washed, dried, and concentrated under reduced pressure. The residue is crystallized from diethyl ether to give 4,5-dimethoxy-6-(2,3,4-trimethoxybenzoyl)benzoic acid (7.72 g) as listed in Table 52.

REFERENCE EXAMPLE 28

The corresponding starting compounds are treated in the same manner as in Reference Example 27 to give 4,5-dimethoxy-2-(3,4-methylenedioxy-benzoyl)benzoic acid as listed in Table 52.

REFERENCE EXAMPLE 29

A solution of 2-(4-methoxyphenyl)-4,4-dimethyl-2-oxazoline (11.0 g) in tetrahydrofuran (50 ml) is cooled to −50° C., and thereto is added dropwise a 1.6 M solution of n-butyl lithium in hexane (36.8 ml) over a period of 20 minutes. The mixture is stirred at 40° C. for 30 minutes, and thereto is added dropwise a solution of 3,4,5-trimethoxybenzaldehyde (10.5 g) in tetrahydrofuran (30 ml) at the same temperature over a period of 10 minutes. After reaction at −30T for one hour, to the mixture are added water and ethyl acetate. The ethyl acetate layer is separated, washed, dried, and concentrated under reduced pressure. The residue is crystallized from diethyl ether to give 2-{2-[hydroxy-(3,4,5trimethoxyphenyl)methyl]-4-methoxyphenyl}-4,4-dimethyl-2-oxazoline (16.2 g) as listed in Table 53.

REFERENCE EXAMPLE 30

The corresponding compounds are treated in the same manner as in Reference Example 29 to give 2-[2-hydroxy-(3,4,5-trimethoxyphenyl)methylphenyl]-4,4-dimethyl-2-oxazoline as listed in Table 53.

REFERENCE EXAMPLE 31

A solution of N-methyl-2-chlorobenzamide (13.0 g) in tetrahydrofuran (300 ml) is cooled to −70° C., and thereto is added dropwise a 1.3M solution of sec-butyl lithium in cyclohexane (130 ral) over a period of 20 minutes. The mixture is stirred at −60° C. for 30 minutes, and thereto is added dropwise a solution of 3,4,5-trimethoxybenzaldehyde (15.0 g) in tetrahydrofuran (100 ml) over a period of 10 minutes. The mixture is stirred at the same temperature for one hour, and thereto are added water and ethyl acetate (300 ml). The ethyl acetate layer is separated, washed, dried, and concentrated under reduced pressure. The residue is crystallized from diethyl ether to give N-methyl-2-chloro-6-[hydroxy-(3,4,5-trimethoxyphenyl)methyl]benzamide (19.2 g) as listed in Table 54.

REFERENCE-EXAMPLE 32–35

The corresponding compounds are treated in the same manner as in Reference Example 31 to give the compounds as listed in Table 54.

REFERENCE EXAMPLE 36

To the compound obtained in Reference Example 29 (9.0 g) are added dioxane (38 ml) and conc. hydrochloric acid (19 ml). After reaction at 110° C. for one hour, to the mixture are added water and ethyl acetate (150 ml). The ethyl acetate layer is separated, washed, dried, and concentrated under reduced pressure. The residue is crystallized from diethyl ether to give 5-methoxy-3(3,4,5-trimethoxyphenyl) phthalide (6.14 g) as listed in Table 55.

REFERENCE EXAMPLE 37–41

The corresponding compounds are treated in the same manner as in Reference Example 36 to give the compounds as listed in Table 55.

REFERENCE EXAMPLE 42

To 6-[hydroxy-(3,4,5-trimethoxyphenyl)methyl]-2-methoxymethyloxy-N-methylbenzamide (the compound obtained in Reference Example 35) (17.0 g) are added dioxane (68 ml) and conc. hydrochloric acid (17 ml), and the mixture is stirred at 100° C. for 20 minutes. To the mixture are added water and ethyl acetate (200 ml). The ethyl acetate layer is separated, washed, dried, and concentrated under reduced pressure. The residue is crystallized from diethyl ether. To the collected crystals are added dimethylformamide (90 ml), potassium carbonate (3.35 g), and benzyl bromide (4.14 g), and the mixture is stirred at room temperature for two hours. To the mixture are added water and ethyl acetate (200 ml). The ethyl acetate layer is separated, washed, dried, and concentrated under reduced pressure. The residue is crystallized from diethylether to give 7-benzyloxy-3-(3,4,5-trimethoxyphenyl)phthalide (7.68 g) as listed in Table 55.

REFERENCE EXAMPLE 43

To the compound obtained in Reference Example 36 are added pyridine (45 ml) and a 25% aqueous potassium hydroxide solution (90 ml), and the mixture is warmed to WC. To the mixture is added solid potassium permanganate (5.31 g) in portions, and the mixture is stirred at the same temperature for 1.5 hour. The insoluble materials are removed by filtration, and to the filtrate are added conc. hydrochloric acid (100 ml) and ethyl acetate (300 ml) under ice-cooling. The ethyl acetate layer is separated, washed, dried, and concentrated under reduced pressure. The residue is crystallized from diethyl ether to give 4-methoxy-2-(3,4,5-trimethoxybenzoyl)benzoic acid (7.38 g) as listed in Table 56.

REFERENCE EXAMPLES 44–49

The corresponding compound are treated in the same manner as in Reference Example 43 to give the compounds as listed in Table 56.

REFERENCE EXAMPLE 50

To a solution of 4,5-dimethoxy-2-(3,4,5-trimethoxybenzoyl)benzoic acid (5 g) in dimethylformamide (50 ral) ard added potassium carbonate (3.72 g) and diethyl bromomalonate (2.48 ml), and the mixture is stirred at room temperature overnight. The mixture is evaporated to remove dimethylformamide, and thereto is added chloroform and water. The chloroform layer is separated, and thereto are added dioxane (80 ml) and conc. hydrochloric acid (80 ml). The mixture is heated under reflux for three hours. The reaction mixture is cooled, and the precipitated crystals are collected by filtration washed with acetone, and dried to give 6,7-dimethoxy-4-(3,4,5-trimethoxyphenyl) isocoumarin-3-carboxylic acid (2.85 g) as listed in Table 57.

REFERENCE EXAMPLES 51–59

The corresponding compounds are treated in the same manner as in Reference Example 50 to give the compounds as listed in Table 57.

REFERENCE EXAMPLE 60

To a solution of 2-(3-bromo-4,5-dimethoxybenzoyl)-4,5-dimethoxy-benzoic acid (6 g) in dimethylformamide (110 ml) are added potassium carbonate (4.29 g) and diethyl bromomalonate (3.71 g), and the mixture is stirred at room temperature overnight. The reaction mixture is evaporated to remove dimethylformamide, and to the residue are added ethyl acetate and water. The ethyl acetate layer is separated, washed, dried, and concentrated under reduced pressure. To the residue are added dioxane (35 ml) and conc. hydrochloric acid (35 ml), and the mixture is heated under reflux for five hours. The reaction mixture is cooled, and thereto are added chloroform and water. The chloroform layer is separated, washed, dried, and concentrated under reduced pressure. The residue is crystallized from ether to give 4-(3-bromo-4,5-dimethoxyphenyl)-6,7-dimethoxyisocoumarin-3-carboxylic acid (2.54 g) as listed in Table 58.

REFERENCE EXAMPLES 61–65

The corresponding compounds are treated in the same manner as in Reference Example 60 to give the compounds as listed in Table 58.

REFERENCE EXAMPLE 66

To a solution of 2-(3,5-dibromo-4-methoxybenzoyl)-4,5-dimethoxy-benzoic acid (6.30 g) in dimethylformamide (50 ml) are added potassium carbonate (4.04 g) and dimethyl bromomalonate (3.43 g), and the mixture is stirred at room temperature overnight. To the reaction mixture are added ethyl acetate and water. The ethyl acetate layer is separated, washed, dried, and concentrated under reduced pressure. To the residue are added dioxane (30 ml) and conc. hydrochloric acid (30 ml), and the mixture is heated under reflux for five hours. The reaction mixture is cooled, and thereto are added ethyl acetate and water. The ethyl acetate layer is separated, and washed. The remaining aqueous layer is acidified with 10% hydrochloric acid, and then extracted with ethyl acetate. The extract is washed, and dried. The extracts are combined, and concentrated under reduced pressure. The residue is crystallized from ether to give 4(3,5-dibromo-4-methoxyphenyl)-6,7-diethoxy-isocoumarin-3-carboxylic acid (1.32 g) as listed in Table 58.

REFERENCE EXAMPLE 67

To a solution of 5-benzyloxy-4-methoxy-2-(3,4,5-trimethoxybenzoyl)-benzoic acid (90 g) in dimethylformamide (900 MI) are added potassium carbonate (60.5 g) and di-tert-butyl bromomalonate (64.6 g), and the mixture is stirred at room temperature for three hours. To the reaction mixture are added ethyl acetate and water. The ethyl acetate layer is separated, washed, dried, and concentrated under reduced pressure. To the residue is added a 4M solution of hydrogen chloride in ethyl acetate (500 ml), and the mixture is stirred at room temperature for five hours. The precipitated crystals are collected by filtration, washed, dried, and dissolved in a mixture of acetic acid (40 ml) and dioxane (80 ml). The mixture is heated under reflux for five hours, and the precipitated crystals are collected by filtration. washed, and dried to give 7-benzyloxy-6-methoxy-4-(3,4,5-trimethoxyphenyl)isocoumarin-3-carboxylic acid (70.0 g) as listed in Table 59.

REFERENCE EXAMPLES 68–70

The corresponding compounds are treated in the same manner as in Reference Example 67 to give the compounds. as listed in Table 59.

REFERENCE EXAMPLE 71

The compound obtained in Reference Example 67 (13.9 g) is added to a mixture of 2M aqueous sodium hydroxide solution (100 ml) and methanol (100 ml), and the mixture is stirred at room temperature for four hours. The mixture is concentrated under reduced pressure, and the remaining aqueous layer is adjusted to pH 2 with 10% hydrochloric acid. The mixture is extracted with ethyl acetate, and the extract is washed, dried, and concentrated under reduced pressure. The residue is crystallized from diethyl ether to give 7-benzyloxy-3hydroxy-6-methoxy-4-(3,4,5-trimethoxyphenyl)-3,4-dihydroisocoumarin-3-carboxylic acid (12.78 g) as listed in Table 60.

REFERENCE EXAMPLES 72–86

The corresponding compounds are treated in the same manner as in Reference Example 71 to give the compounds as listed in Table 60.

REFERENCE EXAMPLE 107

(1) A solution of 2-bromo-5-benzyloxybenzaldehydedimethylacetal (8.14 g) in tetrahydrofuran (40 ml) is cooled at −WC under nitrogen atmosphere, and a 1.6M n-butyl lithium (16.6 ml) is added thereto dropwise. The mixture is stirred for 10 minutes, and then a solution of N,N-dimethyl-3,4-dimethoxy-5-methoxy-methoxybenzamide (6.50 g) in tetrahydrofuran is added thereto dropwise. After being warmed at ice-cooling temperature slowly, the mixture is poured into a saturated aqueous ammonium chloride solution, and extracted with ethyl acetate. The extract is washed, dried, and concentrated under reduced pressure to give a crude 2-(3,4-dimethoxy-5-methoxymethoxy-benzoyl)-5-benzyloxy-benzaldehydedimethylacetal.

(2) To a solution of the compound thus obtained in tetrahydrofuran (80 ml) is added a 2M aqueous hydrochloric acid solution (20 ml), and stirred at room temperature overnight. The solvent is evaporated, and to the residue are added water and ethyl acetate. The ethyl acetate layer is separated, washed, dried, and concentrated under reduced pressure to give 2-(3,4-dimethoxy-5-methoxymethoxybenzoyl)-5-benzyloxybenzaldehyde (5.66 g).

(3) The residual oil thus obtained is dissolved in dioxane (60 ml), and resorcinol (2.14 g) and acetate buffer (pH 3.8) (50 ml) are added thereto. To the mixture is added dropwise slowly an aqueous sodium chlorite solution, and the mixture is stirred at room temperature overnight. After the reaction, the reaction mixture is adjusted to pH 1 with conc. hydrochloric acid solution, and extracted with chloroform. The chloroform layer is washed, dried, and concentrated under reduced pressure to give 2-(3,4-dimethoxy-5-methoxymethoxybenzoyl)~-5-benzyloxybenzoic acid.

(4) The compound thus obtained is dissolved in dimethylformamide (30 ml). Potassium carbonate (1.79 g) and di-tert-butyl bromomalonate (3.83 g) are added thereto under ice-cooling, and the mixture is stirred at room temperature overnight. Then potassium carbonate (1.79 g) is added thereto. After being stirred overnight, the mixture is poured into water. The mixture is extracted with ethyl acetate, and the extract is washed, dried, and concentrated under reduced pressure. To the residue is added a 4M solution of hydrogen chloride in ethyl acetate (35 ral), and the mixture is stirred overnight. The mixture is concentrated under reduced pressure and then co-evaporated with dioxane. The residue is dissolved in dioxane (50 ml) and acetic acid (30 ml), and the mixture is heated under reflux for 4 hours. The mixture is concentrated under reduced pressure and co-evaporated with toluene. The residue is dissolved in dimethylformamide (50 ml), and to the mixture diisopropylethylamine (9.3 m]) and methoxymethyl chloride (4.0 ml) are added under ice-cooling temperature. The mixture is stirred overnight, and poured into water. The mixture is extracted with ethyl acetate, and the extract is washed, dried, and concentrated under reduced pressure. The residue is purified by silica gel column chromatography (solvent; hexane:chloroform:ethyl acetate=5:5:1) to give 7-benzyloxy-4-(3',4dimethoxy-5-methoxymethoxyphenyl)-3-methoxymethoxycarbonyloxy-isocoumarin (1.82 g).

(5) The compound thus obtained is dissolved in tetrahydrofuran (15 ml) and methanol (5 ml), and to the solution a 2M aqueous sodium hydroxide solution (3.39 ml) is added. The mixture is stirred for 20 minutes, and then a 2M aqueous hydrochloric acid solution is added thereto. The mixture is concentrated under reduced pressure, and water and ethyl acetate are added thereto. The ethyl acetate layer is washed, dried, and concentrated under reduced pressure to give 7-benzyloxy-3-hydroxy-4-(3,4-dimethoxy-5-methoxymethoxyphenyl)-3,4-dihydroisocoumarin-3-carboxylic acid.

The following tables are those referred to in the previous examples, and the legends and annotations (e.g., * and **) are used consistently from table to table. The information is presented not to limit the invention, but to exemplify it.

TABLE 1

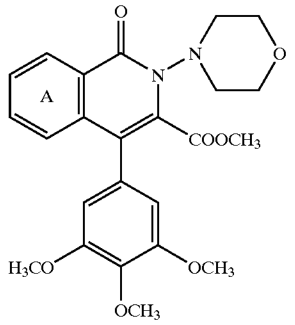

| Ex. No. | Ring A | Physicochemical properties |
|---|---|---|
| 1 | 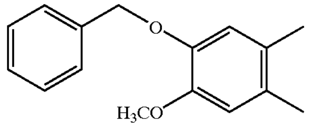 | m.p. 173–174° C. |
| 2 | 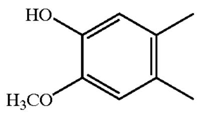 | m.p. 231–233° C. |
| 3* | 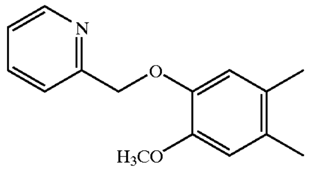 | m.p. 200–203° C. (decomp.) |

*monohydrochloride

TABLE 2
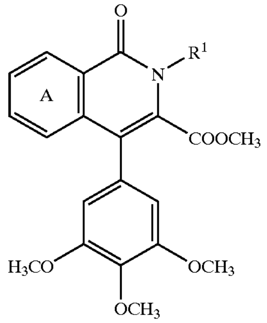
| Ex. No. | Ring A | $R^1$ | Physicochemical properties |
|---|---|---|---|
| 4 | 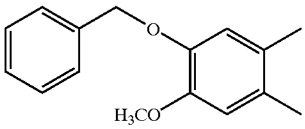 | 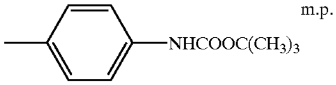 | m.p. 140–141° C. |
| 5 | 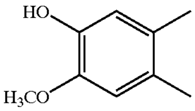 | 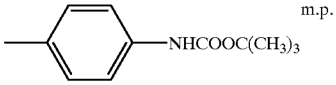 | m.p. 160–161° C. |
| 6 (1) | 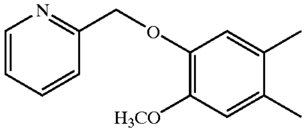 | 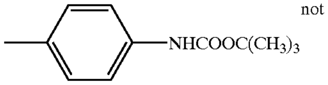 | not purified |
| 6 (2)** | 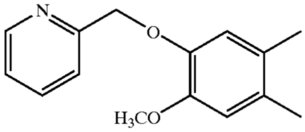 | 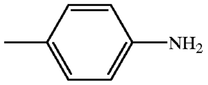 | m.p. 186–190° C. (decomp.) |
| 7** | 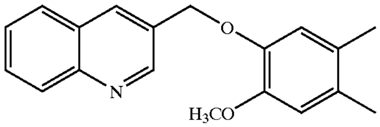 | 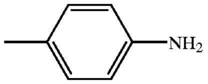 | m.p. 184–185° C. (decomp.) |
| 8 | 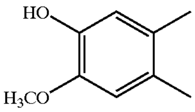 | 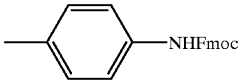 | m.p. 204–206° C. |
| 9* | 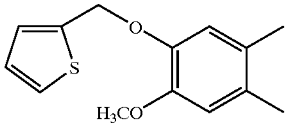 | 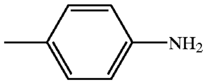 | m.p. 146–148° C. (decomp.) |
*monohydrochloride
**dihydrochloride
Fmoc: 9-fluorenylmethyloxycarbonyl group TABLE 3
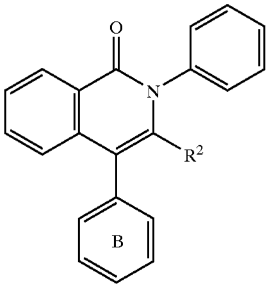
| Ex. No. | Ring B | $R^2$ | Physicochemical properties |
|---|---|---|---|
| 10 | 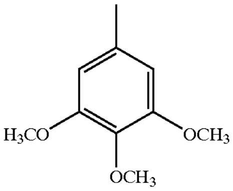 | —$COOCH_3$ | m.p. 190–191° C. |
| 11 | 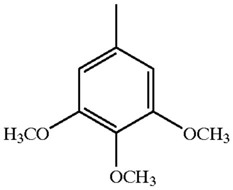 | —$COOC_2H_5$ | m.p. 169–170° C. |
| 11a | 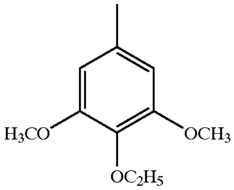 | —$COOC_2H_5$ | m.p. 141–143° C. |
| 12 | 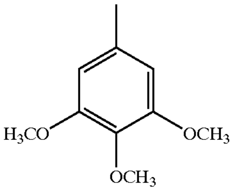 | 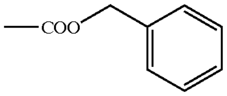 | m.p. 145–147° C. |
| 12a | 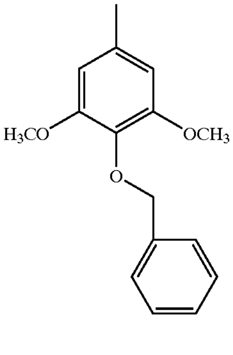 | 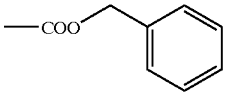 | m.p. 128–130° C. |

TABLE 3-continued
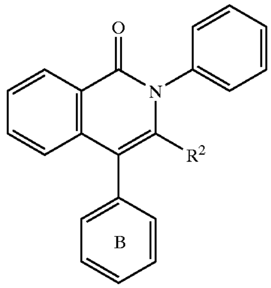
| Ex. No. | Ring B | $R^2$ | Physicochemical properties |
|---|---|---|---|
| 13 | 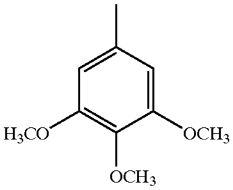 | $—COO(CH_2)_3CH_3$ | m.p. 144–146° C. |
| 13a | 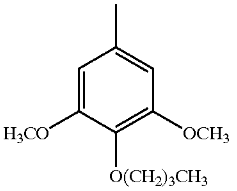 | $—COO(CH_2)_3CH_3$ | m.p. 76–78° C. |
TABLE 4
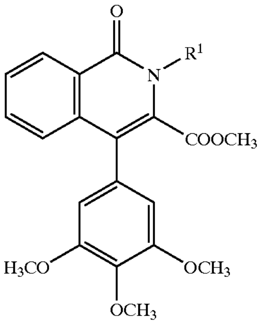
| Ex. No. | $R^1$ | Physicochemical properties |
|---|---|---|
| 14 | 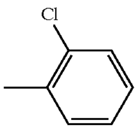 | m.p. 177–179° C. |
| 15 | 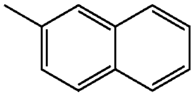 | m.p. 229–231° C. |
| 16 | 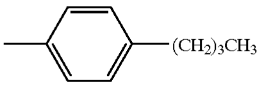 | m.p. 145–147° C. |

TABLE 4-continued
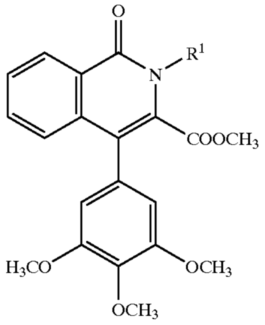
| Ex. No. | $R^1$ | Physicochemical properties |
|---|---|---|
| 17 | 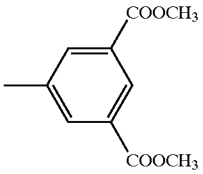 | m.p. 212–214° C. |
| 18 | 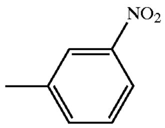 | m.p. 204–206° C. |
| 19 | $—N(CH_3)_2$ | m.p. 173–175° C. |
| 20 | 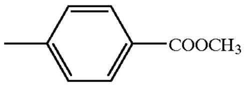 | m.p. 213–215° C. |
| 21 (1) (2)**** | 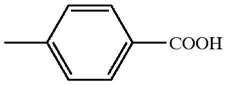 | (1) m.p. 254–256° C. (2) m.p. 259–261° C. (decomp.) |
| 22 | 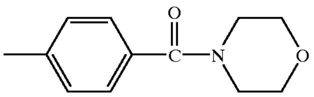 | m.p. 215–217° C. |
| 23 | 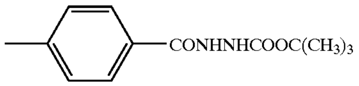 | m.p. 223–225° C. (decomp.) |
| 24* | 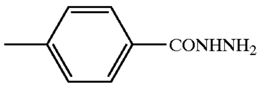 | m.p. 175–177° C. (decomp.) |
| 25 | 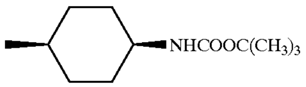 (cis) | m.p. 182–183° C. |
| 26 | 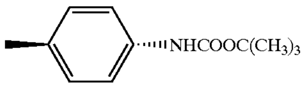 (trans) | m.p. 217–218° C. |

TABLE 4-continued
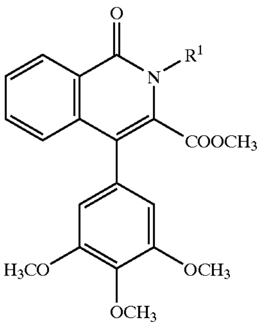
| Ex. No. | $R^1$ | Physicochemical properties |
| --- | --- | --- |
| 27* | 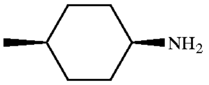 | m.p. 167–169° C. (decomp.) |
| 28* | 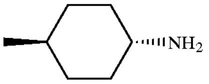 | m.p. 255–257° C. (decomp.) |
| 29 | 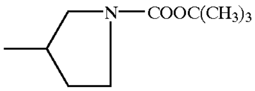 | m.p. 141–142° C. |
| 30* | 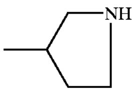 | m.p. 214–216° C. (decomp.) |
| 31 | 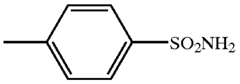 | m.p. 258–260° C. |
| 32 | 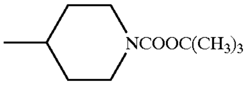 | m.p. 120–122° C. |
| 33 | 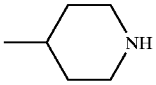 | m.p. 186–189° C. |
| 34 | 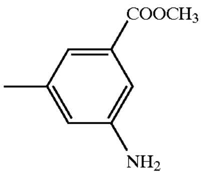 | m.p. 180–181° C. |
| 35 | 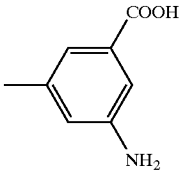 | m.p. 156–157° C. |
| 36 | 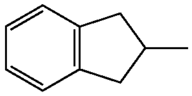 | m.p. 204–207° C. |

TABLE 4-continued
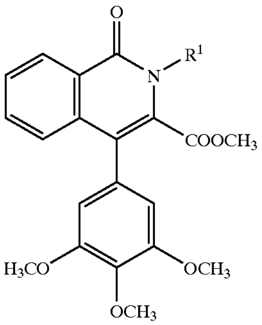
| Ex. No. | $R^1$ | Physicochemical properties |
|---|---|---|
| 37 | 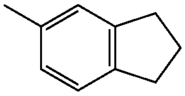 | m.p. 223–224° C. |
| 38 | 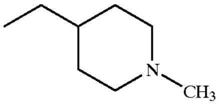 | m.p. 178–184° C. |
| 39 | 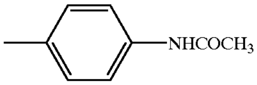 | m.p. 198–202° C. |
| 40* | 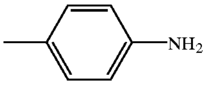 | m.p. 164–168° C. (decomp.) |
| 41 | 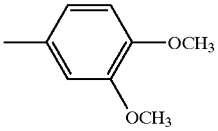 | m.p. 190–192° C. |
| 42 | 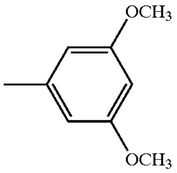 | m.p. 170–172° C. |
| 43* | 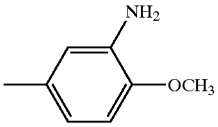 | m.p. 174–178° C. (decomp.) |
| 44 | 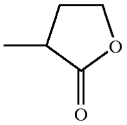 | m.p. 213–215° C. |
| 45 | 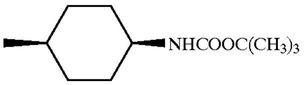 (cis) | m.p. >220° C. |

TABLE 4-continued
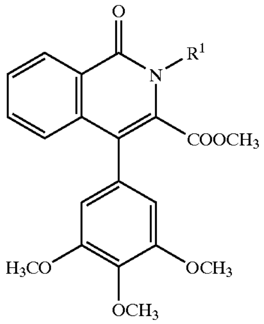
| Ex. No. | $R^1$ | Physicochemical properties |
|---|---|---|
| 46* | 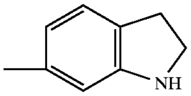 | m.p. 170–178° C. (decomp.) |
| 47 | 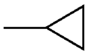 | m.p. 172–173° C. |
| 48 | 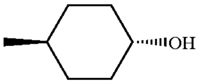 | m.p. 165–166° C. |
| 49 | $—C_2H_5$ | m.p. 171–173° C. |
| 50 | 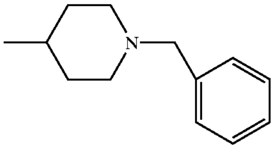 | m.p. 166–168° C. |
| 51 | 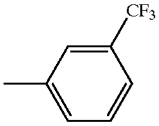 | m.p. 120–123° C. |
| 52 | 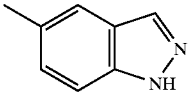 | m.p. 244–246° C. |
| 53 | 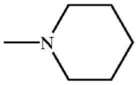 | m.p. 174–175° C. |
| 54 | $—(CH_2)_3OH$ | m.p. 148–150° C. |
| 55* | 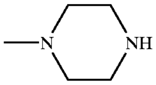 | m.p. 245–247° C. (decomp.) |
| 56 | 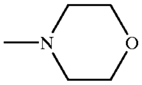 | m.p. 163–165° C. |
| 57 | 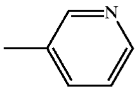 | m.p. 173–175° C. |

TABLE 4-continued
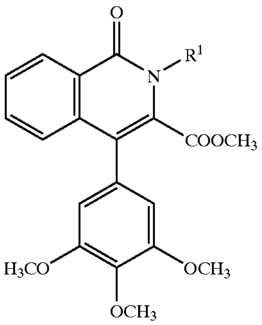
| Ex. No. | $R^1$ | Physicochemical properties |
|---|---|---|
| 58 | 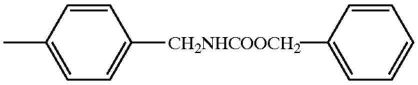 | m.p. 137–140° C. |
| 59* | 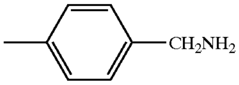 | m.p. 230–233° C. (decomp.) |
| 60 | 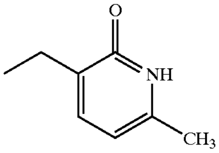 | m.p. 214–215° C. |
| 61 | 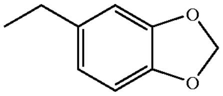 | m.p. 125–127° C. |
| 62* | 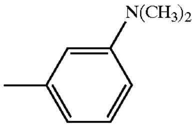 | m.p. 137–139° C. (decomp.) |
| 63* | 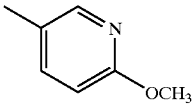 | m.p. 85–86° C. |
| 64 | 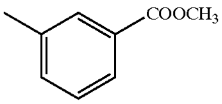 | m.p. 207–208° C. |
| 65 | 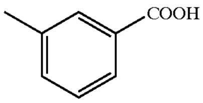 | m.p. 268–269° C. |
*monohydrochloride
****sodium salt

TABLE 5

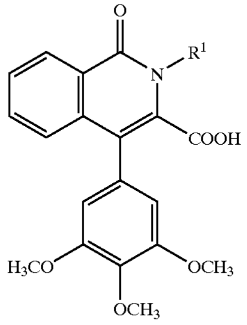

| Ex. No. | $R^1$ | Physicochemical properties |
|---|---|---|
| 66 | —$NHCOOC(CH_3)_3$ | m.p. 200–201° C. (decomp.) |

TABLE 6

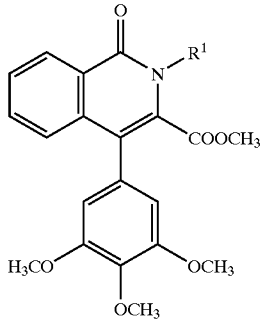

| Ex. No. | $R^1$ | Physicochemical properties |
|---|---|---|
| 67 | —$NHCOOC(CH_3)_3$ | m.p. 206–208° C. |
| 68 | —$NH_2$ | m.p. 209–211° C. |
| 69 | —$NHCOCH_3$ | m.p. 136–139° C. |
| 70 | —$N(COCH_3)_2$ | m.p. 184–185° C. |
| 71 | —$N(CH_3)(COOC(CH_3)_3)$ | — |
| 72 | —$NHCH_3$ | m.p. 218–220° C. |
| 73 | —$N(CH_2CH_2OH)(COOC(CH_3)_3)$ | — |
| 74 | —$NHCH_2CH_2OH$ | m.p. 167–168° C. |
| 75 | —$NHCH_2CH_2OCOCH_3$ | m.p. 126–127° C. |
| 76 | —$NHCH_2CH_2CH_3$ | m.p. 147–148° C. |
| 77 | —$NHCH_2CH_3$ | m.p. 149–151° C. |
| 78 | 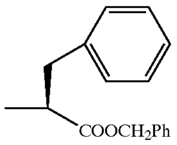 | — |
| 79 | 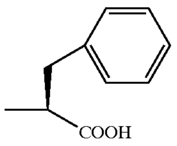 | m.p. 191–194° C. |
| 80 | 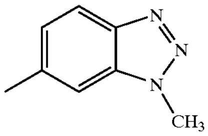 | m.p. 155–157° C. |

Ph: phenyl group

TABLE 7

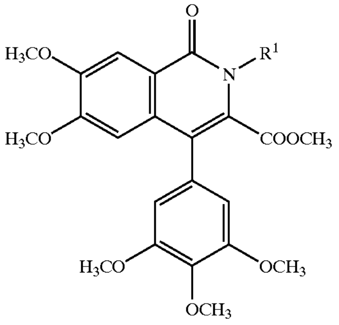

| Ex. No. | $R^1$ | Physicochemical properties |
|---|---|---|
| 81 | 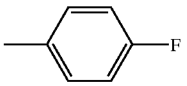 | m.p. 199–200° C. |
| 82 | 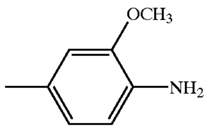 | m.p. 238–239° C. |
| 83 | 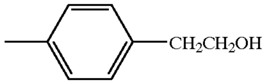 | m.p. 148–152° C. |
| 84 | 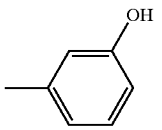 | m.p. 230–231° C. |
| 85 | 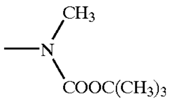 | — |
| 86 | —$NHCH_3$ | m.p. 189–190° C. |
| 87 | 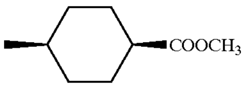 (cis) | m.p. 110–113° C. |
| 88 | 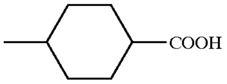 | m.p. 193–198° C. |
| 89 | 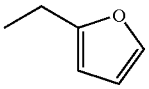 | m.p. 142–143° C. |
| 90 | 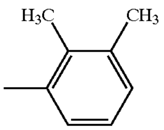 | m.p. 202–203° C. |

TABLE 7-continued
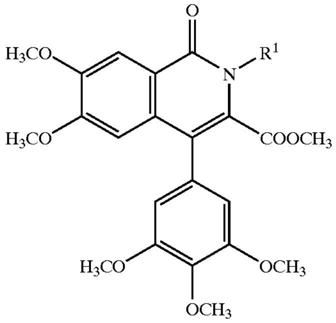
| Ex. No. | $R^1$ | Physicochemical properties |
|---|---|---|
| 91 | 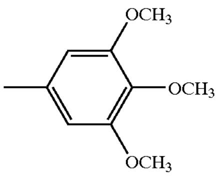 | m.p. 232–233° C. |
| 92 (1)<br>(2)* | 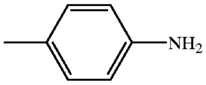 | (1) m.p. 203–205° C.<br>(2) m.p. >230 |
| 93 | 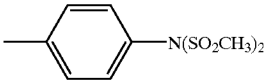 | m.p. >230° C. |
| 94 | 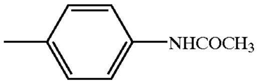 | m.p. 235–237° C. |
| 95 | 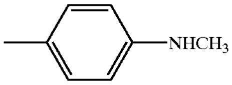 | m.p. 239–241° C. |
| 96 | 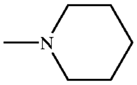 | m.p. 125–128° C. |
| 97 | 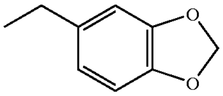 | m.p. 185–186° C. |
| 98 | 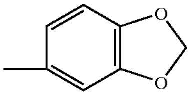 | m.p. >250° C. |
*monohydrochloride
TABLE 8
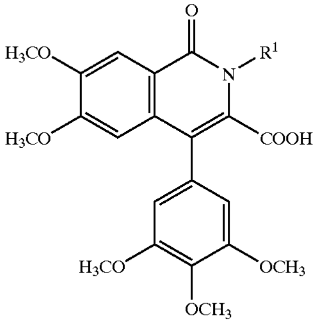
| Ex. No. | $R^1$ | Physicochemical properties |
|---|---|---|
| 99 (1)<br>(2)**** | H | (1) m.p. >250° C.<br>(2) m.p. >250° C. |
| 100 | 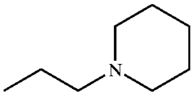 | m.p. 198–200° C. |
****sodium salt
TABLE 9
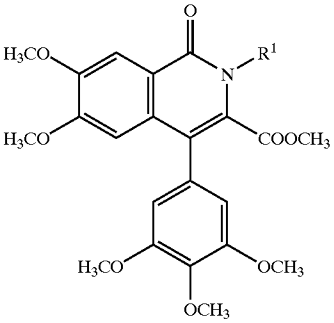
| Ex. No. | $R^1$ | Physicochemical properties |
|---|---|---|
| 101 | 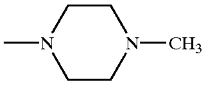 | m.p. > 250° C. |
| 102 | 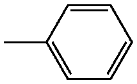 | m.p. 214–216° C. |
| 103 | 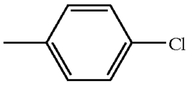 | m.p. 194–195° C. |
| 104 | 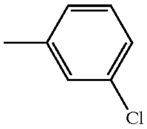 | m.p. 233–235° C. |
| 105 | 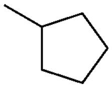 | m.p. 132–134° C. |

TABLE 9-continued
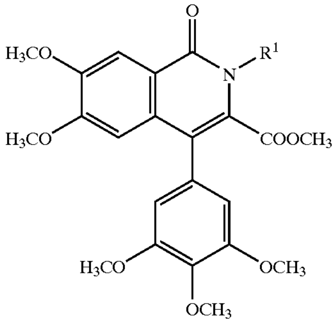
| Ex. No. | $R^1$ | Physicochemical properties |
|---|---|---|
| 106 | 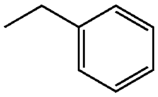 | m.p. 182–183° C. |
| 107* | 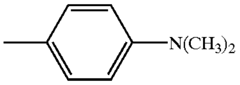 | m.p. 226–228° C. |
| 108* | 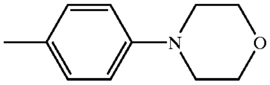 | m.p. 223–227° C. (decomp.) |
| 109 | 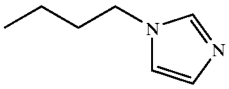 | m.p. 158–160° C. |
| 110 | 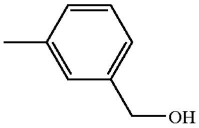 | m.p. 204–205° C. |
| 111 | 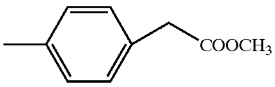 | m.p. 187–188° C. |
| 112**** | 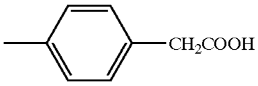 | m.p. 132–136° C. (decomp.) |
| 113 | —H | m.p. 204–207° C. |
| 114* | 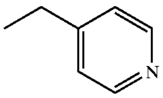 | m.p. 218–220° C. (decomp.) |
| 115 | 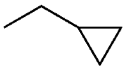 | m.p. 117–119° C. |
TABLE 9-continued
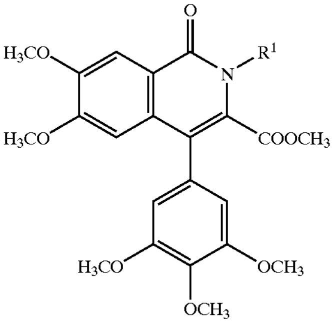
| Ex. No. | $R^1$ | Physicochemical properties |
|---|---|---|
| 116* | 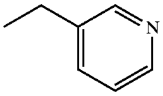 | m.p. 209–211° C. (decomp.) |
| 117* | 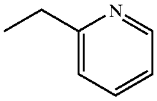 | m.p. 155–157° C. (decomp.) |
| 118 | 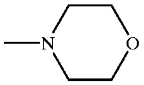 | m.p. 219–220° C. |
*monohydrochloride
****sodium salt
TABLE 10
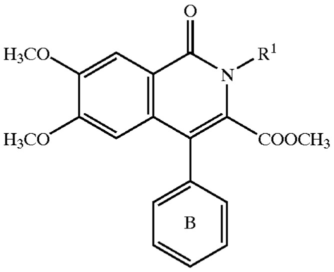
| Ex. No. | Ring B | $R^1$ | Physico-chemical properties |
|---|---|---|---|
| 119 | 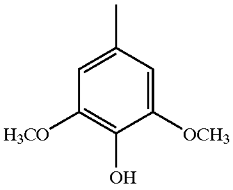 | 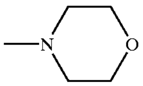 | m.p. > 250° C. |

TABLE 11
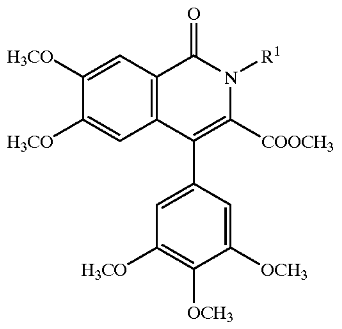
| Ex. No. | $R^1$ | Physicochemical properties |
|---|---|---|
| 120* | 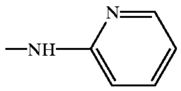 | m.p. 178–179° C. (decomp.) |
| 121 | 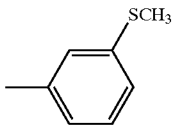 | m.p. 217–218° C. |
| 122 | 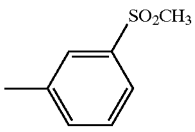 | m.p. > 250° C. |
TABLE 11-continued
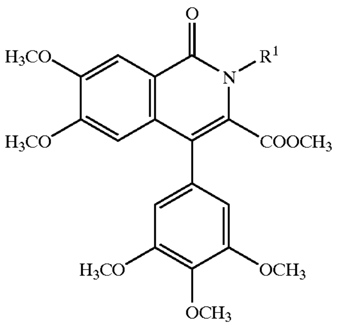
| Ex. No. | $R^1$ | Physicochemical properties |
|---|---|---|
| 123 | 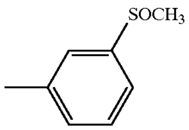 | m.p. 241–244° C. |
| 124 | 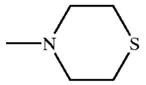 | m.p. 215–218° C. |
| 125 | 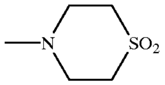 | m.p. 226–227° C. (decomp.) |
| 126 | 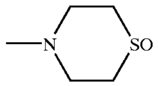 | m.p. > 250° C. |
*monohydrochloride
TABLE 12
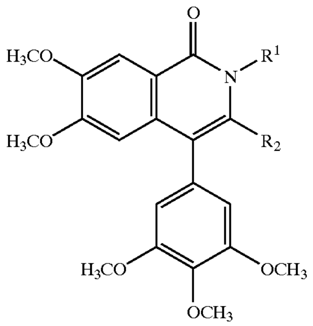
| Ex. No. | $R^1$ | $R^2$ | Physicochemical properties |
|---|---|---|---|
| 127 | $—CH_3$ | $—COOCH_3$ | m.p. 170–171° C. |
| 128 | $—CH_3$ | —COOH | m.p. > 270° C. |
| 129 | $—CH_3$ | 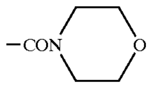 | m.p. 188–190° C. |

TABLE 12-continued
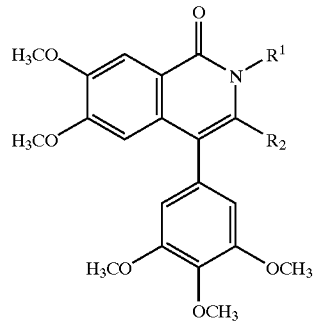
| Ex. No. | $R^1$ | $R^2$ | Physicochemical properties |
|---|---|---|---|
| 130 | —$CH_3$ | 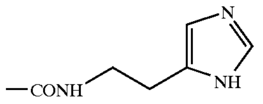 | m.p. > 210° C. |
| 131 | —$CH_3$ | 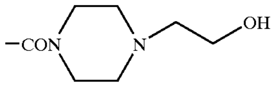 | m.p. 133–134° C. |
| 132 | 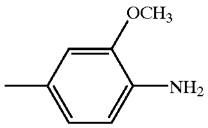 | —$COOCH_2Si(CH_3)_3$ | m.p. 191–192° C. |
TABLE 13
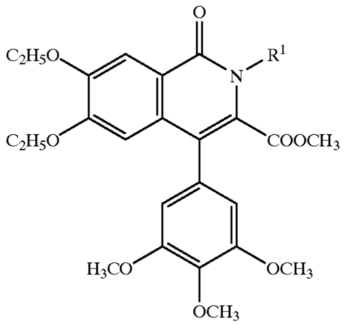
| Ex. No. | $R^1$ | Physicochemical properties |
|---|---|---|
| 133 | 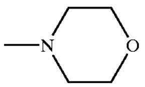 | m.p. 195–197° C. |
| 134 | 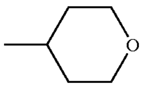 | m.p. 182–184° C. |
| 135 | 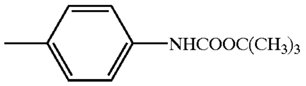 | m.p. 204–206° C. |
TABLE 13-continued
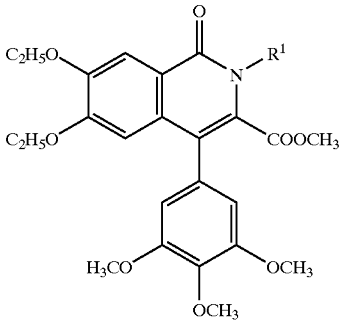
| Ex. No. | $R^1$ | Physicochemical properties |
|---|---|---|
| 136<br>(1)*<br>(2) | 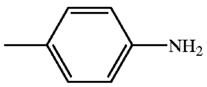 | (1)m.p. 222–225° C.<br>(decomp.)<br>(2)m.p. 170–172° C. |
| 137 | 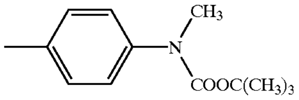 | m.p. 161–163° C. |
| 138* | 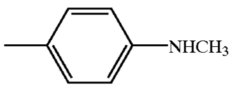 | m.p. 206–208° C.<br>(decomp.) |

TABLE 13-continued
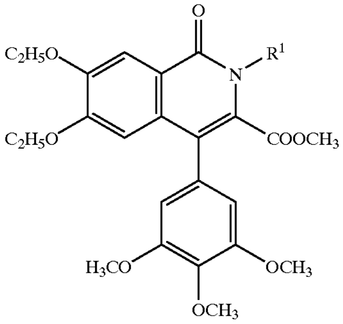
| Ex. No. | $R^1$ | Physicochemical properties |
|---|---|---|
| 139 | 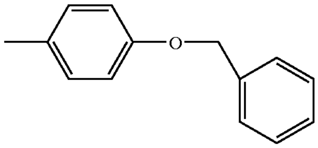 | m.p. 145–147° C. |
TABLE 13-continued
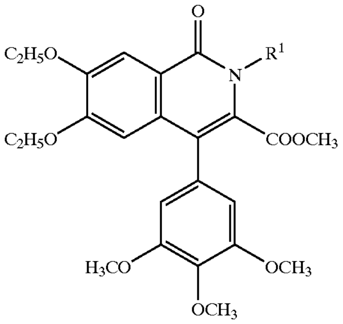
| Ex. No. | $R^1$ | Physicochemical properties |
|---|---|---|
| 140 | 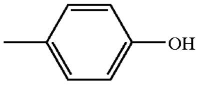 | m.p. 197–199° C. |
*monohydrochloride
TABLE 14
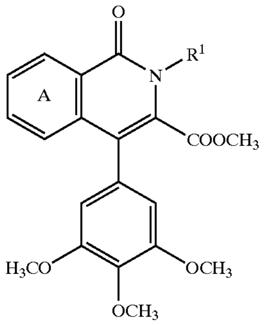
| Ex. No. | Ring A | $R^1$ | Physicochemical properties |
|---|---|---|---|
| 141 | 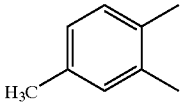 | 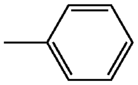 | m.p. 169–170° C. |
| 142 | 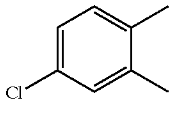 | 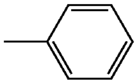 | m.p. 196–198° C. |
| 143 | 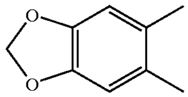 | 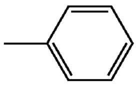 | m.p. 223–225° C. |

TABLE 14-continued
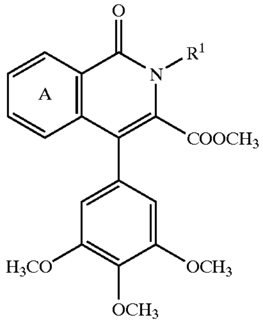
| Ex. No. | Ring A | $R^1$ | Physicochemical properties |
|---|---|---|---|
| 144 | 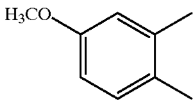 | 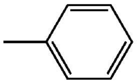 | m.p. 209–211° C. |
| 145 | 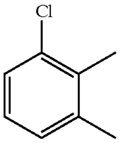 | 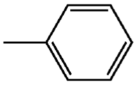 | m.p. 182–183° C. |
| 146 | 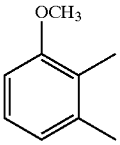 | 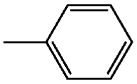 | m.p. 216–217° C. |
| 147 | 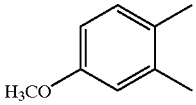 | 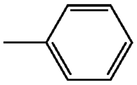 | m.p. 206–208° C. |
| 148 | 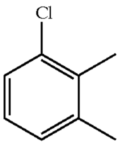 | 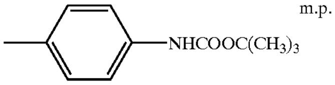 | m.p. 235–237° C. |
| 149* | 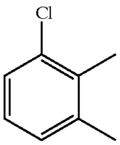 | 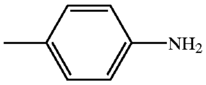 | m.p. 210–212° C. (decomp.) |
| 150 | 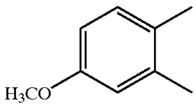 | 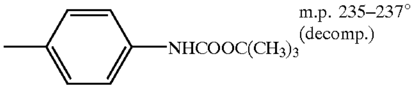 | m.p. 235–237° C. (decomp.) |
| 151 | 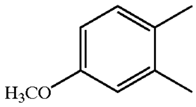 | 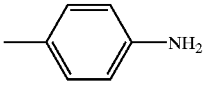 | m.p. 210–211° C. |
*monohydrochloride TABLE 15
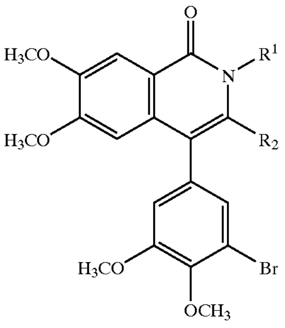
| Ex. No. | $R^1$ | $R^2$ | Physicochemical properties |
|---|---|---|---|
| 152 | 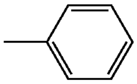 | —COOH | m.p. 184–186° C. |
| 153 | 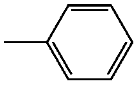 | —$COOCH_3$ | m.p. 223–225° C. |
TABLE 15-continued
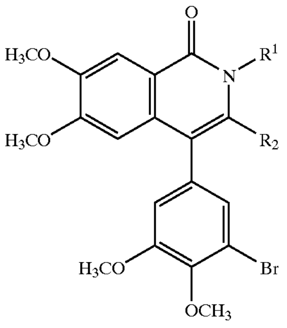
| Ex. No. | $R^1$ | $R^2$ | Physicochemical properties |
|---|---|---|---|
| 154 | 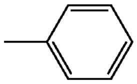 | —$CONH_2$ | m.p. 258–261° C. |
| 155 | 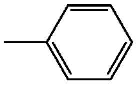 | —$CONHCH_3$ | m.p. 249–252° C. |
TABLE 16
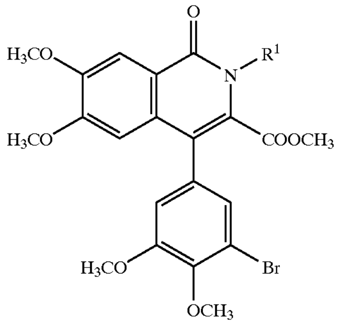
| Ex. No. | $R^1$ | Physicochemical properties |
|---|---|---|
| 156 | 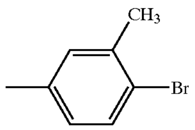 | m.p. 198–200° C. |
| 157 | 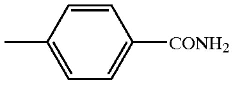 | m.p. > 250° C. |
| 158 | 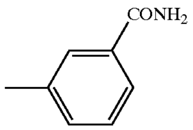 | m.p. 261–263° C. |
| 159 | —$CH_2COOCH_3$ | m.p. 185–186° C. |
| 160 | —$CH_2COOC_2H_5$ | m.p. 156–157° C. |

TABLE 16-continued
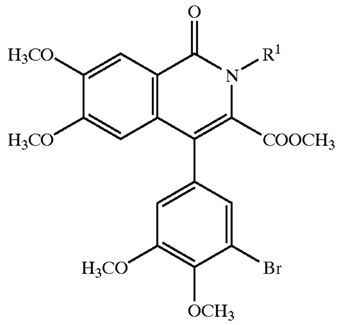
| Ex. No. | $R^1$ | Physicochemical properties |
|---|---|---|
| 161 | $—CH_2COOH$ | m.p. 200–202° C. |
| 162 | $—C_2H_4OC_2H_4OH$ | m.p. 144–146° C. |
| 163 | 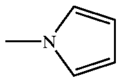 | m.p. 224–225° C. |
| 164 | $—C_2H_4NHCOOC(CH_3)_3$ | m.p. 174–176° C. |
| 165* | $—C_2H_4NH_2$ | m.p. 188–190° C. (decomp.) |
| 166 | 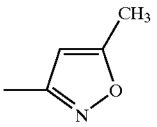 | m.p. 209–211° C. |
| 167 | 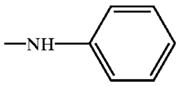 | m.p. 132–135° C. |
| 168 | 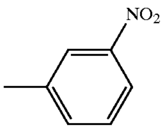 | m.p. 245–246° C. |
| 169 | $—C_2H_4OCH_3$ | m.p. 154–156° C. |
| 170 | 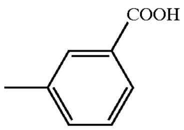 | m.p. 246–247° C. |
| 171 | 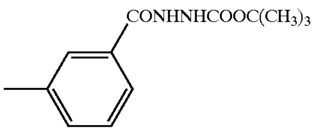 | m.p. 201–202° C. |
| 172 | 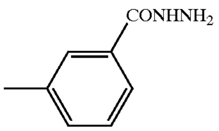 | m.p. 162–163° C. |
| 173 | 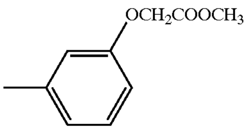 | m.p. 184–185° C. |

TABLE 16-continued
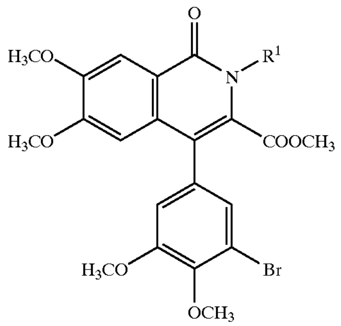
| Ex. No. | $R^1$ | Physicochemical properties |
| --- | --- | --- |
| 174 | 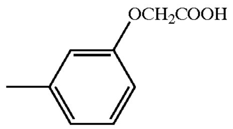 | m.p. 252–253° C. |
| 175 | 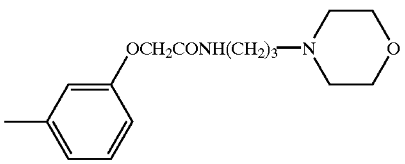 | m.p. 118–119° C. |
| 176 | 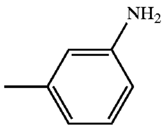 | m.p. 241–242° C. |
| 177 | 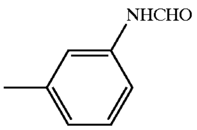 | m.p. > 250° C. |
| 178 | 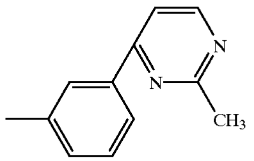 | m.p. 131–132° C. |
| 179 | 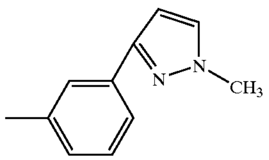 | m.p. 211–212° C. |
| 180 | 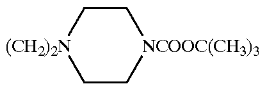 | m.p. 153–154° C. |
| 181** | 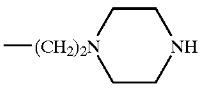 | m.p. 210–211° C. (decomp.) |

TABLE 16-continued
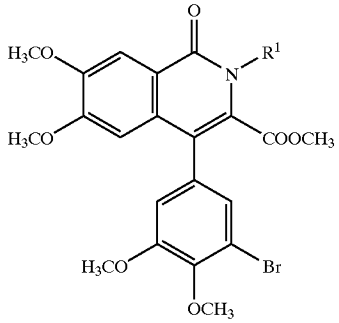
| Ex. No. | $R^1$ | Physicochemical properties |
|---|---|---|
| 182* | 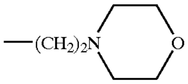 | m.p. 216–217° C. (decomp.) |
| 183 | $—NH_2$ | m.p. 215–216° C. |
| 184 | $—(CH_2)_3OH$ | m.p. 105–106° C. |
| 185 | 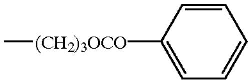 | m.p. 119–120° C. |
| 186 | $—(CH_2)_3CH_3$ | m.p. 140–141° C. |
| 187 | $—CH_2CONH_2$ | m.p. 213–216° C. |
| 188 | 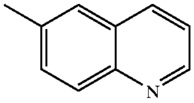 | m.p. > 230° C. |
| 189 | 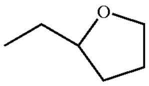 | m.p. 180–182° C. |
| 190 | 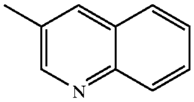 | m.p. 122–124° C. |
| 191 | 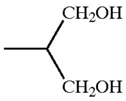 | m.p. 193–196° C. |
| 192 | $—(CH_2)_3N(CH_3)_2$ | m.p. 151–154° C. |
| 193 | $—(CH_2)_3NHCOOC(CH_3)_3$ | m.p. 129–132° C. |
| 194 | $—(CH_2)_3OCH_3$ | m.p. 138–140° C. |
| 195 | 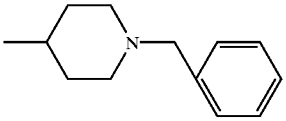 | m.p. 129–131° C. |
| 196 | 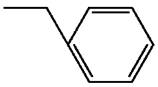 | m.p. 187–189° C. |
| 197 | $—(CH_2)_2CH_3$ | m.p. 166–168° C. |

TABLE 16-continued
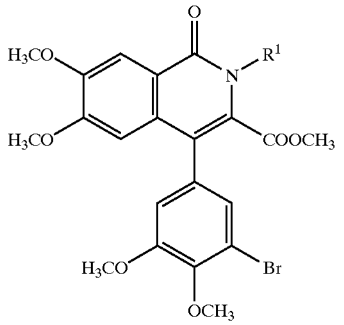
| Ex. No. | $R^1$ | Physicochemical properties |
|---|---|---|
| 198 | 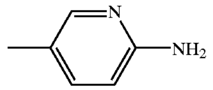 | m.p. 223–226° C. (decomp.) |
| 199* | $—(CH_2)_4NH_2$ | m.p. 172–178° C. (decomp.) |
| 200* | 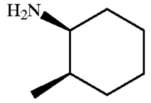 | m.p. 210–214° C. (decomp.) |
| 201* | 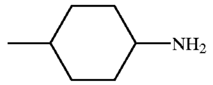 | m.p. 189–192° C. (decomp.) |
| 202 | 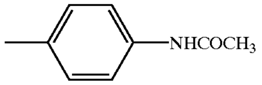 | m.p. 192–194° C. |
| 203 | 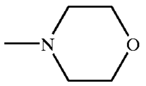 | m.p. 195–196° C. |
| 204 | 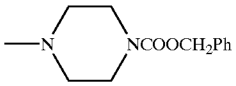 | m.p. 218–222° C. |
| 205* | 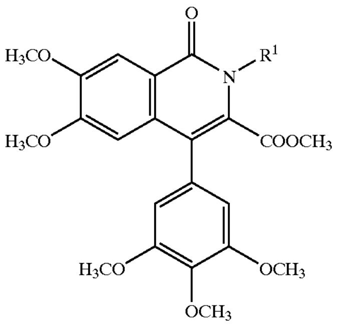 | m.p. 244–246° C. (decomp.) |
| 206 | 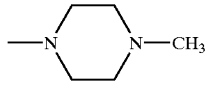 | m.p. 135–136° C. |
| 207* | $—(CH_2)_3NH_2$ | m.p. 210–212° C. (decomp.) |
*monohydrochloride
**dihydrochloride
Ph: phenyl group TABLE 17
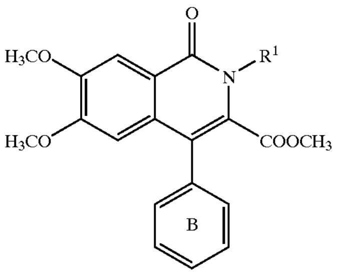
| Ex. No. | $R^1$ | Ring B | Physicochemical properties |
|---|---|---|---|
| 208* | 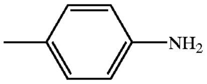 | 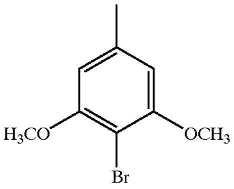 | m.p. > 230° C. |
| 209* | 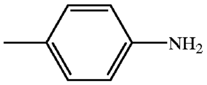 | 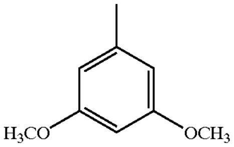 | m.p. > 230° C. |
| 210 | 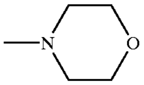 | 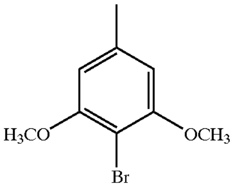 | m.p. > 230° C. |
| 211 | 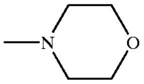 | 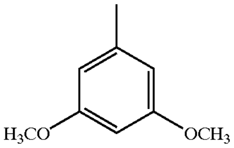 | m.p. 206–208° C. |
| 212 | 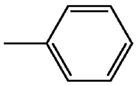 | 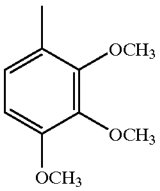 | m.p. 239–241° C. |
*monohydrochloride TABLE 18
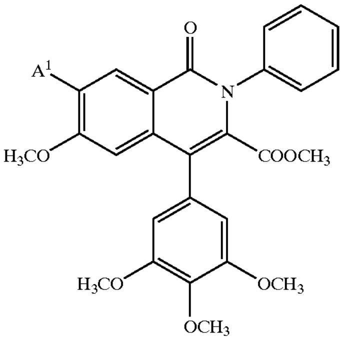
| Ex. No. | $A^1$ | Physicochemical properties |
|---|---|---|
| 213 | $PhCH_2O$— | m.p. 235–237° C. |
| 214 | HO— | m.p. 210–212° C. |
| 215* | 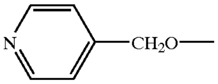 | m.p. 151–152° C. |
| 216* | 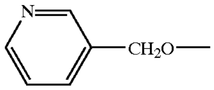 | m.p. 145–146° C. |
| 217* | 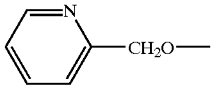 | m.p. 107–109° C. |
TABLE 18-continued
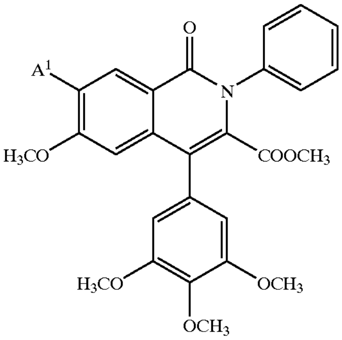
| Ex. No. | $A^1$ | Physicochemical properties |
|---|---|---|
| 218 | 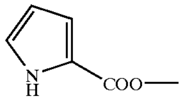 | m.p. 234–235° C. |
| 219 | 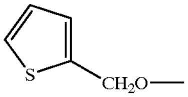 | m.p. 215–216° C. |
| 220 | 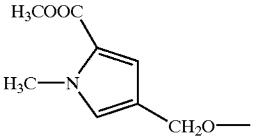 | m.p. 193–195° C. |
*monohydrochloride
Ph: phenyl group
TABLE 19
| Ex. No. | $A^1$ | $R^1$ | Physicochemical properties |
|---|---|---|---|
| 221 | $PhCH_2O$— | 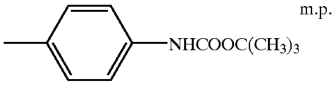 | m.p. 148–149° C. |
| 222* | $PhCH_2O$— | 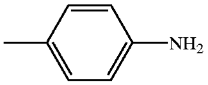 | m.p. 207–208° C. (decomp.) |
| 223 | HO— | 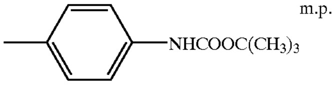 | m.p. 230–231° C. |
| 224* | HO— | 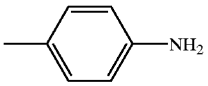 | m.p. 254–255° C. (decomp.) |
| 225** | 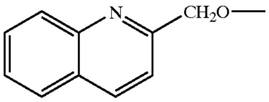 | 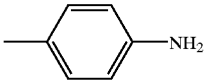 | m.p. 194–197° C. (decomp.) |

TABLE 19-continued
| Ex. No. | $A^1$ | $R^1$ | Physicochemical properties |
|---|---|---|---|
| 226** | 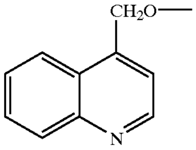 | 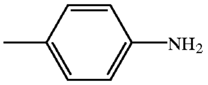 | m.p. 193–197° C. (decomp.) |
| 227** | 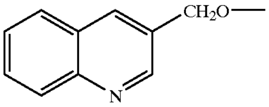 | 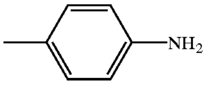 | m.p. 203–206° C. (decomp.) |
*monohydrochloride
**dihydrochloride
Ph: phenyl group
TABLE 20
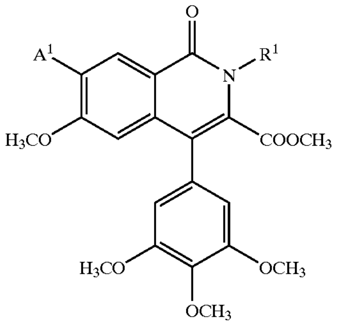
| Ex. No. | $A^1$ | $R^1$ | Physicochemical properties |
|---|---|---|---|
| 228 | $PhCH_2O$— | 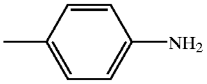 | m.p. 161–163° C. (decomp.) |
| 229 | HO— | 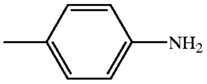 | m.p. 170–172° C. (decomp.) |
| 230(1) | $(CH_3)_3COOCCH_2O$— | 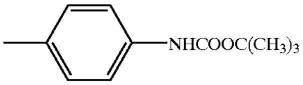 | m.p. 203–204° C. |
| 230(2)* | $HOOCCH_2O$— | 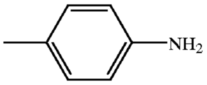 | m.p. 170–172° C. (decomp.) |
| 231(1) | 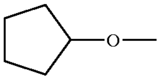 | 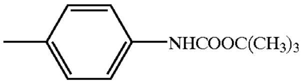 | m.p. 156–158° C. |
| 231(2)* | 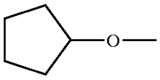 | 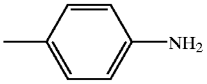 | m.p. 168–170° C. (decomp.) |

TABLE 20-continued
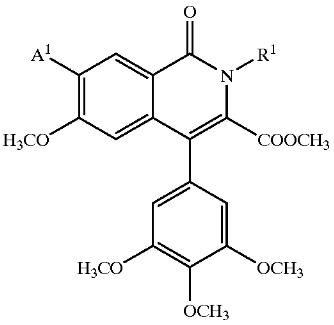
| Ex. No. | $A^1$ | $R^1$ | Physicochemical properties |
| --- | --- | --- | --- |
| 232(1) | $(CH_3)_2NCH_2CH_2O$— | 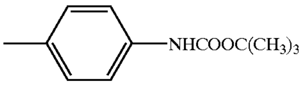 | m.p. 203–204° C. |
| 232(2)** | $(CH_3)_2NCH_2CH_2O$— | 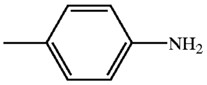 | m.p. > 220° C. |
| 233(1) | $CH_3O(CH_2)_2O(CH_2)_2O$— | 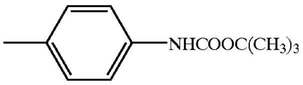 | m.p. 152–154° C. |
| 233(2)* | $CH_3O(CH_2)_2O(CH_2)_2O$— | 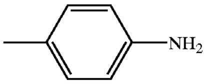 | m.p. 138–145° C. (decomp.) |
| 234(1) | $CH_3CH_2O$— | 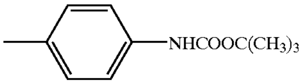 | m.p. 227–229° C. |
| 234(2)* | $CH_3CH_2O$— | 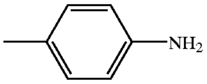 | m.p. 197–200° C. (decomp.) |
| 235(1) | $CH_3O(CH_2)_2O$— | 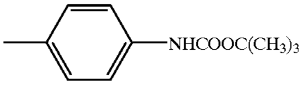 | m.p. 245–247° C. |
| 235(2) | $CH_3O(CH_2)_2O$— | 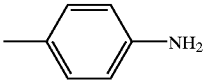 | m.p. 165–170° C. (decomp.) |
| 236(1) | 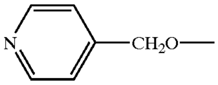 | 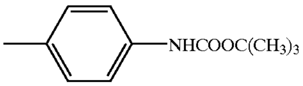 | m.p. 143–145° C. |
| 236(2)** | 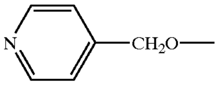 | 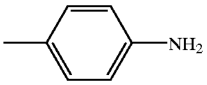 | m.p. 191–196° C. (decomp.) |
| 237(1) | 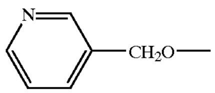 | 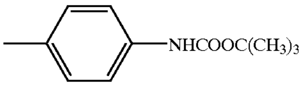 | m.p. 131–132° C. |

TABLE 20-continued
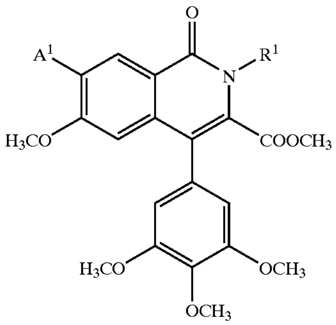
| Ex. No. | $A^1$ | $R^1$ | Physicochemical properties |
|---|---|---|---|
| 237(2)** | 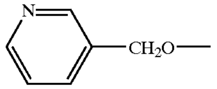 | 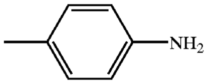 | m.p. 186–190° C. (decomp.) |
| 238(1) | 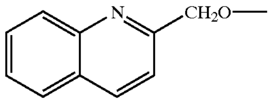 | 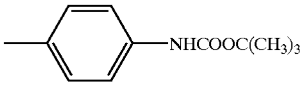 | m.p. 172–173° C. |
| 238(2)** | 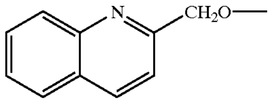 | 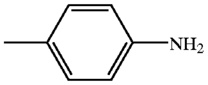 | m.p. 183–186° C. (decomp.) |
| 239(1) | $HO(CH_2)_2O$— | 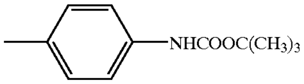 | m.p. 139–140° C. |
| 239(2)* | $HO(CH_2)_2O$— | 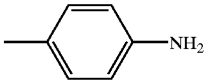 | m.p. 174–176° C. (decomp.) |
| 240(1) | $Ph(CH_2)_2O$— | 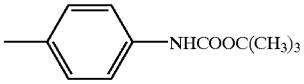 | m.p. 224–225° C. |
| 240(2)* | $Ph(CH_2)_2O$— | 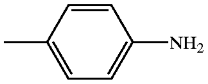 | m.p. 146–149° C. (decomp.) |
| 241(1) | $PhCOCH_2O$— | 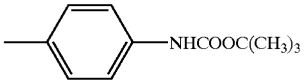 | m.p. 218–219° C. |
| 241(2)* | $PhCOCH_2O$— | 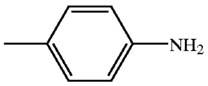 | m.p. 175–177° C. (decomp.) |
| 242(1) | 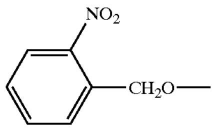 | 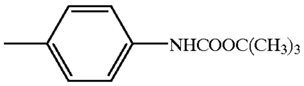 | m.p. 149–151° C. |

TABLE 20-continued
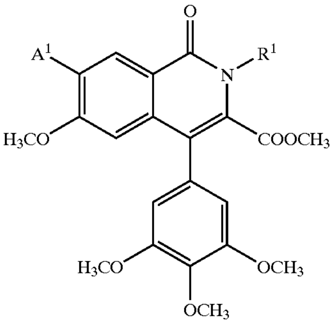
| Ex. No. | $A^1$ | $R^1$ | Physicochemical properties |
|---|---|---|---|
| 242(2)* | 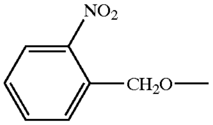 | 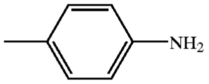 | m.p. 154–156° C. (decomp.) |
| 243(1) | 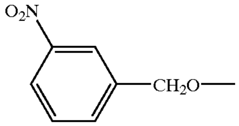 | 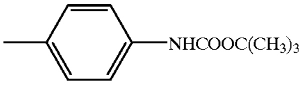 | m.p. 138–139° C. |
| 243(2)* | 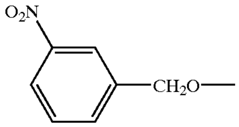 | 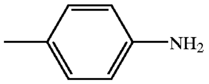 | m.p. 225–227° C. (decomp.) |
| 244(1) | 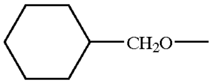 | 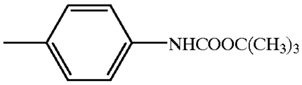 | Powder |
| 244(2)* | 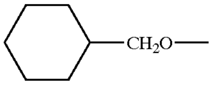 | 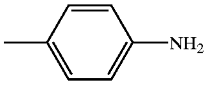 | m.p. 166–167° C. (decomp.) |
| 245(1) | $H_3COOCCH_2O$— | 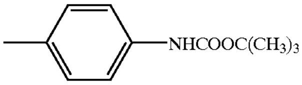 | m.p. 205–206° C. |
| 245(2)* | $H_3COOCCH_2O$— | 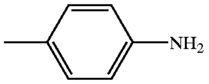 | m.p. 195–197° C. (decomp.) |
| 246(1) | 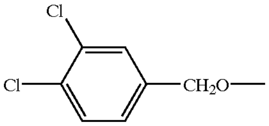 | 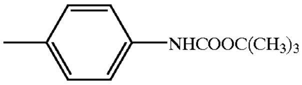 | m.p. 193–195° C. |
| 246(2)* | 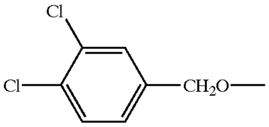 | 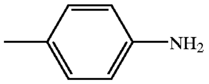 | m.p. 237–239° C. (decomp.) |
| 247(1) | 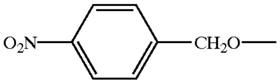 | 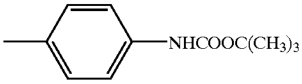 | m.p. 183–185° C. |

TABLE 20-continued
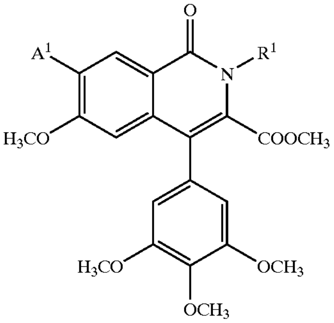
| Ex. No. | $A^1$ | $R^1$ | Physicochemical properties |
|---|---|---|---|
| 247(2)* | 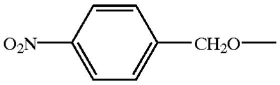 | 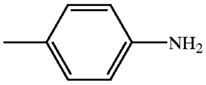 | m.p. 235–237° C. (decomp.) |
| 248(1) | 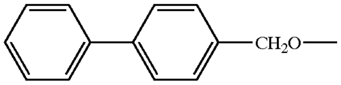 | 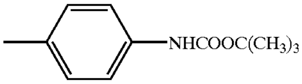 | m.p. 216–217° C. |
| 248(2)* | 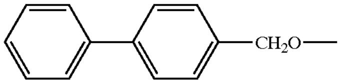 | 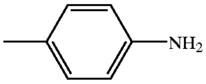 | m.p. 151–153° C. (decomp.) |
| 249(1) | 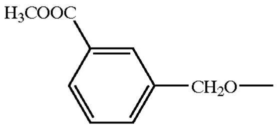 | 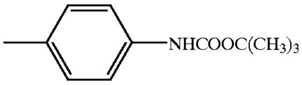 | m.p. 190–191° C. |
| 249(2)* | 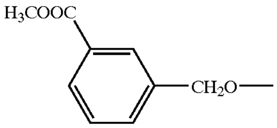 | 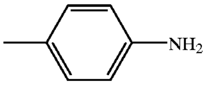 | m.p. 205–208° C. (decomp.) |
| 250(1) | 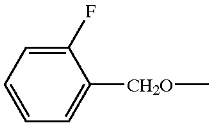 | 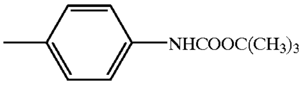 | m.p. 176–178° C. |
| 250(2)* | 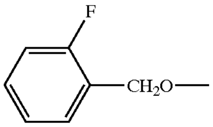 | 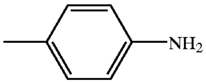 | m.p. 167–169° C. (decomp.) |
| 251(1) | 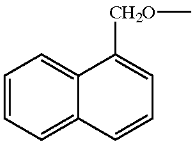 | 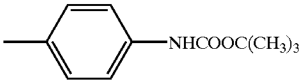 | m.p. 230–232° C. (decomp.) |
| 251(2)* | 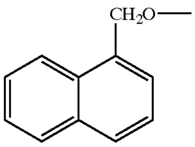 | 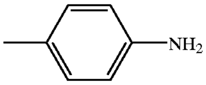 | m.p. 156–158° C. (decomp.) |

TABLE 20-continued
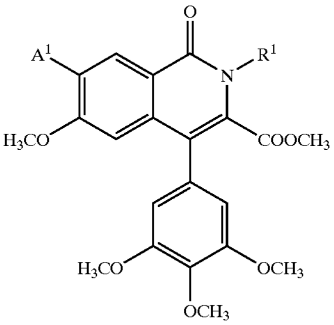
| Ex. No. | $A^1$ | $R^1$ | Physicochemical properties |
|---|---|---|---|
| 252(1) | 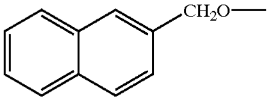 | 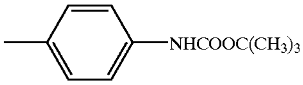 | m.p. 216–217° C. |
| 252(2)* | 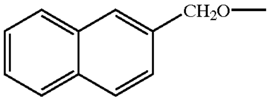 | 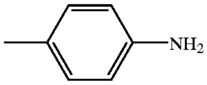 | m.p. 185–190° C. (decomp.) |
| 253(1) | $CH_2$═$CHCH_2O$— | 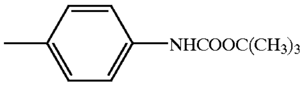 | m.p. 229–230° C. |
| 253(2)* | $CH_2$═$CHCH_2O$— | 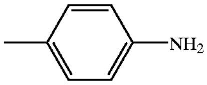 | m.p. 197–200° C. (decomp.) |
| 254(2)* | 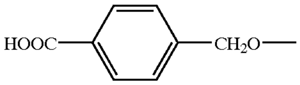 | 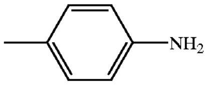 | m.p. > 230° C. |
| 254(3)* | 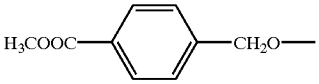 | 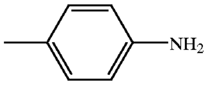 | m.p. 192–195° C. (decomp.) |
| 255(1) | 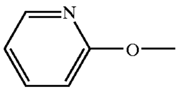 | 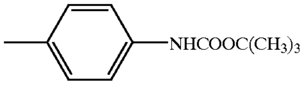 | m.p. 223–224° C. |
| 255(2)** | 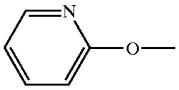 | 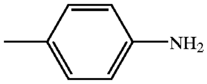 | m.p. 186–188° C. (decomp.) |
| 256(1) | 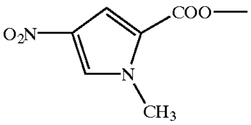 | 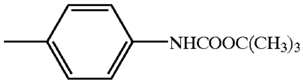 | m.p. 232–233° C. |
| 256(2)* | 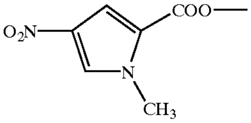 | 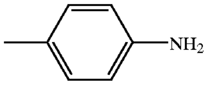 | m.p. 220–223° C. (decomp.) |

TABLE 20-continued
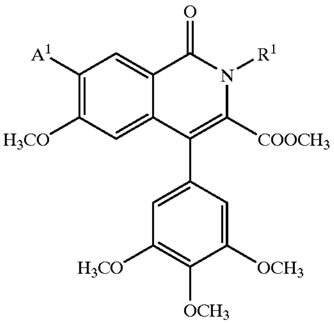
| Ex. No. | $A^1$ | $R^1$ | Physicochemical properties |
|---|---|---|---|
| 257(1) | PhCOO— | 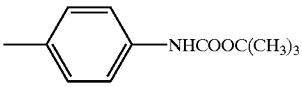 | m.p. 234–235° C. |
| 257(2)* | PhCOO— | 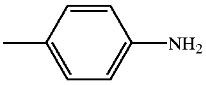 | m.p. 175–176° C. (decomp.) |
| 258(1) | 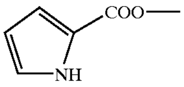 | 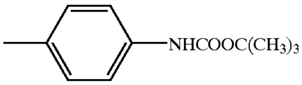 | — |
| 258(2)* | 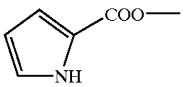 | 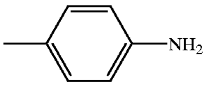 | m.p. 180–182° C. (decomp.) |
| 259(1) | 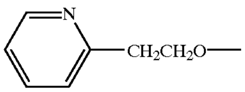 | 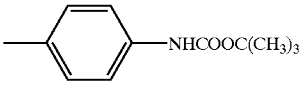 | m.p. 213–215° C. |
| 259(2)** | 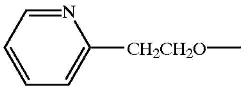 | 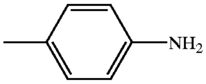 | m.p. 178–182° C. (decomp.) |
| 260(1) | 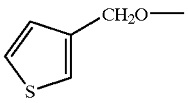 | 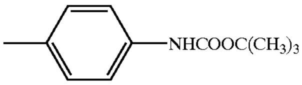 | m.p. 143–145° C. |
| 260(2)* | 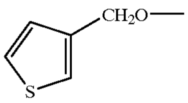 | 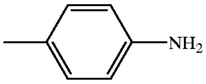 | m.p. 151–155° C. (decomp.) |
| 261(1) | 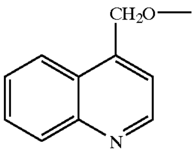 | 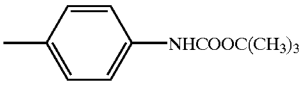 | m.p. 145–146° C. |
| 261(2)** | 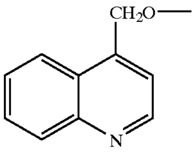 | 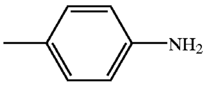 | m.p. 196–200° C. (decomp.) |

TABLE 20-continued
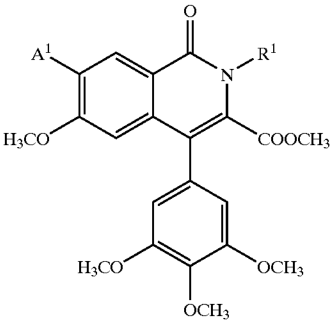
| Ex. No. | $A^1$ | $R^1$ | Physicochemical properties |
|---|---|---|---|
| 262(1) | 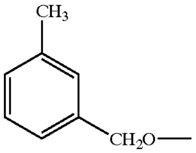 | 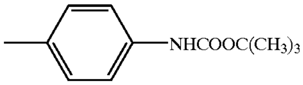 | m.p. 142–144° C. |
| 262(2)* | 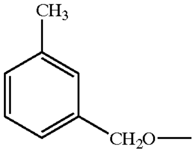 | 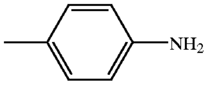 | m.p. 165–168° C. (decomp.) |
| 263(1) | 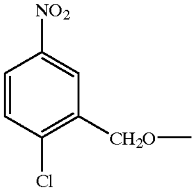 | 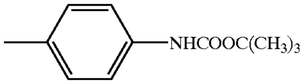 | m.p. 138–139° C. |
| 263(2)* | 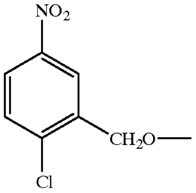 | 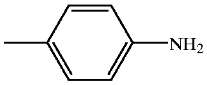 | m.p. 159–160° C. (decomp.) |
| 264(1) | 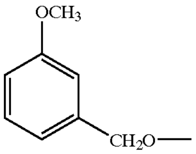 | 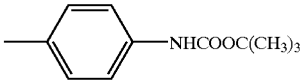 | — |
| 264(2)* | 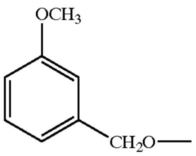 | 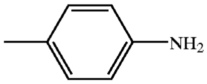 | m.p. 160–164° C. (decomp.) |
| 265(1) | 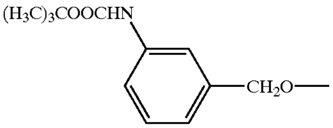 | 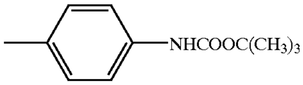 | — |

TABLE 20-continued
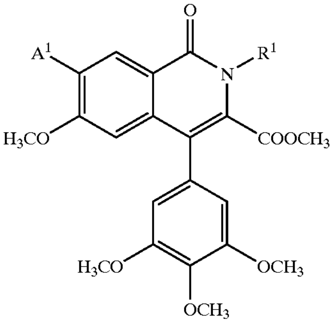
| Ex. No. | $A^1$ | $R^1$ | Physicochemical properties |
|---|---|---|---|
| 265(2)** | 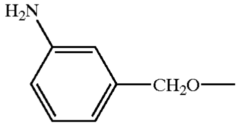 | 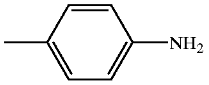 | m.p. 218–219° C. (decomp.) |
| 266(1) | 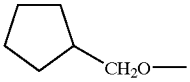 | 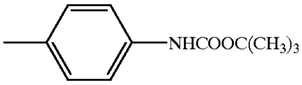 | — |
| 266(2)* | 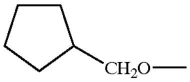 | 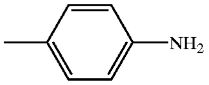 | m.p. 161–162° C. (decomp.) |
| 267(1) | 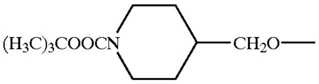 | 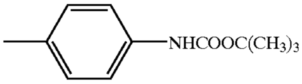 | m.p. 116–119° C. |
| 267(2)** | 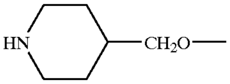 | 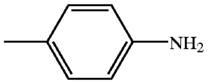 | m.p. 225–227° C. (decomp.) |
| 268(1) | 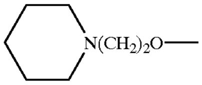 | 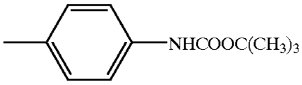 | m.p. 209–210° C. |
| 268(2)** | 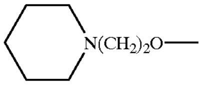 | 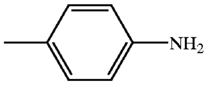 | m.p. 83–84° C. (decomp.) |
| 269(1) | 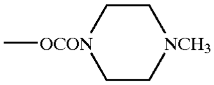 | 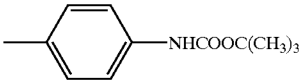 | m.p. 245–247° C. (decomp.) |
| 269(2)** | 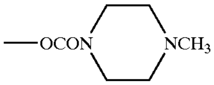 | 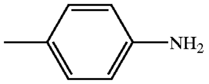 | m.p. 216–218° C. (decomp.) |
| 270(1) | $—OCON(C_2H_5)_2$ | 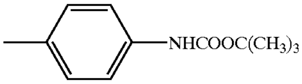 | m.p. 237–240° C. (decomp.) |
| 270(2)* | $—OCON(C_2H_5)_2$ | 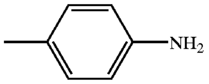 | m.p. 186–188° C. (decomp.) |

TABLE 20-continued
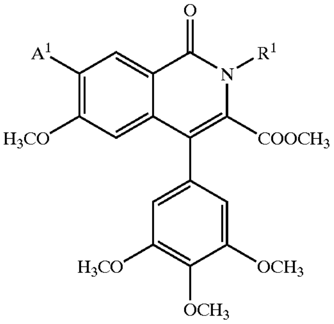
| Ex. No. | A[1] | R[1] | Physicochemical properties |
|---|---|---|---|
| 271(1) | 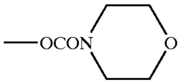 | 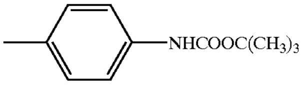 | m.p. > 250° C. |
| 271(2)* | 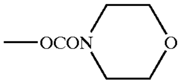 | 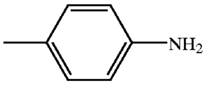 | m.p. 179–180° C. (decomp.) |
| 272(2) | 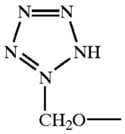 | 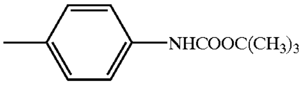 | m.p. 193–194° C. |
| 272(3)* | 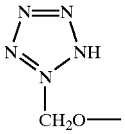 | 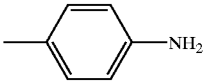 | m.p. > 230° C. |
| 273(1) | 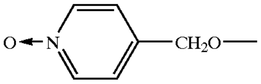 | 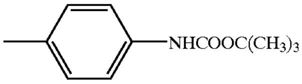 | m.p. 159–160° C. |
| 273(2)* | 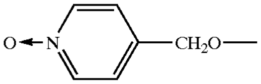 | 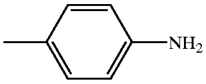 | m.p. 178–180° C. (decomp.) |
| 274(1) | 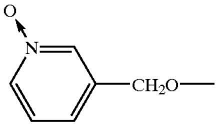 | 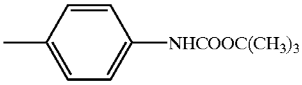 | m.p. 141–142° C. |
| 274(2)* | 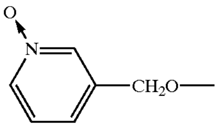 | 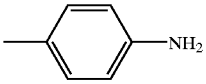 | m.p. 177–179° C. (decomp.) |
| 275(1) | 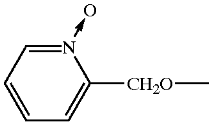 | 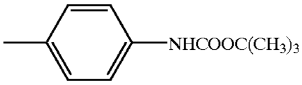 | m.p. 148–149° C. |

TABLE 20-continued
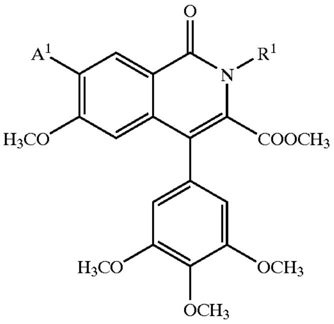
| Ex. No. | $A^1$ | $R^1$ | Physicochemical properties |
|---|---|---|---|
| 275(2)* | 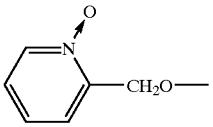 | 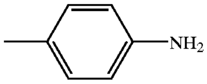 | m.p. 180–183° C. (decomp.) |
| 276(1) | $—OCH_2CONH_2$ | 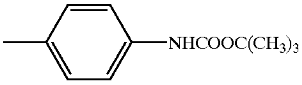 | m.p. 227–228° C. |
| 276(2)* | $—OCH_2CONH_2$ | 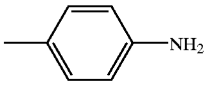 | m.p. 195–197° C. (decomp.) |
| 277(1) | 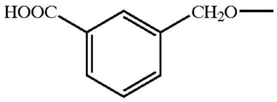 | 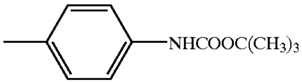 | — |
| 277(2)* | 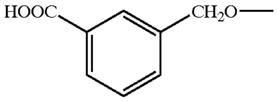 | 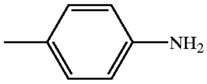 | m.p. 171–174° C. (decomp.) |
*monohydrochloride
**dihydrochloride
Ph: phenyl group
TABLE 21
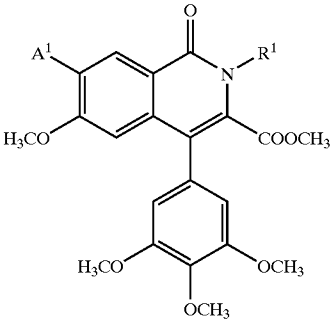
| Ex. No. | $A^1$ | $R^1$ | Physicochemical properties |
|---|---|---|---|
| 278* | 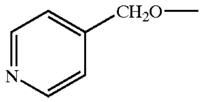 | 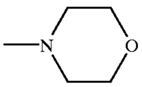 | m.p. 221–223° C. (decomp.) |
TABLE 21-continued
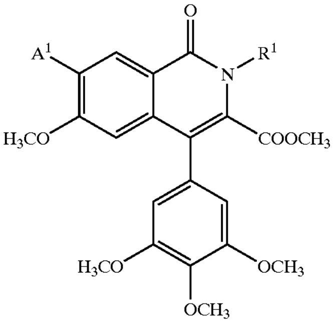
| Ex. No. | $A^1$ | $R^1$ | Physicochemical properties |
|---|---|---|---|
| 279* | 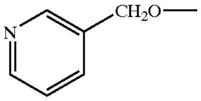 | 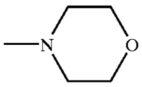 | m.p. 108–110° C. (decomp.) |
*monohydrochloride TABLE 22
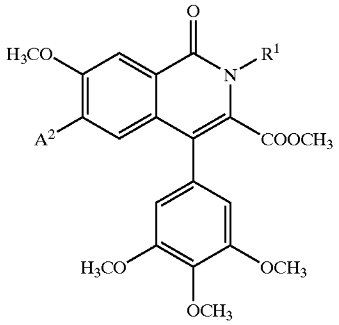
| Ex. No. | $A^2$ | $R^1$ | Physicochemical properties |
|---|---|---|---|
| 280 | $PhCH_2O$— | 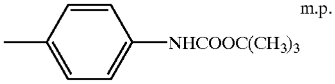 | m.p. 198–199° C. |
| 281 | HO— | 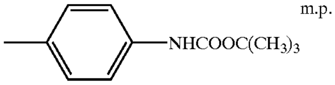 | m.p. 228–229° C. |
| 282* | $PhCH_2O$— | 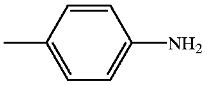 | m.p. 174–177° C. (decomp.) |
| 283* | HO— | 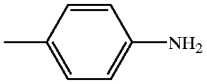 | m.p. 175–180° C. (decomp.) |
| 284(1) | $CH_3O(CH_2)_2O(CH_2)_2O$— | 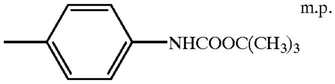 | m.p. 200–202° C. |
| 284(2)* | $CH_3O(CH_2)_2O(CH_2)_2O$— | 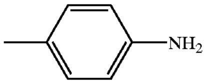 | m.p. 175–180° C. (decomp.) |
| 285(1) | $CH_3CH_2O$— | 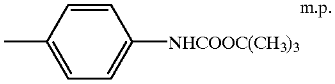 | m.p. 196–198° C. |
| 285(2)* | $CH_3CH_2O$— | 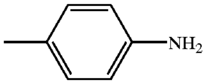 | m.p. 189–190° C. (decomp.) |
| 286(1) | $CH_3O(CH_2)_2O$— | 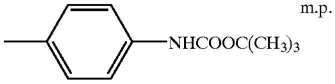 | m.p. 186–187° C. |
| 286(2)* | $CH_3O(CH_2)_2O$— | 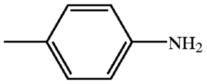 | m.p. 205–210° C. (decomp.) |
| 287(1) | $HO(CH_2)_2O$— | 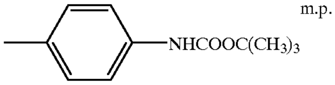 | m.p. 138–139° C. |

TABLE 22-continued
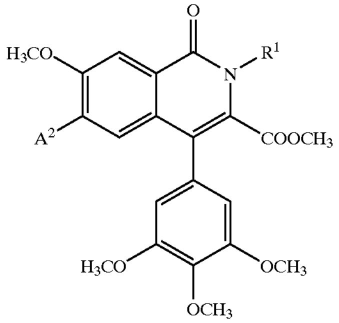
| Ex. No. | $A^2$ | $R^1$ | Physicochemical properties |
|---|---|---|---|
| 287(2)* | $HO(CH_2)_2O$— | 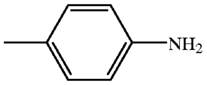 | m.p. 195–200° C. (decomp.) |
| 288(1) | 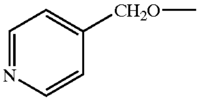 | 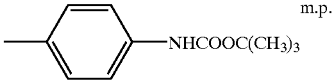 | m.p. 219–221° C. |
| 288(2)** | 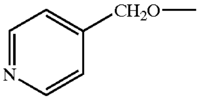 | 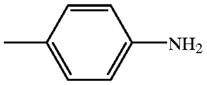 | m.p. 215–220° C. (decomp.) |
| 289(1) | 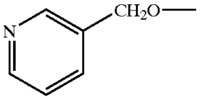 | 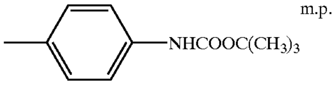 | m.p. 189–190° C. |
| 289(2)** | 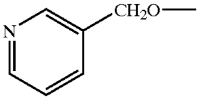 | 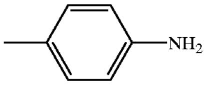 | m.p. 208–210° C. (decomp.) |
| 290(1) | 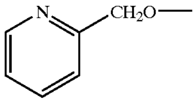 | 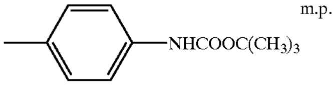 | m.p. 171–173° C. |
| 290(2)** | 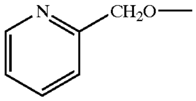 | 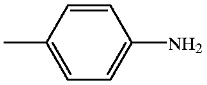 | m.p. 188–189° C. (decomp.) |

TABLE 22-continued
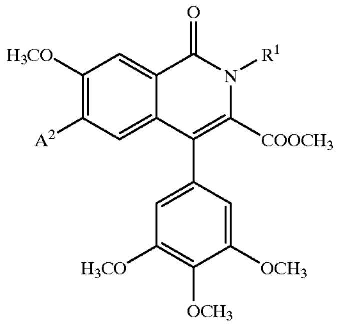
| Ex. No. | $A^2$ | $R^1$ | Physicochemical properties |
|---|---|---|---|
| 291(1) | 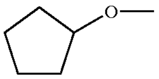 | 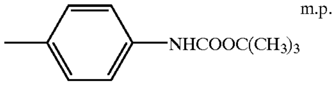 | m.p. 221–223° C. |
| 291(2)* | 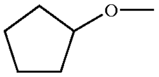 | 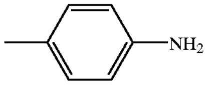 | m.p. 160–162° C. (decomp.) |
| 292(1) | 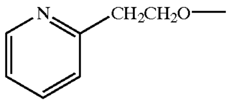 | 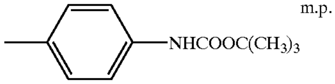 | m.p. 202–203° C. |
| 292(2)** | 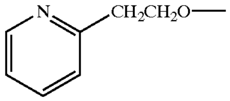 | 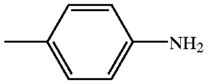 | m.p. 187–190° C. (decomp.) |
*monohydrochloride
**dihydrochloride
Ph: phenyl group
TABLE 23
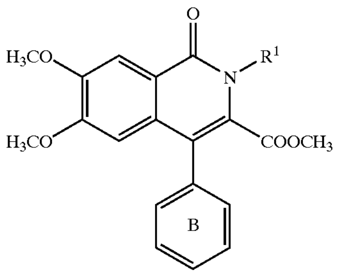
| Ex. No. | $R^1$ | Ring B | Physicochemical properties |
|---|---|---|---|
| 293 | 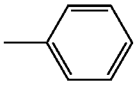 | 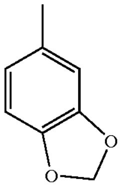 | m.p. 234–235° C. |
TABLE 23-continued
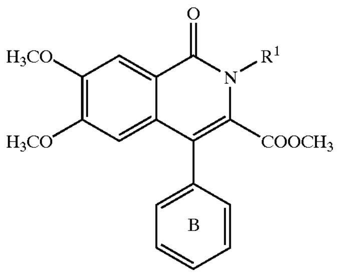
| Ex. No. | $R^1$ | Ring B | Physicochemical properties |
|---|---|---|---|
| 294 | 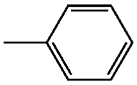 | 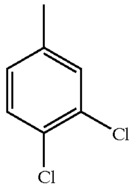 | m.p. 228–230° C. |

TABLE 24
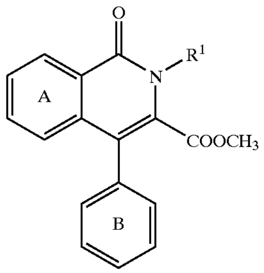
| Ex. No. | Ring A | Ring B | $R^1$ | Physicochemical properties |
|---|---|---|---|---|
| 295* | 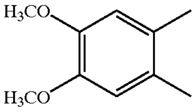 | 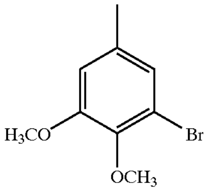 | 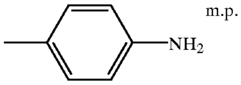 | m.p. > 220° C. |
| 296 | 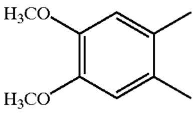 | 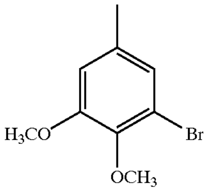 | 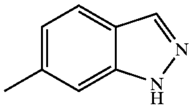 | m.p. 168–171° C. |
| 297 | 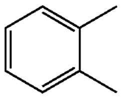 | 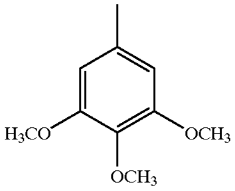 | 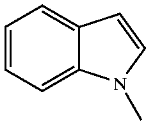 | m.p. 176–178° C. |
| 298 | 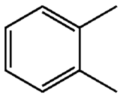 | 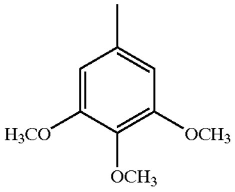 | $—NHCOCF_3$ | m.p. 167–169° C. |
| 299 | 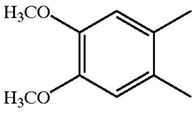 | 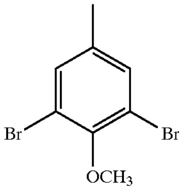 | 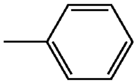 | m.p. 189–191° C. |
*monohydrochloride TABLE 25
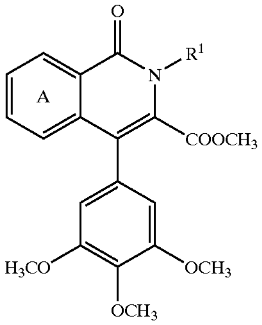
| Ex. No. | Ring A | $R^1$ | Physicochemical properties |
|---|---|---|---|
| 300** | 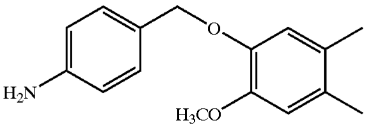 | 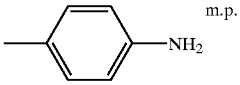 | m.p. 184–186° C. |
| 301* | 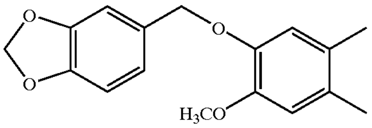 | 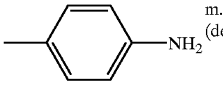 | m.p. 165–168° C. (decomp.) |
| 302* | 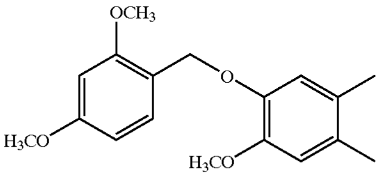 | 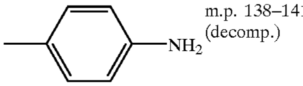 | m.p. 138–141° C. (decomp.) |
| 303* | 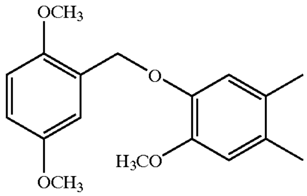 | 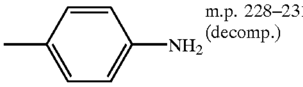 | m.p. 228–231° C. (decomp.) |
| 304* | 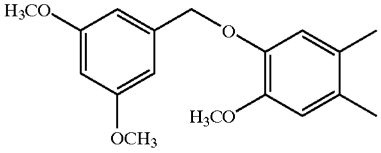 | 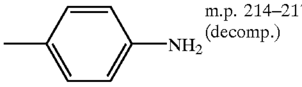 | m.p. 214–217° C. (decomp.) |
| 305* | 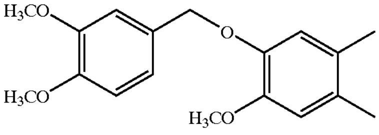 | 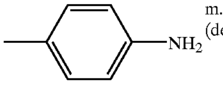 | m.p. 136–138° C. (decomp.) |
| 306* | 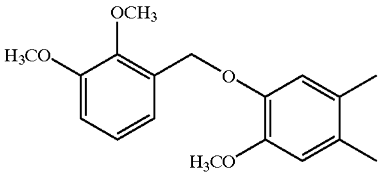 | 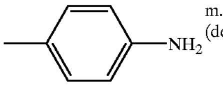 | m.p. 144–146° C. (decomp.) |

TABLE 25-continued
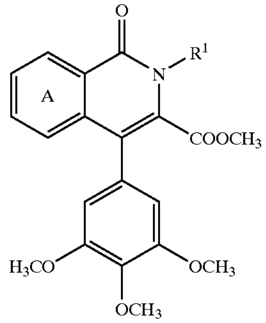
| Ex. No. | Ring A | $R^1$ | Physicochemical properties |
|---|---|---|---|
| 307* | 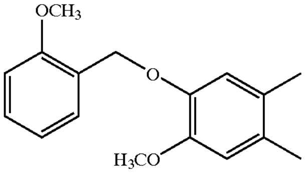 | 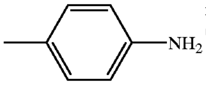 | m.p. 146–148° C. (decomp.) |
| 308* | 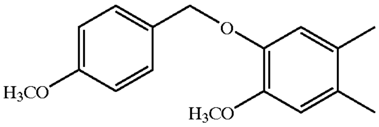 | 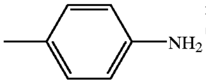 | m.p. 141–144° C. (decomp.) |
*: monohydrochloride
**: dihydrochloride
TABLE 26
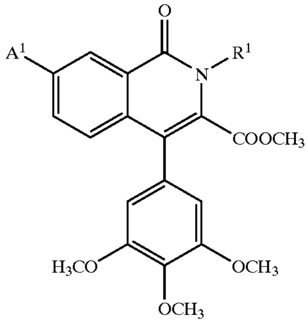
| Ex. No. | $A^1$ | $R^1$ | Physicochemical properties |
|---|---|---|---|
| 309** | 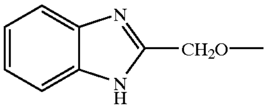 | 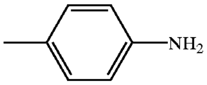 | m.p. 242–243° C. (decomp.) |
| 310* | 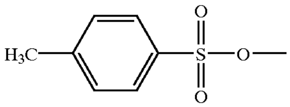 | 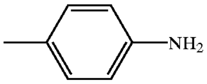 | m.p. 190–195° C. (decomp.) |
| 311(1) | 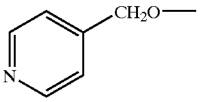 | 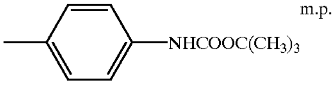 | m.p. 150–151° C. |

TABLE 26-continued
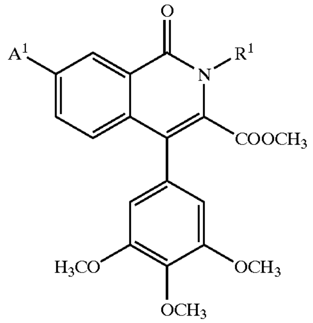
| Ex. No. | $A^1$ | $R^1$ | Physicochemical properties |
|---|---|---|---|
| 311(2)** | 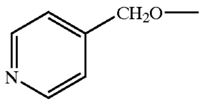 | 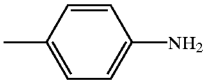 | m.p. 232–233° C. (decomp.) |
| 312(1) | 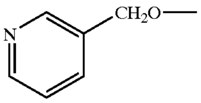 | 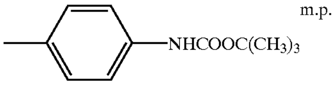 | m.p. 144–145° C. |
| 312(2)** | 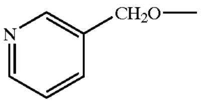 | 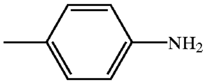 | m.p. 208–209° C. (decomp.) |
| 313(1) | 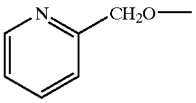 | 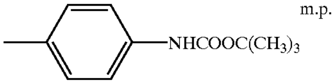 | m.p. 136–138° C. |
| 313(2)** | 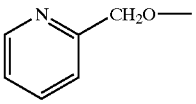 | 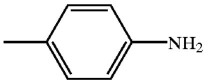 | m.p. 207–208° C. (decomp.) |
| 314* | 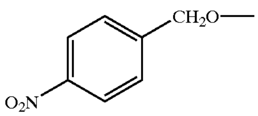 | 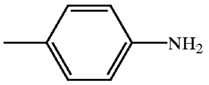 | m.p. 240–242° C. (decomp.) |
| 315* | 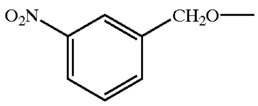 | 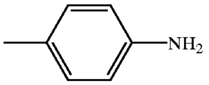 | m.p. 232–235° C. (decomp.) |
| 316* | 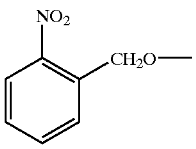 | 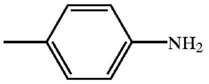 | m.p. 181–183° C. (decomp.) |
*: monohydrochloride,
**: dihydrochloride TABLE 27
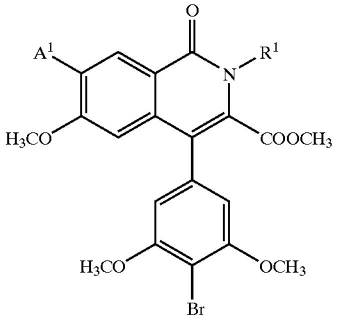
| Ex. No. | $A^1$ | $R^1$ | Physicochemical properties |
|---|---|---|---|
| 317 | 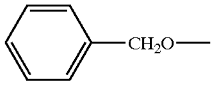 | 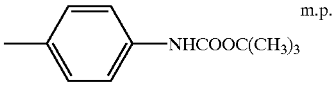 | m.p. 168–169° C. |
| 318* | 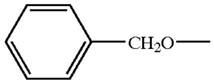 | 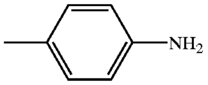 | m.p. 194–196° C. (decomp.) |
| 319(1) (2)* | HO— | 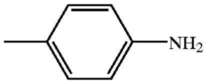 | (1)m.p. 171–172° C. (2)m.p. 238–242° C. (decomp.) |
| 320** | 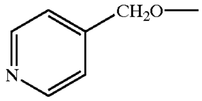 | 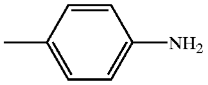 | m.p. 213–214° C. (decomp.) |
| 321** | 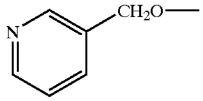 | 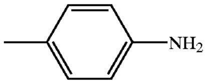 | m.p. 196–199° C. (decomp.) |
| 322** | 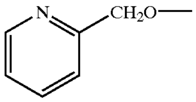 | 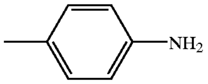 | m.p. 186–188° C. (decomp.) |
| 323** | 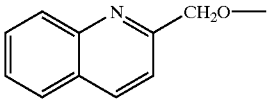 | 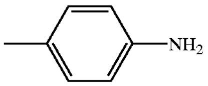 | m.p. 240–243° C. (decomp.) |
*: monohydrochloride
**: dihydrochloride TABLE 28
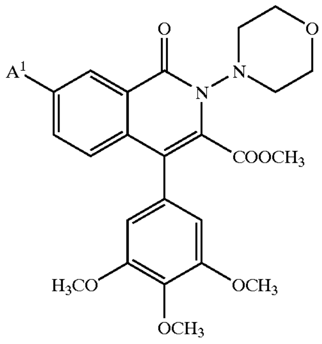
| Ex. No. | $A^1$ | Physicochemical properties |
|---|---|---|
| 324 | 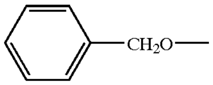 | m.p. 173–174° C. |
| 325 | HO— | m.p. >250° C. |
| 326* | 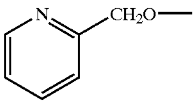 | m.p. 193–196° C. (decomp.) |
TABLE 28-continued
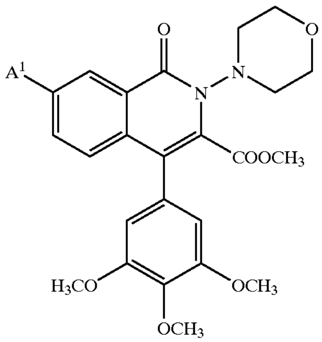
| Ex. No. | $A^1$ | Physicochemical properties |
|---|---|---|
| 327* | 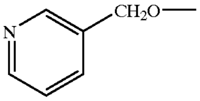 | m.p. 135–138° C. (decomp.) |
| 328* | 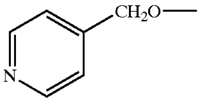 | m.p. 138–139° C. (decomp.) |
*: monohydrochloride
TABLE 29
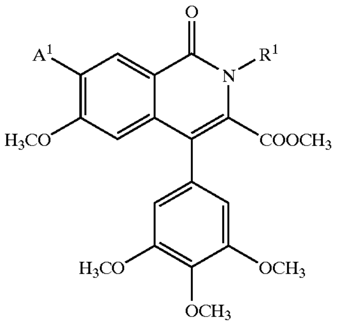
| Ex. No. | $A^1$ | $R^1$ | Physicochemical properties |
|---|---|---|---|
| 329 | 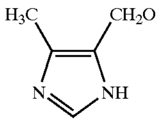 | 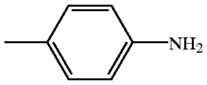 | m.p. 175–178° C. (decomp.) |
| 330(1) | 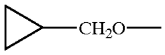 | 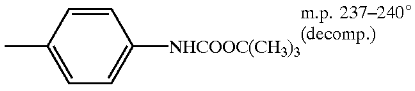 | m.p. 237–240° C. (decomp.) |
| 330(2)* | 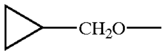 | 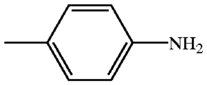 | m.p. 210–212° C. (decomp.) |

TABLE 29-continued
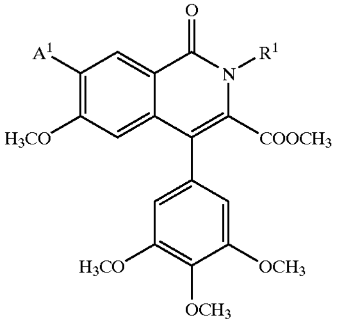
| Ex. No. | $A^1$ | $R^1$ | Physicochemical properties |
|---|---|---|---|
| 331** | 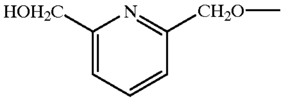 | 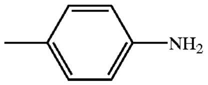 | m.p. 193–195° C. (decomp.) |
| 332** | 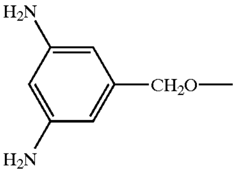 | 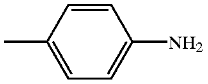 | m.p. 210–212° C. (decomp.) |
| 333** | 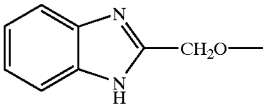 | 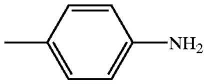 | m.p. 210–215° C. (decomp.) |
*: monohydrochloride
**: dihydrochloride
***: trihydrochloride.
TABLE 30
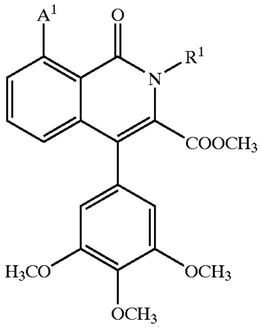
| Ex. No. | $A^1$ | $R^1$ | Physicochemical properties |
|---|---|---|---|
| 334 | H | 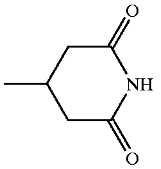 | m.p. 203–205° C. |
| 335 | 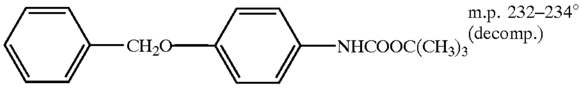 | | m.p. 232–234° C. (decomp.) |

TABLE 30-continued
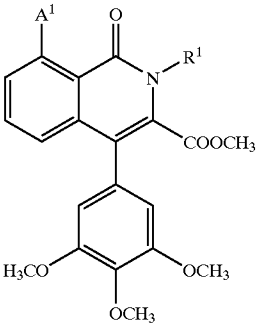
| Ex. No. | $A^1$ | $R^1$ | Physicochemical properties |
|---|---|---|---|
| 336 | 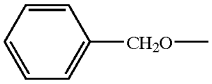 | 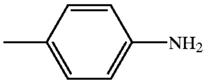 | m.p. 241–243° C. |
| 337 | HO— | 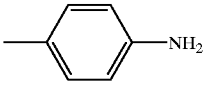 | m.p. 222–224° C. (decomp.) |
*: monohydrochloride
TABLE 31
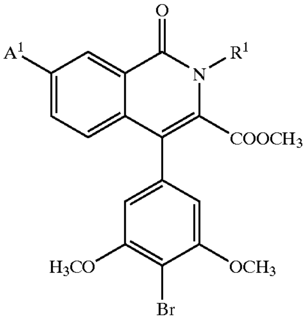
| Ex. No. | $A^1$ | $R^1$ | Physicochemical properties |
|---|---|---|---|
| 338 | 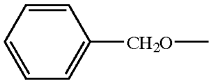 | 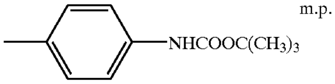 | m.p. 143–145° C. |
| 339* | 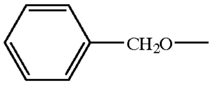 | 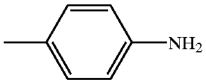 | m.p. 168–171° C. |
| 340(1) (2)* | HO— | 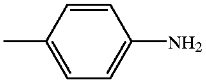 | (1)m.p. >250° C. (2)m.p. 247–249° C. (decomp.) |
*: monohydrochloride

TABLE 32

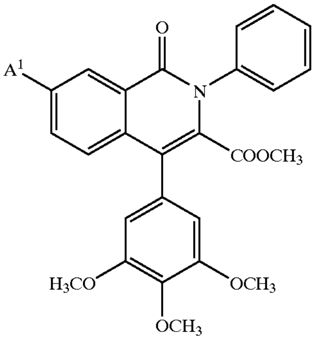

| Ex. No. | $A^1$ | Physicochemical properties |
|---|---|---|
| 341 | 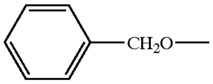 | m.p. 148–149° C. |
| 342 | HO— | m.p. 236–238° C. |
| 343* | 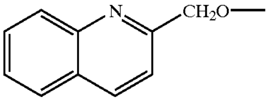 | m.p. 209–212° C. (decomp.) |
| 344* | 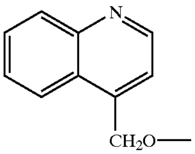 | m.p. 171–172° C. (decomp.) |
| 345* | 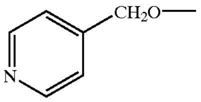 | m.p. 228–230° C. (decomp.) |
| 346* | 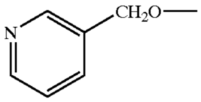 | m.p. 151–153° C. (decomp.) |
| 347* | 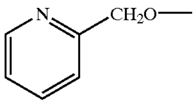 | m.p. 126–128° C. (decomp.) |

*: monohydrochloride

TABLE 33

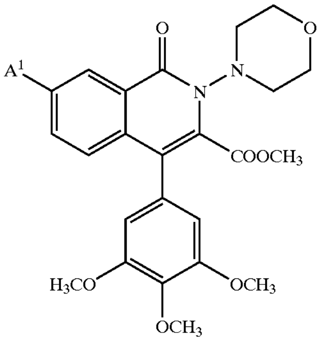

| Ex. No. | $A^1$ | Physicochemical properties |
|---|---|---|
| 348* | 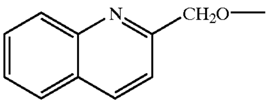 | m.p. 142–147° C. (decomp.) |

TABLE 34

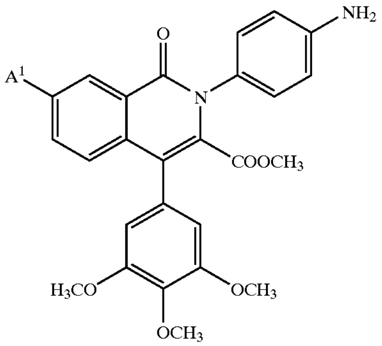

| Ex. No. | $A^1$ | Physicochemical properties |
|---|---|---|
| 349** | 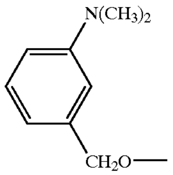 | m.p. 170–173° C. (decomp.) |
| 350** | 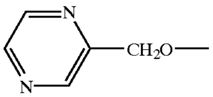 | m.p. 188–192° C. (decomp.) |
| 351* | 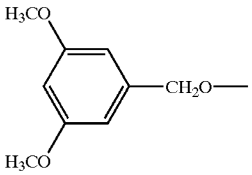 | m.p. 208–213° C. (decomp.) |
| 352* | 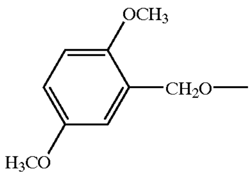 | m.p. 121–123° C. (decomp.) |

*: monohydrochloride
**: dihydrochloride

TABLE 35

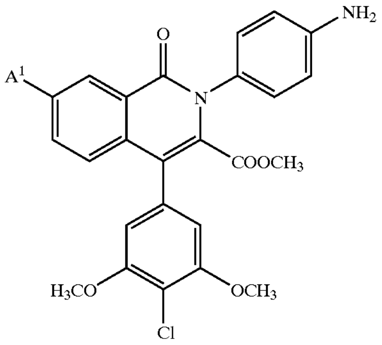

| Ex. No. | $A^1$ | Physicochemical properties |
|---|---|---|
| 353* | 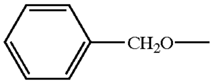 | m.p. 203–205° C. (decomp.) |
| 354 | HO— | m.p. >250° C. |

TABLE 35-continued

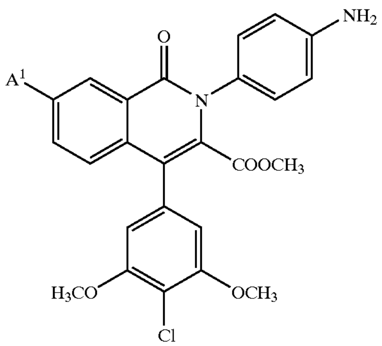

| Ex. No. | $A^1$ | Physicochemical properties |
|---|---|---|
| 355** | 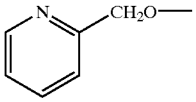 | m.p. 210–213° C. (decomp.) |
| 356** | 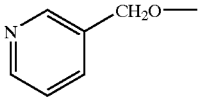 | m.p. 213–216° C. (decomp.) |
| 357** | 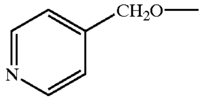 | m.p. 222–225° C. (decomp.) |
| 358** | 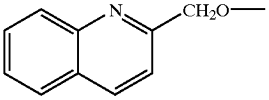 | m.p. 210–215° C. (decomp.) |

*: monohydrochloride
**: dihydrochloride

TABLE 36

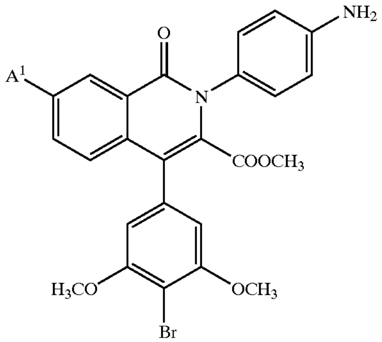

| Ex. No. | $A^1$ | Physicochemical properties |
|---|---|---|
| 359** | 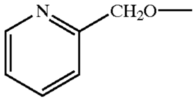 | m.p. 194–197° C. (decomp.) |
| 360** | 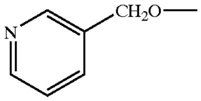 | m.p. 204–206° C. (decomp.) |
| 361** | 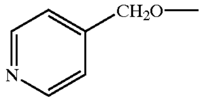 | m.p. 205–208° C. (decomp.) |

TABLE 36-continued

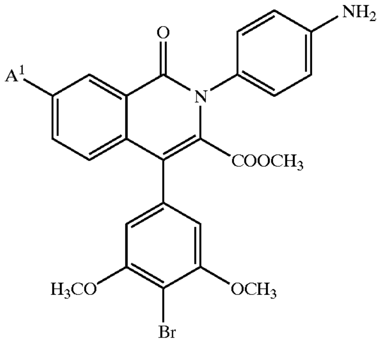

| Ex. No. | $A^1$ | Physicochemical properties |
|---|---|---|
| 362** | 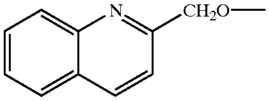 | m.p. 235–239° C. (decomp.) |
| 363* | 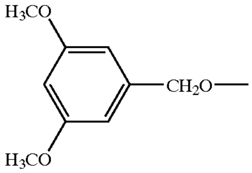 | m.p. 235–238° C. (decomp.) |
| 364** | 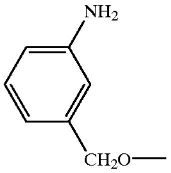 | m.p. 208–210° C. (decomp.) |

*: monohydrochloride
**: dihydrochloride

TABLE 37

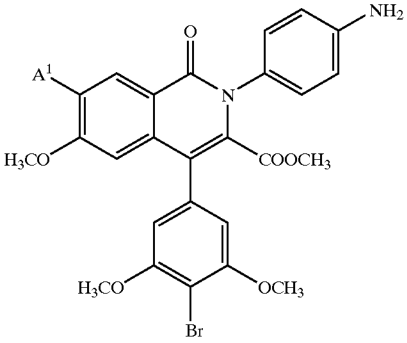

| Ex. No. | $A^1$ | Physicochemical properties |
|---|---|---|
| 365* | 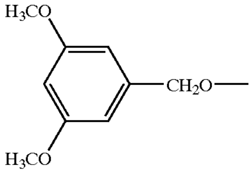 | m.p. 184–187° C. (decomp.) |

TABLE 37-continued
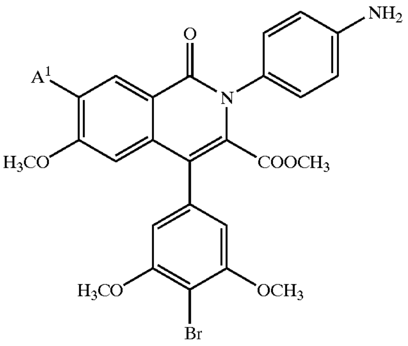
| Ex. No. | $A^1$ | Physicochemical properties |
|---|---|---|
| 366* | 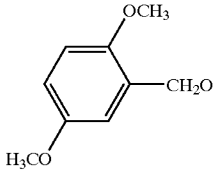 | m.p. 178–182° C. (decomp.) |
| 367* | $NCCH_2O$— | m.p. 172–175° C. (decomp.) |
TABLE 37-continued
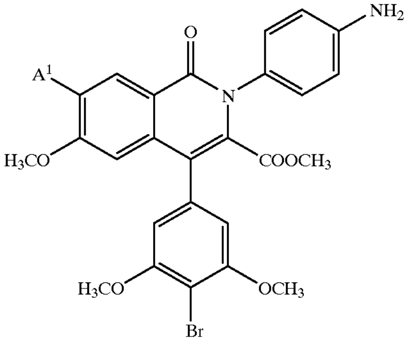
| Ex. No. | $A^1$ | Physicochemical properties |
|---|---|---|
| 368** | 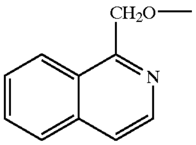 | m.p. 215–218° C. (decomp.) |
*: monohydrochloride
**: dihydrochloride
TABLE 38
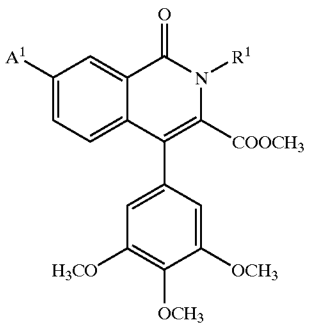
| Ex. No. | $A^1$ | $R^1$ | Physicochemical properties |
|---|---|---|---|
| 369 | HO— | 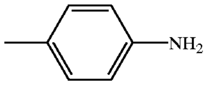 | m.p. 149–151° C. |
| 370 | HO— | 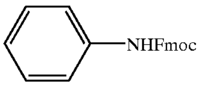 | m.p. >250° C. |
| 371*** | 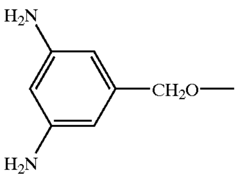 | 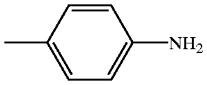 | m.p. 190–200° C. (decomp.) |

TABLE 38-continued
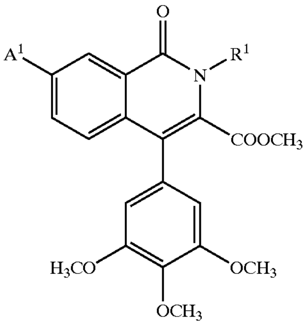
| Ex. No. | $A^1$ | $R^1$ | Physicochemical properties |
| --- | --- | --- | --- |
| 372** | 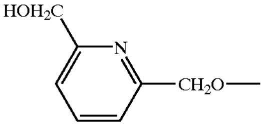 | 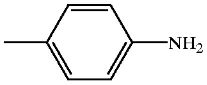 | m.p. 185–190° C. (decomp.) |
| 373(1) | 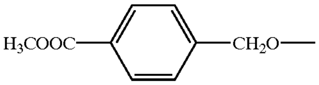 | 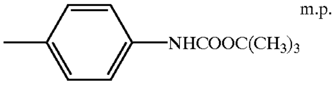 | m.p. 148–150° C. |
| 373(2)* | 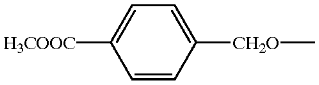 | 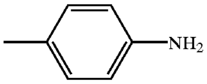 | m.p. 221–224° C. (decomp.) |
| 374 | 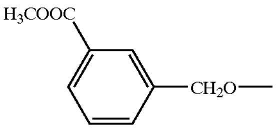 | 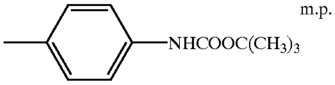 | m.p. 206–209° C. |
| 375(1) | 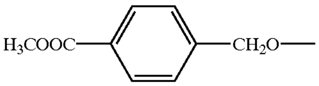 | 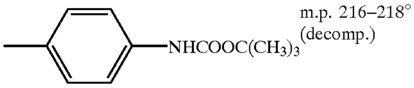 | m.p. 216–218° C. (decomp.) |
| 375(2)* | 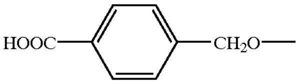 | 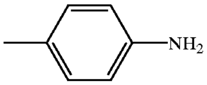 | m.p. 237–240° C. (decomp.) |
*: monohydrochloride
**: dihydrochloride
***: trihydrochloride
Fmoc: 9-fluorenylmethyloxycarbonyl group TABLE 39
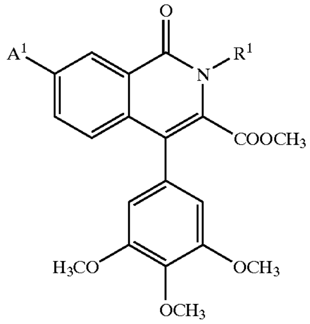
| Ex. No. | $A^1$ | $R^2$ | Physicochemical properties |
|---|---|---|---|
| 376(1) | 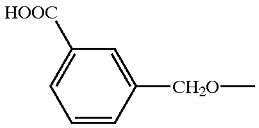 | 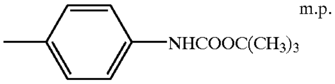 | m.p. 150–153° C. |
| 376(2)* | 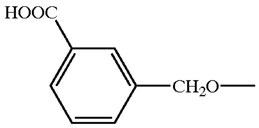 | 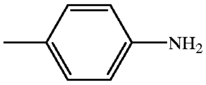 | m.p. 164–165° C. (decomp.) |
| 377** | 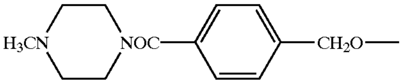 | 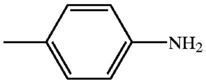 | m.p. 212–215° C. (decomp.) |
| 378** | 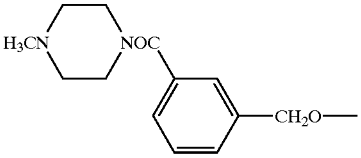 | 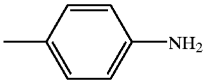 | m.p. 215–218° C. (decomp.) |
| 379** | 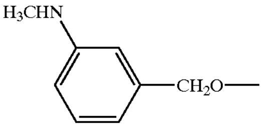 | 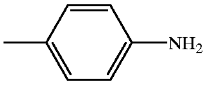 | m.p. 215–218° C. (decomp.) |
| 380* | 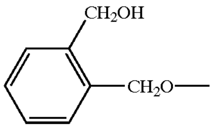 | 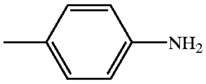 | m.p. >230° C. |
| 381* | 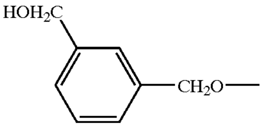 | 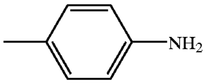 | m.p. 126–130° C. (decomp.) |
| 382* | 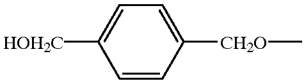 | 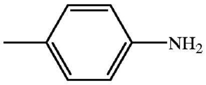 | m.p. 133–138° C. (decomp.) |
*: monohydrochloride
**: dihydrochloride TABLE 40
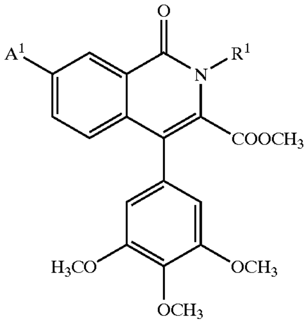
| Ex. No. | $A^1$ | $R^1$ | Physicochemical properties |
|---|---|---|---|
| 383 | 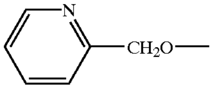 | 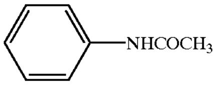 | m.p. 194–198° C. |
| 384(1) | 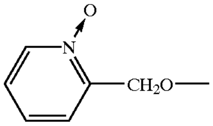 | 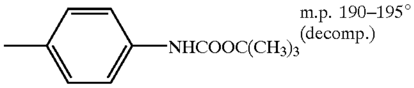 | m.p. 190–195° C. (decomp.) |
| 384(2) | 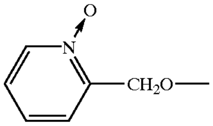 | 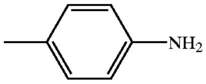 | m.p. 190–195° C. (decomp.) |
| 385* | 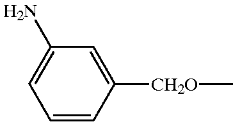 | 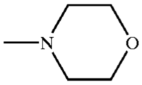 | m.p. 226–228° C. (decomp.) |
| 386 | 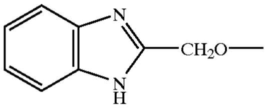 | 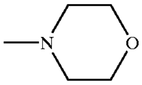 | m.p. 232–234° C. |
*: monohydrochloride
TABLE 41
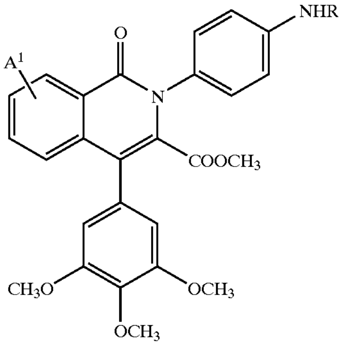
(R=H in Examples 384–393, and R=$SO_2CH_3$ in Example 394)
| Ex. No. | $A^1$ | Substituted position of $A^1$ | Physicochemical properties |
|---|---|---|---|
| 387 | HO— | 8 | m.p. 233–235° C. |

TABLE 41-continued
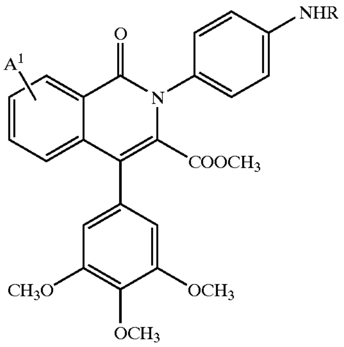
(R=H in Examples 384–393, and R=$SO_2CH_3$ in Example 394)
| Ex. No. | $A^1$ | Substituted position of $A^1$ | Physicochemical properties |
|---|---|---|---|
| 388** | 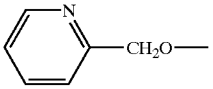 | 8 | m.p. 201–204° C. (decomp.) |
| 389** | 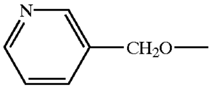 | 8 | m.p. 222–224° C. (decomp.) |
| 390** | 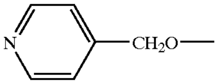 | 8 | m.p. 239–244° C. (decomp.) |
| 391** | 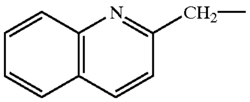 | 8 | m.p. 220–224° C. (decomp.) |
| 392* | 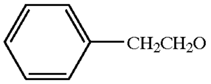 | 8 | m.p. 224–228° C. (decomp.) |
| 393** | 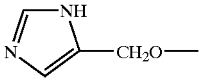 | 7 | m.p. 211–215° C. (decomp.) |
| 394 | 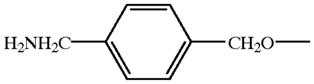 | 7 | m.p. 135–137° C. |
*: monohydrochloride
**: dihydrochloride TABLE 42
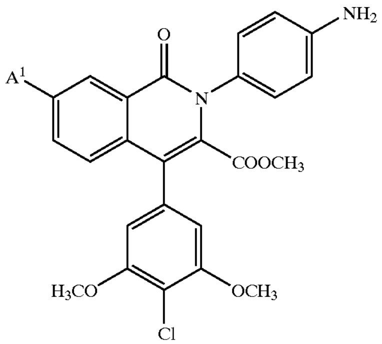
| Ex. No. | $A^1$ | Physicochemical properties |
|---|---|---|
| 395** | 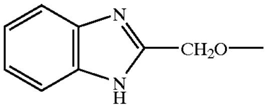 | m.p. 248–252° C. (decomp.) |
| 396* | 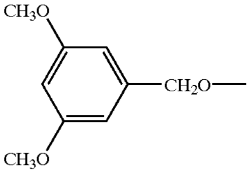 | m.p. 234–238° C. (decomp.) |
TABLE 42-continued
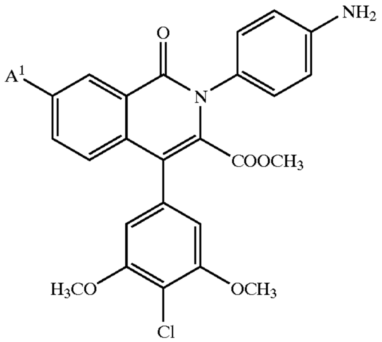
| Ex. No. | $A^1$ | Physicochemical properties |
|---|---|---|
| 397** | 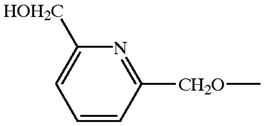 | m.p. 226–230° C. (decomp.) |
| 398** | 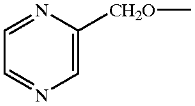 | m.p. 201–205° C. (decomp.) |
*: monohydrochloride
**: dihydrochloride
TABLE 43
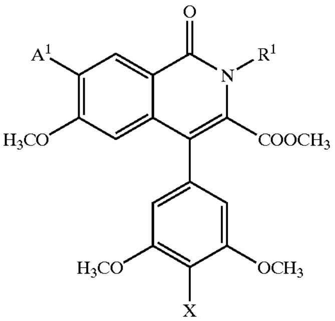
(X=Br in Example 399, and X=$CH_3$ in Examples 400–407)
| Ex. No. | $A^1$ | $R^1$ | Physicochemical properties |
|---|---|---|---|
| 399* | 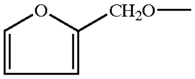 | 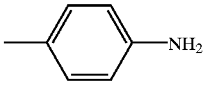 | m.p. 185–188° C. (decomp.) |
| 400 | 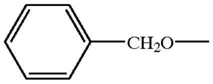 | 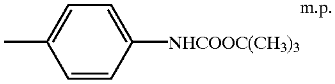 | m.p. 164–165° C. |
| 401* | 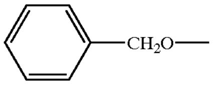 | 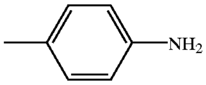 | m.p. 205–208° C. (decomp.) |
| 402 | HO— | 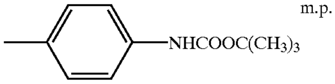 | m.p. >250° C. |

TABLE 43-continued
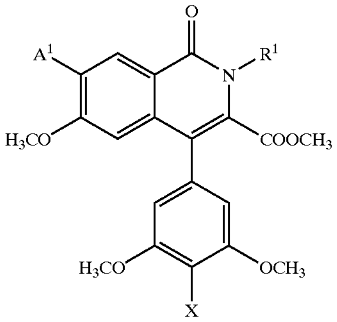
(X=Br in Example 399, and X=$CH_3$ in Examples 400–407)
| Ex. No. | $A^1$ | $R^1$ | Physicochemical properties |
|---|---|---|---|
| 403* | HO— | 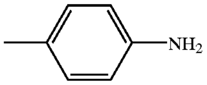 | m.p. 235–240° C. (decomp.) |
| 404** | 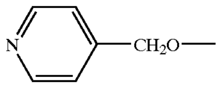 | 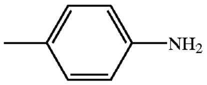 | m.p. 210–213° C. (decomp.) |
| 405** | 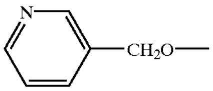 | 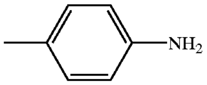 | m.p. 212–217° C. (decomp.) |
| 406** | 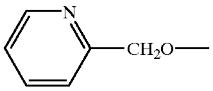 | 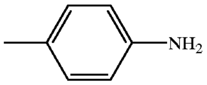 | m.p. 206–209° C. (decomp.) |
| 407** | 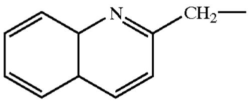 | 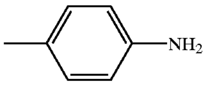 | m.p. 198–201° C. (decomp.) |
*: monohydrochloride
**: dihydrochloride
TABLE 44
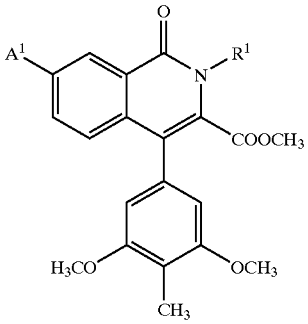
| Ex. No. | $A^1$ | $R^1$ | Physicochemical properties |
|---|---|---|---|
| 408 | 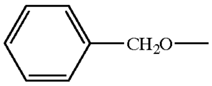 | 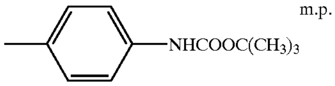 | m.p. 132–134° C. |
| 409* | 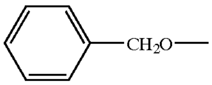 | 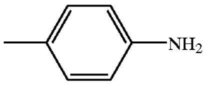 | m.p. 188–191° C. (decomp.) |

TABLE 44-continued
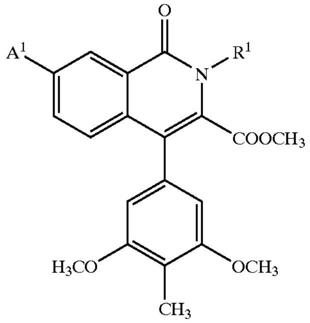
| Ex. No. | $A^1$ | $R^1$ | Physicochemical properties |
|---|---|---|---|
| 410 | HO— | 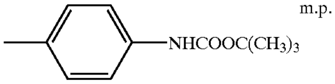 | m.p. 234–235° C. |
| 411* | HO— | 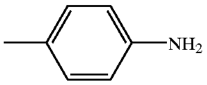 | m.p. 245–249° C. (decomp.) |
| 412** | 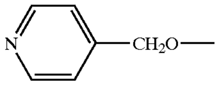 | 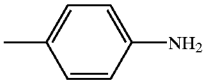 | m.p. 229–234° C. (decomp.) |
| 413** | 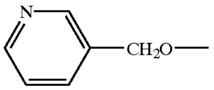 | 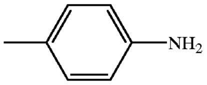 | m.p. 200–205° C. (decomp.) |
| 414** | 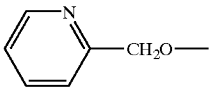 | 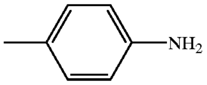 | m.p. 203–206° C. (decomp.) |
*: monohydrochloride
**: dihydrochloride
TABLE 45
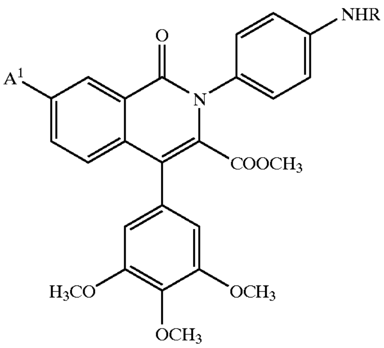
| Ex. No. | $A^1$ | Physicochemical properties |
|---|---|---|
| 415** | 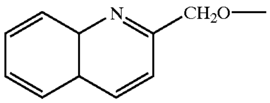 | m.p. 205–209° C. (decomp.) |
TABLE 45-continued
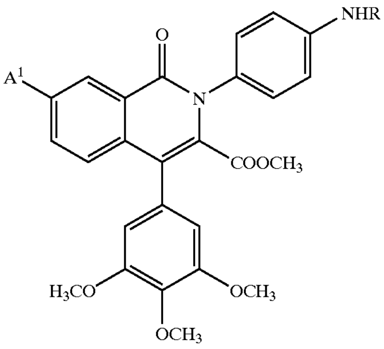
| Ex. No. | $A^1$ | Physicochemical properties |
|---|---|---|
| 416** | 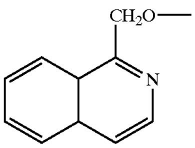 | m.p. 194–198° C. (decomp.) |

TABLE 45-continued

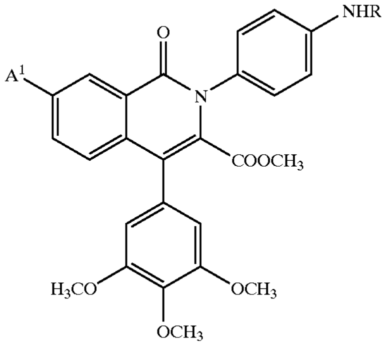

| Ex. No. | $A^1$ | Physicochemical properties |
| --- | --- | --- |
| 417*** | 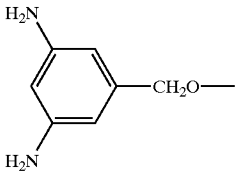 | m.p. 190–200° C. (decomp.) |
| 418** | 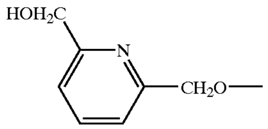 | m.p. 185–189° C. (decomp.) |
| 419** | 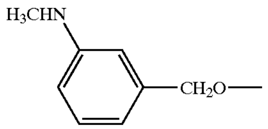 | m.p. 198–202° C. (decomp.) |
| 420* | 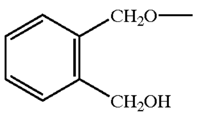 | m.p. 237–243° C. (decomp.) |
| 421** | 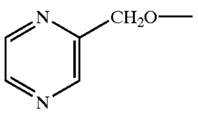 | m.p. 168–171° C. (decomp.) |

*: monohydrochloride
**: dihydrochloride
***: trihydrochloride

TABLE 46

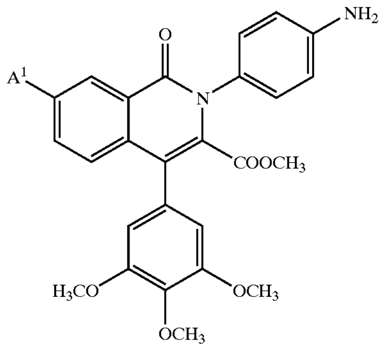

| Ex. No. | $A^1$ | Physicochemical properties |
| --- | --- | --- |
| 422(1) | 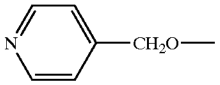 | m.p. 230–231° C. |
| 422(2) | 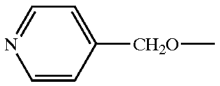 | monosulfate m.p. 232–236° C. (decomp.) |
| 423 | 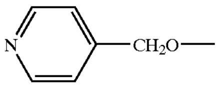 | dimethanesulfonate m.p. >250° C. |
| 424 | 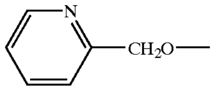 | monosulfate m.p. 221–223° C. (decomp.) |
| 425 | 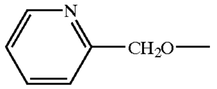 | dimethanesulfonate m.p. 190–193° C. |

TABLE 47

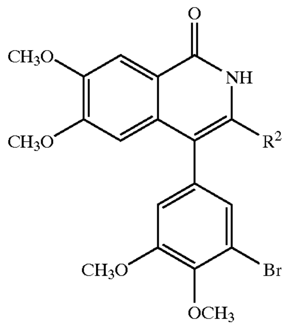

| Ex. No. | $R^2$ | Physicochemical properties |
| --- | --- | --- |
| 426 | —COOH | m.p. >220° C. |
| 427 | $—COOCH_3$ | m.p. 204–206° C. |

TABLE 48
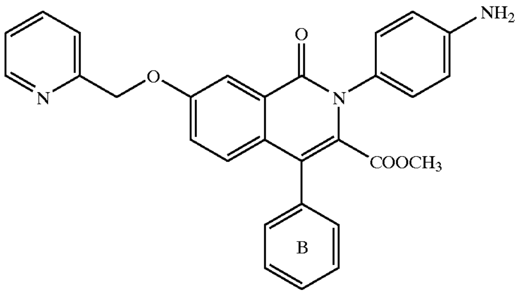
| Ex. No. | Ring B | Physicochemical properties |
| --- | --- | --- |
| 428(3)** | 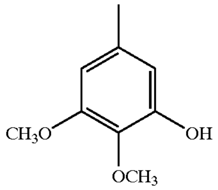 | m.p. 196–199° C. (decomp.) |
| 429 | 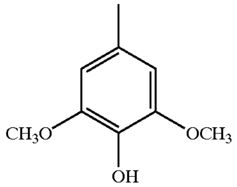 | m.p. 202–205° C. |
**: dihydrochloride
TABLE 49
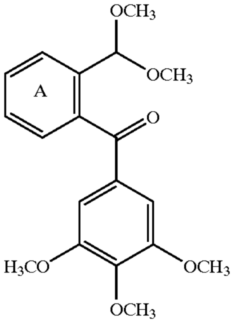
| Ref. Ex. No. | Ring A | Physicochemical properties |
| --- | --- | --- |
| 1 | 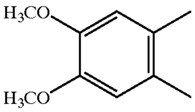 | m.p. 146–148° C. |
| 2 | 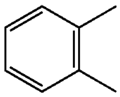 | m.p. 87–89° C. |
TABLE 49-continued
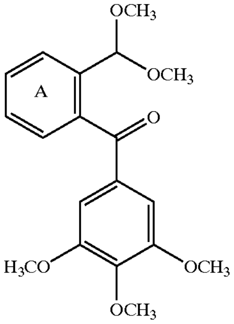
| Ref. Ex. No. | Ring A | Physicochemical properties |
| --- | --- | --- |
| 3 | 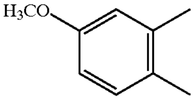 | m.p. 129–131° C. |
| 4 | 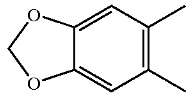 | m.p. 121–123° C. |
| 5 | 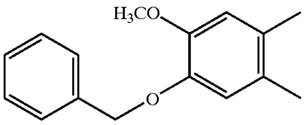 | Oil |
| 6 | 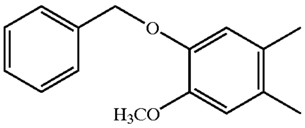 | not purified |
| 7 | 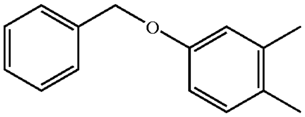 | m.p. 230–231° C. |
| 8 | 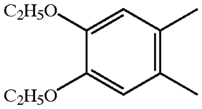 | m.p. 80–82° C. |

TABLE 50
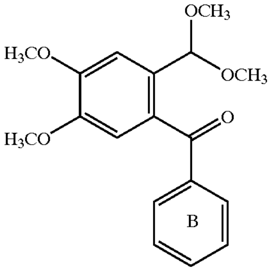
| Ref. Ex. No. | Ring B | Physicochemical properties |
|---|---|---|
| 9 | 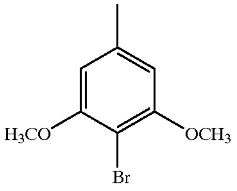 | m.p. 170–172° C. |
| 10 | 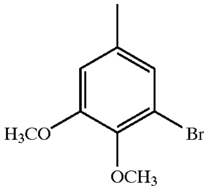 | Oil |
| 11 | 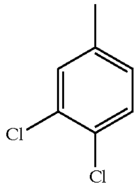 | Oil |
| 12 | 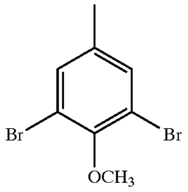 | Oil |
| 13 | 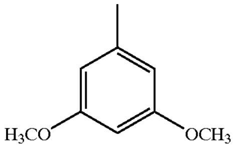 | Oil |
TABLE 51
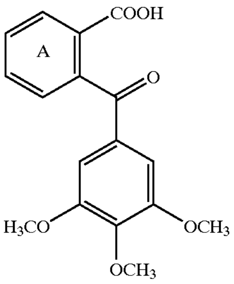
| Ref. Ex. No. | Ring A | Physicochemical properties |
|---|---|---|
| 14 | 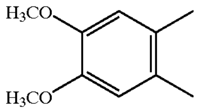 | m.p. 182–184° C. |
| 15 | 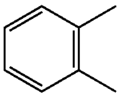 | m.p. 169–171° C. |
| 16 | 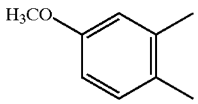 | m.p. 197–199° C. |
| 17 | 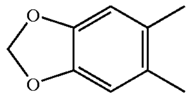 | m.p. 214–216° C. |
| 18 | 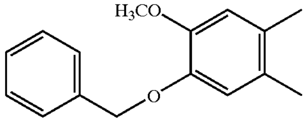 | m.p. 146–147° C. |
| 19 | 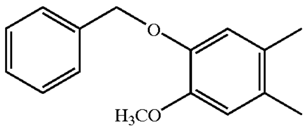 | m.p. 93–94° C. |
| 20 | 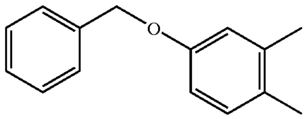 | m.p. 161–162° C. |
| 21 | 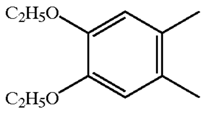 | m.p. 194–196° C. |

TABLE 52

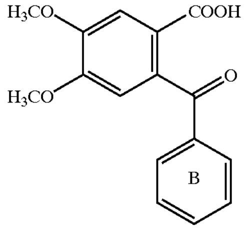

| Ref. Ex. No. | Ring A | Physicochemical properties |
|---|---|---|
| 22 | 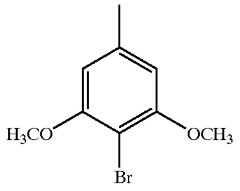 | m.p. >230° C. |
| 23 | 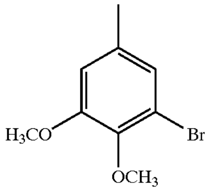 | m.p. 180–182° C. |
| 24 | 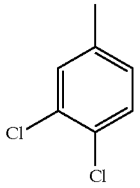 | m.p. 189–191° C. |
| 25 | 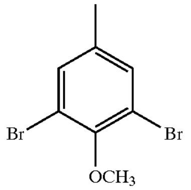 | m.p. 213–216° C. |
| 26 | 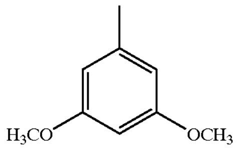 | Oil |
| 27 | 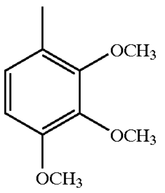 | m.p. 166–168° C. |

TABLE 52-continued

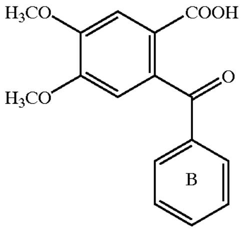

| Ref. Ex. No. | Ring A | Physicochemical properties |
|---|---|---|
| 28 | 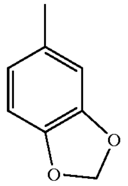 | m.p. 200–202° C. |

TABLE 53

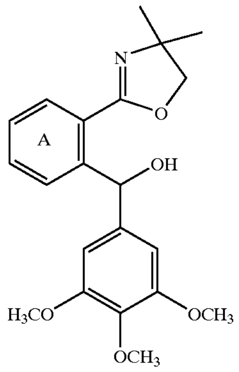

| Ref. Ex. No. | Ring A | Physicochemical properties |
|---|---|---|
| 29 | 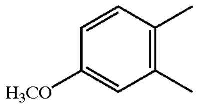 | m.p. 109–110° C. |
| 30 | 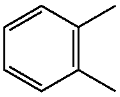 | Oil |

REFERENCE EXAMPLE 31

A solution of N-methyl-2-chlorobenzamide (13.0 g) in tetrahydrofuran (300 ml) is cooled to −70° C., and thereto is added dropwise a 1.3M solution of sec-butyl lithium in cyclohexane (130 ml) over a period of 20 minutes. The mixture is stirred at −60° C. for 30 minutes, and thereto is added dropwise a solution of 3,4,5-trimethoxybenzaldehyde (15.0 g) in tetrahydrofuran (100 ml) over a period of 10 minutes. The mixture is stirred at the same temperature for one hour, and thereto are added water and ethyl acetate (300 ml). The ethyl acetate layer is separated, washed, dried, and concentrated under reduced pressure. The residue is crystallized from diethyl ether to give N-methyl-2-chloro-6-[hydroxy-(3,4,5-trimethoxyphenyl)methyl]benzamide (19.2 g) as listed in Table 54.

REFERENCE EXAMPLE 32–35
The corresponding compounds are treated in the same manner as in Reference Example 31 to give the compounds as listed in Table 54.
TABLE 54
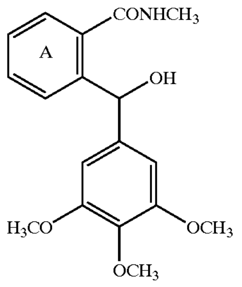
| Ref. Ex. No. | Ring A | Physicochemical properties |
|---|---|---|
| 31 | 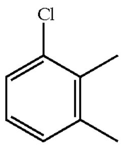 | m.p. 185–187° C. |
| 32 | 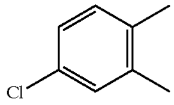 | Not purified |
| 33 | 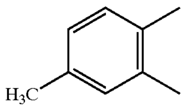 | m.p. 138–140° C. |
| 34 | 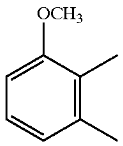 | m.p. 169–171° C. |
| 35 | 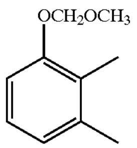 | m.p. 148–149° C. |
TABLE 55
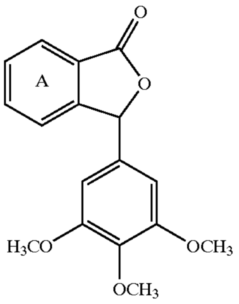
| Ref. Ex. No. | Ring A | Physicochemical properties |
|---|---|---|
| 36 | 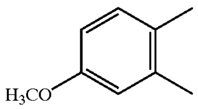 | m.p. 114–115° C. |
| 37 | 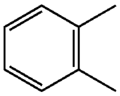 | m.p. 126–127° C. |
| 38 | 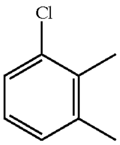 | m.p. 199–201° C. |
| 39 | 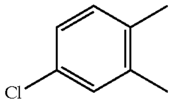 | m.p. 155–156° C. |
| 40 | 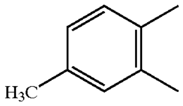 | m.p. 107–110° C. |
| 41 | 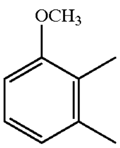 | m.p. 140–141° C. |
| 42 | 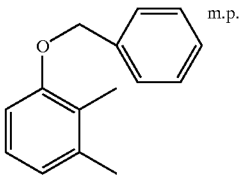 | m.p. 148–149° C. |

TABLE 56
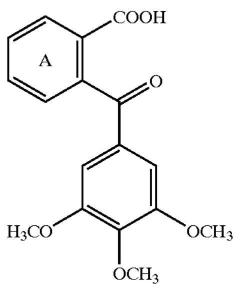
| Ref. Ex. No. | Ring A | Physicochemical properties |
|---|---|---|
| 43 | 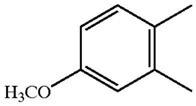 | m.p. 207–209° C. |
| 44 | 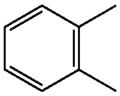 | m.p. 169–171° C. |
| 45 | 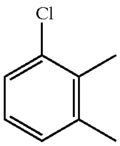 | m.p. 169–171° C. |
| 46 | 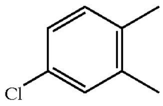 | m.p. 219–220° C. |
| 47 | 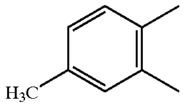 | m.p. 182–183° C. |
| 48 | 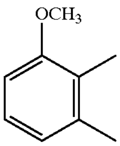 | m.p. 160–162° C. |
| 49 | 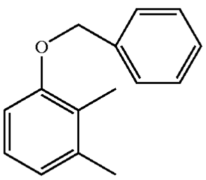 | m.p. 153–155° C. |
TABLE 57
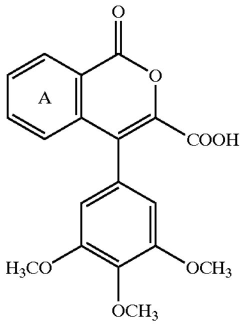
| Ref. Ex. No. | Ring A | Physicochemical properties |
|---|---|---|
| 50 | 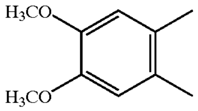 | m.p. > 250° C. |
| 51 | 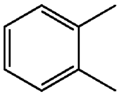 | m.p. 237–239° C. |
| 52 | 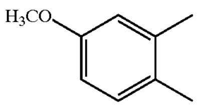 | m.p. 264–266° C. |
| 53 | 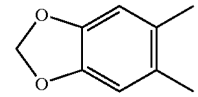 | m.p. 259–262° C. |
| 54 | 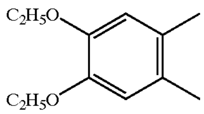 | m.p. > 250° C. |
| 55 | 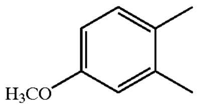 | m.p. 219–221° C. |
| 56 | 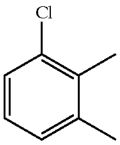 | m.p. 234–236° C. |
| 57 | 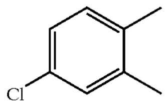 | m.p. > 250° C. |
| 58 | 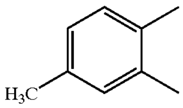 | m.p. 233–235° C. (decomp.) |
| 59 | 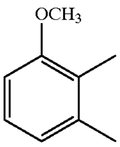 | m.p. 245–248° C. |

TABLE 58
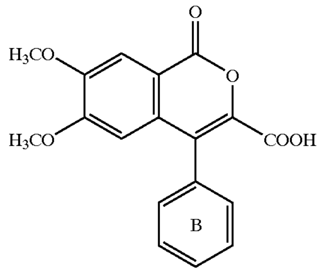
| Ref. Ex. No. | Ring B | Physicochemical properties |
|---|---|---|
| 60 | 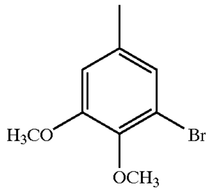 | m.p. 260–262° C. |
| 61 | 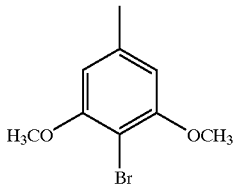 | Not purified |
| 62 | 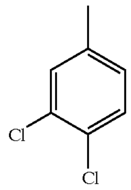 | m.p. 274–277° C. |
| 63 | 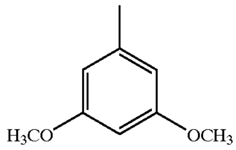 | m.p. 238–240° C. |
| 64 | 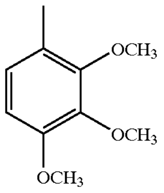 | m.p. 215–218° C. |
| 65 | 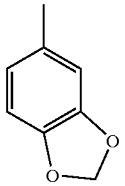 | m.p. 203–205° C. |
TABLE 58-continued
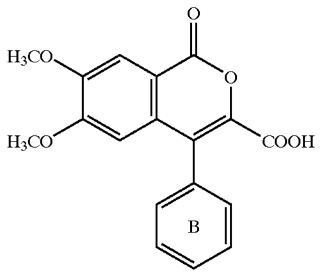
| Ref. Ex. No. | Ring B | Physicochemical properties |
|---|---|---|
| 66 | 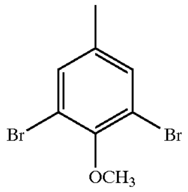 | m.p. > 250° C. |
TABLE 59
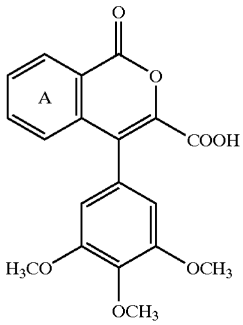
| Ref. Ex. No. | Ring A | Physicochemical properties |
|---|---|---|
| 67 | 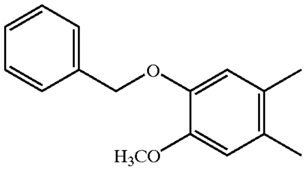 | m.p. > 250° C. |
| 68 | 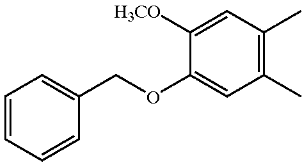 | m.p. 242–244° C. |
| 69 | 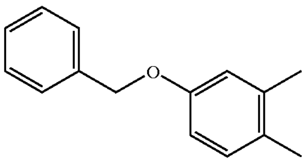 | m.p. 236–238° C. |

TABLE 59-continued
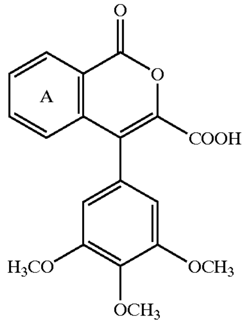
| Ref. Ex. No. | Ring A | Physicochemical properties |
|---|---|---|
| 70 | 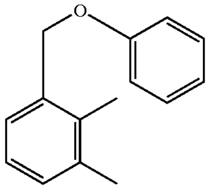 | m.p. 212–214° C. |
TABLE 60
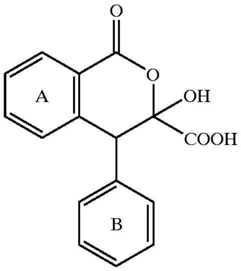
| Ref. Ex. No. | Ring A | Ring B | Physicochemical properties |
|---|---|---|---|
| 71 | 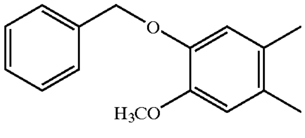 | 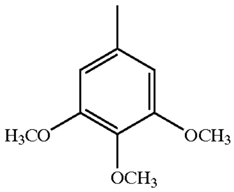 | m.p. 160–163° C. |
| 72 | 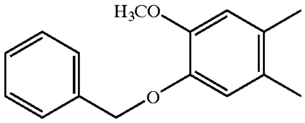 | 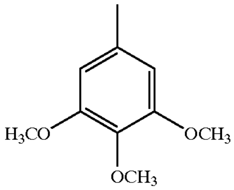 | m.p. 114–116° C. |

TABLE 60-continued
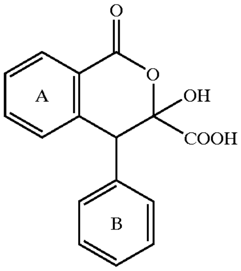
| Ref. Ex. No. | Ring A | Ring B | Physicochemical properties |
|---|---|---|---|
| 73 | 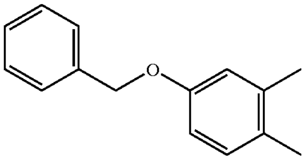 | 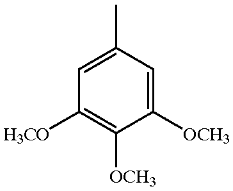 | m.p. 105–106° C. |
| 74 | 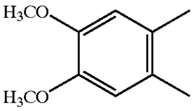 | 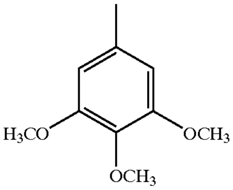 | m.p. 207–208° C. |
| 75 | 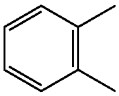 | 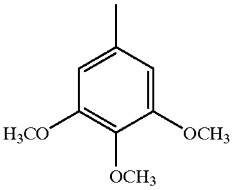 | Powder |
| 76 | 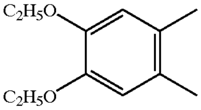 | 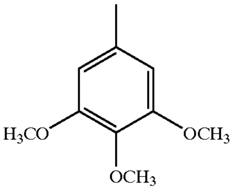 | m.p. > 250° C. |
| 77 | 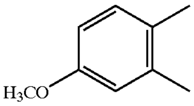 | 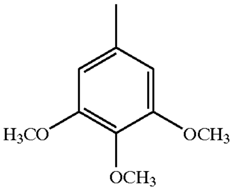 | Not purified |
| 78 | 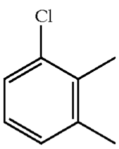 | 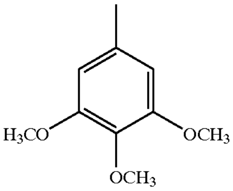 | Not purified |

TABLE 60-continued
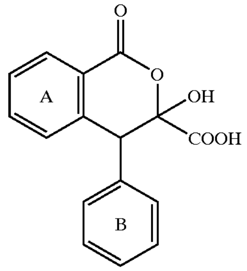
| Ref. Ex. No. | Ring A | Ring B | Physicochemical properties |
|---|---|---|---|
| 79 | 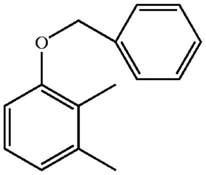 | 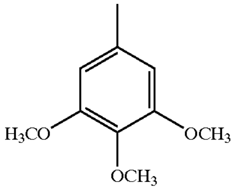 | m.p. 118–120° C. |
| 80 | 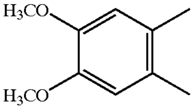 | 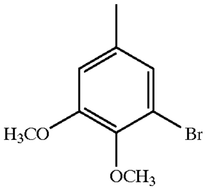 | m.p. 258–260° C. |
| 81 | 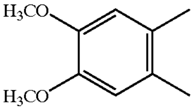 | 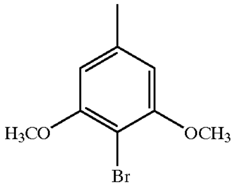 | Powder |
| 82 | 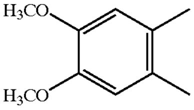 | 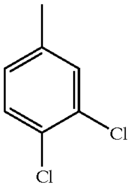 | Not purified |
| 83 | 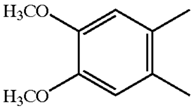 | 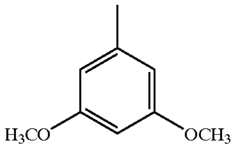 | m.p. 165–168° C. |
| 84 | 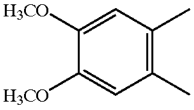 | 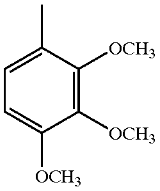 | Not purified |

TABLE 60-continued
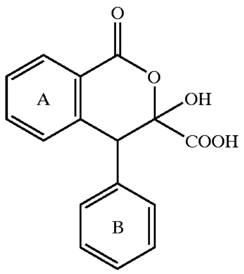
| Ref. Ex. No. | Ring A | Ring B | Physicochemical properties |
|---|---|---|---|
| 85 | 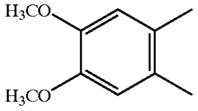 | 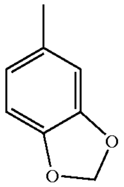 | Not purified |
| 86 | 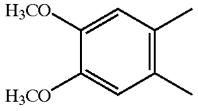 | 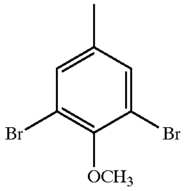 | Not purified |
TABLE 61
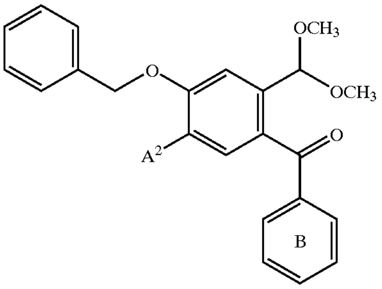
| Ref. Ex. No. | $A^2$ | Ring B | Physicochemical properties |
|---|---|---|---|
| 87 | $CH_3O$— | 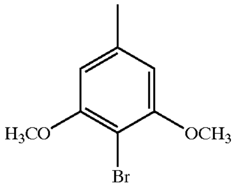 | not purified |
| 88 | $CH_3O$— | 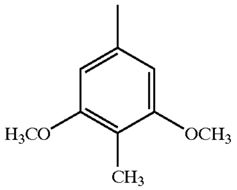 | not purified |
TABLE 61-continued
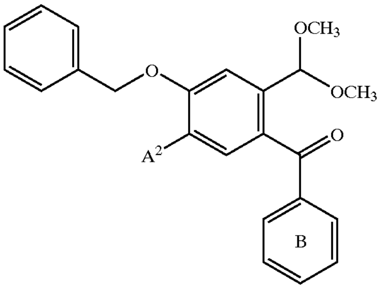
| Ref. Ex. No. | $A^2$ | Ring B | Physicochemical properties |
|---|---|---|---|
| 89 | H | 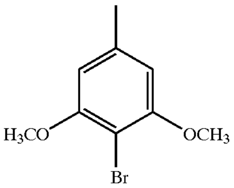 | not purified |
| 90 | H | 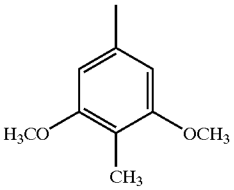 | m.p. 134–136° C. |

TABLE 61-continued
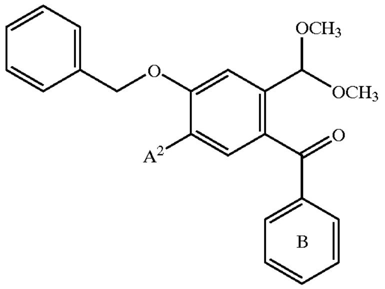
| Ref. Ex. No. | $A^2$ | Ring B | Physicochemical properties |
|---|---|---|---|
| 91 | H | 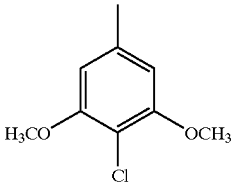 | m.p. 162–164° C. |
TABLE 62
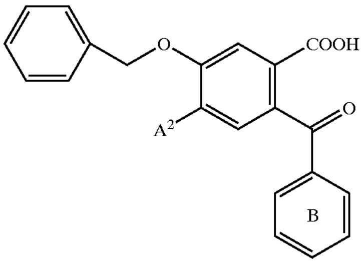
| Ref. Ex. No. | $A^2$ | Ring B | Physicochemical properties |
|---|---|---|---|
| 92 | $CH_3O$— | 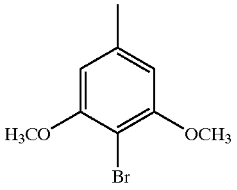 | m.p. 111–112° C. |
| 93 | $CH_3O$— | 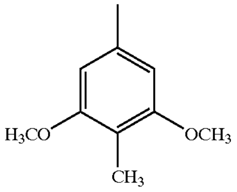 | m.p. 183–184° C. |
| 94 | H | 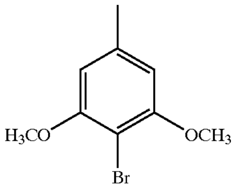 | m.p. 179–180° C. |
TABLE 62-continued
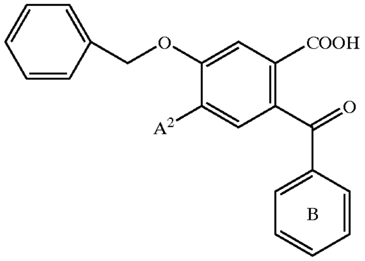
| Ref. Ex. No. | $A^2$ | Ring B | Physicochemical properties |
|---|---|---|---|
| 95 | H | 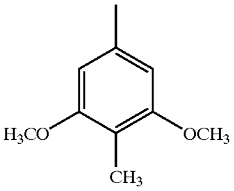 | m.p. 173–175° C. |
| 96 | H | 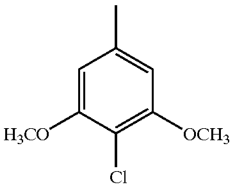 | m.p. 173–175° C. |
TABLE 63
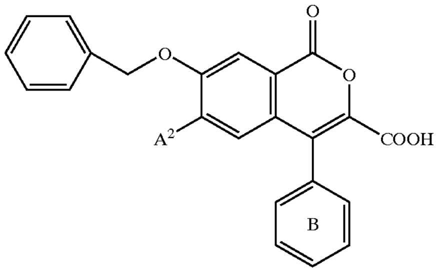
| Ref. Ex. No. | $A^2$ | Ring B | Physicochemical properties |
|---|---|---|---|
| 97 | $CH_3O$— | 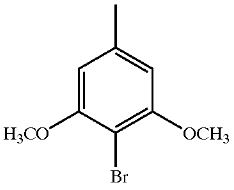 | m.p. > 250° C. |
| 98 | $CH_3O$— | 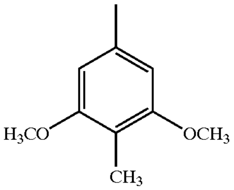 | m.p. > 250° C. |

TABLE 63-continued

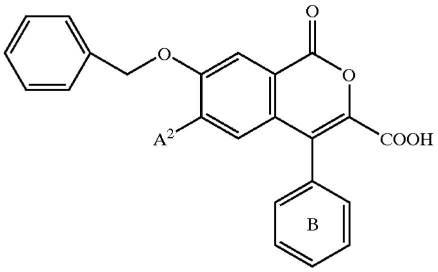

| Ref. Ex. No. | $A^2$ | Ring B | Physicochemical properties |
|---|---|---|---|
| 99 | H | 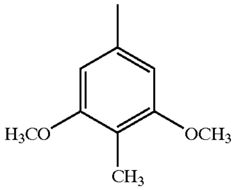 | m.p. > 250° C. |
| 100 | H | 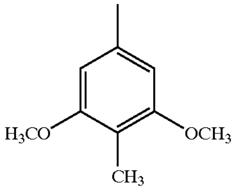 | m.p. 245–246° C. |
| 101 | H | 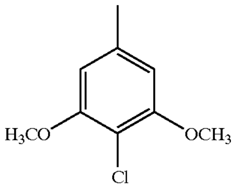 | m.p. > 250° C. |

TABLE 64

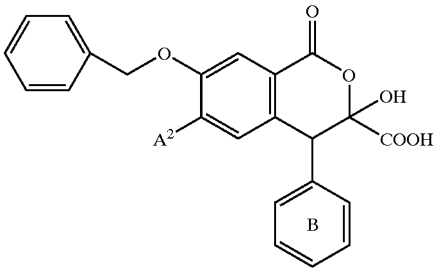

| Ref. Ex. No. | $A^2$ | Ring B | Physicochemical properties |
|---|---|---|---|
| 102 | $CH_3O$— | 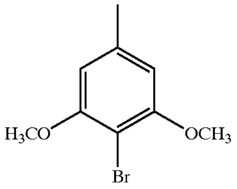 | m.p. 200–204° C. (decomp.) |

TABLE 64-continued

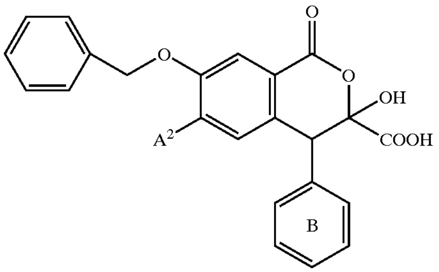

| Ref. Ex. No. | $A^2$ | Ring B | Physicochemical properties |
|---|---|---|---|
| 103 | $CH_3O$— | 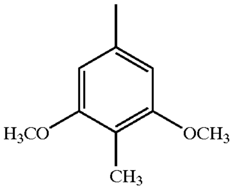 | m.p. 144–145° C. (decomp.) |
| 104 | H | 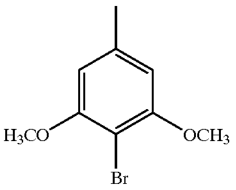 | m.p. 113–115° C. |
| 105 | H | 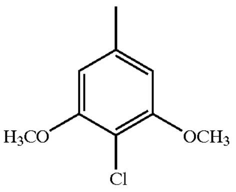 | m.p. 146–148° C. |
| 106 | H | 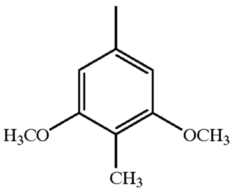 | m.p. 129–134° C. (decomp.) |

It will be understood that various changes and modifications can be made in the details of procedure, formulation and use without departing from the spirit of the invention, especially as defined in the following claims.

We claim:

1. A method of treating a mammal having precancerous lesions sensitive to a compound below comprising administering a pharmacologically effective amount of a compound of Formula I or pharmaceutically acceptable salt thereof:

(I)

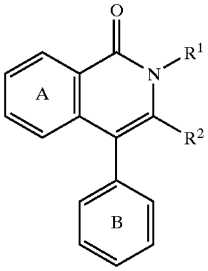

wherein

Ring A and Ring B are the same or different and each a substituted or unsubstituted benzene ring, R1 is morpholine, R2 is —COOR3, and R3 is alkyl.

2. A method for inhibiting the growth of neoplastic cells sensitive to a compound below comprising exposing the cells to a growth inhibiting effective amount of a compound of Formula I or pharmaceutically acceptable salt thereof:

(I)

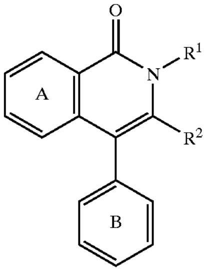

wherein

Ring A and Ring B are the same or different and each a substituted or unsubstituted benzene ring, R1 is morpholine, R2 is —COOR3, and R3 is alkyl.

* * * * *